(12) United States Patent
Uto et al.

(10) Patent No.: US 8,735,425 B2
(45) Date of Patent: May 27, 2014

(54) TETRAHYDROISOQUINOLINE DERIVATIVE

(75) Inventors: Yoshikazu Uto, Chiba (JP); Hiroshi Karasawa, Tokyo (JP); Kiyosumi Takaishi, Tokyo (JP)

(73) Assignee: Daiichi Sankyo Company, Limited, Tokyo (JP)

(*) Notice: Subject to any disclaimer, the term of this patent is extended or adjusted under 35 U.S.C. 154(b) by 930 days.

(21) Appl. No.: 12/878,170

(22) Filed: Sep. 9, 2010

(65) Prior Publication Data
US 2011/0034481 A1 Feb. 10, 2011

Related U.S. Application Data

(63) Continuation of application No. PCT/JP2009/055738, filed on Mar. 24, 2009.

(30) Foreign Application Priority Data

Mar. 26, 2008 (JP) ................. 2008-079901

(51) Int. Cl.
*C07D 217/06* (2006.01)
*A61K 31/47* (2006.01)

(52) U.S. Cl.
CPC .............. *C07D 217/06* (2013.01); *A61K 31/47* (2013.01)
USPC ......................... 514/310; 546/143

(58) Field of Classification Search
None
See application file for complete search history.

(56) References Cited

U.S. PATENT DOCUMENTS

| | | | |
|---|---|---|---|
| 2002/0127627 A1 | 9/2002 | Ramharack et al. | |
| 2007/0249620 A1 | 10/2007 | Kurata et al. | |

FOREIGN PATENT DOCUMENTS

| | | |
|---|---|---|
| EP | 1764360 A1 | 3/2007 |
| EP | 1 837 332 A1 | 9/2007 |
| GB | 1077173 | 7/1967 |
| JP | 53-124237 | 10/1978 |
| JP | 62-255480 | 11/1987 |
| JP | 2000-026294 | 1/2000 |
| JP | 2002-306199 | 10/2002 |
| JP | 2004/0196723 | 7/2004 |
| JP | 2007-131584 A | 5/2007 |
| JP | 2007-191471 A | 8/2007 |
| WO | WO 03-007955 | 1/2003 |
| WO | WO 03-045926 | 6/2003 |
| WO | WO 03/086306 A2 | 10/2003 |
| WO | WO 2005/009950 A2 | 2/2005 |
| WO | WO 2005-011656 | 2/2005 |
| WO | WO 2005/072740 A2 | 8/2005 |
| WO | WO 2006/019020 A1 | 8/2005 |
| WO | WO 2006/004200 A1 | 1/2006 |
| WO | WO 2006/009741 | 1/2006 |
| WO | WO 2006-058649 | 6/2006 |
| WO | WO 2006/095922 A1 | 9/2006 |
| WO | WO 2007/074753 A1 | 7/2007 |

OTHER PUBLICATIONS

Lima et al., "Bioisosterism: A Useful Strategy for Molecular Modification and Drug Design," *Curr. Med. Chem.* (2005), 12(1): pp. 23-49.

Itagaki, Eiji, ed. "STEP Series, Metabolism, Endocrinology," Kaibashobo, Ltd., 1st ed.: pp. 105 (1998).

Zimmet, P. et al. "Global and societal implications of the diabetes epidemic," *Nature*, vol. 414, pp. 782-787 (Dec. 13, 2001).

Engstrom, R.G. et al. "The effects of 5-hydroxy-5-(f'-Chlorophenyl)-2, 3-Dihydro-5H-Imidazo (2,1-a) Isoindole (Mazindol, SaH 42-548) on the Metabolism of Brain Norepinephrine," *Arch. Int. Pharmacodyn.*, vol. 214, pp. 308-321 (1975).

(Continued)

*Primary Examiner* — Zinna Northington Davis
(74) *Attorney, Agent, or Firm* — Dorsey and Whitney LLP

(57) ABSTRACT

The present invention relates to a compound or a pharmacologically acceptable salt thereof having an excellent DGAT inhibitory effect and feeding suppressant effect. The present invention provides a compound represented by the general formula (I), or pharmacologically acceptable salt thereof:

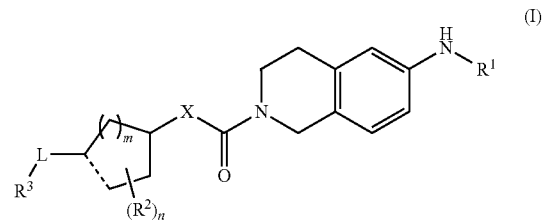

[wherein, $R^1$ represents a phenylaminocarbonyl group that may be substituted with 1 to 5 group(s) independently selected from Substituent Group A, a benzoxazol-2-yl group that may be substituted with 1 to 3 group(s) independently selected from Substituent Group A, or the like; $R^2$ independently represents a $C_1$-$C_6$ alkyl group; $R^3$ represents a group represented by the formula —C(=O)—O—$R^4$ or the like; $R^4$ represents a hydrogen atom, a $C_1$-$C_6$ alkyl group that may be substituted with 1 to 3 group(s) independently selected from Substituent Group B, or the like; X represents an oxygen atom, a methylene group, or a group represented by the formula —NH—, or the like; L represents a single bond, a methylene group, or the like; . . . represents a single bond or a double bond; m represents 1 or 2; n represents an integer of 0 to 5; Substituent Group A represents a halogen atom, a $C_1$-$C_6$ alkyl group, a $C_1$-$C_6$ halogenated alkyl group, a $C_1$-$C_6$ alkoxy group, or the like; and Substituent Group B represents a $C_3$-$C_6$ cycloalkyl group, a phenyl group, a carboxyl group, or the like].

41 Claims, No Drawings

(56) References Cited

OTHER PUBLICATIONS

Bray, George A. et al. "A double-blind randomized placebo-controlled trial of sibutramine," *Obesity Research*, vol. 4, No. 3, pp. 263-270 (1996).

Davidson, Michael H. et al. "Weight control and risk factor reduction in obese subjects treated for 2 years with orlistat: a randomized controlled trial," *JAMA*, vol. 281, pp. 235-242 (1999).

Coleman, R. et al. "Triacyglycerol Synthesis in Isolated Fat Cells," *The Jour. of Biol. Chem.*, vol. 251, No. 15, pp. 4537-4543 (1976).

Coleman, Rosalind. "Diacylglycerol Acyltransferase and Monoacylglycerol Acyltransferase from Liver and Intestine," *Methods in Enzymology*, vol. 209, pp. 98-104 (1992).

Lehner, Richard et al. "Biosynthesis of Triacylglycerols," *Prog. Lipid. Res.*, vol. 35, No. 2, pp. 169-201 (1996).

Bell, Robert M. "Enzymes of glycerolipid synthesis in eukaryotes," *Ann. Rev. Biochem.*, vol. 49, pp. 459-487 (1980).

Cases, S. et al. "Identification of a gene encoding an acyl CoA:diacylglycerol acyltransferase, a key enzyme in triacylglycerol synthesis," *Proc. Natl. Acad. Sci.*, vol. 95, pp. 13018-13023 (Oct. 1998).

Cases, S. et al. "Cloning of DGAT2, a second mammalian diacylglycerol acyltransferase, and related family members," *Jour. of Biol. Chem.*, vol. 276, No. 42, pp. 38870-38876 (2001).

Coleman, Rosalind A. et al. "Enzymes of triacylglycerol synthesis and their regulation," *Progress in Lipid Research*, vol. 43, pp. 134-176 (2004).

Smith, Steven J. et al. "Obesity resistance and multiple mechanisms of triglyceride synthesis in mice lacking Dgat," Nature Genetics, vol. 25, pp. 87-90 (May 2000).

Chen, Hubert C. et al. "Increased insulin and leptin sensitivity in mice lacking acyl CoA:diacylglycerol acyltransferase 1," *Jour. of Clin. Invest.*, vol. 109, No. 8, pp. 1049-1055 (Apr. 2002).

Buhman, Kimberly K. et al. "DGAT1 is not essential for intestinal triacylglycerol absorption or chylomicron synthesis," *Jour. of Biol. Chem.*, vol. 277, No. 28, pp. 25474-25479 (2002).

Gaziano, J. Michael et al. "Fasting triglycerides, high-density lipoprotein, and risk of myocardial infarction," *Circulation*, vol. 96, pp. 2520-2525 (1997).

Yamaguchi, Kanji et al. "Diacylglycerol acyltransferase 1 anti-sense oligonucleotides reduce hepatic fibrosis in mice with nonalcoholic steatohepatitis," *Hepatology*, vol. 47, pp. 625-635 (2008).

Strader, April D. et al. "Gastrointestinal hormones and food intake," *Gastroenterology*, vol. 128, pp. 175-191 (2005).

Campfield, L. Arthur et al. "Recombinant mouse OB protein: evidence for a peripheral signal linking adiposity and central neural networks," Science, vol. 269, pp. 546-549 (Jul. 29, 1995).

Tomodo, Hiroshi et al. "Amidepsines, inhibitors of diacylglycerol acyltransferase produced by *Humicola* sp. FO-2942," *Jour. of Antibiotics*, vol. 48, No. 9, pp. 937-941 (1995).

Yang, D. J. et al. "New Isochromophilones VII and VIII Produced by *Penicillium* sp. FO-4164," *Jour. of Antibiotics*, vol. 49, No. 3, pp. 223-229 (Mar. 1996).

Tomoda, Hiroshi et al. "Roselipins, Inhibitors of Diacylglycerol Acyltransferase, produced by *Gliocladium roseum* KF-1040," *Jour. of Antibiotics*, vol. 52, No. 8, pp. 689-694 (Aug. 1999).

Tabata, N. et al. "Xanthohumols, Diacylglycerol acyltransferase inhibitors, from *Humulus lupulus*," *Phytochemistry*, vol. 46, No. 4, pp. 683-687 (1997).

Zhao, Gang et al. "Validation of diacyl glycerolacyltransferase I as a novel target for the treatment of obesity and dyslipidemia using a potent and selective small molecule inhibitor," *J. Med. Chem.*, vol. 51, pp. 380-383 (2008).

Yen, Chi-Liang Eric, et al. "DGAT enzymes and triacyglycerol biosynthesis," *Journal of Lipid Research*, vol. 49, pp. 2283-2301 (2008).

Subauste, Angela et al. "DGAT: novel therapeutic target for obesity and type 2 diabetes mellitus," *Current Drug Targets—Immune, Endocrine & Metabolic Disorders*, vol. 3, pp. 263-270 (2003).

Chen, Hubert C. et al. "Role of Adipocyte-Derived Factors in Enhancing Insulin Signaling in Skeletal Muscle and White Adipose Tissue of Mice Lacking Acyl CoA:Diacyglycerol Acyltransferase 1," Diabetes, vol. 53, pp. 1445-1451 (Jun. 2004).

King, Andrew J. et al. "Diacylglycerol acyltransferase 1 (DGAT-1) inhibition lowers serum triglycerides in the Zucker fatty rat and the hyperlipidemic hamster," *Am. Soc. Pharm. Exp. Ther.*, pp. 1-28 (2009).

Chen et al. "Inhibition of Triglyceride Synthesis as a Treatment Strategy for Obesity: Lessons fro mDGAT1-Deficient Mice," *Arterioscler. Thrombl. Vasc. Biol.*, vol. 25, pp. 482-486 (Nov. 2004).

Husain et al. "Search for Potent Anthelmintics-Part X$^1$N1-*p*-4-(Phenyl/*p*-Tolyl)-1-Piperazino]Phenyl-N$^3$-Alkyl/Aryl Ureas and Thioureas," *Journal of the Indian Chemical Society*, vol. 56, pp. 919-920 (1979).

Meerpoel, Lieven et al. "Synthesis and in 1,36-38 Vitro and in Vivo Structure-Activity Relationships of Novel Antifungal Triazoles for Dermatology," *Journal of Medicinal Chemistry*, vol. 48, No. 6, pp. 2184-2193 (2005).

TETRAHYDROISOQUINOLINE DERIVATIVE

CROSS REFERENCE TO RELATED APPLICATIONS

This application is a Continuation of PCT Patent Application No. PCT/JP2009/055738, filed Mar. 24, 2009, which claims priority to Japanese Patent Application No. 2008-079901, filed Mar. 26, 2008, the contents of each of which are hereby incorporated in their entirety by reference.

TECHNICAL FIELD

The present invention relates to a compound or a pharmacologically acceptable salt thereof having a particular chemical structure having an excellent acyl-coenzyme A: diacylglycerol acyltransferase (Acyl-CoA: diacylglycerol acyltransferase, hereinafter, also referred to as DGAT) inhibitory effect and an excellent feeding suppressant effect.

BACKGROUND ART

Adiposity is a condition of having a significantly greater body weight than normal as a result of accumulation of neutral fats (triacylglycerol or triglyceride, hereinafter also referred to as TG) in fat cells due to continuous excess energy intake compared to energy consumption (Non-Patent Document 1). Adiposity leads to life-style related disease (e.g., hyperlipidemia, hypertriglyceridemia, diabetes, hypertension, and arteriosclerosis), cerebrovascular disorder, coronary artery disease, respiratory abnormality, lower back pain, knee osteoarthritis, gout, cholelithiasis, and so on. Adiposity with a complication of these diseases or adiposity which may later lead to such a complication is defined as obesity and treated as a disease.

Moreover, in recent years, obesity has been shown to be one of the major causes of a life-style related disease called metabolic syndrome (Non-Patent Document 2). It has been reported that in individuals with obesity, fatty acids and factors such as TNF-α are released from accumulated visceral fats, and induce insulin resistance in skeletal muscles, the liver, and fat tissue while facilitating the synthesis of neutral fats in the liver, resulting in hyperlipidemia. Furthermore, an increase in serum insulin concentration induced by the insulin resistance increases peripheral vascular resistance via increased renal reabsorption of Na ions and activation of sympathetic nerves, causing hypertension. Hyperlipidemia, diabetes, and hypertension caused by obesity are also thought to trigger angiopathy such as cerebrovascular disorder or coronary artery disease caused by arteriosclerosis, resulting in severe, life-threatening clinical conditions.

Currently, drug therapy has been practiced on obesity based on the provisions of each country, and centrally acting anorectics such as mazindol (Non-Patent Document 3) and sibutramine (Non-Patent Document 4) and lipid absorption inhibitors such as the pancreatic lipase inhibitor orlistat are prescribed mainly for the purpose of controlling calorie intake. These drugs offer low satisfaction with treatment, although achieving some therapeutic effects. The centrally acting anorectics have adverse effects such as dry mouth, constipation, gastric discomfort, and in some cases, auditory hallucination and visual hallucination. Orlistat (Non-Patent Document 5) may cause adverse effects in the gastrointestinal tract, such as diarrhea, incontinence, steatorrhea, and flatus. Accordingly, there is a need for the development of more potent drugs with fewer adverse effects. Under such circumstances, active research and development has been conducted with the aim of developing novel anti-obesity drugs, most of which are anorectics.

Animals and plants store lipids as insoluble TG and produce energy by catabolizing TG according to need. TG taken from food is hydrolyzed into free fatty acid and monoacylglycerol in the lumen of the small intestine by the action of bile acid and pancreatic lipase. Micelles composed of free fatty acid, monoacylglycerol, and bile acid are absorbed into small intestinal epithelial cells in which TG is then re-synthesized in the endoplasmic reticulum by the action of acyl-coenzyme A synthetase (hereinafter, referred to as ACS), acyl-coenzyme A: monoacylglycerol acyltransferase, and DGAT. TG is combined with phospholipid, cholesterol, and apolipoprotein and secreted in the form of chylomicron into the lymph vessels in the stomach and intestine. TG is then secreted into the blood through the lymphatic trunk and transferred to the periphery for use. On the other hand, TG is also synthesized in fat tissue from glycerol 3-phosphate and free fatty acid by the action of ACS, glycerol 3-phosphate acyltransferase, lysophosphatidic acid acyltransferase, and DGAT (Non-Patent Document 6). TG taken excessively is thus accumulated in fat tissue, resulting in obesity.

DGAT, an intracellular enzyme found in the endoplasmic reticulum, catalyzes the most important reaction in the final step in the pathway of TG synthesis. i.e., the reaction of transferring acyl groups of acyl-coenzyme A to the 3 position of 1,2-diacylglycerol (Non-Patent Documents 7 to 9). It has been reported that DGAT has two isozymes DGAT1 (Non-Patent Document 10) and DGAT2 (Non-Patent Document 11). Since DGAT1 and DGAT2 are highly expressed in the small intestine and fat tissue and in the liver and fat tissue, respectively, it is believed that DGAT1 is involved mainly in fat absorption from the small intestine and fat accumulation in fat tissue and DGAT2 is involved mainly in TG synthesis or VLDL (very low density lipoprotein) secretion in the liver and fat accumulation in fat tissue. Although the difference between the roles of DGAT1 and DGAT2 has not yet been fully elucidated, the association of DGAT with obesity, lipid metabolism, glucose metabolism, and the like has been suggested (Non-Patent Document 12). DGAT is a key enzyme of TG synthesis in gastrointestinal epithelial cells and fat tissue. Drugs which inhibit DGAT suppress the TG synthesis and thus suppress fat absorption in the gastrointestinal tract and fat accumulation in fat tissue. Accordingly, such drugs are expected to be useful as therapeutic or preventive agents for, for example, adiposity, obesity, hyperlipidemia, hypertriglyceridemia, lipidosis, insulin resistance syndrome, diabetes, nonalcoholic steatohepatitis, or hyperlipidemia, hypertriglyceridemia, lipidosis, insulin resistance syndrome, diabetes, nonalcoholic steatohepatitis, hypertension, arteriosclerosis, cerebrovascular disorder, or coronary artery disease caused by obesity (Non-Patent Documents 13 to 17).

Anorectics directly or indirectly regulate the system of appetite control, and their mechanisms of action are broadly classified into central and peripheral actions. The centrally acting anorectics directly suppress appetite through their action on the hypothalamic neuronal system containing the feeding and satiety centers or on the monoaminergic neuronal system in the brain regulating this hypothalamic neuronal system. On the other hand, the peripherally acting anorectics indirectly suppress appetite through their action on the mechanism of detecting and transmitting information on nutrition intake from diets or accumulation of excess energy.

In recent years, the mechanism has been increasingly evident, in which, for example, gastrointestinal hormone (CCK, GLP-1, PYY, etc.) (Non-Patent Document 18) secreted in close relation to the digestion and absorption of food, or leptin (Non-Patent Document 19) secreted from fat cells in response to the amount of energy accumulated (amount of fats) conveys hormonal or neuronal signals regulating appetites from the periphery to the central nervous system. Novel anorectics associated with these peripheral signals are expected to serve as more effective anti-obesity drugs with fewer adverse reactions.

Patent Document 1 discloses compounds structurally similar to compounds of the present invention. This document describes compounds comprising two substituted phenyl groups bound via urea and amide bonds or via urea and ester bonds with a tetrahydroisoquinoline ring, and use thereof as a DGAT inhibitor. Moreover, Patent Document 2 describes use of these compounds as a feeding suppressant. However, these patent documents merely disclose compounds wherein a nitrogen atom on the tetrahydroisoquinoline ring is substituted by a substituted phenyl group via an amide or ester bond. On the other hand, in the compounds of the present invention, a nitrogen atom on a tetrahydroisoquinoline ring is substituted by a substituted cycloalkyl or cycloalkenyl group via an ester bond or the like.

In addition, some compounds having a DGAT inhibitory effect are known. However, all differ from the compounds of the present invention in their structures (e.g., Patent Documents 3, 4, and 5 and Non-Patent Documents 20 to 24). Also, some compounds having a feeding suppressant effect are known. However, all differ from the compounds of the present invention in their structures (see e.g., Patent Documents 6 and 7).

Patent Document 1: US No. 2007/0249620
Patent Document 2: International Publication No. WO2007/074753 Pamphlet
Patent Document 3: Japanese Patent Laid-Open No. 2007-131584
Patent Document 4: International Publication No. WO2006/019020 Pamphlet
Patent Document 5: Japanese Patent Laid-Open No. 2002-306199
Patent Document 6: International Publication No. WO2005/072740 Pamphlet
Patent Document 7: EP No. 1411881
Non-Patent Document 1: Eiji Itagaki, "STEP series, Metabolism, Endocrinology", KAIBASHOBO, LTD. 1st ed., 1998, p. 105
Non-Patent Document 2: Zimmet, P. et al., Nature, 2001, vol. 414, p. 782-787
Non-Patent Document 3: Engstrom, R. G. et al., Arch. Intern. Pharmacodyn., 1975, vol. 214, p. 308-321
Non-Patent Document 4: Bray, G. A. et al., Obes. Res., 1996, vol. 4, p. 263-270
Non-Patent Document 5: Davidson, M. H. et al., The Journal of the American Medical Association, 1999, vol. 281, p. 235-242
Non-Patent Document 6: Coleman, R., Bell, R., J. Biol. Chem., 1976, vol. 251, p. 4537-4543
Non-Patent Document 7: Coleman, R., Methods in Enzymology, 1992, vol. 209, p. 98-104
Non-Patent Document 8: Lehner, R., Kuksis, A., Prog. Lipid Res., 1996, vol. 35, p. 169-201
Non-Patent Document 9: R. Bell., Ann. Rev. Biochem., 1980, vol. 49, p. 459-487
Non-Patent Document 10: Cases, S. et al., Proc. Natl. Acad. Sci. USA., 1998, vol. 95, p. 13018-13023
Non-Patent Document 11: Cases, S. et al., J. Biol. Chem., 2001, vol. 276, p. 38870-38876
Non-Patent Document 12: Coleman, R. A., Lee, D. P., Progress in Lipid Research, 2004, vol. 43, p. 134-176
Non-Patent Document 13: Smith, S. J. et al., Nat. Genet., 2000, vol. 25, p. 87-90
Non-Patent Document 14: Chen, H. C., J. Clin. Invest., 2002, vol. 109, p. 1049-1055
Non-Patent Document 15: Buhman, K. K., J. Biol. Chem., 2002, vol. 277, p. 25474-25479
Non-Patent Document 16: Gaziano, J., et al., Circulation, 1997, vol. 96, p. 2520-2525
Non-Patent Document 17: Yamaguchi, K. et al., Hepatology, 2008, vol. 47, p. 625-635
Non-Patent Document 18: Strader, A. D. et al., Gastroenterology, 2005, vol. 128, p. 175-191
Non-Patent Document 19: Campfield, L. A. et al., Science, 1995, vol. 269, p. 546-549
Non-Patent Document 20: Tomoda, H. et al., J. Antibiot. (Tokyo), 1995, vol. 48, p. 937-941
Non-Patent Document 21: Yang, D. J. et al., J. Antibiot. (Tokyo), 1996, vol. 49, p. 223-229
Non-Patent Document 22: Tomoda, H. et al., J. Antibiot. (Tokyo), 1999, vol. 52, p. 689-694
Non-Patent Document 23: Tabata, N. et al., Phytochemistry, 1997, vol. 46, p. 683-687
Non-Patent Document 24: Gang Zhao et al., J. Med. Chem., 2008, vol. 51, p. 380-383

DISCLOSURE OF THE INVENTION

Problems to be Solved by the Invention

The present inventors have conducted diligent studies for compounds having a DGAT inhibitory effect and a feeding suppressant effect and consequently found that compounds having a particular chemical structure have an excellent DGAT inhibitory effect, particularly, a high inhibitory effect against DGAT1. The present inventors have also found that these compounds have an excellent feeding suppressant effect. The present inventors have further found that these compounds are useful as an active ingredient for pharmaceutical agents intended for the prevention and/or treatment of a disease selected from the group consisting of adiposity, obesity, hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, ischemic heart disease, and bulimia, or as an active ingredient for pharmaceutical agents intended for the treatment and/or prevention of a disease selected from the group consisting of hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, hypertension, cerebrovascular disorder, coronary artery disease, fatty liver, respiratory abnormality, lower back pain, knee osteoarthritis, gout, and cholelithiasis caused by obesity.

Furthermore, the present inventors have found that these compounds are also excellent in terms of high safety, long-lasting effect, low transfer into the central nervous system, and high enzymatic selectivity. Based on these findings, the present invention has been completed.

Means for Solving the Problems

The present invention relates to:
(1) A compound represented by the general formula (I):

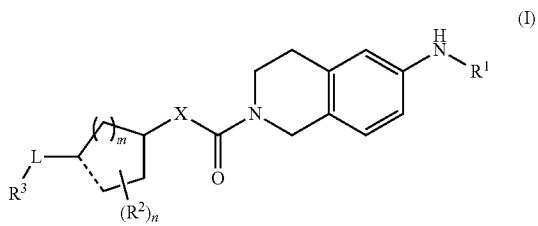

[wherein
$R^1$ represents a phenylaminocarbonyl group that may be substituted with 1 to 5 group(s) independently selected from Substituent Group A, a heteroarylaminocarbonyl group that may be substituted with 1 to 3 group(s) independently selected from Substituent Group A, a benzoxazol-2-yl group that may be substituted with 1 to 3 group(s) independently selected from Substituent Group A, a benzothiazol-2-yl group that may be substituted with 1 to 3 group(s) independently selected from Substituent Group A, a ($C_1$-$C_6$ alkyl that may be monosubstituted with a $C_3$-$C_6$ cycloalkyl group)aminocarbonyl group, a ($C_3$-$C_6$ cycloalkyl)aminocarbonyl group or an adamantylaminocarbonyl group;

$R^2$ independently represents a $C_1$-$C_6$ alkyl group;

$R^3$ represents a heterocyclic group that may be substituted with 1 to 3 group(s) independently selected from Substituent Group A, a group represented by the formula —C(=O)—O—$R^4$ or a group represented by the formula —C(=O)—N($R^5$)$R^6$;

$R^4$ represents a hydrogen atom, a $C_1$-$C_6$ alkyl group that may be substituted with 1 to 3 group(s) independently selected from Substituent Group B or a $C_3$-$C_6$ cycloalkyl group that may be monosubstituted with a carboxyl group;

$R^5$ represents a hydrogen atom, a $C_1$-$C_6$ alkyl group that may be substituted with 1 to 3 group(s) independently selected from Substituent Group B, a $C_3$-$C_6$ cycloalkyl group that may be monosubstituted with a carboxyl group or a heterocyclic group that may be substituted with 1 to 3 group(s) independently selected from Substituent Group A;

$R^6$ represents a hydrogen atom, a $C_1$-$C_6$ alkyl group that may be substituted with 1 to 3 group(s) independently selected from Substituent Group B or a $C_3$-$C_6$ cycloalkyl group that may be monosubstituted with a carboxyl group;

when both $R^5$ and $R^6$ are a $C_1$-$C_6$ alkyl group that may be substituted with 1 to 3 group(s) independently selected from Substituent Group B, their carbon atoms may bind to each other to form a 4- to 6-membered saturated ring;

X represents an oxygen atom, a methylene group, a group represented by the formula —NH—, a methylene group monosubstituted with a $C_1$-$C_6$ alkyl group or a group represented by the formula —N($R^7$)—;

$R^7$ represents a $C_1$-$C_6$ alkyl group;

L represents a single bond, a methylene group, a 1,1-dimethylmethylene group, an ethylene group, a group represented by the formula —CH= or a methylene group monosubstituted with a $C_1$-$C_6$ alkyl group;

. . . represents a single bond or a double bond (however, . . . represents a single bond when L represents a group represented by the formula —CH=);

m represents 1 or 2;

n represents an integer of 0 to 5;

Substituent Group A represents the group of substituents selected from a halogen atom, a $C_1$-$C_6$ alkyl group, a $C_1$-$C_6$ halogenated alkyl group, a $C_1$-$C_6$ alkoxy group, a $C_1$-$C_6$ halogenated alkoxy group, a ($C_1$-$C_6$ alkoxy)-($C_1$-$C_6$ alkyl) group, a $C_1$-$C_6$ alkylthio group, a carboxyl group, a $C_2$-$C_7$ alkylcarbonyl group, a $C_2$-$C_7$ alkoxycarbonyl group, an amino group, a mono-$C_2$-$C_7$ alkylcarbonylamino group, a mono-$C_1$-$C_6$ alkylsulfonylamino group, a mono-$C_1$-$C_6$ alkylamino group, a di-($C_1$-$C_6$ alkyl)amino group, a cyano group, a nitro group, a hydroxy group, a $C_1$-$C_6$ alkylsulfinyl group, and an oxo group; and Substituent Group B represents the group of substituents selected from a $C_3$-$C_6$ cycloalkyl group, a phenyl group, a carboxyl group, an amino group, and a hydroxy group]

or a pharmacologically acceptable salt thereof.

Preferably, the present invention relates to:

(2) The compound or pharmacologically acceptable salt thereof according to (1), wherein $R^1$ is a phenylaminocarbonyl group that may be substituted with 1 to 5 group(s) independently selected from Substituent Group A, a heteroarylaminocarbonyl group that may be substituted with 1 to 3 group(s) independently selected from Substituent Group A, a benzoxazol-2-yl group that may be substituted with 1 to 3 group(s) independently selected from Substituent Group A or a benzothiazol-2-yl group that may be substituted with 1 to 3 group(s) independently selected from Substituent Group A; $R^5$ is a hydrogen atom, a $C_1$-$C_6$ alkyl group that may be substituted with 1 to 3 group(s) independently selected from Substituent Group B or a $C_3$-$C_6$ cycloalkyl group that may be monosubstituted with a carboxyl group; X is an oxygen atom, a methylene group or a group represented by the formula —NH—; L is a single bond, a methylene group, a 1,1-dimethylmethylene group, an ethylene group or a group represented by the formula —CH=; and Substituent Group A is the group of substituents selected from a halogen atom, a $C_1$-$C_6$ alkyl group, a $C_1$-$C_6$ halogenated alkyl group, a $C_1$-$C_6$ alkoxy group, a $C_1$-$C_6$ halogenated alkoxy group, a ($C_1$-$C_6$ alkoxy)-($C_1$-$C_6$ alkyl) group, a $C_1$-$C_6$ alkylthio group, a carboxyl group, a $C_2$-$C_7$ alkylcarbonyl group, a $C_2$-$C_7$ alkoxycarbonyl group, an amino group, a mono-$C_2$-$C_7$ alkylcarbonylamino group, a mono-$C_1$-$C_6$ alkylsulfonylamino group, a mono-$C_1$-$C_6$ alkylamino group, a di-($C_1$-$C_6$ alkyl)amino group, a cyano group, a nitro group, and a hydroxy group;

(3) The compound or pharmacologically acceptable salt thereof according to (1), wherein the general formula (I) is the general formula (II) or (III):

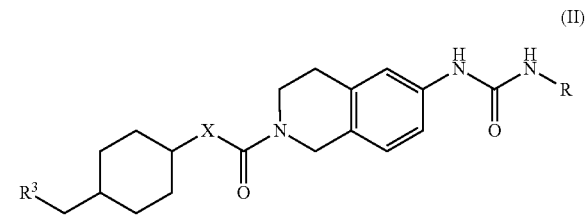

-continued

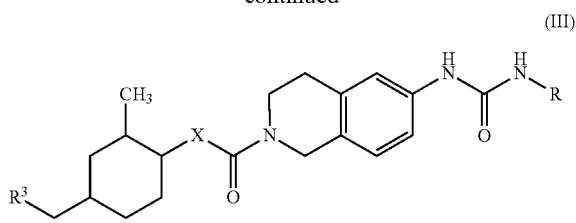
(III)

wherein
R represents a phenyl group that may be substituted with 1 to 5 group(s) independently selected from Substituent Group A or a $C_3$-$C_6$ cycloalkyl group; and
$R^3$, X, and Substituent Group A are as defined in the general formula (I);

(4) The compound or pharmacologically acceptable salt thereof according to (1), wherein
the general formula (I) is the general formula (II):

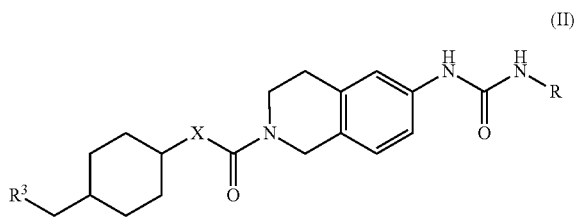
(II)

wherein
R represents a phenyl group that may be substituted with 1 to 5 group(s) independently selected from Substituent Group A or a $C_3$-$C_6$ cycloalkyl group; and
$R^3$, X, and Substituent Group A are as defined in the general formula (I);

(5) The compound or pharmacologically acceptable salt thereof according to (3) or (4), wherein
R is a phenyl group that may be substituted with 1 to 3 group(s) independently selected from a halogen atom, a $C_1$-$C_6$ alkyl group, a $C_1$-$C_6$ halogenated alkyl group, a $C_1$-$C_6$ alkoxy group, and a $C_1$-$C_6$ halogenated alkoxy group, or a $C_3$-$C_6$ cycloalkyl group;

(6) The compound or pharmacologically acceptable salt thereof according to (3) or (4), wherein
R is a phenyl group, a 2-fluorophenyl group, a 3-fluorophenyl group, a 3-methylphenyl group, a 3-ethylphenyl group, a 3-methoxyphenyl group, a 3-ethoxyphenyl group, a 4-trifluoromethylphenyl group, a 3-trifluoromethoxyphenyl group, a 3,4-difluorophenyl group, a 2-fluoro-5-methoxyphenyl group, a 2,4,5-trifluorophenyl group, a 3,4,5-trifluorophenyl group or a cyclopentyl group;

(7) The compound or pharmacologically acceptable salt thereof according to (3) or (4), wherein
R is a phenyl group, a 2-fluorophenyl group, a 3-fluorophenyl group, a 3-methylphenyl group, a 3-ethylphenyl group, a 3-methoxyphenyl group, a 3-ethoxyphenyl group, a 3-trifluoromethoxyphenyl group, a 3,4-difluorophenyl group, a 2-fluoro-5-methoxyphenyl group or a 2,4,5-fluorophenyl group;

(8) The compound or pharmacologically acceptable salt thereof according to (3) or (4), wherein
R is a 2-fluorophenyl group, a 3-isopropylphenyl group, a 3-ethoxyphenyl group, a 2-ethoxy-5-fluorophenyl group, a 2,4,5-trifluorophenyl group or a 3,4,5-trifluorophenyl group;

(9) The compound or pharmacologically acceptable salt thereof according to any one of (1) to (8), wherein
$R^3$ is a heterocyclic group capable of serving as a carboxylic acid equivalent or a carboxyl group;

(10) The compound or pharmacologically acceptable salt thereof according to any one of (1) to (8), wherein
$R^3$ is a 4-carboxyoxazol-2-yl group, a 5-oxo-4,5-dihydro-[1,2,4]oxadiazol-3-yl group, a 5-hydroxy-2H-pyrazol-3-yl group, a 3-hydroxyisoxazol-5-yl group, a tetrazol-5-yl group or a carboxyl group;

(11) The compound or pharmacologically acceptable salt thereof according to any one of (1) to (8), wherein
$R^3$ is a carboxyl group;

(12) The compound or pharmacologically acceptable salt thereof according to any one of (1) to (11), wherein
X is an oxygen atom or a methylene group;

(13) The compound or pharmacologically acceptable salt thereof according to any one of (1) to (11), wherein
X is an oxygen atom;

(14) The compound or pharmacologically acceptable salt thereof according to (1), wherein
the general formula (I) is the general formula (II) or (III), wherein R is a phenyl group that may be substituted with 1 to 3 group(s) independently selected from a halogen atom, a $C_1$-$C_6$ alkyl group, a $C_1$-$C_6$ halogenated alkyl group, a $C_1$-$C_6$ alkoxy group, and a $C_1$-$C_6$ halogenated alkoxy group or a $C_3$-$C_6$ cycloalkyl group; $R^3$ is a heterocyclic group capable of serving as a carboxylic acid equivalent or a carboxyl group; and X is an oxygen atom or a methylene group;

(15) The compound or pharmacologically acceptable salt thereof according to (1), wherein
the general formula (I) is the general formula (II) or (III), wherein R is a phenyl group, a 2-fluorophenyl group, a 3-fluorophenyl group, a 3-methylphenyl group, a 3-ethylphenyl group, a 3-methoxyphenyl group, a 3-ethoxyphenyl group, a 4-trifluoromethylphenyl group, a 3-trifluoromethoxyphenyl group, a 3,4-difluorophenyl group, a 2-fluoro-5-methoxyphenyl group, a 2,4,5-trifluorophenyl group, a 3,4,5-trifluorophenyl group or a cyclopentyl group; $R^3$ is a 4-carboxyoxazol-2-yl group, a 5-oxo-4,5-dihydro-[1,2,4]oxadiazol-3-yl group, a 5-hydroxy-2H-pyrazol-3-yl group, a 3-hydroxyisoxazol-5-yl group, a tetrazol-5-yl group or a carboxyl group; and X is an oxygen atom;

(16) The compound or pharmacologically acceptable salt thereof according to (1), wherein
the general formula (I) is the general formula (II) or (III), wherein R is a phenyl group, a 2-fluorophenyl group, a 3-fluorophenyl group, a 3-methylphenyl group, a 3-ethylphenyl group, a 3-methoxyphenyl group, a 3-ethoxyphenyl group, a 3-trifluoromethoxyphenyl group, a 3,4-difluorophenyl group, a 2-fluoro-5-methoxyphenyl group or a 2,4,5-trifluorophenyl group; $R^3$ is a carboxyl group; and X is an oxygen atom;

(17) The compound or pharmacologically acceptable salt thereof according to (1), wherein
the general formula (I) is the general formula (II), wherein R is a phenyl group that may be substituted with 1 to 3 group(s) independently selected from a halogen atom, a $C_1$-$C_6$ alkyl group, a $C_1$-$C_6$ halogenated alkyl group, a $C_1$-$C_6$ alkoxy group, and a $C_1$-$C_6$ halogenated alkoxy group or a $C_3$-$C_6$ cycloalkyl group; $R^3$ is a heterocyclic group capable of serving as a carboxylic acid equivalent or a carboxyl group; and X is an oxygen atom or a methylene group;

(18) The compound or pharmacologically acceptable salt thereof according to (1), wherein
the general formula (I) is the general formula (II), wherein R is a phenyl group, a 2-fluorophenyl group, a 3-fluorophenyl group, a 3-methylphenyl group, a 3-ethylphenyl group, a 3-methoxyphenyl group, a 3-ethoxyphenyl group, a 4-trifluoromethylphenyl group, a 3-trifluoromethoxyphenyl group, a 3,4-difluorophenyl group, a 2-fluoro-5-methoxyphenyl group, a 2,4,5-trifluorophenyl group, a 3,4,5-trifluorophenyl group or a cyclopentyl group; $R^3$ is a 4-carboxyoxazol-2-yl group, a 5-oxo-4,5-dihydro-[1,2,4]oxadiazol-3-yl group, a 5-hydroxy-2H-pyrazol-3-yl group, a 3-hydroxyisoxazol-5-yl group, a tetrazol-5-yl group or a carboxyl group; and X is an oxygen atom;

(19) The compound or pharmacologically acceptable salt thereof according to (1), wherein the general formula (I) is the general formula (II), wherein R is a phenyl group, a 2-fluorophenyl group, a 3-fluorophenyl group, a 3-methylphenyl group, a 3-ethylphenyl group, a 3-methoxyphenyl group, a 3-ethoxyphenyl group, a 3-trifluoromethoxyphenyl group, a 3,4-difluorophenyl group, a 2-fluoro-5-methoxyphenyl group or a 2,4,5-trifluorophenyl group; $R^3$ is a carboxyl group; and X is an oxygen atom;

(20) The compound or pharmacologically acceptable salt thereof according to (1), wherein the compound represented by the general formula (I) is trans-6-[3-(2-fluoro-phenyl)-ureido]-3,4-dihydro-1H-isoquinoline-2-carboxylic acid 4-carboxymethyl-cyclohexyl ester,
6-[3-(2-fluoro-phenyl)-ureido]-3,4-dihydro-1H-isoquinoline-2-carboxylic acid t-4-carboxymethyl-c-2-methyl-r-1-cyclohexyl ester,
6-[3-(2-fluoro-phenyl)-ureido]-3,4-dihydro-1H-isoquinoline-2-carboxylic acid t-4-carboxymethyl-t-2-methyl-r-1-cyclohexyl ester,
[4-(2-{6-[3-(2-fluoro-phenyl)-ureido]-3,4-dihydro-1H-isoquinolin-2-yl}-2-oxoethyl)-cyclohexyl]-acetic acid,
trans-6-[3-(3-ethoxy-phenyl)-ureido]-3,4-dihydro-1H-isoquinoline-2-carboxylic acid 4-carboxymethyl-cyclohexyl ester,
trans-6-[3-(2,4,5-trifluoro-phenyl)-ureido]-3,4-dihydro-1H-isoquinoline-2-carboxylic acid 4-carboxymethyl-cyclohexyl ester,
trans-6-[3-(3,4,5-trifluoro-phenyl)-ureido]-3,4-dihydro-1H-isoquinoline-2-carboxylic acid 4-carboxymethyl-cyclohexyl ester,
trans-6-[3-(3-methoxy-phenyl)-ureido]-3,4-dihydro-1H-isoquinoline-2-carboxylic acid 4-carboxymethyl-cyclohexyl ester,
trans-6-(3-phenyl-ureido)-3,4-dihydro-1H-isoquinoline-2-carboxylic acid 4-carboxymethyl-cyclohexyl ester,
trans-6-[3-(3-trifluoromethoxy-phenyl)-ureido]-3,4-dihydro-1H-isoquinoline-2-carboxylic acid 4-carboxymethyl-cyclohexyl ester,
trans-6-[3-(3,4-difluoro-phenyl)-ureido]-3,4-dihydro-1H-isoquinoline-2-carboxylic acid 4-carboxymethyl-cyclohexyl ester,
trans-6-[3-(2-fluoro-5-methoxy-phenyl)-ureido]-3,4-dihydro-1H-isoquinoline-2-carboxylic acid 4-carboxymethyl-cyclohexyl ester,
trans-6-[3-(3-fluoro-phenyl)-ureido]-3,4-dihydro-1H-isoquinoline-2-carboxyl is acid 4-carboxymethyl-cyclohexyl ester,
trans-6-(3-m-tolyl-ureido)-3,4-dihydro-1H-isoquinoline-2-carboxylic acid 4-carboxymethyl-cyclohexyl ester,
trans-6-[3-(4-trifluoromethyl-phenyl)-ureido]-3,4-dihydro-1H-isoquinoline-2-carboxylic acid 4-carboxymethyl-cyclohexyl ester,
trans-6-[3-(3-ethyl-phenyl)-ureido]-3,4-dihydro-1H-isoquinoline-2-carboxylic acid 4-carboxymethyl-cyclohexyl ester,
trans-6-(3-cyclopentyl-ureido)-3,4-dihydro-1H-isoquinoline-2-carboxylic acid 4-carboxymethyl-cyclohexyl ester,
6-[3-(3-ethoxy-phenyl)-ureido]-3,4-dihydro-1H-isoquinoline-2-carboxylic acid t-4-carboxymethyl-t-2-methyl-r-1-cyclohexyl ester,
6-[3-(3-methoxy-phenyl)-ureido]-3,4-dihydro-1H-isoquinoline-2-carboxylic acid t-4-carboxymethyl-t-2-methyl-r-1-cyclohexyl ester or
6-[3-(3-trifluoromethoxy-phenyl)-ureido]-3,4-dihydro-1H-isoquinoline-2-carboxylic acid t-4-carboxymethyl-t-2-methyl-r-1-cyclohexyl ester;

(21) The compound or pharmacologically acceptable salt thereof according to (1), wherein the compound represented by the general formula (I) is trans-6-[3-(2-fluoro-phenyl)-ureido]-3,4-dihydro-1H-isoquinoline-2-carboxylic acid 4-carboxymethyl-cyclohexyl ester,
trans-6-[3-(3-ethoxy-phenyl)-ureido]-3,4-dihydro-1H-isoquinoline-2-carboxylic acid 4-carboxymethyl-cyclohexyl ester,
trans-6-[3-(2,4,5-trifluoro-phenyl)-ureido]-3,4-dihydro-1H-isoquinoline-2-carboxylic acid 4-carboxymethyl-cyclohexyl ester,
trans-6-[3-(3-methoxy-phenyl)-ureido]-3,4-dihydro-1H-isoquinoline-2-carboxylic acid 4-carboxymethyl-cyclohexyl ester,
trans-6-(3-phenyl-ureido)-3,4-dihydro-1H-isoquinoline-2-carboxylic acid 4-carboxymethyl-cyclohexyl ester,
trans-6-[3-(3-trifluoromethoxy-phenyl)-ureido]-3,4-dihydro-1H-isoquinoline-2-carboxylic acid 4-carboxymethyl-cyclohexyl ester,
trans-6-[3-(3,4-difluoro-phenyl)-ureido]-3,4-dihydro-1H-isoquinoline-2-carboxylic acid 4-carboxymethyl-cyclohexyl ester,
trans-6-[3-(2-fluoro-5-methoxy-phenyl)-ureido]-3,4-dihydro-1H-isoquinoline-2-carboxylic acid 4-carboxymethyl-cyclohexyl ester,
trans-6-[3-(3-fluoro-phenyl)-ureido]-3,4-dihydro-1H-isoquinoline-2-carboxylic acid 4-carboxymethyl-cyclohexyl ester,
trans-6-(3-m-tolyl-ureido)-3,4-dihydro-1H-isoquinoline-2-carboxylic acid 4-carboxymethyl-cyclohexyl ester or
trans-6-[3-(3-ethyl-phenyl)-ureido]-3,4-dihydro-1H-isoquinoline-2-carboxylic acid 4-carboxymethyl-cyclohexyl ester;

(22) The compound according to (1), wherein the compound represented by the general formula (I) is trans-6-[3-(2-fluoro-phenyl)-ureido]-3,4-dihydro-1H-isoquinoline-2-carboxylic acid 4-carboxymethyl-cyclohexyl ester,
trans-6-[3-(3-ethoxy-phenyl)-ureido]-3,4-dihydro-1H-isoquinoline-2-carboxylic acid 4-carboxymethyl-cyclohexyl ester,
trans-6-[3-(2,4,5-trifluoro-phenyl)-ureido]-3,4-dihydro-1H-isoquinoline-2-carboxyl is acid 4-carboxymethyl-cyclohexyl ester,
trans-6-[3-(3-methoxy-phenyl)-ureido]-3,4-dihydro-1H-isoquinoline-2-carboxylic acid 4-carboxymethyl-cyclohexyl ester,
trans-6-(3-phenyl-ureido)-3,4-dihydro-1H-isoquinoline-2-carboxylic acid 4-carboxymethyl-cyclohexyl ester,
trans-6-[3-(3-trifluoromethoxy-phenyl)-ureido]-3,4-dihydro-1H-isoquinoline-2-carboxylic acid 4-carboxymethyl-cyclohexyl ester,
trans-6-[3-(3,4-difluoro-phenyl)-ureido]-3,4-dihydro-1H-isoquinoline-2-carboxylic acid 4-carboxymethyl-cyclohexyl ester, trans-6-[3-(2-fluoro-5-methoxy-phenyl)-ureido]-3,4-dihydro-1H-isoquinoline-2-carboxylic acid 4-carboxymethyl-cyclohexyl ester,
trans-6-[3-(3-fluoro-phenyl)-ureido]-3,4-dihydro-1H-isoquinoline-2-carboxylic acid 4-carboxymethyl-cyclohexyl ester,
trans-6-(3-m-tolyl-ureido)-3,4-dihydro-1H-isoquinoline-2-carboxylic acid 4-carboxymethyl-cyclohexyl ester or
trans-6-[3-(3-ethyl-phenyl)-ureido]-3,4-dihydro-1H-isoquinoline-2-carboxylic acid 4-carboxymethyl-cyclohexyl ester;

(23) The compound or pharmacologically acceptable salt thereof according to (1), wherein the compound represented by the general formula (I) is
trans-6-[3-(2-fluoro-phenyl)-ureido]-3,4-dihydro-H-isoquinoline-2-carboxylic acid 4-carboxymethyl-cyclohexyl ester,
trans-6-[3-(2-isopropyl-phenyl)-ureido]-3,4-dihydro-1H-isoquinoline-2-carboxylic acid 4-carboxymethyl-cyclohexyl ester,
trans-6-[3-(2-methoxy-phenyl)-ureido]-3,4-dihydro-1H-isoquinoline-2-carboxylic acid 4-carboxymethyl-cyclohexyl ester,
trans-6-[3-(2-ethoxy-phenyl)-ureido]-3,4-dihydro-1H-isoquinoline-2-carboxylic acid 4-carboxymethyl-cyclohexyl ester,
trans-6-[3-(3-isopropyl-phenyl)-ureido]-3,4-dihydro-1H-isoquinoline-2-carboxylic acid 4-carboxymethyl-cyclohexyl ester,
trans-6-[3-(3-ethoxy-phenyl)-ureido]-3,4-dihydro-1H-isoquinoline-2-carboxylic acid 4-carboxymethyl-cyclohexyl ester,
trans-6-[3-(3-isopropoxy-phenyl)-ureido]-3,4-dihydro-1H-isoquinoline-2-carboxylic acid 4-carboxymethyl-cyclohexyl ester,
trans-6-[3-(5-fluoro-2-methoxy-phenyl)-ureido]-3,4-dihydro-1H-isoquinoline-2-carboxylic acid 4-carboxymethyl-cyclohexyl ester,
trans-6-[3-(2-ethoxy-5-fluoro-phenyl)-ureido]-3,4-dihydro-1H-isoquinoline-2-carboxylic acid 4-carboxymethyl-cyclohexyl ester,
trans-6-[3-(2-methoxy-5-methyl-phenyl)-ureido]-3,4-dihydro-1H-isoquinoline-2-carboxylic acid 4-carboxymethyl-cyclohexyl ester,
trans-6-[3-(2,4,5-trifluoro-phenyl)-ureido]-3,4-dihydro-1H-isoquinoline-2-carboxylic acid 4-carboxymethyl-cyclohexyl ester,
trans-6-[3-(3,4,5-trifluoro-phenyl)-ureido]-3,4-dihydro-1H-isoquinoline-2-carboxylic acid 4-carboxymethyl-cyclohexyl ester,
6-[3-(2-fluoro-phenyl)-ureido]-3,4-dihydro-1H-isoquinoline-2-carboxylic acid t-4-carboxymethyl-c-2-methyl-r-1-cyclohexyl ester or
6-[3-(2-fluoro-phenyl)-ureido]-3,4-dihydro-1H-isoquinoline-2-carboxylic acid t-4-carboxymethyl-t-2-methyl-r-1-cyclohexyl ester;

(24) The compound or pharmacologically acceptable salt thereof according to (1), wherein the compound represented by the general formula (I) is
trans-6-[3-(2-fluoro-phenyl)-ureido]-3,4-dihydro-1H-isoquinoline-2-carboxylic acid 4-carboxymethyl-cyclohexyl ester,
trans-6-[3-(3-isopropyl-phenyl)-ureido]-3,4-dihydro-1H-isoquinoline-2-carboxylic acid 4-carboxymethyl-cyclohexyl ester,
trans-6-[3-(3-ethoxy-phenyl)-ureido]-3,4-dihydro-1H-isoquinoline-2-carboxylic acid 4-carboxymethyl-cyclohexyl ester,
trans-6-[3-(2-ethoxy-5-fluoro-phenyl)-ureido]-3,4-dihydro-1H-isoquinoline-2-carboxylic acid 4-carboxymethyl-cyclohexyl ester,
trans-6-[3-(2,4,5-trifluoro-phenyl)-ureido]-3,4-dihydro-1H-isoquinoline-2-carboxylic acid 4-carboxymethyl-cyclohexyl ester,
trans-6-[3-(3,4,5-trifluoro-phenyl)-ureido]-3,4-dihydro-1H-isoquinoline-2-carboxylic acid 4-carboxymethyl-cyclohexyl ester,
6-[3-(2-fluoro-phenyl)-ureido]-3,4-dihydro-1H-isoquinoline-2-carboxylic acid t-4-carboxymethyl-c-2-methyl-r-1-cyclohexyl ester or
6-[3-(2-fluoro-phenyl)-ureido]-3,4-dihydro-1H-isoquinoline-2-carboxylic acid t-4-carboxymethyl-t-2-methyl-r-1-cyclohexyl ester;

(25) The compound according to (1), wherein the compound represented by the general formula (I) is
trans-6-[3-(2-fluoro-phenyl)-ureido]-3,4-dihydro-1H-isoquinoline-2-carboxylic acid 4-carboxymethyl-cyclohexyl ester,
trans-6-[3-(3-isopropyl-phenyl)-ureido]-3,4-dihydro-1H-isoquinoline-2-carboxylic acid 4-carboxymethyl-cyclohexyl ester,
trans-6-[3-(3-ethoxy-phenyl)-ureido]-3,4-dihydro-1H-isoquinoline-2-carboxylic acid 4-carboxymethyl-cyclohexyl ester,
trans-6-[3-(2-ethoxy-5-fluoro-phenyl)-ureido]-3,4-dihydro-1H-isoquinoline-2-carboxylic acid 4-carboxymethyl-cyclohexyl ester,
trans-6-[3-(2,4,5-trifluoro-phenyl)-ureido]-3,4-dihydro-1H-isoquinoline-2-carboxylic acid 4-carboxymethyl-cyclohexyl ester,
trans-6-[3-(3,4,5-trifluoro-phenyl)-ureido]-3,4-dihydro-1H-isoquinoline-2-carboxyl is acid 4-carboxymethyl-cyclohexyl ester,
6-[3-(2-fluoro-phenyl)-ureido]-3,4-dihydro-1H-isoquinoline-2-carboxylic acid t-4-carboxymethyl-c-2-methyl-r-1-cyclohexyl ester or
6-[3-(2-fluoro-phenyl)-ureido]-3,4-dihydro-1H-isoquinoline-2-carboxylic acid t-4-carboxymethyl-t-2-methyl-r-1-cyclohexyl ester;

(26) An acyl-coenzyme A: diacylglycerol acyltransferase inhibitor comprising as an active ingredient thereof a compound or pharmacologically acceptable salt thereof according to any one of (1) to (25);

(27) A feeding suppressant and/or an anorectic comprising as an active ingredient thereof a compound or pharmacologically acceptable salt thereof according to any one of (1) to (25);

(28) A pharmaceutical composition comprising as an active ingredient thereof a compound or pharmacologically acceptable salt thereof according to any one of (1) to (25);

(29) The pharmaceutical composition according to (28), wherein the pharmaceutical composition has an acyl-coenzyme A: diacylglycerol acyltransferase inhibitory effect;

(30) The pharmaceutical composition according to (28), wherein the pharmaceutical composition has a feeding suppressant effect and/or an anorectic effect;

(31) The pharmaceutical composition according to (28), wherein the pharmaceutical composition is intended for the treatment and/or prevention of a disease which is treated and/or prevented by an acyl-coenzyme A: diacylglycerol acyltransferase inhibitory effect;

(32) The pharmaceutical composition according to (28), wherein the pharmaceutical composition is intended for the treatment and/or prevention of a disease caused by increased acyl-coenzyme A: diacylglycerol acyltransferase activity;

(33) The pharmaceutical composition according to (28), wherein the pharmaceutical composition is intended for the treatment and/or prevention of a disease whose symptoms are treated, improved, alleviated and/or prevented by inhibiting acyl-coenzyme A: diacylglycerol acyltransferase such that triglyceride synthesis is inhibited, resulting in suppressed absorption of triglyceride;

(34) The pharmaceutical composition according to (28), wherein the pharmaceutical composition is intended for the treatment and/or prevention of a disease whose symptoms are treated, improved, alleviated and/or prevented by inhibiting acyl-coenzyme A: diacylglycerol acyltransferase such that triglyceride synthesis is inhibited;

(35) The pharmaceutical composition according to (28), wherein the pharmaceutical composition is intended for the treatment and/or prevention of adiposity, obesity, hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, ischemic heart disease, or bulimia;

(36) The pharmaceutical composition according to (28), wherein the pharmaceutical composition is intended for the treatment and/or prevention of adiposity or obesity;

(37) The pharmaceutical composition according to (28), wherein the pharmaceutical composition is intended for the treatment and/or prevention of hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, hypertension, cerebrovascular disorder, coronary artery disease, fatty liver, respiratory abnormality, lower back pain, knee osteoarthritis, gout, or cholelithiasis caused by obesity;

(38) The pharmaceutical composition according to (28), wherein the pharmaceutical composition is intended for the treatment and/or prevention of hyperlipidemia, hypertriglyceridemia, diabetes, arteriosclerosis, or hypertension caused by obesity;

(39) The pharmaceutical composition according to (28), wherein the pharmaceutical composition is intended for the suppression of fat absorption from the small intestine;

(40) Use of a compound or pharmacologically acceptable salt thereof according to any one of (1) to (25) for producing a pharmaceutical composition;

(41) The use according to (40), wherein the pharmaceutical composition is a composition intended for the inhibition of acyl-coenzyme A: diacylglycerol acyltransferase;

(42) The use according to (40), wherein the pharmaceutical composition is a composition intended for the suppression of feeding and/or appetite;

(43) The use according to (40), wherein the pharmaceutical composition is a composition intended for the treatment and/or prevention of adiposity, obesity, hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, ischemic heart disease, or bulimia;

(44) The use according to (40), wherein the pharmaceutical composition is a composition intended for the treatment and/or prevention of adiposity or obesity;

(45) The use according to (40), wherein the pharmaceutical composition is a composition intended for the treatment and/or prevention of hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, hypertension, cerebrovascular disorder, coronary artery disease, fatty liver, respiratory abnormality, lower back pain, knee osteoarthritis, gout, or cholelithiasis caused by obesity;

(46) The use according to (40), wherein the pharmaceutical composition is a composition intended for the treatment and/or prevention of hyperlipidemia, hypertriglyceridemia, diabetes, arteriosclerosis, or hypertension caused by obesity;

(47) The use according to (40), wherein the pharmaceutical composition is a composition intended for the suppression of fat absorption from the small intestine;

(48) A method for inhibiting acyl-coenzyme A: diacylglycerol acyltransferase, comprising administering a pharmacologically effective amount of a compound or pharmacologically acceptable salt thereof according to any one of (1) to (25) to a warm-blooded animal;

(49) A method for suppressing feeding and/or appetite, comprising administering a pharmacologically effective amount of a compound or pharmacologically acceptable salt thereof according to any one of (1) to (25) to a warm-blooded animal;

(50) A method for treating and/or preventing a disease, comprising administering a pharmacologically effective amount of a compound or pharmacologically acceptable salt thereof according to any one of (1) to (25) to a warm-blooded animal;

(51) The method according to (50), wherein the disease is adiposity, obesity, hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, ischemic heart disease, or bulimia;

(52) The method according to (50), wherein the disease is adiposity or obesity;

(53) The method according to (50), wherein the disease is hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, hypertension, cerebrovascular disorder, coronary artery disease, fatty liver, respiratory abnormality, lower back pain, knee osteoarthritis, gout, or cholelithiasis caused by obesity;

(54) The method according to (50), wherein the disease is hyperlipidemia, hypertriglyceridemia, diabetes, arteriosclerosis, or hypertension caused by obesity;

(55) A method for suppressing fat absorption from the small intestine, comprising administering a pharmacologically effective amount of a compound or pharmacologically acceptable salt thereof according to any one of (1) to (25) to a warm-blooded animal; and

(56) The method according to any one of (48) to (55), wherein the warm-blooded animal is a human.

In the present invention, a "halogen atom" refers to a fluorine atom, a chlorine atom, a bromine atom or an iodine atom. The halogen atom is preferably a fluorine atom or a chlorine atom, and more preferably a fluorine atom.

In the present invention, a "$C_1$-$C_6$ alkyl group" refers to a linear or branched alkyl group having 1 to 6 carbon atom(s). Examples thereof include a methyl group, an ethyl group, a propyl group, an isopropyl group, a butyl group, an isobutyl group, an s-butyl group, a t-butyl group, a pentyl group, an isopentyl group, a 2-methylbutyl group, a neopentyl group, a 1-ethylpropyl group, a hexyl group, an isohexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group and a 1,2-dimethylbutyl group. The $C_1$-$C_6$ alkyl group is preferably a linear or branched alkyl group having 1 to 4 carbon atom(s) ($C_1$-$C_4$ alkyl group), more preferably a methyl group or an ethyl group ($C_1$-$C_2$ alkyl group), and even more preferably a methyl group for $R^2$ and In the present invention, a "$C_1$-$C_6$ halogenated alkyl group" refers to a group in which 1 to 5 of the same or different above-mentioned "halogen atom" are bonded to the above-mentioned "$C_1$-$C_6$ alkyl group". Examples thereof include a trifluoromethyl group, a trichloromethyl group, a difluoromethyl group, a dichloromethyl group, a dibromomethyl group, a fluoromethyl group, a 2,2,2-trifluoroethyl group, a 2,2,2-trichloroethyl group, a 2-bromoethyl group, a 2-chloroethyl group and a 2-fluoroethyl group. The $C_1$-$C_6$ halogenated alkyl group is preferably a group in which 1 to 5 of the same or different above-mentioned "halogen atom" are bonded to the above-mentioned "$C_1$-$C_4$ alkyl group" ($C_1$-$C_4$ halogenated alkyl group), more preferably a group in which 1 to 5 of the same or different above-mentioned "halogen atom" are bonded to the above-mentioned "$C_1$-$C_2$ alkyl group" ($C_1$-$C_2$ halogenated alkyl group), and even more preferably a trifluoromethyl group.

In the present invention, a "$C_1$-$C_6$ alkoxy group" refers to a group in which the above-mentioned "$C_1$-$C_6$ alkyl group" is bonded to an oxygen atom, and is a linear or branched alkoxy group having 1 to 6 carbon atom(s). Examples thereof include a methoxy group, an ethoxy group, a propoxy group, an isopropoxy group, a butoxy group, an isobutoxy group, an s-butoxy group, a t-butoxy group, a pentoxy group, a 2-methylbutoxy group, a 3-ethylpropoxy group, a hexyloxy group and 2,3-dimethylbutoxy group. The $C_1$-$C_6$ alkoxy group is preferably a linear or branched alkoxy group having 1 to 4 carbon atom(s) ($C_1$-$C_4$ alkoxy group), and more preferably a methoxy group or an ethoxy group ($C_1$-$C_2$ alkoxy group).

In the present invention, a "$C_1$-$C_6$ halogenated alkoxy group" refers to a group in which 1 to 5 of the same or different above-mentioned "halogen atom" are bonded to the above-mentioned "$C_1$-$C_6$ alkoxy group". Examples thereof include a trifluoromethoxy group, a trichloromethoxy group, a difluoromethoxy group, a dichloromethoxy group, a dibromomethoxy group, a fluoromethoxy group, a 2,2,2-trifluoroethoxy group, a 2,2,2-trichloroethoxy group, a 2-fluoroethoxy group and a pentafluoroethoxy group. The $C_1$-$C_6$ halogenated alkoxy group is preferably a group in which 1 to 5 of the same or different above-mentioned "halogen atom" are bonded to the above-mentioned "$C_1$-$C_4$ alkoxy group" ($C_1$-$C_4$ halogenated alkoxy group), more preferably a group in which 1 to 5 of the same or different above-mentioned "halogen atom" are bonded to the above-mentioned "$C_1$-$C_2$ alkoxy group" ($C_1$-$C_2$ halogenated alkoxy group), and even more preferably a trifluoromethoxy group.

In the present invention, a "($C_1$-$C_6$ alkoxy)-($C_1$-$C_6$ alkyl) group" refers to a group in which one above-mentioned "$C_1$-$C_6$ alkoxy group" is bonded to the above-mentioned "$C_1$-$C_6$ alkyl group". Examples thereof include a methoxymethyl group, an ethoxymethyl group, a propoxymethyl group, an isopropoxymethyl group, a butoxymethyl group, an s-butoxymethyl group, a t-butoxymethyl group, a 2-methoxyethyl group and a 3-isopropoxypropyl group. The ($C_1$-$C_6$ alkoxy)-($C_1$-$C_6$ alkyl) group is preferably a group in which one above-mentioned "$C_1$-$C_4$ alkoxy group" is bonded to the above-mentioned "$C_1$-$C_4$ alkyl group" (($C_1$-$C_4$ alkoxy)-($C_1$-$C_4$ alkyl) group), more preferably a group in which one above-mentioned "$C_1$-$C_2$ alkoxy group" is bonded to the above-mentioned "$C_1$-$C_2$ alkyl group" (($C_1$-$C_2$ alkoxy)-($C_1$-$C_2$ alkyl) group), and even more preferably a methoxymethyl group.

In the present invention, a "$C_1$-$C_6$ alkylthio group" refers to a group in which one above-mentioned "$C_1$-$C_6$ alkyl group" is bonded to a sulfur atom, and is a linear or branched alkylthio group having 1 to 6 carbon atom(s). Examples thereof include a methylthio group, an ethylthio group, a propylthio group, an isopropylthio group, a butylthio group, an isobutylthio group, an s-butylthio group, a pentylthio group, a 1-ethylpropylthio group and a hexylthio group. The $C_1$-$C_6$ alkylthio group is preferably a linear or branched alkylthio group having 1 to 4 carbon atom(s) ($C_1$-$C_4$ alkylthio group), more preferably a methylthio group or an ethylthio group ($C_1$-$C_2$ alkylthio group), and even more preferably a methylthio group.

In the present invention, a "$C_1$-$C_6$ alkylsulfinyl group" refers to a group in which one above-mentioned "$C_1$-$C_6$ alkyl group" is bonded to a sulfinyl group, and is a linear or branched alkylsulfinyl group having 1 to 6 carbon atom(s). Examples thereof include a methylsulfinyl group, an ethylsulfinyl group, a propylsulfinyl group, an isopropylsulfinyl group, a butylsulfinyl group, a pentylsulfinyl group and a hexylsulfinyl group. The $C_1$-$C_6$ alkylsulfinyl group is preferably a linear or branched alkylsulfinyl group having 1 to 4 carbon atom(s) ($C_1$-$C_4$ alkylsulfinyl group), more preferably a methylsulfinyl group or an ethylsulfinyl group ($C_1$-$C_2$ alkylsulfinyl group), and even more preferably a methylsulfinyl group.

In the present invention, a "$C_2$-$C_7$ alkylcarbonyl group" refers to a group in which one above-mentioned "$C_1$-$C_6$ alkyl group" is bonded to a carbonyl group. Examples thereof include an acetyl group, a propionyl group, a butyryl group, an isobutyryl group, a pentanoyl group, a pivaloyl group and a valeryl group. The $C_2$-$C_7$ alkylcarbonyl group is preferably a group in which one above-mentioned "$C_1$-$C_4$ alkyl group" is bonded to a carbonyl group ($C_2$-$C_5$ alkylcarbonyl group), more preferably an acetyl group or a propionyl group ($C_2$-$C_3$ alkylcarbonyl group), and even more preferably an acetyl group.

In the present invention, a "$C_2$-$C_7$ alkoxycarbonyl group" refers to a group in which one above-mentioned "$C_1$-$C_6$ alkoxy group" is bonded to a carbonyl group. Examples thereof include a methoxycarbonyl group, an ethoxycarbonyl group, a propoxycarbonyl group, an isopropoxycarbonyl group, a butoxycarbonyl group, an isobutoxycarbonyl group, an s-butoxycarbonyl group and a t-butoxycarbonyl group.

The $C_2$-$C_7$ alkoxycarbonyl group is preferably a group in which one above-mentioned "$C_1$-$C_4$ alkoxy group" is bonded to a carbonyl group ($C_2$-$C_5$ alkoxycarbonyl group), more preferably a methoxycarbonyl group or an ethoxycarbonyl group ($C_2$-$C_3$ alkoxycarbonyl group), and even more preferably a methoxycarbonyl group.

In the present invention, a "mono-$C_2$-$C_7$ alkylcarbonylamino group" refers to a group in which a carbonyl group to which is bonded one above-mentioned "$C_1$-$C_6$ alkyl group" is bonded to an amino group. Examples thereof include an acetamide group, an ethylcarbonylamino group, a propylcarbonylamino group, an isopropylcarbonylamino group, a butylcarbonylamino group and an isobutylcarbonylamino group. The mono-$C_2$-$C_7$ alkylcarbonylamino group is preferably a group in which a carbonyl group to which is bonded one above-mentioned "$C_1$-$C_4$ alkyl group" is bonded to an amino group (mono-$C_2$-$C_5$ alkylcarbonylamino group), more preferably an acetamide group or an ethylcarbonylamino group (mono-$C_2$-$C_3$ alkylcarbonylamino group), and even more preferably an acetamide group.

In the present invention, a "mono-$C_1$-$C_6$ alkylsulfonylamino group" refers to a group in which a sulfonyl group to which is bonded one above-mentioned "$C_1$-$C_6$ alkyl group" is bonded to an amino group. Examples thereof include a methylsulfonylamino group, an ethylsulfonylamino group, a propylsulfonylamino group, an isopropylsulfonylamino group, a butylsulfonylamino group, a t-butylsulfonylamino group and a 2-ethylbutylsulfonylamino group. The mono-$C_1$-$C_6$ alkylsulfonylamino group is preferably a group in which a sulfonyl group to which is bonded one above-mentioned "$C_1$-$C_4$ alkyl group" is bonded to an amino group (mono-$C_1$-$C_4$ alkylsulfonylamino group), more preferably a methylsulfonylamino group or an ethylsulfonylamino group (mono-$C_1$-$C_2$ alkylsulfonylamino group), and even more preferably a methylsulfonylamino group.

In the present invention, a "mono-$C_1$-$C_6$ alkylamino group" refers to a group in which one above-mentioned "$C_1$-$C_6$ alkyl group" is bonded to an amino group. Examples thereof include a methylamino group, an ethylamino group, a propylamino group, an isopropylamino group, a butylamino group, an isobutylamino group, an s-butylamino group, a t-butylamino group, a pentylamino group, an isopentylamino group, a 2-methylbutylamino group, a neopentylamino group, a 1-ethylpropylamino group, a hexylamino group and an isohexylamino group. The mono-$C_1$-$C_6$ alkylamino group is preferably a group in which one above-mentioned "$C_1$-$C_4$ alkyl group" is bonded to an amino group (mono-$C_1$-$C_4$ alkylamino group), more preferably a methylamino group or an ethylamino group (mono-$C_1$-$C_2$ alkylamino group), and even more preferably a methylamino group.

In the present invention, a "di-($C_1$-$C_6$ alkyl)amino group" refers to a group in which two of the same or different above-mentioned "$C_1$-$C_6$ alkyl group" is bonded to an amino group. Examples thereof a dimethylamino group, a diethylamino group, a dipropylamino group, a diisopropylamino group, a dibutylamino group, a diisobutylamino group, a dipentylamino group, a diisopentylamino group, a dineopentylamino group, a dihexylamino group, an N-ethyl-N-methylamino group, an N-methyl-N-propylamino group, an N-isopropyl-N-methylamino group, an N-butyl-N-methylamino group, an N-isobutyl-N-methylamino group, an N-methyl-N-pentylamino group, an N-isopentyl-N-methylamino group, an N-ethyl-N-propylamino group, an N-ethyl-N-isopropylamino group, an N-butyl-N-ethylamino group and an N-ethyl-N-isopentylamino group. The di-($C_1$-$C_6$ alkyl)amino group is preferably a group in which two of the same or different above-mentioned "$C_1$-$C_4$ alkyl group" is bonded to an amino group (di-($C_1$-$C_4$ alkyl)amino group), more preferably a dimethylamino group, a diethylamino group or an N-ethyl-N-methylamino group (di-($C_1$-$C_2$ alkyl)amino group), and even more preferably a dimethylamino group.

In the present invention, a "$C_3$-$C_6$ cycloalkyl group" refers to a cyclopropyl group, a cyclobutyl group, a cyclopentyl group or a cyclohexyl group and is preferably a cyclopentyl group for R or a cyclopropyl group for the other moieties.

In the present invention, a "phenylaminocarbonyl group that may be substituted with 1 to 5 group(s) independently selected from Substituent Group A" refers to a group in which an amino group to which is bonded a phenyl group (that may be substituted with 1 to 5 group(s) independently selected from Substituent Group A) is bonded to a carbonyl group, and is preferably a phenylaminocarbonyl group that may be substituted with 1 to 3 group(s) independently selected from a halogen atom, a $C_1$-$C_6$ alkyl group, a $C_1$-$C_6$ halogenated alkyl group, a $C_1$-$C_6$ alkoxy group, and a $C_1$-$C_6$ halogenated alkoxy group, more preferably a phenylaminocarbonyl group, a 2-fluorophenylaminocarbonyl group, a 3-fluorophenylaminocarbonyl group, a 3-methylphenylaminocarbonyl group, a 3-ethylphenylaminocarbonyl group, a 3-methoxyphenylaminocarbonyl group, a 3-ethoxyphenylaminocarbonyl group, a 4-trifluoromethylphenylaminocarbonyl group, a 3-trifluoromethoxyphenylaminocarbonyl group, a 3,4-difluorophenylaminocarbonyl group, a 2-fluoro-5-methoxyphenylaminocarbonyl group, a 2,4,5-trifluorophenylaminocarbonyl group or a 3,4,5-trifluorophenylaminocarbonyl group, and even more preferably a phenylaminocarbonyl group, a 2-fluorophenylaminocarbonyl group, a 3-fluorophenylaminocarbonyl group, a 3-methylphenylaminocarbonyl group, a 3-ethylphenylaminocarbonyl group, a 3-methoxyphenylaminocarbonyl group, a 3-ethoxyphenylaminocarbonyl group, a 3-trifluoromethoxyphenylaminocarbonyl group, a 3,4-difluorophenylaminocarbonyl group, a 2-fluoro-5-methoxyphenylaminocarbonyl group or a 2,4,5-trifluorophenylaminocarbonyl group.

In the present invention, a "phenyl group that may be substituted with 1 to 5 group(s) independently selected from Substituent Group A" is preferably a phenyl group that may be substituted with 1 to 3 group(s) independently selected from a halogen atom, a $C_1$-$C_6$ alkyl group, a $C_1$-$C_6$ halogenated alkyl group, a $C_1$-$C_6$ alkoxy group, and a $C_1$-$C_6$ halogenated alkoxy group, more preferably a phenyl group, a 2-fluorophenyl group, a 3-fluorophenyl group, a 3-methylphenyl group, a 3-ethylphenyl group, a 3-methoxyphenyl group, a 3-ethoxyphenyl group, a 4-trifluoromethylphenyl group, a 3-trifluoromethoxyphenyl group, a 3,4-difluorophenyl group, a 2-fluoro-5-methoxyphenyl group, a 2,4,5-trifluorophenyl group or a 3,4,5-trifluorophenyl group, and even more preferably a phenyl group, a 2-fluorophenyl group, a 3-fluorophenyl group, a 3-methylphenyl group, a 3-ethylphenyl group, a 3-methoxyphenyl group, a 3-ethoxyphenyl group, a 3-trifluoromethoxyphenyl group, a 3,4-difluorophenyl group, a 2-fluoro-5-methoxyphenyl group or a 2,4,5-trifluorophenyl group.

In the present invention, a "heteroaryl group" refers to a 4- to 7-membered heteroaryl group that contains 1 to 3 sulfur atom(s), oxygen atom(s) and/or nitrogen atom(s), and may further contain 1 or 2 nitrogen atom(s), and in which the sulfur atom(s) may be bonded to 2 oxygen atoms. Examples thereof include a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,3,4-oxadiazolyl group, a 1,3,4-thiadiazolyl group, a triazolyl group, a tetrazolyl group, a thiadiazolyl group, a pyranyl group, a pyridyl group, a pyridazinyl group, a pyrimidinyl group and a pyrazinyl group. The heteroaryl group may be condensed with another aromatic cyclic group such as benzene ring. Examples of such heteroaryl group include a benzothienyl group, a benzothiazolyl group, a benzoxazolyl group, a quinolyl group and an indolyl group. The heteroaryl group is preferably a pyrazolyl group, an isoxazolyl group, a thiazolyl group, a pyridyl group or a pyrazinyl group, and more preferably a 5-pyrazolyl group, a 3-isoxazolyl group, a 2-thiazolyl group, a 2-pyridyl group, a 3-pyridyl group, a 4-pyridyl group or a 2-pyrazinyl group.

In the present invention, a "heteroarylaminocarbonyl group that may be substituted with 1 to 3 group(s) independently selected from Substituent Group A" refers to a group in which an amino group to which is bonded above-mentioned "heteroaryl group" (that may be substituted with 1 to 3 group(s) independently selected from Substituent Group A) is bonded to a carbonyl group, and is preferably a pyrazolyl, isoxazolyl, thiazolyl, pyridyl or pyrazinyl group that may be substituted with 1 to 3 group(s) independently selected from a halogen atom, a $C_1$-$C_6$ alkyl group, and a $C_1$-$C_6$ alkoxy group, more preferably a 5-pyrazolyl, 3-isoxazolyl, 2-thiazolyl, 2-pyridyl, 3-pyridyl, 4-pyridyl or 2-pyrazinyl group that may be substituted with 1 to 3 group(s) independently selected from a chlorine atom, a methyl group, and a methoxy group.

In the present invention, a "benzoxazol-2-yl group that may be substituted with 1 to 3 group(s) independently selected from Substituent Group A" is preferably a benzoxazol-2-yl group or a 6-chloro-benzoxazol-2-yl group.

In the present invention, a "benzothiazol-2-yl group that may be substituted with 1 to 3 group(s) independently selected from Substituent Group A" is preferably a benzothiazol-2-yl group.

In the present invention, a "($C_1$-$C_6$ alkyl that may be monosubstituted with a $C_3$-$C_6$ cycloalkyl group)aminocarbonyl group" refers to a group in which an amino group to which is bonded above-mentioned "$C_1$-$C_6$ alkyl group" (that may be monosubstituted with above-mentioned "$C_3$-$C_6$ cycloalkyl group") is bonded to a carbonyl group, and is preferably a cyclohexylmethylaminocarbonyl group.

In the present invention, a "($C_3$-$C_6$ cycloalkyl)aminocarbonyl group" is a cyclopropylaminocarbonyl group, a cyclobutylaminocarbonyl group, a cyclopentylaminocarbonyl group or a cyclohexylaminocarbonyl group, preferably a cyclopentylaminocarbonyl group or a cyclohexylaminocarbonyl group, and more preferably a cyclopentylaminocarbonyl group.

In the present invention, a "heterocyclic group" refers to a 4- to 7-membered heterocyclic group that contains 1 to 3 sulfur atom(s), oxygen atom(s) and/or nitrogen atom(s), and may further contain 1 or 2 nitrogen atom(s), and in which the sulfur atom(s) may be bonded to 2 oxygen atoms. Examples thereof include: "aromatic heterocyclic group" such as a furyl group, a thienyl group, a pyrrolyl group, an azepinyl group, a pyrazolyl group, an imidazolyl group, an oxazolyl group, an isoxazolyl group, a thiazolyl group, an isothiazolyl group, a 1,3,4-oxadiazolyl group, a 1,3,4-thiadiazolyl group, a triazolyl group, a tetrazolyl group, a thiadiazolyl group, a pyranyl group, a pyridyl group, a pyridazinyl group, a pyrimidinyl group and a pyrazinyl group; and "partially or completely reduced saturated heterocyclic group" such as a tetrahydropyranyl group, a tetrahydrothienyl group, a morpholinyl group, a thiomorpholinyl group, a pyrrolidinyl group, a pyrrolinyl group, an imidazolidinyl group, a pyrazolidinyl group, a piperidinyl group, a piperazinyl group, an oxazolinyl group, an oxazolidinyl group, an isoxazolidinyl group, a thiazolinyl group, a thiazolidinyl group, a dioxolanyl group, a dioxanyl group and a 5,6-dihydro-4H-1,3-oxazine group. The heterocyclic group may be condensed with another cyclic group such as benzene ring ("condensed heterobicyclic group"). Examples of such a condensed heterobicyclic group include a benzothienyl group, a benzothiazolyl group, a benzoxazolyl group, an isobenzofuranyl group, a 1,3-dihydroisobenzofuranyl group, a quinolyl group, a 1,3-benzodioxolanyl group, a 1,4-benzodioxanyl group, an indolyl group, an isoindolyl group and an indolinyl group. The heterocyclic group is preferably an oxazole group, a 4,5-dihydro-[1,2,4]oxadiazole group, a pyrazole group, an isoxazole group or a tetrazole group, and more preferably an oxazol-2-yl group, a 4,5-dihydro-[1,2,4]oxadiazol-3-yl group, a 2H-pyrazol-3-yl group, an isoxazol-5-yl group or a tetrazol-5-yl group.

In the present invention, a "carboxylic acid (carboxyl group) equivalent" refers to hydroxamic acid (R—CO—NH—OH), acylcyanamide (R—CO—NH—CN) or acylsulfonamide (R—CO—NH—SO$_2$—R'); planar heterocycles (e.g., tetrazole); or non-planar acidic groups containing sulfur or phosphorus. They exhibit in vivo chemical, biological, physical, and physiochemical properties and behaviors similar to those of carboxylic acid and have acidity equivalent to that of carboxylic acid. For example, functional groups or heterocycles, such as hydroxamic acid, acylcyanamide, tetrazole, mercaptazole, sulfinylazole, sulfonylazole, isoxazole, isothiazole, hydroxythiadiazole, hydroxy-γ-pyrone, phosphinic acid, phosphonic acid, phosphonamide, sulfonic acid, sulphonamide, and acylsulphonamide have been reported in the document (The Practice of Medicinal Chemistry (First Part), p. 248, TECHNOMICS, INC., First Edition). Other such carboxylic acid equivalents are described in, for example, Bioorg. Med. Chem. Lett. 15 (2005) 4053-4056; and Lipinski, C. A. and Chenard, B. L. Pestic. Sci. 1990, 290, 227-240.

In the present invention, examples of a "heterocyclic group capable of serving as a carboxylic acid equivalent" include a 4-carboxyoxazol-2-yl group, a 5-oxo-4,5-dihydro-[1,2,4]oxadiazol-3-yl group, a 5-hydroxy-2H-pyrazol-3-yl group, a 3-hydroxyisoxazol-5-yl group and a tetrazol-5-yl group.

In the present invention, a "heterocyclic group that may be substituted with 1 to 3 group(s) independently selected from Substituent Group A" refers to the above-mentioned "heterocyclic group" that may be substituted with 1 to 3 group(s) independently selected from Substituent Group A, and is preferably a heterocyclic group capable of serving as a carboxylic acid equivalent, and more preferably a 4-carboxyoxazol-2-yl group, a 5-oxo-4,5-dihydro-[1,2,4]oxadiazol-3-yl group, a 5-hydroxy-2H-pyrazol-3-yl group, a 3-hydroxyisoxazol-5-yl group or a tetrazol-5-yl group for $R^3$ or more preferably a tetrazol-5-yl group for $R^5$.

In the present invention, a "group represented by the formula —C(=O)—O—$R^4$" is preferably a carboxyl group.

In the present invention, a "group represented by the formula —C(=O)—N($R^5$)$R^6$" is preferably a 1-carboxy-1-methyl-1-ethylcarbamoyl group.

In the present invention, a "$C_1$-$C_6$ alkyl group that may be substituted with 1 to 3 group(s) independently selected from Substituent Group B" refers to the above-mentioned "$C_1$-$C_6$ alkyl group" that may be substituted with 1 to 3 group(s) independently selected from Substituent Group B, and is preferably a methyl group or a 2,3-dihydropropyl group for $R^4$ or preferably a methyl group, a carboxymethyl group, a 1-carboxy-1-ethyl group or a 1-carboxy-1-methyl-1-ethyl group for $R^5$ and $R^6$.

In the present invention, a "$C_3$-$C_6$ cycloalkyl group that may be monosubstituted with a carboxyl group" refers to the above-mentioned "$C_3$-$C_6$ cycloalkyl group" that may be monosubstituted with a carboxyl group, and is preferably a 1-carboxycyclopropyl group.

In the present invention, a "4- to 6-membered saturated ring" in the sentence "when both $R^5$ and $R^6$ are a $C_1$-$C_6$ alkyl group that may be substituted with 1 to 3 group(s) independently selected from Substituent Group B, their carbon atoms may bind to each other to form a 4- to 6-membered saturated ring" refers to a 4- to 6-membered saturated ring formed through the bond between carbon atoms of the $C_1$-$C_6$ alkyl group represented by $R^5$ and the $C_1$-$C_6$ alkyl group represented by $R^6$, together with the nitrogen atom respectively bound by $R^5$ and $R^6$. The 4- to 6-membered saturated ring is preferably a pyrrolidine group.

In the present invention, a "methylene group monosubstituted with a $C_1$-$C_6$ alkyl group" refers to a methylene group monosubstituted with the "$C_1$-$C_6$ alkyl group" exemplified above and is preferably a methylmethylene group.

In the present invention, the "group represented by the formula —N($R^7$)—" is preferably a group represented by the formula —N(CH$_3$)—.

In the present invention, the general formula (I) is preferably the general formula (II) or (III), more preferably the general formula (II).

In the present invention, $R^1$ is preferably a phenylaminocarbonyl group that may be substituted with 1 to 3 group(s) independently selected from a halogen atom, a $C_1$-$C_6$ alkyl group, a $C_1$-$C_6$ halogenated alkyl group, a $C_1$-$C_6$ alkoxy group, and a $C_1$-$C_6$ halogenated alkoxy group, or a ($C_3$-$C_6$ cycloalkyl)aminocarbonyl group, more preferably a phenylaminocarbonyl group, a 2-fluorophenylaminocarbonyl group, a 3-fluorophenylaminocarbonyl group, a 3-methylphenylaminocarbonyl group, a 3-ethylphenylaminocarbonyl group, a 3-methoxyphenylaminocarbonyl group, a 3-ethoxyphenylaminocarbonyl group, a 4-trifluoromethylphenylaminocarbonyl group, a 3-trifluoromethoxyphenylaminocarbonyl group, a 3,4-difluorophenylaminocarbonyl group, a 2-fluoro-5-methoxyphenylaminocarbonyl group, a 2,4,5-trifluorophenylaminocarbonyl group, a 3,4,5-trifluorophenylaminocarbonyl group or a cyclopentylaminocarbonyl group, and even more preferably a phenylaminocarbonyl group, a 2-fluorophenylaminocarbonyl group, a 3-fluorophenylaminocarbonyl group, a 3-methylphenylaminocarbonyl group, a 3-ethylphenylaminocarbonyl group, a 3-methoxyphenylaminocarbonyl group, a 3-ethoxyphenylaminocarbonyl group, a 3-trifluoromethoxyphenylaminocarbonyl group, a 3,4-difluorophenylaminocarbonyl group, a 2-fluoro-5-methoxyphenylaminocarbonyl group or a 2,4,5-trifluorophenylaminocarbonyl group.

In the present invention, R is preferably a phenyl group that may be substituted with 1 to 3 group(s) independently selected from a halogen atom, a $C_1$-$C_6$ alkyl group, a $C_1$-$C_6$ halogenated alkyl group, a $C_1$-$C_6$ alkoxy group, and a $C_1$-$C_6$ halogenated alkoxy group, or a $C_3$-$C_6$ cycloalkyl group, more preferably a phenyl group, a 2-fluorophenyl group, a 3-fluorophenyl group, a 3-methylphenyl group, a 3-ethylphenyl group, a 3-methoxyphenyl group, a 3-ethoxyphenyl group, a 4-trifluoromethylphenyl group, a 3-trifluoromethoxyphenyl group, a 3,4-difluorophenyl group, a 2-fluoro-5-methoxyphenyl group, a 2,4,5-trifluorophenyl group, a 3,4,5-trifluorophenyl group or a cyclopentyl group, and even more preferably a phenyl group, a 2-fluorophenyl group, a 3-fluorophenyl group, a 3-methylphenyl group, a 3-ethylphenyl group, a 3-methoxyphenyl group, a 3-ethoxyphenyl group, a 3-trifluoromethoxyphenyl group, a 3,4-difluorophenyl group, a 2-fluoro-5-methoxyphenyl group or a 2,4,5-trifluorophenyl group.

In the present invention, $R^2$ is preferably a methyl group.

In the present invention, $R^3$ is preferably a heterocyclic group capable of serving as a carboxylic acid equivalent or a carboxyl group, more preferably a 4-carboxyoxazol-2-yl group, a 5-oxo-4,5-dihydro-[1,2,4]oxadiazol-3-yl group, a 5-hydroxy-2H-pyrazol-3-yl group, a 3-hydroxyisoxazol-5-yl group, a tetrazol-5-yl group or a carboxyl group, and even more preferably a carboxyl group.

In the present invention, $R^4$ is preferably a hydrogen atom.
In the present invention, $R^5$ is preferably a methyl group.
In the present invention, $R^6$ is preferably a hydrogen atom.
In the present invention, $R^7$ is preferably a methyl group.
In the present invention, X is preferably an oxygen atom or a methylene group, and more preferably an oxygen atom.
In the present invention, L is preferably a methylene group.
In the present invention, . . . is preferably a single bond.
In the present invention, m is preferably 2.
In the present invention, n is preferably 0 or 1, and more preferably 0.
In the present invention, when n is 1, $R^2$ preferably binds to the carbon atom adjacent to the carbon atom bound with X.

The compound or pharmacologically acceptable salt thereof represented by the general formula (I) of the present invention has all isomers (such as a keto-enol isomer, a diastereomer, an optical isomer, a rotamer, etc.).

The compound or pharmacologically acceptable salt thereof represented by the general formula (I) of the present invention has various isomers because asymmetric carbon atom(s) exist in the molecule. These isomers and mixtures of these isomers of the present invention are all represented by a single formula, specifically, the general formula (I). Accordingly, the present invention includes all of these isomers and mixtures of these isomers in arbitrary ratios.

The aforementioned stereoisomers can be obtained by synthesizing the compound of the present invention using an optically active raw material compound or using an asymmetric synthesis or asymmetric induction technique or by isolating the synthesized compound of the present invention by a common optical resolution or separation method if desired.

A "pharmacologically acceptable salt thereof" refers to a salt that is free of prominent toxicity and which can be used as a pharmaceutical. The compound represented by the general formula (I) of the present invention can be converted to a salt by reacting with an acid in the case the compound has a basic group such as an amino group, or by reacting with a base in the case of having an acidic group such as a carboxyl group.

Examples of salts based on a basic group include salts of hydrohalic acids such as hydrofluorides, hydrochlorides, hydrobromides or hydroiodides, salts of inorganic acids such as nitrates, perchlorates, sulfates or phosphates; $C_1$-$C_6$ alkylsulfonates such as methanesulfonates, trifluoromethanesulfonates or ethanesulfonates, arylsulfonates such as benzenesulfonates or p-toluenesulfonates; salts of organic acids such as acetates, malates, fumarates, succinates, citrates, ascorbates, tartrates, oxalates or maleates; and, salts of amino acids such as salts of glycine, lysine, arginine, ornithine, glutamic acid and aspartic acid.

On the other hand, examples of salts based on acidic groups include metal salts such as alkali metal salts such as sodium salts, potassium salts or lithium salts, alkaline earth metal salts such as calcium salts or magnesium salts, metal salts such as aluminum salts or iron salts; amine salts such as inorganic salts such as ammonium salts, or organic salts such as salts of t-octylamine, dibenzylamine, morpholine, glucosamine, phenylglycine alkyl esters, ethylenediamine, N-methylglucamine, guanidine, diethylamine, triethylamine, dicyclohexylamine, N,N'-dibenzylethylenediamine, chloroprocaine, procaine, diethanolamine, N-benzylphenethylamine, piperazine, tetramethylammonium or tris(hydroxymethyl)aminomethane; and, salts of amino acids such as salts of glycine, lysine, arginine, ornithine, glutamic acid and aspartic acid.

The compound or pharmacologically acceptable salt thereof represented by the general formula (I) of the present invention may become a hydrate by incorporating water molecule(s) by being left in the atmosphere or by recrystallizing, and such hydrates are also included in the salts of the present invention.

The compound or pharmacologically acceptable salt thereof represented by the general formula (I) of the present invention may become a solvate by absorbing another type of solvent, and such solvates are also included in the salts of the present invention.

Advantages of the Invention

A compound of the present invention represented by the general formula (I) or a pharmacologically acceptable salt thereof has an excellent DGAT inhibitory effect and feeding suppressant effect and is thus useful as a pharmaceutical agent intended for the prevention and/or treatment of a disease selected from the group consisting of adiposity, obesity, hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, ischemic heart disease, and bulimia, or a disease selected from the group consisting of hyperlipidemia, hypertriglyceridemia, lipidosis, insulin resistance syndrome, impaired glucose tolerance, diabetes, diabetic complications (including diabetic peripheral neuropathy, diabetic nephropathy, diabetic retinopathy, and diabetic macroangiopathy), cataract, gestational diabetes mellitus, nonalcoholic steatohepatitis, polycystic ovary syndrome, arteriosclerosis, atherosclerosis, diabetic atherosclerosis, hypertension, cerebrovascular disorder, coronary artery disease, fatty liver, respiratory abnormality, lower back pain, knee osteoarthritis, gout, and cholelithiasis caused by obesity, in warm-blooded animals (preferably, mammals including humans). Moreover, the novel compound represented by the general formula (I) or the pharmacologically acceptable salt thereof provided by the present invention has an excellent DGAT inhibitory effect and is thus useful as an active ingredient for a pharmaceutical agent intended for the prevention and/or treatment of any of the above diseases in warm-blooded animals (preferably, mammals including humans). Preferably, the compound of the present invention represented by the general formula (I) or the pharmacologically acceptable salt thereof can be used as a pharmaceutical agent intended for the treatment of any of the diseases described above.

BEST MODE FOR CARRYING OUT THE INVENTION

The compound represented by the general formula (I) of the present invention can be produced according to Processes A to C described below.

Solvents used in the reactions in each step of Processes A to C are not particularly limited as long as they do not inhibit the reaction and dissolve starting materials to some extent. For example, the solvents are selected from the solvent group consisting of: hydrocarbons such as pentane, hexane, octane, petroleum ether, ligroin or cyclohexane; amides such as formamide, N,N-dimethylformamide, N,N-dimethylacetamide, N-methyl-2-pyrrolidone, N-methyl-2-pyrrolidinone or hexamethylphosphoric triamide; ethers such as diethyl ether, diisopropyl ether, tetrahydrofuran, dioxane, dimethoxyethane or diethylene glycol dimethyl ether; alcohols such as methanol, ethanol, n-propanol, i-propanol, n-butanol, 2-butanol, 2-methyl-1-propanol, t-butanol, isoamyl alcohol, diethylene glycol, glycerin, octanol, cyclohexanol or methyl cellosolve; sulfoxides such as dimethyl sulfoxide; sulfones such as sulfolane; nitriles such as acetonitrile, propionitrile, butyronitrile or isobutyronitrile; esters such as ethyl formate, ethyl acetate, propyl acetate, butyl acetate or diethyl carbonate; ketones such as acetone, methyl ethyl ketone, 4-methyl-2-pentanone, methyl isobutyl ketone, isophorone or cyclohexanone; nitro compounds such as nitroethane or nitrobenzene; halogenated hydrocarbons such as dichloromethane, 1,2-dichloroethane, chlorobenzene, dichlorobenzene, chloroform or carbon tetrachloride; aromatic hydrocarbons such as benzene, toluene or xylene; carboxylic acids such as acetic acid, formic acid, propionic acid, butyric acid or trifluoroacetic acid; amines such as N-methylmorpholine, triethylamine, tripropylamine, tributylamine, diisopropylethylamine, dicyclohexylamine, N-methylpiperidine, pyridine, 2,6-lutidine, 4-pyrrolidinopyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]non-5-ene (DBN), 1,4-diazabicyclo[2.2.2]octane (DABCO), 1,8-diazabicyclo[5.4.0]undec-7-ene (DBU) or piperidine; water; and, mixed solvents thereof.

Examples of bases used in the reactions in each step of Processes A to C include inorganic bases such as alkali metal carbonates such as sodium carbonate, potassium carbonate, lithium carbonate or cesium carbonate; alkali metal hydrogencarbonates such as sodium hydrogencarbonate, potassium hydrogencarbonate or lithium hydrogencarbonate; alkali metal acetates such as sodium acetate, potassium acetate, lithium acetate or cesium acetate; alkali metal hydrides such as lithium hydride, sodium hydride or potassium hydride; alkali metal hydroxides such as sodium hydroxide, potassium hydroxide, barium hydroxide or lithium hydroxide; and, alkali metal fluorides such as sodium fluoride or potassium fluoride; alkali metal alkoxides such as sodium methoxide, sodium ethoxide, sodium t-butoxide, potassium methoxide, potassium ethoxide, potassium t-butoxide or lithium methoxide; alkali metal trialkyl siloxides such as sodium trimethyl siloxide, potassium trimethyl siloxide or lithium trimethyl siloxide; alkali metal mercaptans such as sodium thiomethoxide or sodium thioethoxide; organic bases such as N-methylmorpholine, triethylamine, tripropylamine, tributylamine, diisopropylethylamine, dicyclohexylamine, N-methylpiperidine, pyridine, 2,6-lutidine, 4-pyrrolidinopyridine, picoline, 4-(N,N-dimethylamino)pyridine, 2,6-di(t-butyl)-4-methylpyridine, quinoline, N,N-diethylaniline, 1,5-diazabicyclo[4.3.0]non-5-ene (DBN), 1,4-diazabicyclo[2.2.2]octane (DABCO) or 1,8-diazabicyclo[5.4.0]undec-7-ene (DBU); organometallic bases such as n-butyl lithium, lithium diisopropylamide or lithium bis(trimethylsilyl)amide; and, amino acids such as proline.

Examples of condensing agents used in the reactions in each step of Processes A to C include O-(7-azabenzotriazol-1-yl)-N,N,N',N'-tetramethyluronium hexafluorophosphate (HATU), 1-propanephosphonic acid cyclic anhydride (T3P), dicyclohexylcarbodiimide (DCCD), 1-ethyl-3-(3-dimethylaminopropyl)carbodiimide hydrochloride (EDCI), isobutyl chloroformate (IBCF), 1,1'-carbonylbis-1H-imidazole (CDI), diethyl cyanophosphonate (DEPC), diphenylphosphoryl azide (DPPA), N-hydroxysuccinimide, 1-hydroxybenzotriazole, N-hydroxy-5-norbornene-2,3-dicarboximide, benzotriazol-1-yloxy-tris(dimethylamino)phosphonium hexafluorophosphate (BOP), triphenylphosphine, and dipyridyl disulfide.

Examples of reducing agents used in the reactions in each step of Processes A to C include alkali metal borohydrides such as sodium borohydride, lithium borohydride, sodium cyanoborohydride or sodium triacetoxyborohydride; borane complexes such as borane-tetrahydrofuran complexes or borane-dimethyl sulfide complexes; aluminum hydride compounds such as diisobutylaluminum hydride, lithium aluminum hydride or lithium ethoxyaluminum hydride; hydride reagents of organic aluminum hydride-based reducing agents such as sodium hydrogen telluride, diisobutylaluminum hydride or sodium bis(methoxyethoxy)aluminum hydride; and alkali metals such as sodium or lithium.

Examples of palladium catalysts used in the reactions in each step of Processes A to C include divalent or zerovalent palladium catalysts such as tetrakis(triphenylphosphine)palladium (0), palladium-active carbon, palladium (II) acetate, palladium (II) trifluoroacetate, palladium black, palladium (II) bromide, palladium (II) chloride, palladium (II) iodide, palladium (II) cyanide, palladium (II) nitrate, palladium (II) oxide, palladium (II) sulfate, dichlorobis(acetonitrile)palladium (II), dichlorobis(benzonitrile)palladium (II), dichloro (1,5-cyclooctadiene)palladium (II), palladium (II) acetylacetonate, palladium (II) sulfide, [1,1'-bis(diphenylphosphino) ferrocene]palladium (II) dichloride, tris (dibenzylideneacetone)dipalladium (0), tetrakis(acetonitrile) palladium (II) tetrafluoroborate, and arylpalladium chloride dimers.

In the reactions in each step of Processes A to C, the reaction temperature varies depending on solvents, starting materials, reagents, etc., and the reaction time varies depending on solvents, starting materials, reagents, reaction temperatures, etc.

In the reactions in each step of Processes A to C, each desired compound is collected from the reaction mixture according to conventional methods after completion of the reaction. The desired compound is obtained as follows, for example. The reaction mixture is appropriately neutralized and insoluble matter, if present, is removed by filtration. Then, water and an immiscible organic solvent such as ethyl acetate are added, and the organic layer containing the desired compound is separated. The organic layer is washed with water or the like and then dried over anhydrous magnesium sulfate, anhydrous sodium sulfate, anhydrous sodium bicarbonate or the like and filtered. Then, the solvent is evaporated. The resulting desired compound may be isolated and purified if necessary by appropriately combining usual methods, for example, methods suitably used for isolation and purification of organic compounds such as recrystallization and reprecipitation and eluting with an appropriate eluent by application of chromatography. The desired compound insoluble in a solvent may be purified by washing the resulting solid crude product with a solvent. The desired compound in each step may also be used as is for the next reaction without purification.

Process A is a process of producing a compound represented by the general formula (Ia) wherein X is an oxygen atom, a group represented by the formula —NH—, or a group represented by the formula —N($R^7$)—.

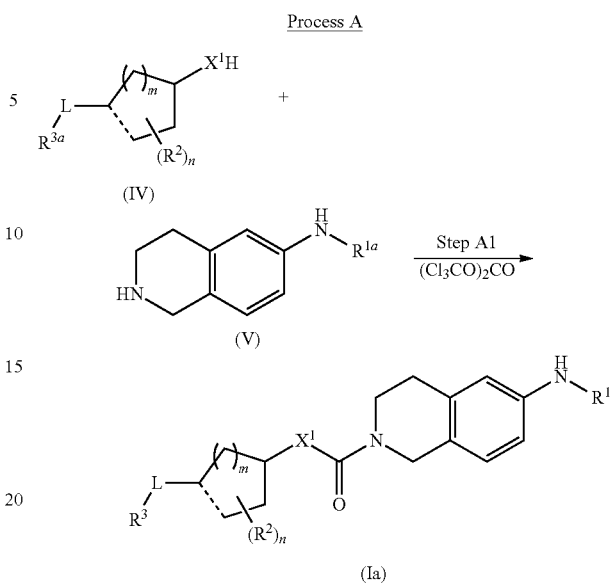

Process A

In the present invention, $R^1$, $R^2$, $R^3$, L, m, and n are as defined above; $X^1$ represents an oxygen atom, a group represented by the formula —NH—, or a group represented by the formula —N($R^7$)— (wherein $R^7$ is as defined above); and $R^{1a}$ and $R^{3a}$ represent the groups of $R^1$ and $R^3$ in which an amino group, hydroxy group and/or carboxyl group contained as a substituent in groups $R^1$ and $R^3$ is an optionally protected amino group, hydroxy group and/or carboxyl group, or represent the same groups as defined for groups $R^1$ and $R^3$.

Step A1

This step is a step of producing the compound represented by the general formula (Ia) and consists of (i) to (ii).

(i) This step is performed by reacting a compound represented by the general formula (IV) with triphosgene in the presence of a base in a solvent.

The compound represented by the general formula (IV) wherein $X^1$ is an oxygen atom, used in this step, is a compound known in the art or is easily produced according to a method known in the art or a method similar thereto using a compound known in the art as a starting material.

The compound represented by the general formula (IV) wherein $X^1$ is a group represented by the formula —NH— or a group represented by the formula —N($R^7$)—, used in this step, is a compound known in the art (e.g., J. Med. Chem., 2000, 43, 1878) or is easily produced according to a method known in the art (e.g., J. Med. Chem., 2000, 43, 1878) or a method similar thereto using a compound known in the art as a starting material.

The solvent used in this step is preferably a halogenated hydrocarbon, more preferably dichloromethane.

The base used in this step is preferably an organic base, more preferably pyridine for $X^1$=an oxygen atom or more preferably triethylamine for $X^1$=a group represented by the formula —NH— or a group represented by the formula —N($R^7$)—.

The reaction temperature in this step is usually −20° C. to 40° C., preferably 0° C. to 25° C.

The reaction time in this step is usually 0.1 hours to 24 hours, preferably 0.5 hours to 2 hours.

(ii) This step is performed by reacting the compound obtained in step (i) with a compound represented by the general formula (V) in the presence of a base in a solvent and then, if desired, removing the protective group(s) for the amino, hydroxy, and/or carboxyl groups in $R^{1a}$ and $R^{3a}$.

The compound represented by the general formula (V), used in this step, is a compound known in the art (e.g., WO2006/4200, Japanese Patent Laid-Open Nos. 2006-45209 and 2007-131584, and US2007/0249620) or is easily produced according to a method known in the art (e.g., WO2006/4200, Japanese Patent Laid-Open Nos. 2006-45209 and 2007-131584, and US2007/0249620) or a method similar thereto using a compound known in the art as a starting material.

The solvent used in this step is preferably a halogenated hydrocarbon, more preferably dichloromethane.

The base used in this step is preferably an organic base, more preferably triethylamine.

The reaction temperature in this step is usually −20° C. to 100° C., preferably 20° C. to 30° C.

The reaction time in this step is usually 0.1 hours to 96 hours, preferably 1 hour to 24 hours.

Process B is a process of producing a compound represented by the general formula (Ib) wherein X is a methylene group or a methylene group monosubstituted with a $C_1$-$C_6$ alkyl group.

The solvent used in this step is preferably an amide, more preferably N,N-dimethylacetamide.

The base used in this step is preferably an organic base, more preferably triethylamine.

The condensing agent used in this step is preferably T3P or BOP.

The reaction temperature in this step is usually −20° C. to 180° C., preferably 0° C. to 60° C.

The reaction time in this step is usually 0.1 hours to 96 hours, preferably 1 hour to 24 hours.

Process C is a process of producing a compound represented by the general formula (IV) used in step A1 of Process A and represented by the general formula (X) or (XII) wherein $R^{3a}$ is a group represented by the formula —C(=O)—O—$R^{4a}$; X' is an oxygen atom; and L is a group represented by the formula —CH= or a methylene group.

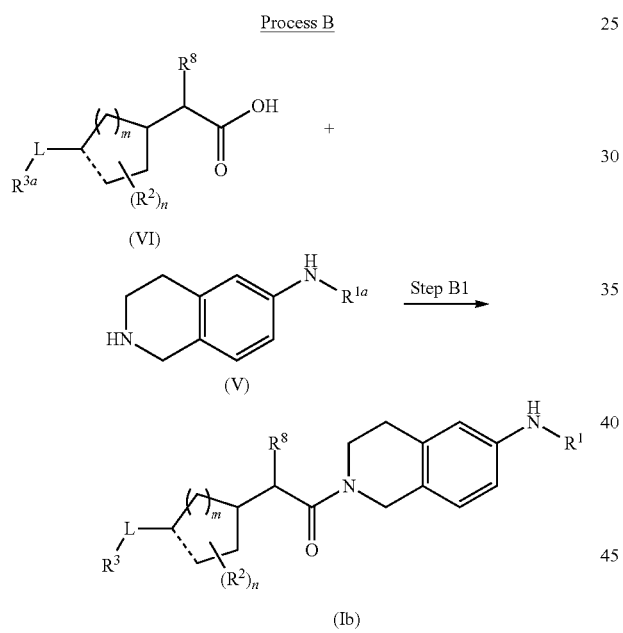

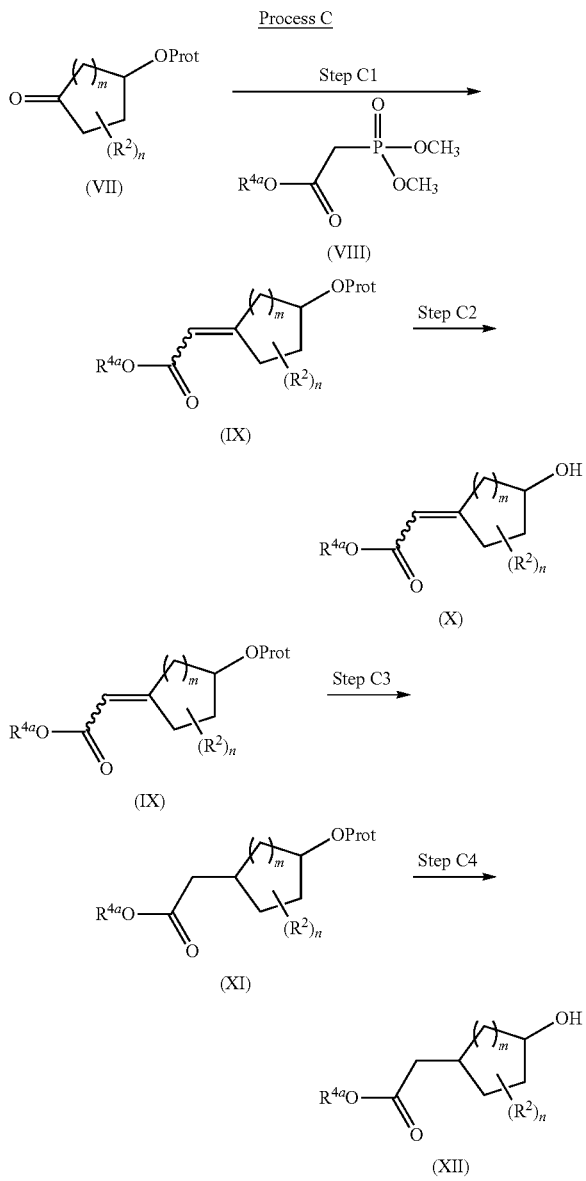

In the present invention, $R^1$, $R^2$, $R^3$, L, m, n, $R^{1a}$, and $R^{3a}$ are as defined above; and $R^8$ represents a hydrogen atom or a $C_1$-$C_6$ alkyl group.

Step B1

This step is a step of producing the compound represented by the general formula (Ib).

This step is performed by reacting a compound represented by the general formula (VI) with the compound represented by the general formula (V) and a condensing agent in the presence of a base in a solvent and then, if desired, removing the protective group(s) for the amino, hydroxy, and/or carboxyl groups in $R^{1a}$ and $R^{3a}$.

The compound represented by the general formula (VI), used in this step, is a compound known in the art (e.g., US2001/9912) or is easily produced according to a method known in the art (e.g., US2001/9912) or a method similar thereto using a compound known in the art as a starting material.

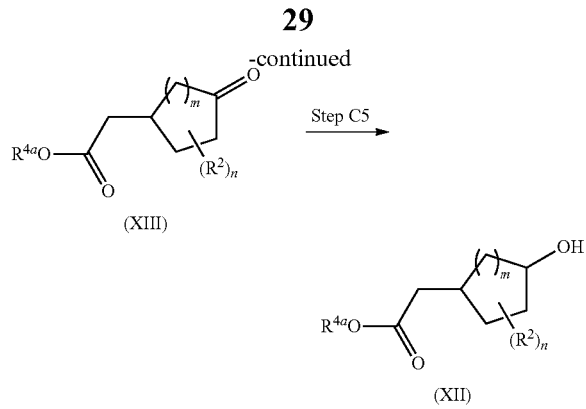

In the present invention, $R^2$, m, and n are as defined above; $R^{4a}$ represents a group in which an amino group, hydroxy group and/or carboxyl group contained as a substituent in group $R^4$ is an optionally protected amino group, hydroxy group and/or carboxyl group, or represents the same groups as defined for groups $R^4$; Prot represents a protective group for the hydroxy group.

Step C1

This step is a step of producing a compound represented by the general formula (IX).

This step is performed by reacting a compound represented by the general formula (VII) with a compound represented by the general formula (VIII) in the presence of a base in a solvent.

The compound represented by the general formula (VII) and the compound represented by the general formula (VIII), used in this step, are respectively a compound known in the art or are easily produced according to a method known in the art or a method similar thereto using a compound known in the art as a starting material.

The solvent used in this step is preferably an amide, more preferably N,N-dimethylformamide.

The base used in this step is preferably an alkali metal hydride, more preferably sodium hydride.

The reaction temperature in this step is usually −20° C. to 100° C., preferably 0° C. to 60° C.

The reaction time in this step is usually 0.1 hours to 96 hours, preferably 1 hour to 24 hours.

Step C2

This step is a step of producing the compound represented by the general formula (X).

This step is performed by removing the protective group for the hydroxy group in the compound represented by the general formula (IX).

Step C3

This step is a step of producing a compound represented by the general formula (XI).

This step is performed by hydrogenating the compound represented by the general formula (IX) in the presence of a palladium catalyst in a solvent in a hydrogen atmosphere.

The solvent used in this step is preferably an alcohol, more preferably ethanol.

The palladium catalyst used in this step is preferably palladium-active carbon.

The reaction temperature in this step is usually 0° C. to 100° C., preferably 20° C. to 80° C.

The reaction time in this step is usually 0.5 hours to 96 hours, preferably 2 hours to 48 hours.

Step C4

This step is a step of producing the compound represented by the general formula (XII).

This step is performed by removing the protective group for the hydroxy group in the compound represented by the general formula (XI).

Step C5

This step is a step of producing the compound represented by the general formula (XII).

This step is performed by reacting a compound represented by the general formula (XIII) with a reducing agent in a solvent.

The compound represented by the general formula (XIII), used in this step, is a compound known in the art (e.g., J. Med. Chem., 2006, 49, 2496) or is easily produced according to a method known in the art (e.g., J. Med. Chem., 2006, 49, 2496) or a method similar thereto using a compound known in the art as a starting material.

The solvent used in this step is preferably an alcohol, more preferably methanol.

The reducing agent used in this step is preferably an alkali metal borohydride, more preferably sodium borohydride.

The reaction temperature in this step is usually −78° C. to 100° C., preferably 0° C. to 30° C.

The reaction time in this step is usually 0.1 hours to 96 hours, preferably 0.5 hours to 24 hours.

In the description above, the protective group for the "amino group which may be protected", the "hydroxy group which may be protected", and the "carboxyl group which may be protected" in the definitions of $R^{1a}$, $R^{3a}$, and $R^{4a}$ refers to a protective group that can be cleaved by a chemical method such as hydrogenolysis, hydrolysis, electrolysis, or photolysis, and represents a protective group generally used in organic synthetic chemistry (see e.g., T. W. Greene et al., Protective Groups in Organic Synthesis, 3rd Edition, John Wiley & Sons, Inc. (1999)).

In the description above, the "protective group" for the "hydroxy group which may be protected" in the definitions of $R^{1a}$, $R^{3a}$, and $R^{4a}$ is not particularly limited as long as it is a protective group for hydroxy groups used in the field of organic synthetic chemistry. Examples thereof include: a formyl group; "alkylcarbonyl groups" such as the "$C_2$-$C_7$ alkylcarbonyl group" exemplified above, halogenated alkylcarbonyl groups (e.g., chloroacetyl, dichloroacetyl, trichloroacetyl, and trifluoroacetyl), alkoxyalkylcarbonyl groups (e.g., methoxyacetyl), and unsaturated alkylcarbonyl groups (e.g., acryloyl, propioloyl, methacryloyl, crotonoyl, isocrotonoyl, and (E)-2-methyl-2-butenoyl); "arylcarbonyl groups" such as arylcarbonyl groups (e.g., benzoyl, α-naphthoyl, and β-naphthoyl), halogenated arylcarbonyl groups (e.g., 2-bromobenzoyl and 4-chlorobenzoyl), $C_1$-$C_6$ alkylated arylcarbonyl groups (e.g., 2,4,6-trimethylbenzoyl and 4-toluoyl), $C_1$-$C_6$ alkoxylated arylcarbonyl groups (e.g., 4-anisoyl), nitrated arylcarbonyl groups (e.g., 4-nitrobenzoyl and 2-nitrobenzoyl), $C_2$-$C_7$ alkoxycarbonylated arylcarbonyl groups (e.g., 2-(methoxycarbonyl)benzoyl), and arylated arylcarbonyl groups (e.g., 4-phenylbenzoyl); "alkoxycarbonyl groups" such as the "$C_2$-$C_7$ alkoxycarbonyl group" exemplified above and $C_1$-$C_7$ alkoxycarbonyl groups substituted by halogen or a tri-($C_1$-$C_6$ alkyl)silyl group (e.g., 2,2,2-trichloroethoxycarbonyl and 2-trimethylsilylethoxycarbonyl); "tetrahydropyranyl or tetrahydrothiopyranyl groups" such as tetrahydropyran-2-yl, 3-bromotetrahydropyran-2-yl, 4-methoxytetrahydropyran-4-yl, tetrahydrothiopyran-2-yl, and 4-methoxytetrahydrothiopyran-4-yl; "tetrahydrofuranyl or tetrahydrothiofuranyl groups" such as tetrahydrofuran-2-yl and tetrahydrothiofuran-2-yl; "silyl groups" such as tri-($C_1$-$C_6$ alkyl)silyl groups (e.g., trimethylsilyl, triethylsilyl, isopropyldimethylsilyl, t-butyldimethylsilyl, methyldiisopropylsilyl, methyldi-t-butylsilyl, and triisopropylsilyl) and ($C_1$-$C_6$ alkyl)diarylsilyl or di-($C_1$-$C_6$ alkyl)arylsilyl groups (e.g., diphenylmethylsilyl, diphenylbutylsilyl, diphenylisopropylsilyl, and phenyldiisopropylsilyl); "alkoxymethyl groups" such as ($C_1$-$C_6$ alkoxy)methyl groups (e.g., methoxymethyl, 1,1-dimethyl-1-methoxymethyl, ethoxymethyl, propoxymethyl; isopropoxymethyl, butoxymethyl, and t-butoxymethyl), ($C_1$-$C_6$ alkoxy)-($C_1$-$C_6$ alkoxy)methyl groups (e.g., 2-methoxyethoxymethyl), and ($C_1$-$C_6$ halogenated alkoxy)methyl (e.g., 2,2,2-trichloroethoxymethyl and bis(2-chloroethoxy)methyl); "substituted ethyl groups" such as ($C_1$-$C_6$ alkoxy)ethyl groups (e.g., 1-ethoxyethyl and 1-(isopropoxy)ethyl) and halogenated ethyl groups (e.g., 2,2,2-trichloroethyl); "aralkyl groups" such as $C_1$-$C_6$ alkyl groups substituted by 1 to 3 aryl groups (e.g., benzyl, α-naphthylmethyl, β-naphthylmethyl, diphenylmethyl, triphenylmethyl, α-naphthyldiphenylmethyl, and 9-anthrylmethyl) and $C_1$-$C_6$ alkyl groups substituted by 1 to 3 aryl groups having an aryl ring substituted by $C_1$-$C_6$ alkyl, $C_1$-$C_6$ alkoxy, nitro, halogen, or a cyano group (e.g., 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzyl, 4-bromobenzyl, and 4-cyanobenzyl); "alkenyloxycarbonyl groups" such as vinyloxycarbonyl and allyloxycarbonyl; and "aralkyloxycarbonyl groups" whose aryl ring may be substituted by 1 or 2 $C_1$-$C_6$ alkoxy or nitro groups, such as benzyloxycarbonyl, 4-methoxybenzyloxycarbonyl, 3,4-dimethoxybenzyloxycarbonyl, 2-nitrobenzyloxycarbonyl, and 4-nitrobenzyloxycarbonyl. The protective group is preferably an alkylcarbonyl group, a silyl group, or an aralkyl group.

In the description above, the "protective group" for the "carboxyl group which may be protected" in the definitions of $R^{1a}$, $R^{3a}$, and $R^{4a}$ is not particularly limited as long as it is a protective group for carboxyl groups used in the field of organic synthetic chemistry. Examples thereof include: the "$C_1$-$C_6$ alkyl group" exemplified above; "$C_2$-$C_6$ alkenyl groups" such as ethenyl, 1-propenyl, 2-propenyl, and 1-methyl-2-propenyl; "$C_2$-$C_6$ alkynyl groups" such as ethynyl, 1-propynyl, 2-propynyl, and 1-methyl-2-propynyl; the "$C_1$-$C_6$ halogenated alkyl group" exemplified above; $C_1$-$C_6$ hydroxyalkyl groups such as hydroxymethyl and 2-hydroxyethyl; ($C_2$-$C_7$ alkylcarbonyl)-($C_1$-$C_6$ alkyl groups) such as acetylmethyl; the "aralkyl groups" exemplified above; and the "silyl groups" exemplified above. The protective group is preferably a $C_1$-$C_6$ alkyl group or an aralkyl group.

In the description above, the "protective group" for the "amino group which may be protected" in the definitions of $R^{1a}$, $R^{3a}$, and $R^{4a}$ is not particularly limited as long as it is a protective group for amino groups used in the field of organic synthetic chemistry. Examples thereof include: those similar to the "alkylcarbonyl groups", the "arylcarbonyl groups", the "alkoxycarbonyl groups", the "silyl groups", the "aralkyl groups", the "alkenyloxycarbonyl groups", and the "aralkyloxycarbonyl groups" exemplified as the "protective group for hydroxy groups"; and "substituted methylene groups that form a Schiff's base" such as N,N-dimethylaminomethylene, benzylidene, 4-methoxybenzylidene, 4-nitrobenzylidene, salicylidene, 5-chlorosalicylidene, diphenylmethylene, and (5-chloro-2-hydroxyphenyl)phenylmethylene. The protective group is preferably an alkylcarbonyl group, an arylcarbonyl group, or an alkoxycarbonyl group, more preferably an alkoxycarbonyl group.

The steps requiring protection/deprotection are performed according to known methods (for example, the methods described in Theodora W. Greene, Peter G. M. Wuts, "Protective Groups in Organic Synthesis," 1999, A Wiley-Interscience Publication, etc.).

The compound or pharmacologically acceptable salt thereof of the present invention can be administered in various forms. Examples of the route of administration include oral administration using tablets, capsules, granules, emulsions, pills, powders, syrups (solutions), and the like and parenteral administration using injections (intravenous, intramuscular, subcutaneous, or intraperitoneal administration), drip infusions, suppositories (rectal administration), and the like. These various formulations can be prepared as drug products according to usual methods using aids usually used in the field of drug formulation such as excipients, binders, disintegrants, lubricants, flavoring agents, dissolving aids, suspending agents, and coating agents in addition to the active ingredient.

In the use as a tablet, examples of carriers that can be used include excipients such as lactose, sucrose, sodium chloride, glucose, urea, starch, calcium carbonate, kaolin, crystalline cellulose, and silicic acid; binders such as water, ethanol, propanol, simple syrup, glucose solution, starch solution, gelatin solution, carboxymethylcellulose, shellac, methylcellulose, potassium phosphate, and polyvinylpyrrolidone; disintegrants such as dry starch, sodium alginate, agar powder, laminaran powder, sodium hydrogencarbonate, calcium carbonate, polyoxyethylene sorbitan fatty acid esters, sodium lauryl sulfate, stearic monoglyceride, starch, and lactose; disintegration inhibitors such as sucrose, stearin, cocoa butter, and hydrogenated oil; absorption enhancers such as quaternary ammonium salts and sodium lauryl sulfate; humectants such as glycerine and starch; adsorbents such as starch, lactose, kaolin, bentonite, and colloidal silicic acid; hibricants such as purified talc, stearate, fluoboric acid powder, and polyethylene glycol, and so forth. Furthermore, tablets coated in usual ways such as, for example, sugar-coated tablets, gelatin-coated tablets, enteric-coated tablets, film-coated tablets, double-layer tablets, and multilayered tablets can be prepared as required.

In the use as a pill, examples of carriers that can be used include excipients such as glucose, lactose, cocoa butter, starch, hydrogenated vegetable oil, kaolin, and talc; binders such as powdered gum arabic, powdered tragacanth, gelatin, and ethanol; disintegrants such as laminaran, and agar, and so forth.

In the use as a suppository, a wide range of carriers known in this field can be used, and examples thereof include polyethylene glycol, cocoa butter, higher alcohols, higher alcohol esters, gelatin, semisynthetic glycerides, and so forth.

In the use as an injection, the formulations can be prepared as solutions, emulsions, or suspensions. Preferably, these solutions, emulsions, and suspensions are sterilized and are isotonic with blood. Solvents for producing these solutions, emulsions, and suspensions are not particularly limited so long as they can be used as diluents for medical use, and examples thereof include water, ethanol, propylene glycol, ethoxylated isostearyl alcohol, polyoxylated isostearyl alcohol, polyoxy ethylene sorbitan fatty acid esters, and so forth. In this case, a sufficient amount of sodium chloride, glucose, or glycerine may be added to the formulation to prepare an isotonic solution, and usual dissolving aids, buffers, soothing agents, and the like may also be added.

Furthermore, coloring agents, preservatives, perfumes, flavoring agents, sweeteners, and the like can be added to the above-mentioned formulation, if necessary. Furthermore, other drugs can also be added.

The amount of active ingredient compound contained in the above-mentioned formulations is not particularly limited, but is usually 0.5 to 70% by weight of the total composition, preferably 1 to 30% by weight.

The dose varies depending on symptoms, age, and the like of the patient (a warm-blooded animal, in particular, a human). In the case of oral administration, the recommended adult daily dosage is from 0.1 mg as the lower limit (preferably 1 mg, more preferably 10 mg) to 2000 mg as the upper limit (preferably 100 mg), which is divided into 1 to 6 doses depending on symptoms.

EXAMPLES

Hereinafter, the present invention will be described more specifically with reference to Examples and Test Examples. However, the scope of the present invention is not intended to be limited to these.

In these Examples, elution in column chromatography was performed under observation by TLC (Thin Layer Chromatography). In the TLC observation, silica gel 60F$_{254}$ manufactured by Merck was adopted as the TLC plate; solvents used as eluting solvents in column chromatography were adopted as developing solvents; and a UV detector was adopted as the detection method. Silica gel SK-85 (230-400 mesh) also manufactured by Merck or Chromatorex NH (200-350 mesh, FUJI SILYSIA CHEMICAL LTD.) was used as silica gel for columns. In addition to usual column chromatography, Biotage automatic chromatography apparatus (SP-1) was appropriately used. The solvents described in each Example were used as eluting solvents at the prescribed ratio (or this ratio was changed appropriately according to need). Abbreviations used in Examples mean the following:

mg: milligram, g: gram, mL: milliliter, MHz: megahertz.

In Examples below, nuclear magnetic resonance (hereinafter, referred to as $^1$H NMR) spectra were indicated in δ values (ppm) in terms of chemical shift values with tetramethylsilane as standards. Splitting patterns were represented by s for singlet, d for doublet, t for triplet, and q for quartet.

Mass spectrometry (hereinafter, referred to as MS) was conducted by the FAB (Fast Atom Bombardment), EI (Electron Ionization), or ESI (Electron Spray Ionization) method.

Example 1 trans-6-[3-(2-fluoro-phenyl)-ureido]-3,4-dihydro-1H-isoquinoline-2-carboxylic acid 4-methoxycarbonylmethyl-cyclohexyl ester

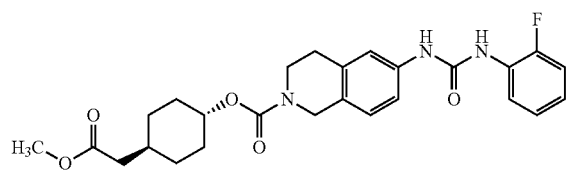 [SMILES: COC(=O)C[C@H]1CC[C@H](OC(=O)N2CCc3cc(NC(=O)Nc4ccccc4F)ccc3C2)CC1]

(1a) (1,4-dioxa-spiro[4.5]dec-8-ylidene)-acetic acid methyl ester

To a DMF (50 mL) solution of trimethyl phosphonoacetate (26 mL), sodium hydride (purity: 55% or higher, 7.03 g) was added in small portions at 0° C. The reaction mixture was warmed to room temperature and stirred for 30 minutes. A DMF (50 mL) solution of 1,4-cyclohexanedione monoethylene ketal (25.2 g) was added, thereto in small portions at room temperature. This suspension was stirred for 19 hours and diluted with a saturated aqueous solution of ammonium chloride, followed by two extractions with ethyl acetate. The organic layer was washed with saturated brine, then dried over sodium sulfate, and then concentrated. The residue was purified by chromatography (hexane/ethyl acetate=5:1) to obtain the title compound (29.7 g, 87%) as a colorless oil.

$^1$H NMR (400 MHz, CDCl$_3$): δ (ppm)=5.75-5.65 (1H, m), 3.99 (4H, s), 3.70 (3H, s), 3.01 (2H, t, J=6.7 Hz), 2.39 (2H, t, J=6.7 Hz), 1.81-1.75 (4H, m);

MS (EI) m/z: 212 (M)$^+$.

(1b) (1,4-dioxa-spiro[4.5]dec-8-yl)-acetic acid methyl ester

An ethanol (50 mL) suspension of (1,4-dioxa-spiro[4.5]dec-8-ylidene)-acetic acid methyl ester (6.57 g) obtained in Example (1a) and palladium carbon (10% by weight) was hydrogen-reduced at room temperature for 24 hours. The reaction mixture was filtered and concentrated. The residue was purified by chromatography (hexane/ethyl acetate=5:1) to obtain the title compound (4.99 g, 75%) as a colorless oil.

$^1$H NMR (400 MHz, CDCl$_3$): δ (ppm)=3.94 (4H, s), 3.67 (3H, s), 2.25 (2H, d, J=7.0 Hz), 1.89-1.81 (1H, m), 1.74 (4H, d, J=9.8 Hz), 1.63-1.53 (2H, m), 1.36-1.25 (2H, m);

MS (EI) m/z: 214 (M)$^+$.

(1c) (4-oxo-cyclohexyl)-acetic acid methyl ester

A 1 N aqueous hydrochloric acid solution (50 mL)/acetone (200 ml) mixture of (1,4-dioxa-spiro[4.5]dec-8-yl)-acetic acid methyl ester (4.99 g) obtained in Example (1b) was stirred at room temperature for 15 hours. The organic solvent was removed using an evaporator. The remaining aqueous solution was subjected to two extractions with ethyl acetate. The organic layer was washed with saturated brine, then dried over sodium sulfate, and then concentrated to obtain the title compound (4.30 g, quantitative yield) as a colorless oil.

$^1$H NMR (400 MHz, CDCl$_3$): δ (ppm)=3.71 (3H, s), 2.41-2.24 (7H, m), 2.12-2.05 (2H, m), 1.54-1.43 (2H, m);

MS (EI) m/z: 170 (M)$^+$.

(1d) trans-(4-hydroxy-cyclohexyl)-acetic acid methyl ester and cis-4-(hydroxy-cyclohexyl)-acetic acid methyl ester To a methanol (50 mL) solution of (4-oxo-cyclohexyl)-acetic acid methyl ester (4.18 g) obtained in Example (1c), sodium borohydride (1.86 g) was added in small portions at 0° C. The reaction mixture was stirred for 1 hour and diluted with a 10% aqueous ammonium chloride solution (100 mL). The organic solvent was removed using an evaporator. The remaining aqueous solution was subjected to two extractions with ethyl acetate. The organic layer was washed with saturated brine, then dried over sodium sulfate, and then concentrated to obtain trans-(4-hydroxy-cyclohexyl)-acetic acid methyl ester (2.56 g, 60%) as a colorless oil and cis-4-hydroxy-cyclohexyl)-acetic acid methyl ester (0.517 g, 12%) as a colorless oil.

Trans Form; $^1$H NMR (400 MHz, CDCl$_3$): δ (ppm)=3.67 (3H, s), 3.67-3.60 (1H, m), 2.20 (2H, d, J=6.7 Hz), 2.00-1.94 (2H, m), 1.82-1.67 (4H, m), 1.35-1.26 (2H, m), 1.10-1.00 (2H, m).

Cis Form; $^1$H NMR (400 MHz, CDCl$_3$): δ (ppm)=4.04-3.96 (1H, m), 3.68 (3H, s), 2.26 (2H, d, J=7.0 Hz), 1.94-1.24 (10H, m).

(1e) trans-6-[3-(2-fluoro-phenyl)-ureido]-3,4-dihydro-1H-isoquinoline-2-carboxylic acid 4-methoxycarbonylmethyl-cyclohexyl ester To a dichloromethane (10 mL) solution of triphosgene (569 mg), a dichloromethane (10 mL) solution of trans-(4-hydroxy-cyclohexyl)-acetic acid methyl ester (850 mg) obtained in Example (1d) and pyridine (0.39 mL) was gradually added dropwise at 0° C. The reaction mixture was warmed to room temperature, then stirred for 3.5 hours, and then concentrated. The residue was vigorously stirred in diisopropyl ether and filtered. The filtrate was concentrated to obtain chloroformate as a colorless oil. A dichloromethane solution (10 mL) of this oil was added at room temperature to a dichloromethane (10 mL) suspension of 1-(2-fluoro-phenyl)-3-(1,2,3,4-tetrahydro-isoquinolin-6-yl)-urea hydrochloride (WO2006004200 A1) (1.03 g) and triethylamine (1.3 mL). After 1 hour, the reaction mixture was concentrated and purified by column chromatography (dichloromethane/ethyl acetate) to obtain the title compound (1.55 g, quantitative yield) as a white solid.

$^1$H NMR (400 MHz, DMSO-d6): δ (ppm)=9.01 (1H, s), 8.52 (1H, d, J=2.7 Hz), 8.15 (1H, ddd, J=11.6, 11.6 and 4.2 Hz), 7.32 (1H, s), 7.25 (1H, dd, J=8.2 and 1.6 Hz), 7.22 (2H, dd, J=8.0 and 1.4 Hz), 7.16-7.08 (1H, m), 7.04-6.98 (1H, m), 4.51-4.44 (3H, m), 3.60-3.55 (2H, m), 3.59 (3H, s), 2.76 (2H, t, J=6.0 Hz), 2.22 (2H, d, J=7.0 Hz), 1.95-1.88 (2H, m), 1.79-1.62 (3H, m), 1.79-1.62 (2H, m), 1.15-1.05 (2H, m);

MS (ESI) m/z: 484 (M+H)$^+$.

Example 2 trans-6-[3-(2-fluoro-phenyl)-ureido]-3,4-dihydro-1H-isoquinoline-2-carboxylic acid 4-carboxymethyl-cyclohexyl ester

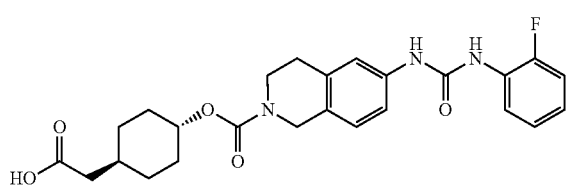 [SMILES: O=C(O)C[C@H]1CC[C@H](OC(=O)N2CCc3cc(NC(=O)Nc4ccccc4F)ccc3C2)CC1]

To a 1,4-dioxane (20 mL) mixture of trans-6-[3-(2-fluoro-phenyl)-ureido]-3,4-dihydro-1H-isoquinoline-2-carboxylic acid 4-methoxycarbonylmethyl-cyclohexyl ester (1.48 g) obtained in Example 1, tetrabutylammonium hydroxide (1.0 mol/L aqueous solution, 4.0 mL) was added at room temperature. The reaction mixture was stirred for 22 hours and concentrated. The residue was acidified with a 1N aqueous hydrochloric acid solution (30 mL), then diluted with ethyl acetate, and vigorously stirred until complete dissolution. The separated organic layer was washed with saturated brine, then dried over sodium sulfate, and then concentrated. The residue was purified by chromatography (dichloromethane/methanol). The obtained solid was recrystallized (isopropyl alcohol) to obtain the title compound (1.04 g, 72%) as a white solid.

$^1$H NMR (400 MHz, DMSO-d6): δ (ppm)=12.1 (1H, s), 9.03 (1H, s), 8.55 (1H, s), 8.16 (1H, dd, J=7.8 and 7.8 Hz), 7.32 (1H, s), 7.26-7.20 (2H, m), 7.16-7.08 (2H, m), 7.04-6.97 (1H, m), 4.52-4.42 (3H, m), 3.57 (2H, t, J=5.9 Hz), 2.76 (2H, t, J=5.9 Hz), 2.12 (2H, d, J=7.1 Hz), 1.97-1.89 (2H, m), 1.79-1.71 (2H, m), 1.70-1.60 (1H, m), 1.40-1.29 (2H, m), 1.14-1.01 (2H, m);

MS (ESI) m/z: 470 (M+H)$^+$.

Example 3 cis-6-[3-(2-fluoro-phenyl)-ureido]-3,4-dihydro-1H-isoquinoline-2-carboxylic acid 4-carboxymethyl-cyclohexyl ester

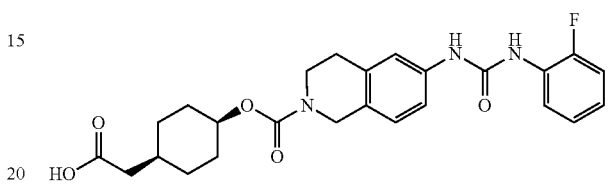

Methyl ester (143 mg, quantitative yield) was obtained in the same way as in Example (1e) from cis-(4-hydroxy-cyclohexyl)-acetic acid methyl ester (62 mg) obtained in Example (1d) and 1-(2-fluoro-phenyl)-3-(1,2,3,4-tetrahydro-isoquinolin-6-yl)-urea hydrochloride (WO2006004200 A1) (83 mg). This methyl ester was hydrolyzed in the same way as in Example 2 to obtain the title compound (86 mg, 71%) as a white solid.

$^1$H NMR (400 MHz, DMSO-d6): δ (ppm)=12.0 (1H, s), 9.01 (1H, s), 8.53 (1H, s), 8.16 (1H, dd, J=9.0 and 9.0 Hz), 7.35-6.95 (6H, m), 4.85-4.77 (1H, m), 4.58-4.39 (2H, m), 3.66-3.53 (2H, m), 2.82-2.74 (2H, m), 2.17 (2H, d, J=7.0 Hz), 2.20-2.08 (1H, m), 1.82-1.69 (3H, m), 1.59-1.47 (3H, m), 1.38-1.22 (2H, m);

MS (ESI) m/z: 469 (M+H)$^+$.

Example 4

[4-({6-[3-(2-fluoro-phenyl)-ureido]-3,4-dihydro-1H-isoquinoline-2-carbonyl}-amino)-cyclohexyl]-acetic acid methyl ester

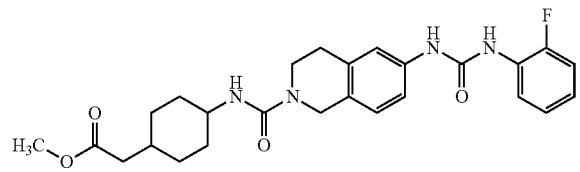 [SMILES: COC(=O)CC1CCC(NC(=O)N2CCc3cc(NC(=O)Nc4ccccc4F)ccc3C2)CC1]

The title compound (84 mg, 54%) was obtained in the same way as in Example (1e) from (4-amino-cyclohexyl)-acetic acid methyl ester (J. Med. Chem. 2000, 9, 1878) (82 mg) and 1-(2-fluoro-phenyl)-3-(1,2,3,4-tetrahydro-isoquinolin-6-yl)-urea hydrochloride (WO2006004200 A1) (103 mg).

$^1$H NMR (400 MHz, DMSO-d6): δ (ppm)=8.99 (1H, s), 8.16 (1H, dd, J=8.4 and 8.4 Hz), 7.33-7.18 (4H, m), 7.14 (1H, dd, J=7.8 and 7.8 Hz), 7.07-6.98 (3H, m), 6.25-6.15 (1H, m), 4.42-4.40 (2H, m), 3.60-3.59 (3H, m), 3.55-3.50 (2H, m), 2.76-2.70 (2H, m), 2.35-2.150 (2H, m), 2.00-1.95 (1H, m), 1.80-1.66 (1H, m), 1.58-1.43 (4H, m), 1.24-1.16 (1H, m), 1.06-0.98 (1H, m);

MS (ESI) m/z: 483 (M+H)$^+$.

Example 5

[4-({6-[3-(2-fluoro-phenyl)-ureido]-3,4-dihydro-1H-isoquinoline-2-carbonyl}-amino)-cyclohexyl]-acetic acid

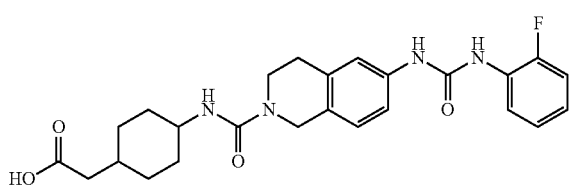 [SMILES: O=C(O)CC1CCC(NC(=O)N2CCc3cc(NC(=O)Nc4ccccc4F)ccc3C2)CC1]

[4-({6-[3-(2-Fluoro-phenyl)-ureido]-3,4-dihydro-1H-isoquinoline-2-carbonyl}-amino)-cyclohexyl]-acetic acid methyl ester (74 mg) obtained in Example 4 was hydrolyzed in the same way as in Example 2 to obtain the title compound (20 mg, 28%) as a white solid.

$^1$H NMR (400 MHz, DMSO-d6): δ (ppm)=12.0 (1H, s), 8.99 (1H, s), 8.52 (1H, s), 8.16 (1H, dd, J=8.8 and 8.8 Hz), 7.35-6.97 (7H, m), 6.20-6.18 (1H, m), 4.46-4.39 (2H, m), 3.55-3.49 (2H, m), 2.77-2.71 (2H, m), 2.10 (2H, d, J=6.7 Hz), 1.97-1.88 (1H, m), 1.83-1.67 (2H, m), 1.63-1.43 (2H, m), 1.31-1.16 (2H, m), 1.07-0.93 (2H, m);

MS (ESI) m/z: 469 (M+H)$^+$.

Example 6 cis-6-[3-(2-fluoro-phenyl)-ureido]-3,4-dihydro-1H-isoquinoline-2-carboxylic acid 3-carboxymethyl-cyclopentyl ester

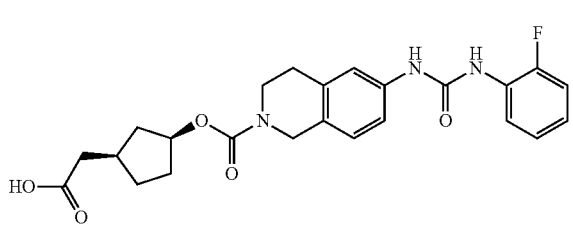 [SMILES: O=C(O)C[C@@H]1CC[C@H](OC(=O)N2CCc3cc(NC(=O)Nc4ccccc4F)ccc3C2)C1]

Methyl ester (469 mg, 90%) was obtained in the same way as in Example (1e) from cis-(3-hydroxy-cyclopentyl)-acetic acid methyl ester (Helvetica Chimica Acta 1992, 75, 1944) (221 mg) and 1-(2-fluoro-phenyl)-3-(1,2,3,4-tetrahydro-isoquinolin-6-yl)-urea hydrochloride (WO2006004200 A1) (321 mg). This methyl ester was hydrolyzed in the same way as in Example 2 to obtain the title compound (455 mg, quantitative yield) as a yellow solid.

$^1$H NMR (400 MHz, DMSO-d6): δ (ppm)=12.1 (1H, brs), 9.04 (1H, s), 8.55 (1H, d, J=2.3 Hz), 8.15 (1H, dt, J=11.6 and 4.2 Hz), 7.32 (1H, brs), 7.25 (1H, dd, J=8.2 and 1.6 Hz), 7.22 (1H, dd, J=8.2 and 1.2 Hz), 7.14 (1H, dd, J=8.6 and 8.6 Hz), 7.10 (1H, d, J=8.2 Hz), 7.03-6.98 (1H, m), 4.99 (1H, t, J=3.7 Hz), 4.47 (2H, brs), 3.57 (2H, t, J=5.6 Hz), 2.77 (2H, t, J=5.9 Hz), 2.31 (2H, d, J=7.1 Hz), 2.23-2.14 (2H, m), 1.84-1.77 (2H, m), 1.73-1.68 (1H, m), 1.37-1.29 (2H, m);

MS (ESI) m/z: 456 (M+H)$^+$.

Example 7 trans-6-[3-(2-fluoro-phenyl)-ureido]-3,4-dihydro-1H-isoquinoline-2-carboxylic acid 3-carboxymethyl-cyclopentyl ester

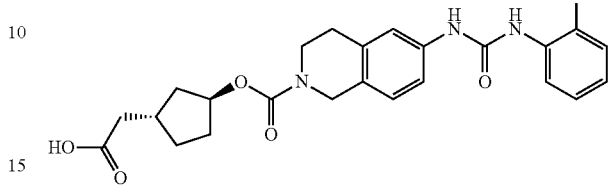

Methyl ester (583 mg, 96%) was obtained in the same way as in Example (1e) from trans-(3-hydroxy-cyclopentyl)-acetic acid methyl ester (Helvetica Chimica Acta 1992, 75, 1944) (280 mg) and 1-(2-fluoro-phenyl)-3-(1,2,3,4-tetrahydro-isoquinolin-6-yl)-urea hydrochloride (WO2006004200 A1) (418 mg). This methyl ester was hydrolyzed in the same way as in Example 2 to obtain the title compound (357 mg, 63%) as an off-white solid.

$^1$H NMR (400 MHz, DMSO-d6): δ (ppm)=12.1 (1H, brs), 9.10 (1H, s), 8.61 (1H, d, J=1.1 Hz), 8.15 (1H, dt, J=11.5 and 4.1 Hz), 7.32 (1H, brs), 7.25 (1H, dd, J=8.0 and 1.4 Hz), 7.24-7.21 (1H, m), 7.16-7.10 (2H, m), 7.03-6.98 (1H, m), 5.05-5.01 (1H, m), 4.46 (2H, brs), 3.56 (2H, t, J=5.7 Hz), 2.76 (2H, t, J=5.9 Hz), 2.39-2.33 (1H, m), 2.26-2.23 (2H, m), 2.04-1.96 (1H, m), 1.94-1.85 (2H, m), 1.66-1.58 (1H, m), 1.48-1.41 (1H, m), 1.23-1.14 (1H, m);

MS (EST) m/z: 456 (M+H)$^+$.

Example 8 trans-6-[3-(2-fluoro-phenyl)-ureido]-3,4-dihydro-1H-isoquinoline-2-carboxylic acid 4-carboxy-cyclohexyl ester

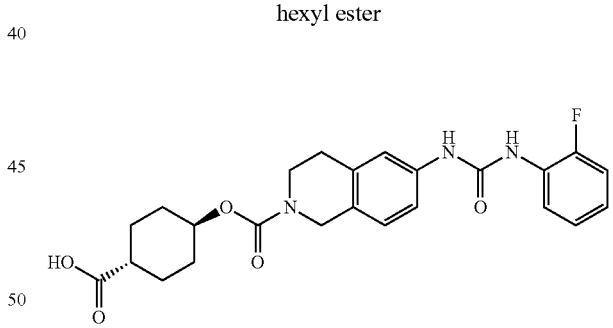

Methyl ester (76 mg, 16%) was obtained in the same way as in Example (1e) from trans-4-carbomethoxycyclohexanol (J. Org. Chem. 1962, 27, 4141.) (221 mg) and 1-(2-fluoro-phenyl)-3-(1,2,3,4-tetrahydro-isoquinolin-6-yl)-urea hydrochloride (WO2006004200 A1) (321 mg). This methyl ester was hydrolyzed in the same way as in Example 2 to obtain the title compound (36 mg, 49%) as a pale yellow solid.

$^1$H NMR (400 MHz, DMSO-d6): δ (ppm)=12.2 (1H, brs), 9.04 (1H, s), 8.55 d, J=2.3 Hz), 8.15 (1H, dt, J=11.7 and 4.1 Hz), 7.33 (1H, brs), 7.25 (1H, dd, J=8.2 and 1.6 Hz), 7.22 (1H, dd, J=8.3 and 1.5 Hz), 7.16-7.09 (2H, m), 7.03-6.98 (1H, m), 4.55-4.50 (1H, m), 4.47 (2H, s), 3.57 (2H, t, J=5.9 Hz), 2.77 (2H, t, J=5.9 Hz), 2.26-2.20 (1H, m), 1.95-1.90 (4H, m), 1.46-1.37 (4H, m);

MS (ESI) m/z: 456 (M+H)$^+$.

Example 9 cis-6-[3-(2-fluoro-phenyl)-ureido]-3,4-dihydro-1H-isoquinoline-2-carboxylic acid 4-carboxy-cyclohexyl ester

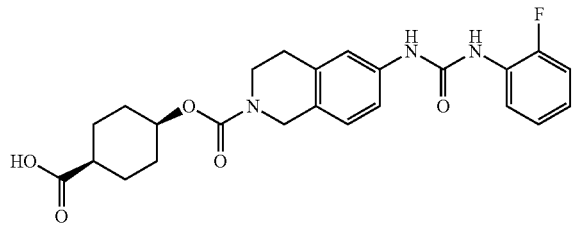 [SMILES: O=C(Nc1ccc2c(c1)CCN(C(=O)O[C@H]1CC[C@@H](C(=O)O)CC1)C2)Nc1ccccc1F]

Methyl ester (469 mg, quantitative yield) was obtained in the same way as in Example (1e) from cis-4-carbomethoxy-cyclohexanol (J. Org. Chem. 1962, 27, 4141.) (249 mg) and 1-(2-fluoro-phenyl)-3-(1,2,3,4-tetrahydro-isoquinolin-6-yl)-urea hydrochloride (WO2006004200 A1) (321 mg). This methyl ester was hydrolyzed in the same way as in Example 2 to obtain the title compound (156 mg, 34%) as a light brown solid.

$^1$H NMR (400 MHz, DMSO-d6): δ (ppm)=12.1 (1H, brs), 9.02 (1H, s), 8.53 (1H, d, J=2.7 Hz), 8.16 (1H, dt, J=11.5 and 4.1 Hz), 7.33 (1H, s), 7.26-7.21 (2H, m), 7.16-7.10 (2H, m), 7.03-6.98 (1H, m), 4.79 (1H, brs), 4.49 (2H, brs), 3.60 (2H, brs), 2.79 (2H, brs), 2.34 (1H, t, J=6.5 Hz), 1.77-1.62 (8H, m);

MS (ESI) m/z: 456 (M+H)$^+$.

Example 10

6-[3-(2-fluoro-phenyl)-ureido]-3,4-dihydro-1H-isoquinoline-2-carboxylic acid 4-(2-carboxy-ethyl)-cyclohexyl ester

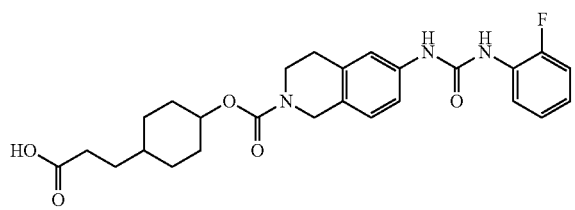 [SMILES: O=C(O)CCC1CCC(OC(=O)N2CCc3cc(NC(=O)Nc4ccccc4F)ccc3C2)CC1]

Methyl ester (429 mg, 66%) was obtained in the same way as in Example (1e) from 3-(4-hydroxycyclohexyl)propionic acid methyl ester (Tetrahedron 1966, 22, 861.) (360 mg) and 1-(2-fluoro-phenyl)-3-(1,2,3,4-tetrahydro-isoquinolin-6-yl)-urea hydrochloride (WO2006004200 A1) (418 mg). This methyl ester was hydrolyzed in the same way as in Example 2 to obtain the title compound (65 mg, 16%) as a yellow solid.

$^1$H NMR (400 MHz, DMSO-d6): δ (ppm)=12.0 (1H, brs), 9.02 (1H, s), 8.54 (1H, d, J=2.3 Hz), 8.16 (1H, dd, J=8.2 and 8.2 Hz), 7.33 (1H, s), 7.27-7.21 (2H, m), 7.16-7.09 (2H, m), 7.03-6.98 (1H, m), 4.83-4.47 (3H, m), 3.64-3.55 (3H, m), 2.79-2.75 (2H, m), 2.23 (2H, dd, J=16.3 and 8.8 Hz), 1.95-1.72 (3H, m), 1.53-1.42 (4H, m), 1.32-1.20 (3H, m);

MS (ESI) m/z: 484 (M+H)$^+$.

Example 11

6-[3-(2-fluoro-phenyl)-ureido]-3,4-dihydro-1H-isoquinoline-2-carboxylic acid 4-carboxymethylene-cyclohexyl ester

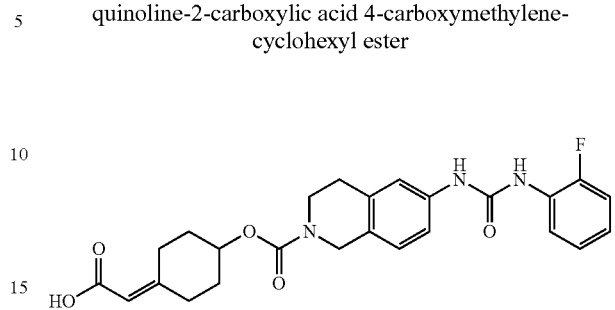

(11a) (4-oxo-cyclohexylidene)-acetic acid methyl ester (1,4-Dioxa-spiro[4.5]dec-8-ylidene)-acetic acid methyl ester (594 mg) obtained in Example (1a) was deprotected in the same way as in Example (1c) to obtain the title compound (395 mg, 84%).

$^1$H NMR (400 MHz, CDCl$_3$): δ (ppm)=5.87 (1H, s), 3.73 (3H, s), 3.22 (2H, dt, J=9.8 and 3.6 Hz), 2.67 (2H, t, J=6.8 Hz), 2.50 (4H, dt, J=7.2 and 7.2 Hz).

(11b) (4-hydroxy-cyclohexylidene)-acetic acid methyl ester

The title compound (335 mg, 84%) was obtained as a colorless oil in the same way as in Example (1d) from (4-oxo-cyclohexylidene)-acetic acid methyl ester (395 mg) obtained in Example (11a).

$^1$H NMR (400 MHz, CDCl$_3$): δ (ppm)=5.67 (1H, s), 3.97-3.93 (1H, m), 3.32 (3H, s), 3.39-3.32 (1H, m), 2.55-2.48 (1H, m), 2.46-2.40 (1H, m), 2.22-2.15 (1H, m), 2.01-1.93 (2H, m), 1.65-1.54 (3H, m).

(11c) 6-[3-(2-fluoro-phenyl)-ureido]-3,4-dihydro-1H-isoquinoline-2-carboxylic acid 4-carboxymethylene-cyclohexyl ester Methyl ester (258 mg, quantitative yield) was obtained in the same way as in Example (1e) from (4-hydroxy-cyclohexylidene)-acetic acid methyl ester (119 mg) obtained in Example (11b) and 1-(2-fluoro-phenyl)-3-(1,2,3,4-tetrahydro-isoquinolin-6-yl)-urea hydrochloride (WO2006004200 A1) (161 mg). This methyl ester was hydrolyzed in the same way as in Example 2 to obtain the title compound (80 mg, 34%) as a white solid.

$^1$H NMR (400 MHz, DMSO-d6): δ (ppm)=12.0 (1H, brs), 9.02 (1H, s), 8.54 (1H, d, J=2.0 Hz), 8.16 (1H, dt, J=11.6 and 4.2 Hz), 7.33 (1H, brs), 7.25 (1H, dd, J=8.2 and 1.2 Hz), 7.23 (1H, dd, J=6.3 and 2.0 Hz), 7.16-7.11 (2H, m), 7.03-6.98 (1H, m), 5.64 (1H, s), 4.88-4.83 (1H, m), 4.54-4.47 (2H, m), 3.63-3.58 (2H, m), 3.00-2.92 (1H, m), 2.83-2.79 (1H, m), 2.78 (2H, t, J=5.6 Hz), 2.42-2.33 (1H, m), 2.26-2.19 (1H, m), 1.91-1.79 (2H, m), 1.74-1.60 (2H, m);

MS (ESI) m/z: 468 (M+H)$^+$.

Example 12

6-[3-(2-fluoro-phenyl)-ureido]-3,4-dihydro-1H-isoquinoline-2-carboxylic acid 4-carboxymethyl-cyclohex-3-enyl-ester

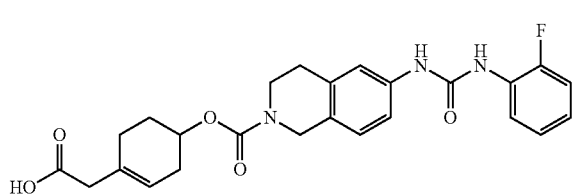 [SMILES: O=C(O)CC1=CCC(OC(=O)N2CCc3cc(NC(=O)Nc4ccccc4F)ccc3C2)CC1]

(12a) (4-oxo-cyclohex-1-enyl)-acetic acid methyl ester (1,4-Dioxa-spiro[4.5]dec-7-en-8-yl)-acetic acid methyl ester (2.21 g) obtained as a by-product in Example (1a) was deprotected in the same way as in Example (1c) to obtain the title compound (996 mg, 57%).

$^1$H NMR (400 MHz, CDCl$_3$): δ (ppm)=5.64 (1H, s), 3.71 (3H, s), 3.12 (2H, s), 2.91-2.90 (2H, m), 2.55-2.51 (4H, m).

(12b) (4-hydroxy-cyclohex-1-enyl)-acetic acid methyl ester

The title compound (677 mg, 67%) was obtained as a colorless oil in the same way as in Example (1d) from (4-oxo-cyclohex-1-enyl)-acetic acid methyl ester (996 mg) obtained in Example (12a).

$^1$H NMR (400 MHz, CDCl$_3$): δ (ppm)=5.47 (1H, s), 3.99-3.95 (1H, m), 3.69 (3H, s), 2.99 (2H, s), 2.40 (1H, d, J=18.4 Hz), 2.17-2.16 (2H, m), 2.09-2.03 (2H, m), 2.09-2.03 (1H, m), 2.09-2.03 (1H, m).

(12c) 6-[3-(2-fluoro-phenyl)-ureido]-3,4-dihydro-1H-isoquinoline-2-carboxylic acid 4-carboxymethyl-cyclohex-3-enyl-ester Methyl ester (256 mg, quantitative yield) was obtained in the same way as in Example (1e) from (4-hydroxy-cyclohex-1-enyl)-acetic acid methyl ester (119 mg) obtained in Example (12b) and 1-(2-fluoro-phenyl)-3-(1,2,3,4-tetrahydro-isoquinolin-6-yl)-urea hydrochloride (WO2006004200 A1) (161 mg). This methyl ester was hydrolyzed in the same way as in Example 2 to obtain the title compound (191 mg, 77%) as an off-white solid.

$^1$H NMR (400 MHz, DMSO-d6): δ (ppm)=12.2 (1H, hrs), 9.04 (1H, s), 8.55 (1H, d, J=1.9 Hz), 8.15 (1H, dt, J=11.5 and 4.1 Hz), 7.32 (1H, hrs), 7.25 (1H, dd, J=8.0 and 1.4 Hz), 7.22 (1H, dd, J=8.2 and 1.6 Hz), 7.16-7.09 (2H, m), 7.03-6.98 (1H, m), 5.41 (1H, s), 4.84-4.81 (1H, m), 4.47 (2H, s), 3.57 (2H, t, J=6.9 Hz), 2.91 (2H, s), 2.76 (2H, t, J=5.9 Hz), 2.50-2.45 (1H, m), 2.39-2.32 (1H, m), 2.14-2.04 (2H, m), 1.83-1.70 (2H, m);

MS (ESI) m/z: 468 (M+H)$^+$.

Example 13 trans-6-[3-(2-fluoro-phenyl)-ureido]-3,4-dihydro-1H-isoquinoline-2-carboxylic acid 4-(carboxy-1-methyl-ethyl)-cyclohexyl ester

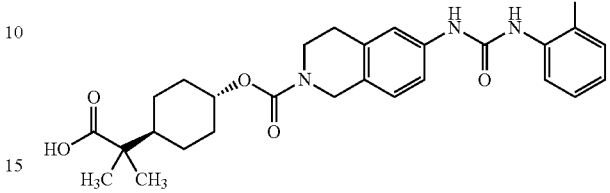

(13a) (1,4-dioxa-spiro[4.5]dec-8-yl)-2-methyl-propionic acid methyl ester

To a tetrahydrofuran (10 mL) solution of (1,4-dioxa-spiro[4.5]dec-8-yl)-acetic acid methyl ester (1.40 g) obtained in Example (1b), LDA (1.8 mol/L heptane/tetrahydrofuran/ethylbenzene, 11 mL) was added at 0° C. After 30 minutes, iodomethane (4.1 mL) was added to the reaction mixture. The formed suspension was warmed to room temperature over 2 hours or longer, then stirred for 18 hours, and diluted with water, followed by extraction with ethyl acetate. The organic layer was washed with a 10% aqueous citric acid solution and saturated brine, then dried over sodium sulfate, and then concentrated. The residue was purified by chromatography (hexane/ethyl acetate=4:1). The obtained oil compound was repeatedly subjected to these steps to obtain the title compound (666 mg, 42%) as a light brown oil.

$^1$H NMR (400 MHz, CDCl$_3$): δ (ppm)=3.94 (4H, s), 3.67 (3H, s), 1.82-1.74 (2H, m), 1.69-1.47 (5H, m), 1.41-1.27 (2H, m), 1.13 (6H, s);

MS (FAB) m/z: 243 (M+H)$^+$.

(13b) 2-methyl-2-(4-oxo-cyclohexyl)-propionic acid methyl ester

The title compound (544 mg, 100%) was obtained as a colorless oil in the same way as in Example (1c) from (1,4-dioxa-spiro[4,5]dec-8-yl)-2-methyl-propionic acid methyl ester (666 mg) obtained in Example (13a).

$^1$H NMR (400 MHz, CDCl$_3$): δ (ppm)=3.70 (3H, s), 2.45-2.30 (4H, m), 2.13-2.04 (1H, m), 1.96-1.90 (2H, m), 1.55-1.44 (2H, m), 1.18 (6H, s);

MS (EI) m/z: 198 (M)$^+$.

(13c) 2-(4-hydroxy-cyclohexyl)-2-methyl-propionic acid methyl ester

The title compound (398 mg, 73%) was obtained as a colorless oil in the same way as in Example (1d) from 2-methyl-2-(4-oxo-cyclohexyl)-propionic acid methyl ester obtained in Example (13b).

$^1$H NMR (400 MHz, CDCl$_3$): δ (ppm)=3.69 (3H, brs), 3.67 (1H, s), 3.60-3.48 (1H, m), 2.14-1.97 (2H, m), 1.73-1.53 (3H, m), 1.35-1.14 (4H, m), 1.11 (6H, s).

(13d) trans-6-[3-(2-fluoro-phenyl)-ureido]-3,4-dihydro-1H-isoquinoline-2-carboxylic acid 4-(carboxy-1-methyl-ethyl)-cyclohexyl ester Methyl ester (123 mg, 96%) was obtained in the same way as in Example (1e) from 2-(4-hydroxy-cyclohexyl)-2-methyl-propionic acid methyl ester (74 mg) obtained in Example (13c) and 1-(2-fluoro-phenyl)-3-(1,2,3,4-tetrahydro-isoquinolin-6-yl)-urea hydrochloride (WO2006004200 A1) (80 mg). This methyl ester was hydrolyzed in the same way as in Example 2 to obtain the title compound (29 mg, 24%) as a white solid.

$^1$H NMR (400 MHz, DMSO-d6): δ (ppm)=12.1 (1H, brs), 9.09 (1H, s), 8.60 (1H, s), 8.15 (1H, dd, J=8.2 and 8.2 Hz), 7.33 (1H, s), 7.26-7.21 (2H, m), 7.16-7.09 (2H, m), 7.03-6.98 (1H, m), 4.50-4.41 (3H, m), 3.57 (2H, t, J=5.9 Hz), 2.76 (2H, t, J=5.1 Hz), 2.03-1.95 (2H, m), 1.66-1.50 (3H, m), 1.38-1.24 (2H, m), 1.19-1.05 (2H, m), 1.02 (6H, s);

MS (ESI) m/z: 498 (M+H)$^+$.

Example 14

6-[3-(2-fluoro-phenyl)-ureido]-3,4-dihydro-1H-isoquinoline-2-carboxylic acid c-4-carboxymethyl-c-2-methyl-r-1-cyclohexyl ester

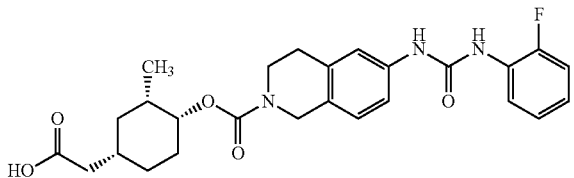 [SMILES: C[C@H]1C[C@@H](CC(=O)O)CC[C@H]1OC(=O)N1CCc2cc(NC(=O)Nc3ccccc3F)ccc2C1]

(14a) cis-7-methyl-1,4-dioxa-spiro[4.5]-decan-8-ol

To a tetrahydrofuran (100 mL) solution of 7-methyl-1,4-dioxa-spiro[4.5]-decan-8-one (Tetrahedron Asymmetry 2001, 12, 1683) (9.50 g), K-Selectride (1.0 mol/L tetrahydrofuran solution, 65 mL) was gradually added at −78° C. After 1 hour, the reaction mixture was warmed to 0° C., and a 1 N aqueous sodium hydroxide solution (120 mL) and 30% aqueous hydrogen peroxide (100 mL) were gradually added thereto. The purified aqueous mixture was stirred overnight, followed by two extractions with dichloromethane. The organic layer was washed with saturated brine, then dried over sodium sulfate, and then concentrated. The residue was purified by chromatography (hexane/ethyl acetate=4:1→2:1→1:1) to obtain the title compound (8.18 g, 85%) as a colorless oil.

$^1$H NMR (400 MHz, CDCl$_3$): δ (ppm)=4.02-3.91 (4H, m), 4.02-3.91 (1H, m), 1.81-1.23 (8H, m), 0.99 (3H, d, J=7.0 Hz).

(14b) cis-4-hydroxy-3-methyl-cyclohexanone

A 1 N hydrochloric acid (250 mL)/acetone (250 mL) mixed solution of cis-7-methyl-1,4-dioxa-spiro[4.5]-decan-8-ol (19.9 g) obtained in Example (14a) was stirred at room temperature for 16 hours. The organic solvent was removed under reduced pressure. The remaining aqueous mixture was subjected to 6 extractions with ethyl acetate. The organic layer was washed with saturated brine, then dried over sodium sulfate, and then concentrated. The residue was dried under reduced pressure to obtain the title compound (14.4 g, 97%) as a colorless oil.

$^1$H NMR (400 MHz, CDCl$_3$): δ (ppm)=4.05-3.99 (1H, m), 2.71-2.61 (1H, m), 2.47 (1H, dd, J=13.3 and 13.3 Hz), 2.28-2.01 (5H, m), 1.94-1.81 (1H, m), 1.07 (3H, d, J=6.7 Hz).

(14c) cis-4-(tert-butyl-dimethyl-silanyloxy)-3-methyl-cyclohexanone

To a dimethylformamide (100 mL) solution of cis-4-hydroxy-3-methyl-cyclohexanone (14.4 g) obtained in Example (14b) and imidazole (15.3 g), tent-butyldimethylsilyl chloride (25.3 g) was added at room temperature. The reaction mixture was stirred for 27 hours, diluted with ethyl acetate, washed with water (twice) and saturated brine, then dried over sodium sulfate, and then concentrated. The residue was purified by chromatography (hexane/ethyl acetate=1:0→40:1→20:1→10:1) to obtain the title compound (21.6 g, 80%) as a colorless oil.

$^1$H NMR (400 MHz, CDCl$_3$): δ (ppm)=3.83-3.79 (1H, m), 2.61-2.49 (1H, m), 2.37 (1H, dd, J=13.3 and 13.3 Hz), 2.11-1.82 (4H, m), 1.73-1.66 (1H, m), 0.89 (3H, d, J=6.7 Hz), 0.83 (9H, s), 0.00 (6H, s).

(14d) cis-{4-(tert-butyl-dimethyl-silanyloxy)-3-methyl-cyclohex-ylidene}-acetic acid methyl ester The title compound (23.0 g, 87%) was obtained as a colorless oil in the same way as in Example (1a) from cis-4-(tert-butyl-dimethyl-silanyloxy)-3-methyl-cyclohexanone (21.6 g) obtained in Example (14c).

$^1$H NMR (400 MHz, CDCl$_3$): δ (ppm) 5.62 (1H, d, J=8.2 Hz), 3.86-3.81 (1H, m), 3.68 (3H, s), 3.45-3.31 (1H, m), 2.57-2.22 (2H, m), 2.08-1.81 (2H, m), 1.74-1.64 (1H, m), 1.62-1.48 (1H, m), 0.95-0.90 (12H, m), 0.08-0.05 (6H, m);

MS (FAB) m/z: 321 (M+Na)$^+$, m/z: 299 (M+H)$^+$.

(14e) cis{4-(tert-butyl-dimethyl-silanyloxy)-3-methyl-cyclohexyl}-1-acetic acid methyl ester (cis relative configuration at C3 vs. C4 and mixture of cis/trans relative configuration at C1 vs. C3 or C1 vs. C4).

The title compound (21.4 g, 92%) was obtained as an oil (diastereomeric mixture) in the same way as in Example (1b) from cis-{4-(tert-butyl-dimethyl-silanyloxy)-3-methyl-cyclohex-ylidene}-acetic acid methyl ester (23.0 g) obtained in Example (14d).

$^1$H NMR (400 MHz, CDCl$_3$): δ (ppm)=3.76-3.71 (1H, m), 3.67 (3H, s), 2.20 (2H, d, J=7.4 Hz), 1.85-1.70 (2H, m), 1.54-1.11 (6H, m), 1.54-1.11 (9H, m), 0.85 (3H, d, J=7.0 Hz), 0.04-0.00 (6H, m);

MS (FAB) m/z: 323 (M+Na)$^+$, m/z: 301 (M+H)$^+$.

(14f) (c-4-hydroxy-c-3-methyl-cyclohexyl)-r-1-acetic acid methyl ester

To a tetrahydrofuran (100 mL) solution of {4-(tert-butyl-dimethyl-silanyloxy)-3-methyl-cyclohexyl}-1-acetic acid methyl ester (21.4 g) obtained in Example (14e), a hydrogen fluoride/pyridine complex (20 mL) was added at room temperature. The reaction mixture was stirred for 19 hours and diluted with water, followed by two extractions with ethyl acetate. The organic layer was washed twice with saturated brine, then dried over sodium sulfate, and then concentrated. The residue was purified by chromatography (hexane/ethyl acetate-2:1→1:1) to obtain the title compound (8.57 g, 65%) as a colorless oil.

$^1$H NMR (400 MHz, CDCl$_3$): δ (ppm)=3.83-3.78 (1H, m), 3.68 (3H, s), 2.22 (2H, dd, J=7.0 and 2.4 Hz), 1.90-1.79 (2H, m), 1.65-1.25 (6H, m), 1.10 (1H, dd, J=25.0 and 12.5 Hz), 0.96 (3H, d, J=7.0 Hz).

(14g) (t-4-hydroxy-t-3-methyl-cyclohexyl)-r-1-arctic acid methyl ester

The title compound was obtained as a colorless oil as a by-product (1.24 g, 9%) in the synthesis of Example (14f).

$^1$H NMR (400 MHz, CDCl$_3$): δ (ppm)=3.76-3.70 (1H, m), 3.67 (3H, s), 2.26-2.17 (2H, m), 2.10-2.00 (1H, m), 1.85-1.74 (3H, m), 1.70-1.50 (2H, m), 1.33-1.20 (2H, m), 1.12-1.02 (1H, m), 0.98 (3H, d, J=–7.0 Hz).

(14h) 6-[3-(2-fluoro-phenyl)-ureido]-3,4-dihydro-1H-isoquinoline-2-carboxylic acid c-4-carboxymethyl-c-2-methyl-r-1-cyclohexyl ester Methyl ester (120 mg, 86%) was obtained in the same way as in Example (1e) from (c-4-hydroxy-c-3-methyl-cyclohexyl)-r-1-acetic acid methyl ester (73 mg) obtained in Example (14f) and 1-(2-fluoro-phenyl)-3-(1,2,3,4-tetrahydro-isoquinolin-6-yl)-urea hydrochloride (WO2006004200 A1) (90 mg). This methyl ester was hydrolyzed in the same way as in Example 2 to obtain the title compound (53 mg, 53%) as a white solid.

$^1$H NMR (400 MHz, DMSO-d6): δ (ppm)=12.0 (1H, brs), 9.12 (1H, s), 8.63 (1H, s), 8.20-8.07 (1H, m), 7.37-6.92 (6H, m), 4.78-4.71 (1H, m), 4.57-4.42 (2H, m), 3.69-3.53 (2H, m), 2.82-2.73 (2H, m), 2.14 (2H, d, J=6.7 Hz), 1.87-1.60 (3M, m), 1.54-1.42 (3H, m), 1.19-0.96 (2H, m), 0.86-0.78 (3H, m);

MS (ESI) m/z: 484 (M+H)$^+$.

Example 15

6-[3-(2-fluoro-phenyl)-ureido]-3,4-dihydro-1H-isoquinoline-2-carboxylic acid t-4-carboxymethyl-c-2-methyl-r-1-cyclohexyl ester

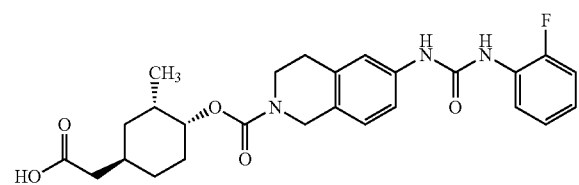 [SMILES: C[C@H]1C[C@H](CC(=O)O)CC[C@H]1OC(=O)N1CCc2cc(NC(=O)Nc3ccccc3F)ccc2C1]

Methyl ester (1.49 g, 80%) was obtained in the same way as in Example (1e) from (t-4-hydroxy-t-3-methyl-cyclohexyl)-r-1-acetic acid methyl ester (841 mg) obtained in Example (14g) and 1-(2-fluoro-phenyl)-3-(1,2,3,4-tetrahydro-isoquinolin-6-yl)-urea hydrochloride (WO2006004200 A1) (1.21 g). This methyl ester was hydrolyzed in the same way as in Example 2 to obtain the title compound (780 mg, 54%) as a white solid.

$^1$H NMR (400 MHz, DMSO-d6): δ (ppm)=12.1 (1H, s), 9.02 (1H, s), 8.54 (1H, s), 8.18-8.14 (1H, m), 7.32 (1H, s), 7.27-7.21 (2H, m), 7.16-7.10 (2H, m), 7.03-6.98 (1H, m), 4.69-4.64 (1H, m), 4.54-4.43 (2H, m), 3.64-3.54 (2H, m), 2.83-2.73 (2H, m), 2.20-1.93 (4H, m), 1.76-1.53 (3H, m), 1.35-1.24 (1H, m), 1.16-1.06 (1H, m), 0.92 (3H, d, J=7.1 Hz), 0.93-0.88 (1H, m);

MS (ESI) m/z: 484 (M+H)$^+$.

Example 16

6-[3-(2-fluoro-phenyl)-ureido]-3,4-dihydro-1H-isoquinoline-2-carboxylic acid t-4-carboxymethyl-t-2-methyl-r-1-cyclohexyl ester

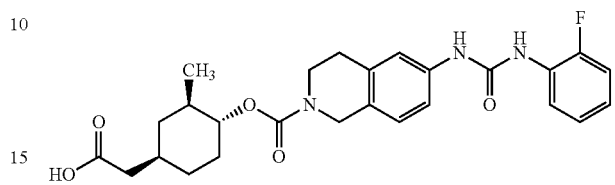

(16a) (t-4-hydroxy-c-3-methyl-cyclohexyl)-r-1-acetic acid methyl ester

To a dichloromethane (100 mL) solution of (c-4-hydroxy-c-3-methyl-cyclohexyl)-r-1-acetic acid methyl ester (8.57 g) obtained in Example (14f), Dess-Martin reagent (23.4 g) was added at room temperature. The reaction mixture was stirred for 20 hours, then diluted with a saturated aqueous solution of sodium bicarbonate, and then filtered. The filtrate was subjected to extraction with dichloromethane. The organic layer was washed twice with a saturated aqueous solution of sodium bicarbonate, then dried over sodium sulfate, and then concentrated. The residue was dried under reduced pressure to obtain ketone (7.55 g). This ketone (7.55 g) was reduced in the same way as in Example (1d) to obtain the title compound (3.10 g, 36%) as a colorless oil.

$^1$H NMR (400 MHz, CDCl$_3$): δ (ppm)=3.68 (3H, s), 3.16-3.09 (1H, m), 2.20 (2H, d, J=7.1 Hz), 2.00-1.94 (1H, m), 1.90-1.70 (3H, m), 1.52 (1H, brs), 1.44-1.25 (2H, m), 1.11-1.04 (1H, m), 1.01 (3H, d, J=6.2 Hz), 0.79 (1H, dt, J=12.4 and 12.5 Hz).

(16b) 6-[3-(2-fluoro-phenyl)-ureido]-3,4-dihydro-1H-isoquinoline-2-carboxylic acid t-4-carboxymethyl-t-2-methyl-r-1-cyclohexyl ester Methyl ester (1.95 g) was obtained in the same way as in Example (1e) from (t-4-hydroxy-c-3-methyl-cyclohexyl)-r-1-acetic acid methyl ester (842 mg) obtained in Example (16a) and 1-(2-fluoro-phenyl)-3-(1,2,3,4-tetrahydro-isoquinolin-6-yl)-urea hydrochloride (WO2006004200 A1) (1.22 g). This methyl ester was hydrolyzed in the same way as in Example 2 to obtain the title compound (1.33 g, 73%, two steps) as a white solid.

$^1$H NMR (400 MHz, DMSO-d6): δ (ppm)=12.1 (1H, s), 9.02 (1H, s), 8.54 (1H, s), 8.16 (1H, dd, J=8.2 and 8.2 Hz), 7.33 (1H, s), 7.27-7.22 (2H, m), 7.16-7.10 (2H, m), 7.03-6.98 (1H, m), 4.54-4.43 (2H, m), 4.22-4.16 (1H, m), 3.64-3.55 (2H, m), 2.77 (2H, t, J=5.9 Hz), 2.11 (2H, d, J=6.7 Hz), 1.96-1.90 (1H, m), 1.77-1.68 (3H, m), 1.66-1.56 (1H, m), 1.35-1.24 (1H, m), 1.11-0.99 (1H, m), 0.90-0.80 (4H, m);

MS (ESI) m/z: 484 (M+H)$^+$.

Example 17

[4-(2-{6-[3-(2-fluoro-phenyl)-ureido]-3,4-dihydro-1H-isoquinolin-2-yl}-2-oxoethyl)-cyclohexyl]-acetic acid

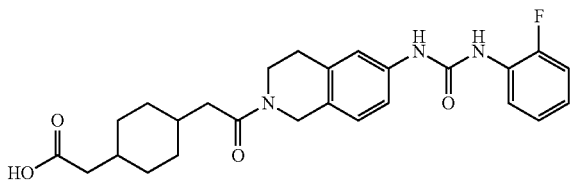 [SMILES: O=C(O)CC1CCC(CC(=O)N2CCc3cc(NC(=O)Nc4ccccc4F)ccc3C2)CC1]

A dimethylformamide (5 mL) solution of (4-methoxycarbonylmethyl-cyclohexyl)-acetic acid (US2001/9912 A1) (378 mg), 1-(2-fluoro-phenyl)-3-(1,2,3,4-tetrahydro-isoquinolin-6-yl)-urea hydrochloride (WO2006004200 A 1) (82 mg), T3P (1.3 mL), and triethylamine (0.62 mL) was stirred for 24 hours. The reaction mixture was diluted with ethyl acetate, washed with a saturated aqueous solution of sodium bicarbonate and saturated brine, then dried over sodium sulfate, and then concentrated. The residue was purified by chromatography (dichloromethane/ethyl acetate) to obtain methyl ester (533 mg, 74%). This methyl ester was hydrolyzed in the same way as in Example 2 to obtain the title compound (456 mg, 88%) as a white solid.

$^1$H NMR (400 MHz, DMSO-d6): δ (ppm)=12.0 (1H, brs), 9.04-9.04 (1H, m), 8.56 (1H, s), 8.17-8.13 (1H, m), 7.35-7.31 (1H, m), 7.26-7.19 (2H, m), 7.16-7.09 (2H, m), 7.03-6.98 (1H, m), 4.59-4.54 (2H, m), 3.66 (2H, t, J=5.5 Hz), 2.81 (1H, t, J=5.1 Hz), 2.72-2.71 (1H, m), 2.28-2.26 (3H, m), 2.08-2.06 (1H, m), 1.97-1.83 (2H, m), 1.73-1.53 (3H, m), 1.50-1.29 (2H, m), 0.97-0.94 (3H, m);
MS (ESI) m/z: 468 (M+H)$^+$.

Example 18 trans-6-[3-(2-fluoro-phenyl)-ureido]-3,4-dihydro-1H-isoquinoline-2-carboxylic acid 4-carbamoylmethyl-cyclohexyl ester

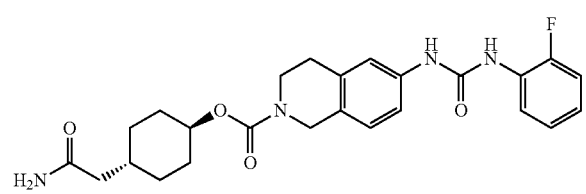 [SMILES: NC(=O)C[C@H]1CC[C@H](OC(=O)N2CCc3cc(NC(=O)Nc4ccccc4F)ccc3C2)CC1]

A DMF (15 mL) solution of trans-6-[3-(2-fluoro-phenyl)-ureido]-3,4-dihydro-1H-isoquinoline-2-carboxylic acid 4-carboxymethyl-cyclohexyl ester (527 mg) obtained in Example 2, HOBt (166 mg), EDCI (236 mg), and ammonia water (0.5 mL) was stirred at room temperature for 2 days. The reaction mixture was diluted with ethyl acetate, washed with a saturated aqueous solution of sodium bicarbonate and saturated brine, then dried, and concentrated. The residue was purified by chromatography (NH silica gel, dichloromethane/methanol=30:1→5:1) to obtain a solid. This solid was recrystallized (isopropanol) to obtain the title compound (89 mg, 17%) as a white solid.

$^1$H NMR (400 MHz, DMSO-d6): δ (ppm)=9.03 (1H, s), 8.55 (1H, d, J=2.7 Hz), 8.15 (1H, dt, J=11.7 and 4.2 Hz), 7.32 (1H, brs), 7.26-7.21 (3H, m), 7.16-7.10 (2H, m), 7.03-6.98 (1H, m), 6.73 (1H, brs), 4.52-4.47 (3H, m), 3.57 (2H, t, J=5.9 Hz), 2.76 (2H, t, J=5.9 Hz), 1.94 (2H, d, J=7.1 Hz), 1.92-1.91 (2H, m), 1.73 (2H, d, J=13.3 Hz), 1.68-1.62 (1H, m), 1.38-1.28 (2H, m), 1.08-0.98 (2H, m);
MS (ESI) m/z: 469 (M+H)$^+$.

Example 19 trans-6-[3-(2-fluoro-phenyl)-ureido]-3,4-dihydro-1H-isoquinoline-2-carboxylic acid 4-[(1-carboxy-1-methyl-1-ethylcarbamoyl)-methyl]-cyclohexyl ester

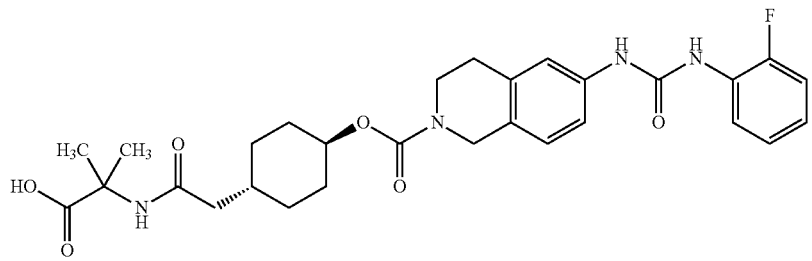 [SMILES: CC(C)(NC(=O)C[C@H]1CC[C@H](OC(=O)N2CCc3cc(NC(=O)Nc4ccccc4F)ccc3C2)CC1)C(=O)O]

Methyl ester (58 mg, 19%) was obtained in the same way as in Example 18 from trans-6-[3-(2-fluoro-phenyl)-ureido]-3,4-dihydro-1H-isoquinoline-2-carboxylic acid 4-carboxymethyl-cyclohexyl ester (246 mg) obtained in Example 2 and 2-amino-2-methyl-propionic acid methyl ester hydrochloride (89 mg). This methyl ester was hydrolyzed in the same way as in Example 2 to obtain the title compound (18 mg, 32%) as a white solid.

$^1$H NMR (400 MHz, DMSO-d6): δ (ppm)=12.2 (1H, brs), 9.11 (1H, s), 8.63 (1H, d, J=2.7 Hz), 8.24 (1H, dt, J=11.7 and 4.2 Hz), 8.07 (1H, s), 7.41 (1H, d, J=1.9 Hz), 7.35-7.30 (2H, m), 7.25-7.18 (2H, m), 7.12-7.08 (1H, m), 4.59-4.53 (3H, m), 3.66 (2H, t, J=5.7 Hz), 2.85 (2H, t, J=5.9 Hz), 2.05-1.99 (4H, m), 1.85-1.80 (2H, m), 1.77-1.70 (2H, m), 1.46-1.35 (2H, m), 1.40 (6H, s), 1.17-1.07 (2H, m);
MS (ESI) m/z: 555 (M+H)$^+$.

Example 20 trans-6-[3-(3-ethoxy-phenyl)-ureido]-3,4-dihydro-1H-isoquinoline-2-carboxylic acid 4-carboxymethyl-cyclohexyl ester

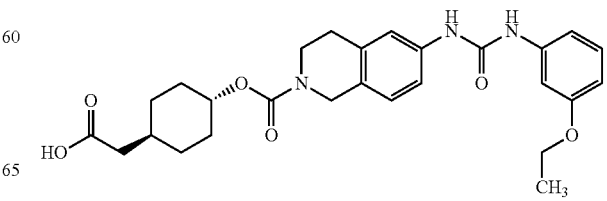

Methyl ester (142 mg, 89%) was obtained in the same way as in Example (1e) from trans-(4-hydroxy-cyclohexyl)-acetic acid methyl ester (81 mg) obtained in Example (1d) and 1-(3-ethoxy-phenyl)-3-(1,2,3,4-tetrahydro-isoquinolin-6-yl)-urea hydrochloride (WO2006004200 A1) (109 mg). This methyl ester was hydrolyzed in the same way as in Example 2 to obtain the title compound (81 mg, 59%) as a white solid.

$^1$H NMR (400 MHz, DMSO-d6): δ (ppm)=12.1 (1H, brs), 8.78 (1H, s), 8.73 (1H, s), 7.35-7.31 (1H, m), 7.24-7.07 (4H, m), 6.92-6.89 (1H, m), 6.56-6.52 (1H, m), 4.53-4.43 (3H, m), 3.99 (2H, q, J=7.1 Hz), 3.57 (2H, t, J=5.9 Hz), 2.75 (2H, t, J=5.9 Hz), 2.11 (2H, d, J=7.0 Hz), 1.98-1.88 (2H, m), 1.79-1.52 (4H, m), 1.39-1.27 (1H, m), 1.32 (3H, t, J=7.1 Hz), 1.12-1.02 (2H, m);
MS (ESI) m/z: 496 (M+H)$^+$.

Example 21 trans-6-[3-(2-methoxy-phenyl)-ureido]-3,4-dihydro-1H-isoquinoline-2-carboxylic acid 4-carboxymethyl-cyclohexyl ester

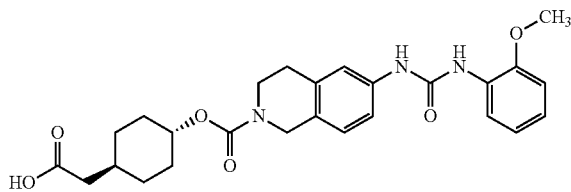 [SMILES: COc1ccccc1NC(=O)Nc1ccc2c(c1)CCN(C(=O)O[C@H]1CC[C@H](CC(=O)O)CC1)C2]

Methyl ester (193 mg, 93%) was obtained in the same way as in Example (1e) from trans-(4-hydroxy-cyclohexyl)-acetic acid methyl ester (101 mg) obtained in Example (1d) and 1-(2-methoxy-phenyl)-3-(1,2,3,4-tetrahydro-isoquinolin-6-yl)-urea hydrochloride (WO2006004200 A 1) (140 mg). This methyl ester was hydrolyzed in the same way as in Example 2 to obtain the title compound (91 mg, 49%) as a white solid.

$^1$H NMR (400 MHz, DMSO-d6): δ (ppm)=12.0 (1H, s), 9.25 (1H, s), 8.20 (1H, s), 8.13 (1H, s), 7.33 (1H, s), 7.23-7.24 (1H, m), 7.12-6.85 (4H, m), 4.54-4.40 (3H, m), 3.88 (3H, s), 3.61-3.53 (2H, m), 2.80-2.72 (2H, m), 2.12 (2H, d, J=7.1 Hz), 1.99-1.87 (2H, m), 1.81-1.60 (3H, m), 1.40-1.27 (2H, m), 1.14-1.00 (2H, m);
MS (ESI) m/z: 482 (M+H)$^+$.

Example 22 trans-6-[3-(5-fluoro-2-methoxy-phenyl)-ureido]-3,4-dihydro-1H-isoquinoline-2-carboxylic acid 4-carboxymethyl-cyclohexyl ester

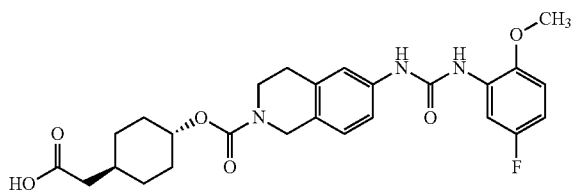 [SMILES: COc1ccc(F)cc1NC(=O)Nc1ccc2c(c1)CCN(C(=O)O[C@H]1CC[C@H](CC(=O)O)CC1)C2]

(22a) 6-[3-(5-fluoro-2-methoxy-phenyl)-ureido]-3,4-dihydro-1H-isoquinoline-2-carboxylic acid tert-butyl ester A tetrahydrofuran (20 mL) solution of 5-fluoro-2-methoxybenzoic acid (1.00 g), DPPA (1.25 mL), and triethylamine (1.6 mL) was heated to reflux for 1 hour. A tetrahydrofuran (10 mL) solution of 6-amino-2N-Boc-1,2,3,4-tetrahydroisoquinoline (1.00 g) was added to the reaction solution. The reaction mixture was further heated to reflux for 5.5 hours, then cooled to room temperature, and then concentrated. The residue was purified by chromatography (dichloromethane/ethyl acetate=20:1→4:1) to obtain the title compound (1.51 g, 90%) as a white solid.

$^1$H NMR (400 MHz, DMSO-d6): δ (ppm)=9.33 (1H, s), 8.38 (1H, s), 8.05-7.97 (1H, m), 7.38-7.28 (1H, m), 7.24-7.16 (1H, m), 7.10-7.05 (1H, m), 7.02-6.97 (1H, m), 6.77-6.69 (1H, m), 4.41 (2H, s), 3.84 (3H, s), 3.51 (2H, t, J=6.1 Hz), 2.73 (2H, t, J=7.0 Hz), 1.41 (9H, s);
MS (FAB) m/z: 416 (M+H)$^+$.

(22b) 1-(5-fluoro-2-methoxy-phenyl)-3-(1,2,3,4-tetrahydro-isoquinolin-6-yl)-urea hydrochloride A suspension of 6-[3-(5-fluoro-2-methoxy-phenyl)-ureido]-3,4-dihydro-1H-isoquinoline-2-carboxylic acid tert-butyl ester (1.20 g) obtained in Example (22a) and 4 N hydrochloric acid (1,4-dioxane solution, 10 mL) was stirred at room temperature for 15 hours and diluted with diisopropyl ether. The precipitate was collected by filtration and dried to obtain the title compound (1.20 g, 94%) as a light beige solid.
MS (ESI) m/z: 316 (M+H)$^+$.

(22c) trans-6-[3-(5-fluoro-2-methoxy-phenyl)-ureido]-3,4-dihydro-1H-isoquinoline-2-carboxylic acid 4-carboxymethyl-cyclohexyl ester Methyl ester (134 mg, 91%) was obtained in the same way as in Example (1e) from trans-(4-hydroxy-cyclohexyl)-acetic acid methyl ester (74 mg) obtained in Example (1d) and 1-(5-fluoro-2-methoxy-phenyl)-3-(1,2,3,4-tetrahydro-isoquinolin-6-yl)-urea hydrochloride (101 mg) obtained in Example (22b). This methyl ester (129 mg) was hydrolyzed in the same way as in Example 2 to obtain the title compound (61 mg, 53%) as an off-white solid.

$^1$H NMR (400 MHz, DMSO-d6): E. (ppm)=12.0 (1H, brs), 9.35 (1H, s), 8.40 (1H, s), 8.02 (1H, dd, J=11.4 and 3.1 Hz), 7.33 (1H, s), 7.23-7.18 (1H, m), 7.13-7.08 (1H, m), 7.01 (1H, dd, J=9.0 and 5.5 Hz), 6.75 (1H, ddd, J=8.6, 8.6 and 3.2 Hz), 4.53-4.43 (3H, m), 3.87 (3H, s), 3.57 (2H, t, J=5.9 Hz), 2.76 (2H, t, J=5.6 Hz), 2.12 (2H, d, J=7.1 Hz), 1.97-1.88 (2H, m), 1.80-1.71 (2H, m), 1.71-1.60 (1H, m), 1.40-1.30 (2H, m), 1.12-1.02 (2H, m);
MS (ESI) m/z: 500 (M+H)$^+$.

Example 23 trans-6-[3-(2-methoxy-5-methyl-phenyl)-ureido]-3,4-dihydro-1H-isoquinoline-2-carboxylic acid 4-carboxymethyl-cyclohexyl ester

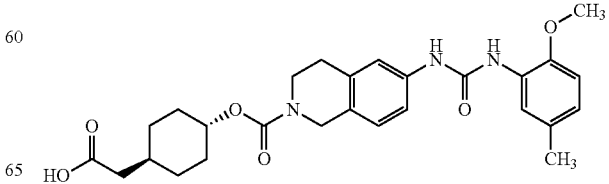

Methyl ester (103 mg, 81%) was obtained in the same way as in Example (1e) from trans-(4-hydroxy-cyclohexyl)-acetic acid methyl ester (65 mg) obtained in Example (1d) and 1-(2-methoxy-5-methyl-phenyl)-3-(1,2,3,4-tetrahydro-isoquinolin-6-yl)-urea hydrochloride (WO2006004200 A1) (88 mg). This methyl ester (92 mg) was hydrolyzed in the same way as in Example 2 to obtain the title compound (38 mg, 43%) as an off-white solid.

$^1$H NMR (400 MHz, DMSO-d6): δ (ppm)=12.1 (1H, brs), 9.24 (1H, s), 8.14 (1H, s), 7.99 (1H, s), 7.35 (1H, s), 7.23-7.15 (1H, m), 7.12-7.05 (1H, m), 6.89 (1H, d, J=8.3 Hz), 6.74 (1H, d, J=9.0 Hz), 4.52-4.41 (3H, m), 3.83 (3H, s), 3.57 (2H, t, J=5.6 Hz), 2.75 (2H, t, J=5.5 Hz), 2.22 (3H, s), 2.12 (2H, d, J=6.7 Hz), 1.98-1.88 (2H, m), 1.81-1.60 (3H, m), 1.42-1.28 (2H, m), 1.14-1.00 (2H, m);

MS (ESI) m/z: 496 (M+H)$^+$.

Example 24 trans-6-[3-(2-methoxy-pyridin-3-yl)-ureido]-3,4-dihydro-1H-isoquinoline-2-carboxylic acid 4-carboxymethyl-cyclohexyl ester

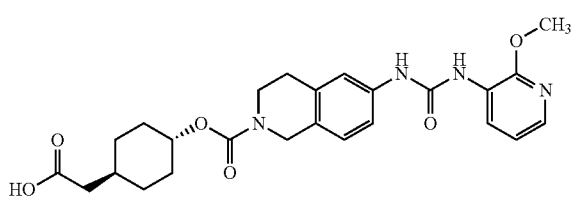 [SMILES: COc1ncccc1NC(=O)Nc1ccc2c(c1)CCN(C(=O)O[C@H]1CC[C@H](CC(=O)O)CC1)C2]

(24a) 6-(4-nitro-phenoxycarbonylamino)-3,4-dihydro-1H-isoquinoline-2-carboxylic acid tert-butyl ester To a dichloromethane (10 mL) solution of 4-nitrophenyl chloroformate (812 mg), a dichloromethane (10 mL) solution of 6-amino-2N-Boc-1,2,3,4-tetrahydroisoquinoline (1.00 g) and pyridine (0.33 mL) was gradually added at 0° C. The reaction mixture was stirred at 0° C. for 1 hour and at room temperature for 2 hours and then concentrated. The residue was vigorously stirred in a mixed solution of diisopropyl ether and water (diisopropyl ether/water). The precipitate was collected by filtration and dried under reduced pressure to obtain the title compound (1.46 g, 88%) as a yellow solid.

$^1$H NMR (400 MHz, CDCl$_3$): δ (ppm)=8.40-8.24 (3H, m), 7.50-6.99 (4H, m), 5.33 (1H, brs), 4.67-4.49 (2H, m), 4.67-4.49 (2H, m), 2.97-2.79 (2H, m), 1.50 (9H, s).

(24b) 6-[3-(2-methoxy-pyridin-3-yl)-ureido]-3,4-dihydro-1H-isoquinoline-2-carboxylic acid tert-butyl ester A mixture of 6-(4-nitro-phenoxycarbonylamino)-3,4-dihydro-1H-isoquinoline-2-carboxylic acid tert-butyl ester (1.46 g) obtained in Example (24a), 3-amino-2-methoxypyridine (441 mg), and acetonitrile (20 mL) was heated to reflux for 5 hours and concentrated. The residue was diluted with ethyl acetate, then washed with a saturated aqueous solution of sodium bicarbonate (twice) and brine, and then concentrated. The residue was purified by chromatography (dichloromethane/ethyl acetate) to obtain the title compound (770 mg, 55%) as an off-white foam.

$^1$H NMR (400 MHz, CDCl$_3$): δ (ppm)=8.46 (1H, d, J=9.4 Hz), 7.79 (1H, d, J=5.1 Hz), 7.52-6.94 (5H, m), 6.89 (1H, dd, J=7.8 and 5.1 Hz), 4.52 (2H, s), 3.93 (3H, s), 3.62 (2H, t, J=5.9 Hz), 2.81-2.72 (2H, m), 1.51 (9H, s);

MS (ESI) m/z: 399 (M+H)$^+$ (24c) 1-(2-methoxy-pyridin-3-yl)-3-(1,2,3,4-tetrahydro-isoquinolin-6-yl)-urea dihydrochloride The title compound (720 mg, quantitative yield) was obtained in the same way as in Example (22b) from 6-[3-(2-methoxy-pyridin-3-yl)-ureido]-3,4-dihydro-1H-isoquinoline-2-carboxylic acid tort-butyl ester (755 mg) obtained in Example (24b).

MS (ESI) m/z: 299 (M+H)$^+$.

(24d) trans-6-[3-(2-methoxy-pyridin-3-yl)-ureido]-3,4-dihydro-1H-isoquinoline-2-carboxylic acid 4-carboxymethyl-cyclohexyl ester Methyl ester (115 mg, 72%) was obtained in the same way as in Example (1e) from trans-(4-hydroxy-cyclohexyl)-acetic acid methyl ester (84 mg) obtained in Example (1d) and 1-(2-methoxy-pyridin-3-yl)-3-(1,2,3,4-tetrahydro-isoquinolin-6-yl)-urea dihydrochloride (119 mg) obtained in Example (24c). This methyl ester (110 mg) was hydrolyzed in the same way as in Example 2 to obtain the title compound (54 mg, 50%) as a white solid.

$^1$H NMR (400 MHz, DMSO-d6): δ (ppm)=12.0 (1H, brs), 9.28 (1H, s), 8.42-8.38 (1H, m), 8.33 (1H, s), 7.80-7.72 (1H, m), 7.32 (1H, s), 7.25-7.19 (1H, m), 7.14-7.07 (1H, m), 6.99-6.91 (1H, m), 4.55-4.41 (3H, m), 3.97 (3H, s), 3.62-3.54 (2H, m), 2.80-2.73 (2H, m), 2.12 (2H, d, J=7.1 Hz), 1.98-1.89 (2H, m), 1.81-1.61 (3H, m), 1.42-1.28 (2H, m), 1.14-1.01 (2H, m);

MS (ESI) m/z: 483 (M+H)$^+$.

Example 25 trans-6-(benzoxazol-2-ylamino)-3,4-dihydro-1H-isoquinoline-2-carboxylic acid 4-carboxymethyl-cyclohexyl ester

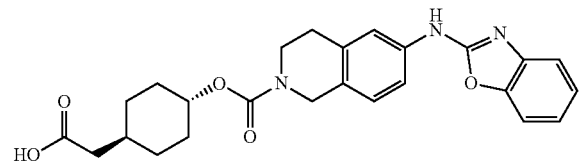 [SMILES: O=C(O)C[C@H]1CC[C@H](OC(=O)N2CCc3cc(Nc4nc5ccccc5o4)ccc3C2)CC1]

(25a) benzoxazol-2-yl-(1,2,3,4-tetrahydro-isoquinolin-6-yl)-amine hydrochloride

A 1-butanol (10 mL) solution of 6-amino-2N-Boc-1,2,3,4-tetrahydroisoquinoline (1.00 g) and 2-chlorobenzoxazole (0.50 mL) was heated to reflux for 11 hours, then cooled to room temperature, and then diluted with ethyl acetate. The precipitate was collected by filtration, then washed with ethyl acetate, and dried under reduced pressure to obtain the title compound (791 mg, 65%) as a beige solid.

MS (ESI) m/z: 266 (M+H)$^+$.

(25b) trans-6-(benzoxazol-2-ylamino)-3,4-dihydro-1H-isoquinoline-2-carboxylic acid 4-carboxymethyl-cyclohexyl ester Methyl ester (103 mg, 72%) was obtained in the same way as in Example (1e) from trans-(4-hydroxy-cyclohexyl)-acetic acid methyl ester (74 mg) obtained in Example (1d) and benzoxazol-2-yl-(1,2,3,4-tetrahydro-isoquinolin-6-yl)-amine hydrochloride (93 mg) obtained in Example (25a). This methyl ester (100 mg) was hydrolyzed in the same way as in Example 2 to obtain the title compound (46 mg, 45%) as a white solid.

$^1$H NMR (400 MHz, DMSO-d6): δ (ppm)=12.1 (1H, brs), 10.6 (1H, s), 7.64-7.45 (3H, m), 7.26-7.11 (4H, m), 4.58-4.46 (3H, m), 3.59 (2H, t, J=5.9 Hz), 2.81 (2H, t, J=5.3 Hz), 2.12 (2H, d, J=6.7 Hz), 1.98-1.88 (2H, m), 1.81-1.61 (3H, m), 1.41-1.28 (2H, m), 1.15-0.99 (2H, m);
MS (ESI) m/z: 450 (M+H)$^+$.

Example 26 trans-6-[3-(2-ethoxy-phenyl)-ureido]-3,4-dihydro-1H-isoquinoline-2-carboxylic acid 4-carboxymethyl-cyclohexyl ester

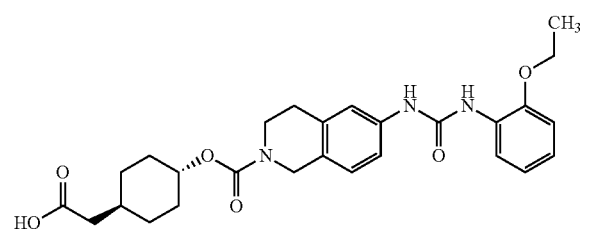 [SMILES: CCOc1ccccc1NC(=O)Nc1ccc2c(c1)CCN(C(=O)O[C@H]1CC[C@H](CC(=O)O)CC1)C2]

(26a) 6-[3-(2-ethoxy-phenyl)-ureido]-3,4-dihydro-1H-isoquinoline-2-carboxylic acid tert-butyl ester A tetrahydrofuran (10 mL) solution of 6-amino-2N-Boc-1,2,3,4-tetrahydroisoquinoline (981 mg) and 2-ethoxyphenyl isocyanate (0.9 mL) was stirred at room temperature for 4 hours and then concentrated. The residue was purified by chromatography (hexane:ethyl acetate=5:1→1:1 and then methylene chloride:ethyl acetate=1:0→1:1) to obtain the title compound (1.62 g, quantitative yield) as a pale yellow solid.

$^1$H NMR (400 MHz, CDCl$_3$): δ (ppm)=8.14 (1H, dd, J=7.7 and 2.2 Hz), 7.32-7.29 (2H, m), 7.22-7.17 (1H, m), 7.06 (1H, d, J=7.0 Hz), 7.01-6.94 (2H, m), 6.85 (1H, dd, J=7.4 and 2.0 Hz), 6.78 (1H, s), 4.54 (2H, s), 4.04 (2H, q, J=7.0 Hz), 3.63 (2H, brs), 2.80 (2H, t, J=5.9 Hz), 1.50 (9H, s), 1.35 (3H, t, J=7.1 Hz).

(26b) 1-(2-ethoxy-phenyl)-3-(1,2,3,4-tetrahydro-isoquinolin-6-yl)-urea hydrochloride The title compound (1.37 g, quantitative yield) was obtained as a yellow solid in the same way as in Example (22b) from 6-[3-(2-ethoxy-phenyl)-ureido]-3,4-dihydro-1H-isoquinoline-2-carboxylic acid tert-butyl ester (1.63 g) obtained in Example (26a).

$^1$H NMR (400 MHz, DMSO-d6): δ (ppm)=9.63 (1H, s), 9.22 (1H, brs), 8.17 (1H, s), 8.11 (1H, dd, J=8.1 and 1.8 Hz), 7.43 (1H, d, J=1.9 Hz), 7.29 (1H, dd, J=8.2 and 2.3 Hz), 7.13 (1H, d, J=8.6 Hz), 7.01 (1H, dd, J=8.2 and 1.5 Hz), 6.93 (1H, dt, J=10.8 and 3.9 Hz), 6.88 (1H, dt, J=10.7 and 3.8 Hz), 4.19 (2H, s), 4.13 (2H, q, J=7.1 Hz), 3.36 (2H, t, J=6.4 Hz), 3.36 (2H, t, J=6.4 Hz), 1.42 (3H, t, J=6.9 Hz).

(26c) trans-6-[3-(2-ethoxy-phenyl)-ureido]-3,4-dihydro-1H-isoquinoline-2-carboxylic acid 4-carboxymethyl-cyclohexyl ester Methyl ester (477 mg, 94%) was obtained in the same way as in Example (1e) from trans-(4-hydroxy-cyclohexyl)-acetic acid methyl ester (241 mg) obtained in Example (1d) and 1-(2-ethoxy-phenyl)-3-(1,2,3,4-tetrahydro-isoquinolin-6-yl)-urea hydrochloride (347 mg) obtained in Example (26b). This methyl ester (477 mg) was hydrolyzed in the same way as in Example 2 to obtain the title compound (362 mg, 78%) as a white solid.

$^1$H NMR (400 MHz, DMSO-d6): δ (ppm)=12.1 (1H, brs), 9.35 (1N, s), 8.12 (1H, dd, J=7.8 and 1.9 Hz), 8.06 (1H, s), 7.34 (1H, s), 7.23 (1H, d, J=7.1 Hz), 7.09 (1H, d, J=8.2 Hz), 7.01 (1H, dd, J=7.8 and 1.5 Hz), 6.92 (1H, dt, J=10.8 and 3.8 Hz), 6.87 (1H, dt, J=10.7 and 3.8 Hz), 4.51-4.47 (3H, m), 4.13 (2H, q, J=7.0 Hz), 3.57 (2H, t, J=5.9 Hz), 2.76 (2H, t, J=5.9 Hz), 2.11 (2H, d, J=7.0 Hz), 1.95-1.91 (2H, m), 1.77-1.73 (2H, m), 1.68-1.62 (1H, m), 1.41 (3H, t, J=6.9 Hz), 1.39-1.29 (2H, m), 1.12-1.02 (2H, m);
MS (ESI) m/z: 496 (M+H)$^+$.

Example 27 trans-6-[3-(2-ethoxy-5-fluoro-phenyl)-ureido]-3,4-dihydro-1H-isoquinoline-2-carboxylic acid 4-carboxymethyl-cyclohexyl ester

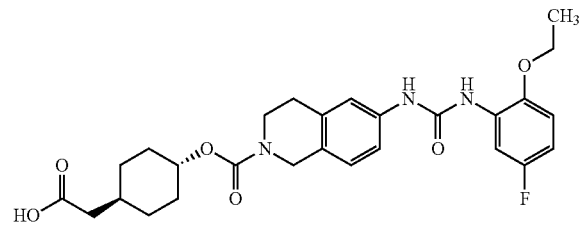 [SMILES: CCOc1ccc(F)cc1NC(=O)Nc1ccc2c(c1)CCN(C(=O)O[C@H]1CC[C@H](CC(=O)O)CC1)C2]

(27a) 6-[3-(2-ethoxy-5-fluoro-phenyl)-ureido]-3,4-dihydro-1H-isoquinoline-2-carboxylic acid tert-butyl ester The title compound (1.56 g, 91%) was obtained as a white solid in the same way as in Example (22a) from 6-amino-2N-Boc-1,2,3,4-tetrahydroisoquinoline (996 mg) and 2-ethoxy-5-fluorobenzoic acid (WO2006004200 A1) (736 mg).

$^1$H NMR (400 MHz, CDCl$_3$): δ (ppm)=8.06 (1H, dd, J=10.9 and 3.2 Hz), 7.39 (1H, brs), 7.19 (1H, brs), 7.15 (1H, m), 6.74 (1H, dd, J=9.0 and 5.1 Hz), 6.66-6.61 (2H, m), 4.55 (2H, s), 4.01 (2H, q, J=6.8 Hz), 3.64 (2H, t, J=5.2 Hz), 2.83 (2H, t, J=5.9 Hz), 1.50 (9H, s), 1.33 (3H, t, J=7.0 Hz).

(27b) 1-(2-ethoxy-5-fluoro-phenyl)-3-(1,2,3,4-tetrahydro-isoquinolin-6-yl)-urea hydrochloride The title compound (1.33 g, 99%) was obtained as a white solid in the same way as in Example (22b) from 6-[3-(2-ethoxy-5-fluoro-phenyl)-ureido]-3,4-dihydro-1H-isoquinoline-2-carboxylic acid tert-butyl ester (1.56 g) obtained in Example (27a).

¹H NMR (400 MHz, DMSO-d6): δ (ppm)=9.79 (1H, s), 9.22 (1H, hrs), 8.38 (1H, s), 8.02 (1H, dd, J=11.3 and 3.1 Hz), 7.44 (1H, d, J=2.0 Hz), 7.29 (1H, dd, J=8.4 and 2.2 Hz), 7.15 (1H, d, J=8.2 Hz), 7.01 (1H, dd, J=9.0 and 5.1 Hz), 6.73 (1H, dt, J=12.5 and 4.3 Hz), 4.20 (2H, hrs), 4.12 (2H, q, J=7.0 Hz), 3.37 (2H, t, J=6.6 Hz), 2.99 (2H, t, J=6.2 Hz), 1.41 (3H, t, J=7.1 Hz).

(27c) trans-6-[3-(2-ethoxy-5-fluoro-phenyl)-ureido]-3,4-dihydro-1H-isoquinoline-2-carboxylic acid 4-carboxymethyl-cyclohexyl ester Methyl ester (532 mg, quantitative yield) was obtained in the same way as in Example (1e) from trans-(4-hydroxy-cyclohexyl)-acetic acid methyl ester (241 mg) obtained in Example (1d) and 1-(2-ethoxy-5-fluoro-phenyl)-3-(1,2,3,4-tetrahydro-isoquinolin-6-yl)-urea hydrochloride (365 mg) obtained in Example (27b). This methyl ester (532 mg) was hydrolyzed in the same way as in Example 2 to obtain the title compound (439 mg, 85%) as a white solid.
¹H NMR (400 MHz, DMSO-d6): δ (ppm)=12.2 (1H, brs), 9.47 (1H, s), 8.25 (1H, s), 8.02 (1H, dd, J=11.8 and 3.1 Hz), 7.35 (1H, s), 7.22 (1H, d, J=7.8 Hz), 7.11 (1H, d, J=8.6 Hz), 7.00 (1H, dd, J=9.0 and 5.4 Hz), 6.72 (1H, dt, J=12.4 and 4.3 Hz), 4.49-4.47 (3H, m), 4.12 (2H, q, J=7.0 Hz), 3.57 (2H, t, J=5.9 Hz), 2.76 (2H, t, J=5.9 Hz), 2.11 (2H, d, J=7.0 Hz), 1.94-1.90 (2H, m), 1.77-1.74 (2H, m), 1.68-1.62 (1H, m), 1.40 (3H, t, J=7.0 Hz), 1.39-1.29 (2H, m), 1.11-1.02 (2H, m);
MS (ESI) m/z: 514 (M+H)⁺.

Example 28 trans-6-[3-(2-isopropyl-phenyl)-ureido]-3,4-dihydro-1H-isoquinoline-2-carboxylic acid 4-carboxymethyl-cyclohexyl ester

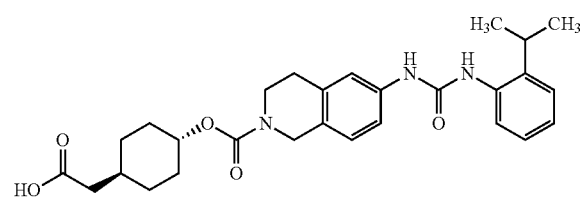 [SMILES: CC(C)c1ccccc1NC(=O)Nc1ccc2c(c1)CCN(C(=O)O[C@H]1CC[C@H](CC(=O)O)CC1)C2]

(28a) 6-[3-(2-isopropyl-phenyl)-ureido]-3,4-dihydro-1H-isoquinoline-2-carboxylic acid tert-butyl ester To a dichloromethane (10 mL) solution of triphosgene (474 mg), a dichloromethane (10 mL) solution of 2-isopropyla-niline (540 mg) and triethylamine (1.2 mL) was gradually added at room temperature. After 2 hours, a dichloromethane (10 mL) solution of 6-amino-2N-Boc-1,2,3,4-tetrahydroiso-quinoline (993 mg) and triethylamine (1.2 mL) was added thereto. The reaction mixture was stirred for 30 minutes and concentrated. The residue was purified by chromatography (dichloromethane/ethyl acetate) to obtain the title compound (1.32 g, 81%) as an off-white solid.
¹H NMR (400 MHz, CDCl₃): δ (ppm)=7.43-7.38 (2H, m), 7.33-7.27 (3H, m), 7.16 (1H, brs), 7.02 (1H, d, J=7.8 Hz), 6.35 (1H, s), 6.18 (1H, s), 4.51 (2H, s), 3.61 (2H, t, J=5.5 Hz), 3.25-3.18 (1H, m), 2.79 (2H, t, J=5.9 Hz), 1.49 (9H, s), 1.22 (6H, d, J=6.7 Hz).

(28b) 1-(2-isopropyl-phenyl)-3-(1,2,3,4-tetrahydro-isoquinolin-6-yl)-urea hydrochloride The title compound (1.12 g, quantitative yield) was obtained as an off-white solid in the same way as in Example (22b) from 6-[3-(2-isopropyl-phenyl)-ureido]-3,4-dihydro-1H-isoquinoline-2-carboxylic acid tert-butyl ester (1.32 g) obtained in Example (28a).
¹H NMR (400 MHz, DMSO-d6): δ (ppm)=9.12-9.06 (3H, m), 7.39 (1H, s), 7.28 (1H, dd, J=8.4 and 2.1 Hz), 7.18-7.17 (1H, m), 7.15-7.12 (2H, m), 6.89 (1H, dd, J=7.8 and 1.5 Hz), 6.53 (1H, dd, J=8.2 and 2.4 Hz), 4.57-4.51 (1H, m), 4.19 (2H, s), 3.38-3.32 (2H, m), 2.98 (2H, t, J=6.2 Hz), 1.26 (6H, d, J=5.8 Hz).

(28c) trans-6-[3-(2-isopropyl-phenyl)-ureido]-3,4-dihydro-1H-isoquinoline-2-carboxylic acid 4-carboxymethyl-cyclohexyl ester Methyl ester (498 mg, 98%) was obtained in the same way as in Example (1e) from trans-(4-hydroxy-cyclohexyl)-acetic acid methyl ester (241 mg) obtained in Example (1d) and 1-(2-isopropyl-phenyl)-3-(1,2,3,4-tetrahydro-isoquinolin-6-yl)-urea hydrochloride (345 mg) obtained in Example (28b). This methyl ester (498 mg) was hydrolyzed in the same way as in Example 2 to obtain the title compound (352 mg, 73%) as an off-white solid.
¹H NMR (400 MHz, DMSO-d6): δ (ppm)=12.1 (1H, brs), 8.95 (1H, s), 7.98 (1H, s), 7.66 (1H, dd, J=7.8 and 1.2 Hz), 7.33 (1H, s), 7.28 (1H, dd, J=7.8 and 1.5 Hz), 7.22 (1H, d, J=9.0 Hz), 7.14 (1H, dt, J=10.7 and 3.9 Hz), 7.09-7.05 (2H, m), 4.48-4.46 (3H, m), 3.57 (2H, t, J=5.9 Hz), 3.18-3.11 (1H, m), 2.75 (2H, t, J=5.6 Hz), 2.11 (2H, d, J=6.6 Hz), 1.94-1.91 (2H, m), 1.77-1.73 (2H, m), 1.68-1.62 (1H, m), 1.39-1.29 (2H, m), 1.19 (6H, d, J=6.7 Hz), 1.12-1.01 (2H, m);
MS (ESI) m/z: 494 (M+H)⁺.

Example 29 trans-6-[3-(3-isopropyl-phenyl)-ureido]-3,4-dihydro-1H-isoquinoline-2-carboxylic acid 4-carboxymethyl-cyclohexyl ester

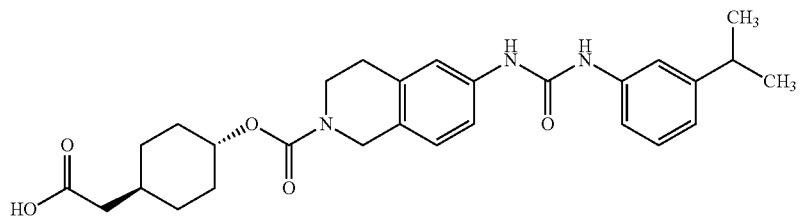

(29a) 6-[3-(3-isopropyl-phenyl)-ureido]-3,4-dihydro-1H-isoquinoline-2-carboxylic acid tert-butyl ester The title compound (1.48 g, 90%) was obtained as a white solid in the same way as in Example (28a) from 3-isopropylaniline (540 mg) and 6-amino-2N-Boc-1,2,3,4-tetrahydroisoquinoline (993 mg).

$^1$H NMR (400 MHz, CDCl$_3$): δ (ppm)=7.28-7.24 (3H, m), 7.18-7.15 (2H, m), 7.01 (2H, d, J=7.5 Hz), 6.76 (2H, brs), 4.52 (2H, s), 3.62 (2H, t, J=4.9 Hz), 2.92-2.85 (1H, m), 2.79 (2H, t, J=5.9 Hz), 1.50 (9H, s), 1.24 (6H, d, J=6.6 Hz).

(29b) 1-(3-isopropyl-phenyl)-3-(1,2,3,4-tetrahydro-isoquinolin-6-yl)-urea hydrochloride The title compound (1.25 g, quantitative yield) was obtained as a pale yellow solid in the same way as in Example (22b) from 6-[3-(3-isopropyl-phenyl)-ureido]-3,4-dihydro-1H-isoquinoline-2-carboxylic acid tert-butyl ester (1.48 g) obtained in Example (29a).

$^1$H NMR (400 MHz, DMSO-d6): δ (ppm)=9.07 (2H, s), 9.01 (1H, s), 7.41 (1H, d, J=1.9 Hz), 7.36 (1H, brs), 7.28 (1H, dd, J=8.4 and 2.1 Hz), 7.26-7.23 (1H, m), 7.19 (1H, dd, J=7.8 and 7.8 Hz), 7.12 (1H, d, J=8.6 Hz), 6.86 (1H, d, J=7.4 Hz), 4.19 (2H, s), 3.37-3.32 (2H, m), 2.97 (2H, t, J=6.1 Hz), 2.87-2.80 (1H, m), 1.19 (6H, d, J=7.1 Hz).

(29c) trans-6-[3-(3-isopropyl-phenyl)-ureido]-3,4-dihydro-1H-isoquinoline-2-carboxylic acid 4-carboxymethyl-cyclohexyl ester Methyl ester (537 mg, quantitative yield) was obtained in the same way as in Example (1e) from trans-(4-hydroxy-cyclohexyl)-acetic acid methyl ester (241 mg) obtained in Example (1d) and 1-(3-isopropyl-phenyl)-3-(1,2,3,4-tetrahydro-isoquinolin-6-yl)-urea hydrochloride (345 mg) obtained in Example (29b). This methyl ester (537 mg) was hydrolyzed in the same way as in Example 2 to obtain the title compound (459 mg, 93%) as a yellow solid.

$^1$H NMR (400 MHz, DMSO-d6): δ (ppm)=12.0 (1H, brs), 8.57 (2H, d. J=10.5 Hz), 7.34 (2H, d, J=7.8 Hz), 7.24-7.16 (3H, m), 7.08 (1H, d, J=8.6 Hz), 7.08 (1H, d, J=8.6 Hz), 4.49-4.46 (3H, m), 3.57 (2H, t, J=5.9 Hz), 2.88-2.81 (1H, m), 2.75 (2H, t, J=5.9 Hz), 2.12 (2H, d, J=7.1 Hz), 1.94-1.91 (2H, m), 1.77-1.74 (2H, m), 1.68-1.62 (1H, m), 1.39-1.29 (2H, m), 1.19 (6H, d, J=7.1 Hz), 1.12-1.02 (2H, m);
MS (ESI) m/z: 494 (M+H)$^+$.

Example 30 trans-6-[3-(3-isopropoxy-phenyl)-ureido]-3,4-dihydro-1H-isoquinoline-2-carboxylic acid 4-carboxymethyl-cyclohexyl ester

(30a) 6-[3-(3-isopropoxy-phenyl)-ureido]-3,4-dihydro-1H-isoquinoline-2-carboxylic acid tert-butyl ester The title compound (1.70 g, quantitative yield) was obtained as an off-white solid in the same way as in Example (28a) from 3-isopropoxyaniline (605 mg) and 6-amino-2N-Boc-1,2,3,4-tetrahydroisoquinoline (993 mg).

$^1$H NMR (400 MHz, CDCl$_3$): δ (ppm)=7.32 (1H, brs), 7.20 (1H, 1, J=8.0 Hz), 7.06-6.98 (2H, m), 7.03 (2H, s), 6.84 (1H, dd, J=7.8 and 1.6 Hz), 6.78 (1H, brs), 6.65 (1H, dd, J=8.4 and 2.2 Hz), 4.58-4.52 (1H, m), 4.52 (2H, s), 3.62 (2H, t, J=5.3 Hz), 2.79 (2H, t, J=6.1 Hz), 1.50 (9H, s), 1.32 (6H, d, J=5.9 Hz).

(30b) 1-(3-isopropoxy-phenyl)-3-(1,2,3,4-tetrahydro-isoquinolin-6-yl)-urea hydrochloride The title compound (1.45 g, quantitative yield) was obtained as an off-white solid in the same way as in Example (22b) from 6-[3-(3-isopropoxy-phenyl)-ureido]-3,4-dihydro-1H-isoquinoline-2-carboxylic acid tert-butyl ester (1.70 g) obtained in Example (30a).

$^1$H NMR (400 MHz, DMSO-d6): δ (ppm)=9.38 (1H, s), 9.11 (1H, brs), 8.21 (1H, s), 7.66 (1H, dd, J=8.0 and 1.4 Hz), 7.41 (1H, d, J=2.4 Hz), 7.31-7.27 (2H, m), 7.16-7.11 (2H, m), 7.07 (1H, dt, J=10.3 and 3.8 Hz), 4.19 (2H, s), 3.38-3.32 (2H, m), 3.24-3.18 (1H, m), 2.97 (2H, t, J=6.5 Hz), 1.19 (6H, d, J=6.6 Hz).

(30c) trans-6-[3-(3-isopropoxy-phenyl)-ureido]-3,4-dihydro-1H-isoquinoline-2-carboxylic acid 4-carboxymethyl-cyclohexyl ester Methyl ester (493 mg, 94%) was obtained in the same way as in Example (1e) from trans-(4-hydroxy-cyclohexyl)-acetic acid methyl ester (241 mg) obtained in Example (1d) and 1-(3-isopropoxy-phenyl)-3-(1,2,3,4-tetrahydro-isoquinolin-6-yl)-urea hydrochloride (361 mg) obtained in Example (30b). This methyl ester (493 mg) was hydrolyzed in the same way as in Example 2 to obtain the title compound (424 mg, 89%) as a pale yellow solid.

$^1$H NMR (400 MHz, DMSO-d6): δ (ppm)=12.1 (1H, brs), 8.68 (2H, d, J=10.9 Hz), 7.32 (1H, s), 7.22 (1H, d, J=7.9 Hz), 7.18-7.16 (1H, m), 7.13 (1H, d, J=8.2 Hz), 7.08 (1H, d, J=8.3 Hz), 6.88 (1H, d, J=7.8 Hz), 6.52 (1H, dd, J=8.2 and 2.3 Hz), 4.58-4.52 (1H, m), 4.49-4.46 (3H, m), 3.57 (2H, t, J=5.9 Hz), 2.75 (2H, t, J=5.9 Hz), 2.12 (2H, d, J=7.0 Hz), 1.94-1.91 (2H, m), 1.77-1.74 (2H, m), 1.68-1.62 (1H, m), 1.39-1.31 (2H, m), 1.26 (6H, d, J=6.2 Hz), 1.11-1.02 (2H, m);
MS (ESI) m/z: 510 (M+H)$^+$.

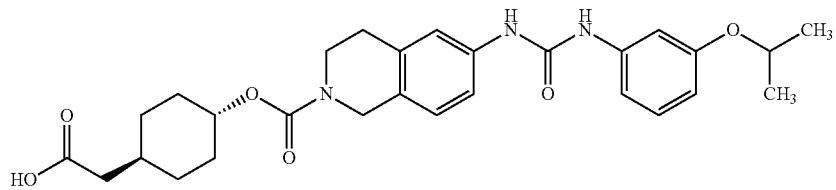 [SMILES: CC(C)Oc1cccc(NC(=O)Nc2ccc3c(c2)CCN(C(=O)O[C@H]2CC[C@H](CC(=O)O)CC2)C3)c1]

Example 31 trans-6-[3-(2,4,5-trifluoro-phenyl)-ureido]-3,4-dihydro-1H-isoquinoline-2-carboxylic acid 4-carboxymethyl-cyclohexyl ester

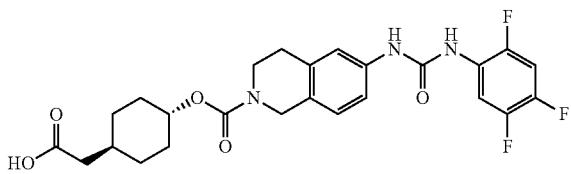 [SMILES: O=C(O)C[C@H]1CC[C@H](OC(=O)N2CCc3cc(NC(=O)Nc4cc(F)c(F)cc4F)ccc3C2)CC1]

(31a) 6-[3-(2,4,5-trifluoro-phenyl)-ureido]-3,4-dihydro-1H-isoquinoline-2-carboxylic acid tert-butyl ester The title compound (1.67 g, 99%) was obtained as a white solid in the same way as in Example (26a) from 6-amino-2N-Boc-1,2,3,4-tetrahydroisoquinoline (993 mg) and 2,4,5-trifluoro-phenyl isocyanate (0.58 mL).

$^1$H NMR (400 MHz, CDCl$_3$): δ (ppm)=8.24-8.16 (1H, m), 7.45-7.25 (1H, m), 7.08 (1H, brs), 6.98-6.91 (2H, m), 6.77 (1H, brs), 6.57 (1H, brs), 4.52 (2H, s), 3.64 (2H, t, J=6.0 Hz), 2.80 (2H, brs), 1.52 (9H, s).

(31b) 1-(2,4,5-trifluoro-phenyl)-3-(1,2,3,4-tetrahydro-isoquinolin-6-yl)-urea hydrochloride The title compound (1.37 g, 96%) was obtained as an off-white solid in the same way as in Example (22b) from 6-[3-(2,4,5-trifluoro-phenyl)-ureido]-3,4-dihydro-1H-isoquinoline-2-carboxylic acid tert-butyl ester (1.67 g) obtained in Example (31a).

$^1$H NMR (400 MHz, DMSO-d6): δ (ppm)=9.33 (1H, s), 8.86 (2H, brs), 8.23-8.16 (1H, m), 7.69-7.61 (1H, m), 7.40 (1H, brs), 7.27 (1H, dd, J=8.4 and 2.1 Hz), 7.14 (1H, d, J=8.6 Hz), 4.18 (2H, s), 3.36-3.32 (2H, m), 2.96 (2H, t, J=6.3 Hz).

(31c) trans-6-[3-(2,4,5-trifluoro-phenyl)-ureido]-3,4-dihydro-1H-isoquinoline-2-carboxylic acid 4-carboxymethyl-cyclohexylester Methyl ester (773 mg, quantitative yield) was obtained in the same way as in Example (1e) from trans-(4-hydroxycyclohexyl)-acetic acid methyl ester (361 mg) obtained in Example (1d) and 1-(2,4,5-trifluoro-phenyl)-3-(1,2,3,4-tetrahydro-isoquinolin-6-yl)-urea hydrochloride (536 mg) obtained in Example (31b). This methyl ester (773 mg) was hydrolyzed in the same way as in Example 2 to obtain the title compound (653 mg, 87%) as a white solid.

$^1$H NMR (400 MHz, DMSO-d6): δ (ppm)=12.1 (1H, brs), 9.12 (1H, s), 8.80 (1H, s), 8.24-8.16 (1H, m), 7.68-7.60 (1H, m), 7.32 (1H, s), 7.22 (1H, d, J=7.8 Hz), 7.11 (1H, d, J=8.2 Hz), 4.49-4.47 (3H, m), 3.57 (2H, t, J=5.8 Hz), 2.76 (2H, t, J=5.8 Hz), 2.11 (2H, d, J=7.0 Hz), 1.95-1.90 (2H, m), 1.77-1.74 (2H, m), 1.68-1.62 (1H, m), 1.39-1.30 (2H, m), 1.12-1.03 (2H, m);

MS (ESI) m/z: 506 (M+H)$^+$.

Example 32 trans-6-[3-(3,4,5-trifluoro-phenyl)-ureido]-3,4-dihydro-1H-isoquinoline-2-carboxylic acid 4-carboxymethyl-cyclohexyl ester

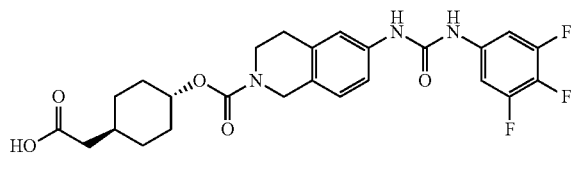 [SMILES: O=C(O)C[C@H]1CC[C@H](OC(=O)N2CCc3cc(NC(=O)Nc4cc(F)c(F)c(F)c4)ccc3C2)CC1]

(32a) 6-[3-(3,4,5-trifluoro-phenyl)-ureido]-3,4-dihydro-1H-isoquinoline-2-carboxylic acid tert-butyl ester The title compound (1.64 g, 97%) was obtained as a yellowish-white solid in the same way as in Example (28a) from 3,4,5-trifluoroaniline (1.22 mL) and 6-amino-2N-Boc-1,2,3,4-tetrahydroisoquinoline (993 mg).

$^1$H NMR (400 MHz, CDCl$_3$): δ (ppm)=7.34-7.26 (4H, m), 7.14-7.10 (2H, m), 6.69 (1H, brs), 4.54 (2H, s), 3.65 (2H, t, J=6.1 Hz), 2.82 (2H, t, J=6.1 Hz), 1.51 (9H, s).

(32b) 1-(3,4,5-trifluoro-phenyl)-3-(1,2,3,4-tetrahydro-isoquinolin-6-yl)-urea hydrochloride The title compound (1.38 g, 99%) was obtained as an off-white solid in the same way as in Example (22b) from 6-[3-(3,4,5-trifluoro-phenyl)-ureido]-3,4-dihydro-1H-isoquinoline-2-carboxylic acid tert-butyl ester (1.64 g) obtained in Example (32a).

$^1$H NMR (400 MHz, DMSO-d6): δ (ppm)=9.59 (1H, s), 9.26 (1H, s), 9.13 (1H, brs), 7.39-7.35 (3H, m), 7.29 (1H, dd, J=8.4 and 2.1 Hz), 7.15 (1H, d, J=8.2 Hz), 4.20 (2H, s), 3.38-3.36 (2H, m), 2.98 (2H, t, J=6.1 Hz).

(32c) trans-6-[3-(3,4,5-trifluoro-phenyl)-ureido]-3,4-dihydro-1H-isoquinoline-2-carboxylic acid 4-carboxymethyl-cyclohexyl ester Methyl ester (779 mg, quantitative yield) was obtained in the same way as in Example (1e) from trans-(4-hydroxycyclohexyl)-acetic acid methyl ester (361 mg) obtained in Example (1d) and 1-(3,4,5-trifluoro-phenyl)-3-(1,2,3,4-tetrahydro-isoquinolin-6-yl)-urea hydrochloride (536 mg) obtained in Example (32b). This methyl ester (779 mg) was hydrolyzed in the same way as in Example 2 to obtain the title compound (678 mg, 89%) as a white solid.

$^1$H NMR (400 MHz, DMSO-d6): δ (ppm)=12.1 (1H, brs), 9.22 (1H, s), 8.99 (1H, s), 7.40 (1H, d, J=6.2 Hz), 7.38 (1H, d, J=6.3 Hz), 7.39 (1H, s), 7.23 (1H, d, J=8.2 Hz), 7.10 (1H, d, J=8.6 Hz), 4.48-4.46 (3H, m), 3.57 (2H, t, J=6.0 Hz), 2.75 (2H, t, J=5.9 Hz), 2.11 (2H, d, J=6.6 Hz), 1.94-1.91 (2H, m), 1.77-1.74 (2H, m), 1.69-1.63 (1H, m), 1.39-1.29 (2H, m), 1.12-1.02 (2H, m);

MS (ESI) m/z: 506 (M+H)$^+$.

Example 33 trans-6-[3-(2-fluoro-phenyl)-ureido]-3,4-dihydro-1H-isoquinoline-2-carboxylic acid 4-dimethylcarbamoylmethyl-cyclohexyl ester

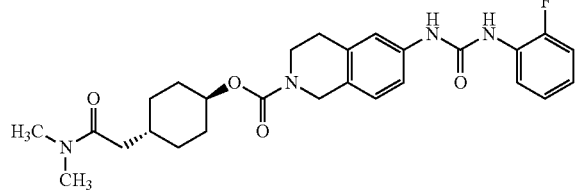

The title compound (100 mg, 35%) was obtained as an off-white solid in the same way as in Example 18 from trans-6-[3-(2-fluoro-phenyl)-ureido]-3,4-dihydro-1H-isoquinoline-2-carboxylic acid 4-carboxymethyl-cyclohexyl ester (268 mg) obtained in Example 2 and dimethylamine hydrochloride (51 mg).

$^1$H NMR (400 MHz, DMSO-d6): δ (ppm)=9.02 (1H, s), 8.54 (1H, d, J=2.4 Hz), 8.16 (1H, dd, J=8.2 and 8.2 Hz), 7.33 (1H, s), 7.26-7.22 (2H, m), 7.16-7.09 (2H, m), 7.03-6.98 (1H, m), 4.51-4.47 (3H, m), 3.57 (2H, t, J=5.9 Hz), 2.95 (3H, s), 2.81 (3H, s), 2.76 (2H, t, J=5.9 Hz), 2.18 (2H, d, J=6.3 Hz), 1.94-1.91 (2H, m), 1.77-1.74 (2H, m), 1.70-1.66 (1H, m), 1.38-1.29 (2H, m), 1.10-1.01 (2H, m);

MS (ESI) m/z: 497 (M+H)$^+$.

Example 34 trans-6-[3-(2-fluoro-phenyl)-ureido]-3,4-dihydro-1H-isoquinoline-2-carboxylic acid 4-methylcarbamoylmethyl-cyclohexyl ester

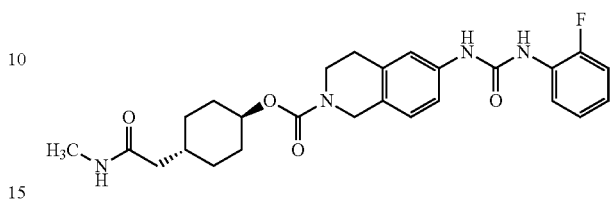

The title compound (119 mg, 37%) was obtained as a light brown solid in the same way as in Example 18 from trans-6-[3-(2-fluoro-phenyl)-ureido]-3,4-dihydro-1H-isoquinoline-2-carboxylic acid 4-carboxymethyl-cyclohexyl ester (317 mg) obtained in Example 2 and methylamine hydrochloride (50 mg).

$^1$H NMR (400 MHz, DMSO-d6): δ (ppm)=9.02 (1H, s), 8.53 (1H, d, J=2.7 Hz), 8.16 (1H, dd, J=8.4 and 8.4 Hz), 7.72 (1H, d, J=4.7 Hz), 7.33 (1H, s), 7.26-7.21 (2H, m), 7.16-7.09 (2H, m), 7.03-6.98 (1H, m), 4.52-4.47 (3H, m), 3.57 (2H, t, J=5.9 Hz), 2.76 (2H, t, J=5.8 Hz), 2.56 (3H, d, J=4.7 Hz), 1.96-1.90 (4H, m), 1.71-1.64 (2H, m), 1.53-1.47 (1H, m), 1.36-1.27 (2H, m), 1.06-1.01 (2H, m);

MS (ESI) m/z: 483 (M+H)$^+$.

Example 35 trans-6-[3-(2-fluoro-phenyl)-ureido]-3,4-dihydro-1H-isoquinoline-2-carboxylic acid 4-[(carboxymethyl-carbamoyl)-methyl]-cyclohexyl ester

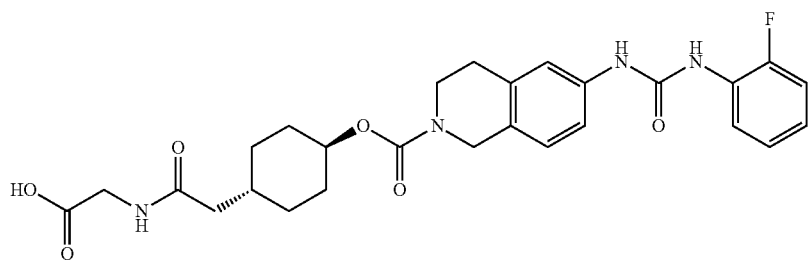 [SMILES: O=C(O)CNC(=O)C[C@H]1CC[C@H](OC(=O)N2CCc3cc(NC(=O)Nc4ccccc4F)ccc3C2)CC1]

Methyl ester (128 mg, 20%) was obtained in the same way as in Example 18 from trans-6-[3-(2-fluoro-phenyl)-ureido]-3,4-dihydro-1H-isoquinoline-2-carboxylic acid 4-carboxymethyl-cyclohexyl ester (551 mg) obtained in Example 2 and glycine methyl ester hydrochloride (162 mg). This methyl ester was hydrolyzed in the same way as in Example 2 to obtain the title compound (51 mg, 41%) as a beige solid.

¹H NMR (400 MHz, DMSO-d6): δ (ppm)=9.12 (1H, s), 8.64 (1H, brs), 8.14 (1H, dd, J=8.4 and 8.4 Hz), 7.92 (1H, brs), 7.33 (1H, s), 7.26-7.21 (2H, m), 7.16-7.09 (2H, m), 7.03-6.99 (1H, m), 4.48-4.47 (3H, m), 3.63 (2H, d, J=5.4 Hz), 3.57 (2H, t, J=5.9 Hz), 2.76 (2H, t, J=5.9 Hz), 2.02 (2H, d, J=6.7 Hz), 1.94-1.90 (2H, m), 1.76-1.73 (2H, m), 1.68-1.63 (1H, m), 1.55-1.51 (1H, m), 1.37-1.25 (2H, m), 1.06-1.01 (2H, m);

MS (ESI) m/z: 527 (M+H)⁺.

Example 36 trans-6-[3-(2-fluoro-phenyl)-ureido]-3,4-dihydro-1H-isoquinoline-2-carboxylic acid 4-[(1-carboxy-ethylcarbamoyl)-methyl]-cyclohexyl ester

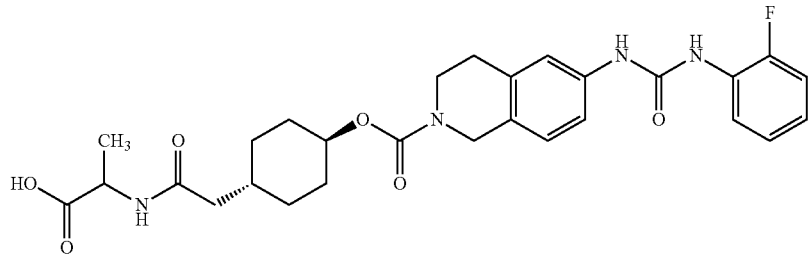 [SMILES: CC(NC(=O)C[C@H]1CC[C@H](OC(=O)N2CCc3cc(NC(=O)Nc4ccccc4F)ccc3C2)CC1)C(=O)O]

Methyl ester (51 mg, 16%) was obtained in the same way as in Example 18 from trans-6-[3-(2-fluoro-phenyl)-ureido]-3,4-dihydro-1H-isoquinoline-2-carboxylic acid 4-carboxymethyl-cyclohexyl ester (275 mg) obtained in Example 2 and alanine methyl ester hydrochloride (racemate, 90 mg). This methyl ester was hydrolyzed in the same way as in Example 2 to obtain the title compound (25 mg, 50%) as an off-white solid.

¹H NMR (400 MHz, DMSO-d6): δ (ppm)=9.74 (1H, s), 9.23 (1H, brs), 8.14 (1H, dd, J=7.7 and 7.7 Hz), 7.61 (1H, brs), 7.46 (1H, s), 7.36-7.28 (2H, m), 7.23-7.16 (2H, m), 7.12-7.08 (1H, m), 4.59-4.55 (3H, m), 3.94 (1H, t, J=6.8 Hz), 3.65 (2H, t, J=6.0 Hz), 2.83 (2H, t, J=5.7 Hz), 2.13-1.98 (6H, m), 1.87-1.78 (2H, m), 1.75-1.60 (1H, m), 1.55-1.43 (1H, m), 1.25 (3H, d, J=7.0 Hz), 1.15-1.10 (2H, m);

MS (ESI) m/z: 541 (M+H)⁺.

Example 37 trans-6-[3-(2-fluoro-phenyl)-ureido]-3,4-dihydro-1H-isoquinoline-2-carboxylic acid 4-[(1-carboxy-cyclopropylcarbamoyl)-methyl]-cyclohexyl ester

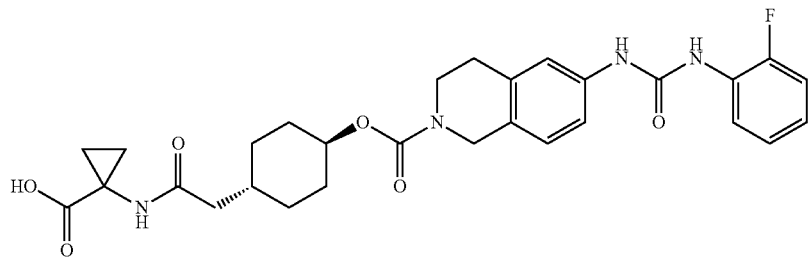 [SMILES: O=C(C[C@H]1CC[C@H](OC(=O)N2CCc3cc(NC(=O)Nc4ccccc4F)ccc3C2)CC1)NC1(C(=O)O)CC1]

Methyl ester (98 mg, 35%) was obtained in the same way as in Example 18 from trans-6-[3-(2-fluoro-phenyl)-ureido]-3,4-dihydro-1H-isoquinoline-2-carboxylic acid 4-carboxymethyl-cyclohexyl ester (235 mg) obtained in Example 2 and 1-amino-cyclopropanecarboxylic acid methyl ester hydrochloride (76 mg). This methyl ester was hydrolyzed in the same way as in Example 2 to obtain the title compound (16 mg, 17%) as a white solid.

$^1$H NMR (400 MHz, DMSO-d6): δ (ppm)=9.11 brs), 8.63 (1H, brs), 8.30 (1H, s), 8.13 (1H, dd, J=7.7 and 7.7 Hz), 7.33 (1H, d, J=1.6 Hz), 7.26-7.21 (2H, m), 7.15-7.09 (2H, m), 7.03-6.98 (1H, m), 4.49-4.47 (3H, m), 3.57 (2H, t, J=6.2 Hz), 2.76 (2H, t, J=5.7 Hz), 1.94 (2H, d, J=7.0 Hz), 1.94-1.89 (2H, m), 1.78-1.74 (2H, m), 1.69-1.64 (1H, m), 1.36-1.25 (4H, m), 1.08-1.00 (2H, m), 0.92-0.89 (2H, m);
MS (ESI) m/z: 553 (M+H)$^+$.

Example 38 trans-6-[3-(2-fluoro-phenyl)-ureido]-3,4-dihydro-1H-isoquinoline-2-carboxylic acid 4-[2-(2-carboxy-pyrrolidin-1-yl)-2-oxo-ethyl]-cyclohexyl ester

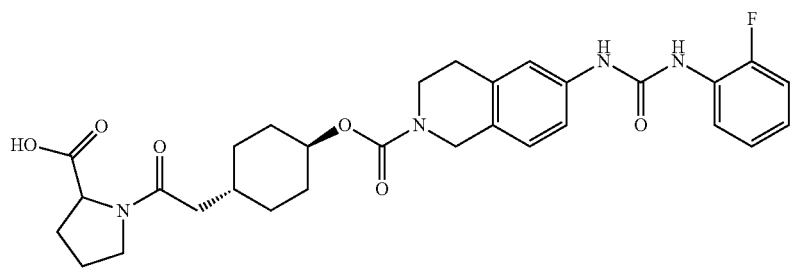 [SMILES: O=C(Nc1ccc2c(c1)CCN(C(=O)O[C@H]1CC[C@H](CC(=O)N3CCCC3C(=O)O)CC1)C2)Nc1ccccc1F]

Methyl ester (233 mg, 80%) was obtained in the same way as in Example 18 from trans-6-[3-(2-fluoro-phenyl)-ureido]-3,4-dihydro-1H-isoquinoline-2-carboxylic acid 4-carboxymethyl-cyclohexyl ester (235 mg) obtained in Example 2 and proline methyl ester hydrochloride (racemate, 83 mg). This methyl ester was hydrolyzed in the same way as in Example 2 to obtain the title compound (209 mg, 92%) as a yellow solid.

$^1$H NMR (400 MHz, DMSO-d6): δ (ppm)=12.4 (1H, brs), 9.04 (1H, s), 8.56 (1H, s), 8.15 (1H, dd, J=8.4 and 8.5 Hz), 7.32 (1H, s), 7.26-7.21 (2H, m), 7.15-7.09 (2H, m), 7.03-6.98 (1H, m), 4.47-4.39 (3H, m), 4.21 (1H, dd, J=8.2 and 3.5 Hz), 3.57 (2H, t, J=5.9 Hz), 3.53-3.49 (2H, m), 2.76 (2H, t, J=5.0 Hz), 2.23-2.08 (3H, m), 1.94-1.88 (4H, m), 1.85-1.71 (4H, m), 1.38-1.28 (2H, m), 1.12-1.00 (2H, m);
MS (ESI) m/z: 567 (M+H)$^+$.

Example 39 trans-6-[3-(2-fluoro-phenyl)-ureido]-3,4-dihydro-1H-isoquinoline-2-carboxylic acid 4-(4-carboxy-oxazol-2-ylmethyl)-cyclohexyl ester

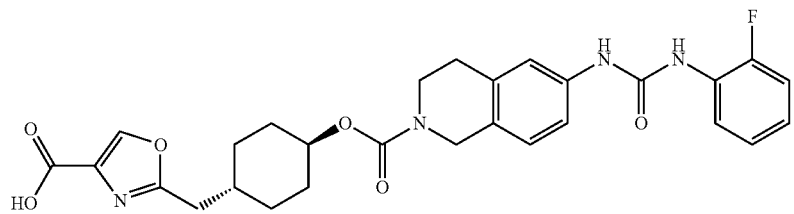 [SMILES: O=C(Nc1ccc2c(c1)CCN(C(=O)O[C@H]1CC[C@H](Cc3nc(C(=O)O)co3)CC1)C2)Nc1ccccc1F]

(39a) trans-6-[3-(2-fluoro-phenyl)-ureido]-3,4-dihydro-1H-isoquinoline-2-carboxylic acid 4-[(2-hydroxy-1-methoxycarbonyl-ethylcarbamoyl)-methyl]-cyclohexyl ester The title compound (199 mg, 23%) was obtained as a white solid in the same way as in Example 18 from trans-6-[3-(2-fluoro-phenyl)-ureido]-3,4-dihydro-1H-isoquinoline-2-carboxylic acid 4-carboxymethyl-cyclohexyl ester (268 mg) obtained in Example 2 and serine methyl ester hydrochloride (racemate, 51 mg).

$^1$H NMR (400 MHz, DMSO-d6): δ (ppm)=9.06 (1H, s), 8.58 (1H, s), 8.17-8.11 (2H, m), 7.33 (1H, s), 7.26-7.21 (2H, m), 7.16-7.09 (2H, m), 7.03-7.00 (1H, m), 5.01 (1H, t, J=5.6 Hz), 4.52-4.47 (3H, m), 4.36-4.31 (1H, m), 3.70-3.63 (1H, m), 3.62 (3H, s), 3.57 (2H, t, J=6.0 Hz), 2.76 (2H, t, J=5.8 Hz), 2.07 (2H, dd, J=6.9 and 3.0 Hz), 1.94-1.91 (2H, m), 1.77-1.65 (3H, m), 1.37-1.27 (2H, m), 1.10-1.00 (2H, m);
MS (ESI) m/z: 571 (M+H)$^+$.

(39b) trans-6-[3-(2-fluoro-phenyl)-ureido]-3,4-dihydro-1H-isoquinoline-2-carboxylic acid 4-(4-carboxy-oxazol-2-ylmethyl)-cyclohexyl ester To a dichloromethane (8 mL) suspension of trans-6-[3-(2-fluoro-phenyl)-ureido]-3,4-dihydro-1H-isoquinoline-2-carboxylic acid 4-[(2-hydroxy-1-methoxycarbonyl-ethylcarbamoyl)-methyl]-cyclohexyl ester (199 mg) obtained in Example (39a), Deoxo-Fluor (0.071 mL) was added at −10° C. After 30 minutes, the reaction mixture was concentrated, diluted with ethyl acetate, washed with a saturated aqueous solution of sodium bicarbonate and saturated brine, then dried over sodium sulfate, and then concentrated. The residue was purified by column chromatography (dichloromethane/ethyl acetate) to obtain oxazoline (55 mg). To a dichloromethane (0.5 mL) mixture of this oxazoline (55 mg), DBU (0.017 mL) and bromotrichloromethane (0.011 mL) were added at 0° C. The reaction mixture was warmed to room temperature, then stirred overnight, and then concentrated. The residue was diluted with ethyl acetate, then washed with a saturated aqueous solution of sodium bicarbonate and saturated brine, and then concentrated. The residue was purified by column chromatography (dichloromethane/ethyl acetate) to obtain oxazole (27 mg, 48%) as a white solid. This oxazole (27 mg) was hydrolyzed in the same way as in Example 2 to obtain the title compound (22 mg, 84%) as a yellow solid.

$^1$H NMR (400 MHz, DMSO-d6): δ (ppm)=9.03 (1H, s), 8.61 (1H, s), 8.54 (1H, d, J=2.7 Hz), 8.15 (1H, dd, J=8.2 and 8.2 Hz), 7.32 (1H, d, J=1.6 Hz), 7.26-7.21 (2H, m), 7.16-7.09 (2H, m), 7.03-6.98 (1H, m), 4.53-4.47 (3H, m), 3.57 (2H, t, J=6.0 Hz), 2.76 (2H, t, J=5.6 Hz), 2.70 (2H, d, J=6.6 Hz), 1.96-1.92 (2H, m), 1.80-1.71 (3H, m), 1.40-1.31 (2H, m), 1.19-1.09 (2H, m);

MS (ESI) m/z: 537 (M+H)$^+$.

Example 40 trans-6-[3-(2-fluoro-phenyl)-ureido]-3,4-dihydro-1H-isoquinoline-2-carboxylic acid 4-[(1H-tetrazol-5-ylcarbamoyl)-methyl]-cyclohexyl ester

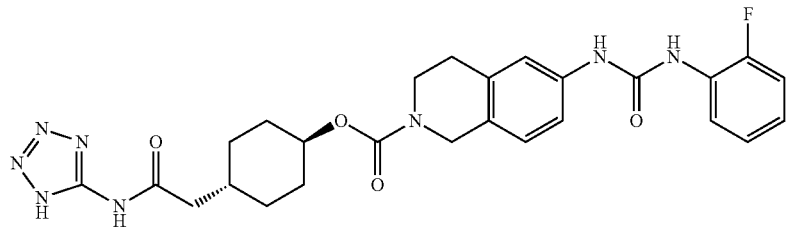 [SMILES: O=C(C[C@H]1CC[C@H](OC(=O)N2CCc3cc(NC(=O)Nc4ccccc4F)ccc3C2)CC1)Nc1nnn[nH]1]

A DMF (4 mL) solution of trans-6-[3-(2-fluoro-phenyl)-ureido]-3,4-dihydro-1H-isoquinoline-2-carboxylic acid 4-carboxymethyl-cyclohexyl ester (188 mg) obtained in Example 2, 1H-tetrazol-5-ylamine (54 mg), BOP reagent (212 mg), and diisopropylethylamine (0.10 mL) was stirred overnight at room temperature. The reaction mixture was diluted with 1 N hydrochloric acid, followed by extraction with ethyl acetate. The organic layer was concentrated and vigorously stirred in water/isopropyl ether. The obtained solid was heated to reflux in methanol and collected by filtration. The title compound (99 mg, 46%) was obtained as a pale yellow solid.

$^1$H NMR (400 MHz, DMSO-d6): δ (ppm)=11.9 (1H, s), 9.00 (1H, s), 8.52 (1H, d, J=2.4 Hz), 8.15 (1H, dd, J=8.2 and 8.2 Hz), 7.32 (1H, s), 7.26-7.21 (2H, m), 7.16-7.09 (2H, m), 7.03-6.98 (1H, m), 4.54-4.47 (3H, m), 3.57 (2H, t, J=6.1 Hz), 2.76 (2H, t, J=5.9 Hz), 2.36 (2H, d, J=6.7 Hz), 1.97-1.93 (2H, m), 1.82-1.75 (3H, m), 1.41-1.31 (2H, m), 1.18-1.08 (2H, m);

MS (ESI) m/z: 537 (M+H)$^+$.

Example 41 trans-6-[3-(2-fluoro-phenyl)-ureido]-3,4-dihydro-1H-isoquinoline-2-carboxylic acid 4-(5-oxo-4,5-dihydro-[1,2,4]oxadiazol-3-ylmethyl)-cyclohexyl ester

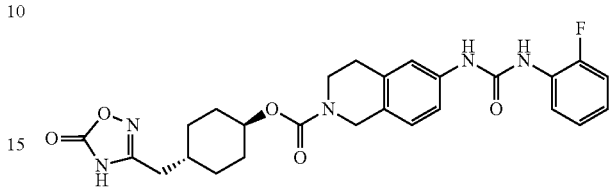

(41a) trans-(4-hydroxy-cyclohexyl)-acetonitrile

The title compound (1.69 g, 53%) was obtained as a clear colorless oil in the same way as in Example (1d) from (4-oxo-cyclohexyl)-acetonitrile (Tetrahedron 1995, 51, 10259.) (3.15 g).

$^1$H NMR (400 MHz, CDCl$_3$): δ (ppm)=3.63-3.56 (1H, m), 2.28 (2H, d, J=6.6 Hz), 2.04 (2H, dd, J=13.3 and 3.9 Hz), 1.90 (2H, dd, J=13.1 and 2.9 Hz), 1.72-1.63 (1H, m), 1.49 (1H, s), 1.37-1.27 (2H, m), 1.24-1.14 (2H, m).

(41b) trans-6-[3-(2-fluoro-phenyl)-ureido]-3,4-dihydro-1H-isoquinoline-2-carboxylic acid 4-cyanomethyl-cyclohexyl ester The title compound (563 mg, quantitative yield) was obtained as a white solid in the same way as in Example (1e) from trans-(4-hydroxy-cyclohexyl)-acetonitrile (WO2006004200 A1) (243 mg) obtained in Example (41a) and 1-(2-fluoro-phenyl)-3-(1,2,3,4-tetrahydro-isoquinolin-6-yl)-urea hydrochloride (403 mg).

$^1$H NMR (400 MHz, DMSO-d6): δ (ppm)=9.05 (1H, s), 8.57 (1H, s), 8.15 (1H, dd, J=8.2 and 8.2 Hz), 7.33 (1H, s), 7.26-7.21 (2H, m), 7.16-7.09 (2H, m), 7.03-7.00 (1H, m), 4.52-4.47 (3H, m), 3.57 (2H, t, J=6.1 Hz), 2.76 (2H, t, J=5.9 Hz), 2.47 (2H, d, J=6.7 Hz), 1.98-1.94 (2H, m), 1.82-1.79 (2H, m), 1.74-1.61 (1H, m), 1.74-1.61 (2H, m), 1.22-1.12 (2H, m).

(41c) trans-6-[3-(2-fluoro-phenyl)-ureido]-3,4-dihydro-1H-isoquinoline-2-carboxylic acid 4-(5-oxo-4,5-dihydro-[1,2,4]oxadiazol-3-ylmethyl)-cyclohexyl ester To an ethanol solution of trans-6-[3-(2-fluoro-phenyl)-ureido]-3,4-dihydro-1H-isoquinoline-2-carboxylic acid 4-cyanomethyl-cyclohexyl ester (563 mg) obtained in Example (41b), hydroxylamine (50% aqueous solution, 0.5 mL) was added. The reaction mixture was heated to reflux overnight and then concentrated. The residue was diluted with ethyl acetate, washed with water and saturated brine, then dried over sodium sulfate, and then concentrated. The residue was purified by column chromatography (Chromatorex NH, dichloromethane/methanol) to obtain a white solid (500 mg, 83%). To a tetrahydrofuran (10 mL) solution of this white solid (500 mg), pyridine (0.096 mL) and 2-ethylcyclohexyl chloroformate (0.20 mL) were added at 0° C. After 2 hours, the reaction mixture was diluted with ethyl acetate, washed with water and saturated brine, then dried over sodium sulfate, and then concentrated. The residue was purified by column chromatography (dichloromethane/ethyl acetate) to obtain white solid (391 mg, 59%). A mixture of this white solid (391 mg) and o-xylene (6 mL) was heated to reflux for 1 hour and concentrated. The residue was vigorously stirred in hexane/isopropyl ether (1:1) and collected by filtration. The title compound (55 mg, 17%) was obtained as an orange solid.

$^1$H NMR (400 MHz, DMSO-d6): δ (ppm)=12.2 (1H, brs), 9.00 (1H, s), 8.70 (1H, d, J=6.2 Hz), 8.15 (1H, dd, J=8.4 and 8.4 Hz), 7.32 (1H, s), 7.25 (1H, dd, J=8.2 and 1.6 Hz), 7.22 (1H, dd, J=8.2 and 1.2 Hz), 7.16-7.09 (2H, m), 7.03-6.98 (1H, m), 4.53-4.47 (3H, m), 3.57 (2H, t, J=5.9 Hz), 2.76 (2H, t, J=5.9 Hz), 2.39 (2H, d, J=7.1 Hz), 1.97-1.93 (2H, m), 1.76-1.72 (2H, m), 1.69-1.63 (1H, m), 1.38-1.24 (2H, m), 1.17-1.07 (2H, m);
MS (ESI) m/z: 510 (M+H)$^+$.

Example 42 trans-6-[3-(2-fluoro-phenyl)-ureido]-3,4-dihydro-1H-isoquinoline-2-carboxylic acid 4-(5-hydroxy-2H-pyrazol-3-ylmethyl)-cyclohexyl ester

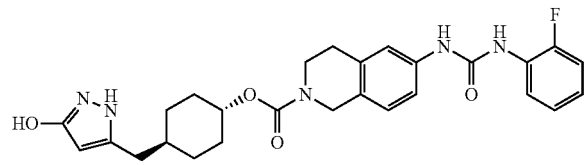 [SMILES: O=C(Nc1ccc2c(c1)CCN(C(=O)O[C@H]1CC[C@H](Cc3cc(O)n[nH]3)CC1)C2)Nc1ccccc1F]

(42a) trans-6-[3-(2-fluoro-phenyl)-ureido]-3,4-dihydro-1H-isoquinoline-2-carboxylic acid 4-(3-ethoxycarbonyl-2-oxo-propyl)-cyclohexyl ester To a dichloromethane (10 mL) suspension of trans-6-[3-(2-fluoro-phenyl)-ureido]-3,4-dihydro-1H-isoquinoline-2-carboxylic acid 4-carboxymethyl-cyclohexyl ester (939 mg) obtained in Example 2, Meldrum's acid (317 mg), dimethylaminopyridine (293 mg), and EDCI (460 mg) were added at 0° C. The reaction mixture was diluted with dichloromethane, washed with 1 N hydrochloric acid and saturated brine, then dried over sodium sulfate, and then concentrated. A mixture of the residue and ethanol (10 mL) was heated to reflux for 4 hours and concentrated. The residue was purified by column chromatography (dichloromethane/ethyl acetate) to obtain the title compound (820 mg, 76%) as a yellowish-white solid.

$^1$H NMR (400 MHz, DMSO-d6): δ (ppm)=9.04 (1H, s), 8.56 (1H, s), 8.15 (1H, dd, J=8.9 and 8.9 Hz), 7.32 (1H, s), 7.27-7.21 (2H, m), 7.16-7.09 (2H, m), 7.03-6.98 (1H, m), 4.50-4.45 (3H, m), 4.09 (2H, q, J=7.2 Hz), 3.57 (2H, t, J=6.0 Hz), 3.57 (2H, s), 2.76 (2H, t, J=5.8 Hz), 2.44 (2H, d, J=6.3 Hz), 1.94-1.89 (2H, m), 1.75-1.67 (3H, m), 1.39-1.29 (2H, m), 1.18 (3H, t, J=7.1 Hz), 1.08-0.98 (2H, m);
MS (ESI) m/z: 540 (M+H)$^+$.

(42b) trans-6-[3-(2-fluoro-phenyl)-ureido]-3,4-dihydro-1H-isoquinoline-2-carboxylic acid 4-(5-hydroxy-2H-pyrazol-3-ylmethyl)-cyclohexyl ester To a mixture of trans-6-[3-(2-fluoro-phenyl)-ureido]-3,4-dihydro-1H-isoquinoline-2-carboxylic acid 4-(3-ethoxycarbonyl-2-oxo-propyl)-cyclohexyl ester (189 mg) obtained in Example (42a) and ethanol (5 mL), hydrazine monohydrate (0.022 mL) was added at 0° C. During the reaction, hydrazine monohydrate was further added thereto, and the mixture was stirred until the reaction substrate was consumed. The reaction mixture was concentrated and purified by column chromatography (dichloromethane/methanol) to obtain a white solid. This white solid was vigorously stirred in isopropyl ether and collected by filtration to obtain the title compound (90 mg, 51%) as a white solid.

$^1$H NMR (400 MHz, DMSO-d6): δ (ppm)=11.2 (1H, brs), 9.28 (1H, brs), 9.06 (1H, s), 8.58 (1H, d, J=2.3 Hz), 8.15 (1H, dd, J=8.4 and 8.4 Hz), 7.32 (1H, s), 7.26-7.21 (2H, m), 7.16-7.09 (2H, m), 7.03-6.99 (1H, m), 5.22 (1H, s), 4.51-4.46 (3H, m), 3.56 (2H, t, J=6.0 Hz), 2.76 (2H, t, J=6.1 Hz), 2.34 (2H, d, J=7.4 Hz), 1.95-1.91 (2H, m), 1.72-1.68 (2H, m), 1.52-1.46 (1H, m), 1.36-1.26 (2H, m), 1.08-0.97 (2H, m);
MS (ESI) m/z: 508 (M+H)$^+$.

Example 43 trans-6-[3-(2-fluoro-phenyl)-ureido]-3,4-dihydro-1H-isoquinoline-2-carboxylic acid 4-(3-hydroxy-isoxazol-5-ylmethyl)-cyclohexyl ester

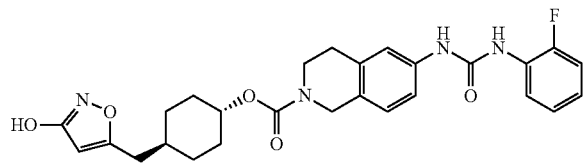 [SMILES: O=C(Nc1ccc2c(c1)CCN(C(=O)O[C@H]1CC[C@H](Cc3cc(O)no3)CC1)C2)Nc1ccccc1F]

To a mixture of trans-6-[3-(2-fluoro-phenyl)-ureido]-3,4-dihydro-1H-isoquinoline-2-carboxylic acid 4-(3-ethoxycarbonyl-2-oxo-propyl)-cyclohexyl ester (127 mg) obtained in Example (42a) and ethanol (3 mL), hydroxylamine hydrochloride (164 mg) was added at room temperature in the same way as in Example (42b). The reaction mixture was heated at 80° C. for 12 hours and concentrated. The residue was purified by column chromatography (dichloromethane/ethyl acetate). The obtained solid was purified by PTLC (dichloromethane/ethyl acetate=1:1) to obtain the title compound (34 mg, 28%) as an orange solid.

$^1$H NMR (400 MHz, DMSO-d6): δ (ppm)=9.02 (1H, s), 8.54 (1H, d, J=2.4 Hz), 8.16 (1H, dd, J=8.0 and 8.0 Hz), 7.32

(1H, s), 7.27-7.21 (2H, m), 7.16-7.09 (2H, m), 7.03-6.98 (1H, m), 4.51-4.46 (3H, m), 4.13 (1H, brs), 3.57 (2H, t, J=5.9 Hz), 2.76 (2H, t, J=5.9 Hz), 2.19-2.15 (2H, m), 1.94-1.91 (2H, m), 1.77-1.74 (2H, m), 1.56-1.48 (1H, m), 1.37-1.27 (2H, m), 1.09-0.99 (2H, m);
MS (ESI) m/z: 509 (M+H)+.

Example 44 trans-6-[3-(2-fluoro-phenyl)-ureido]-3,4-dihydro-1H-isoquinoline-2-carboxylic acid 4-(2H-tetrazol-5-ylmethyl)-cyclohexyl ester

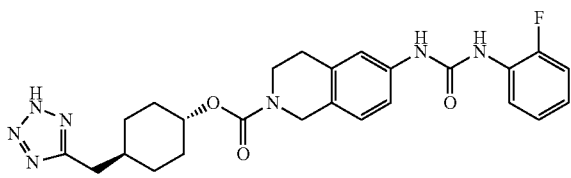 [SMILES: O=C(Nc1ccc2c(c1)CCN(C(=O)O[C@H]1CC[C@H](Cc3nn[nH]n3)CC1)C2)Nc1ccccc1F]

(44a) trans-benzoic acid 4-cyanomethyl-cyclohexyl ester

To a mixture of p-toluenesulfonyl chloride (4.71 g), benzoic acid (2.52 g), N-methylimidazole (4.9 mL), and acetonitrile (50 mL), an acetonitrile (50 mL) solution of trans-(4-hydroxy-cyclohexyl)-acetonitrile (2.87 g) obtained in Example (41a) was added at 0° C. The reaction mixture was warmed to room temperature, then stirred overnight, and then concentrated. The residue was diluted with ethyl acetate, then washed with water and saturated brine, and then concentrated. The residue was purified by column chromatography (hexane/ethyl acetate) to obtain the title compound (4.42 g, 88%) as a white solid.
1H NMR (400 MHz, CDCl3): δ (ppm)=8.04 (2H, dd, J=8.2 and 1.1 Hz), 7.57 (1H, dd, J=7.2 and 7.2 Hz), 7.45 (2H, dd, J=7.6 and 7.6 Hz), 4.98-4.90 (1H, m), 2.32 (2H, d, J=7.0 Hz), 2.21-2.17 (2H, m), 2.02-1.98 (2H, m), 1.83-1.72 (1H, m), 1.61-1.50 (2H, m), 1.36-1.27 (2H, m).

(44b) trans-benzoic acid 4-(2H-tetrazol-5-ylmethyl)-cyclohexyl ester

A mixture of trans-benzoic acid 4-cyanomethyl-cyclohexyl ester (3.42 g) obtained in Example (44a), trimethylsilyl azide (3.7 mL), di-n-butyltin oxide (348 mg), and toluene (30 mL) was heated at 110° C. for 48 hours. The progress of the reaction was stopped using methanol, and the reaction mixture was concentrated. The residue was diluted with ethyl acetate, followed by extraction with a saturated aqueous solution of sodium bicarbonate. The aqueous layer was acidified (pH=2) by the addition of 1 N hydrochloric acid, followed by extraction with ethyl acetate (×2). The organic layer was washed with saturated brine, then dried over sodium sulfate, and then concentrated to obtain the title compound (2.57 g, 64%) as a white solid.
1H NMR (400 MHz, CDCl3): δ (ppm)=8.05 (2H, d, J=7.0 Hz), 7.58 (1H, dd, J=7.4 and 7.4 Hz), 7.46 (2H, dd, J=7.6 and 7.6 Hz), 4.98-4.93 (1H, m), 2.98 (2H, d, J=7.1 Hz), 2.17-2.13 (2H, m), 2.02-1.96 (1H, m), 1.92-1.89 (2H, m), 1.63-1.51 (2H, m), 1.33-1.23 (2H, m).

(44c) trans-benzoic acid 4-[2-(4-methoxy-benzyl)-2H-tetrazol-5-ylmethyl]-cyclohexyl ester To an acetonitrile (20 mL) suspension of trans-benzoic acid 4-(2H-tetrazol-5-ylmethyl)-cyclohexyl ester (1.34 g) obtained in Example (44b), triethylamine (0.68 mL) and 4-methoxybenzyl chloride (0.70 mL) were added at room temperature. The reaction mixture was heated to reflux for 2 hours, cooled to room temperature, concentrated, then diluted with ethyl acetate, and filtered. The filtrate was washed with 1 N hydrochloric acid, then dried over sodium sulfate, and then concentrated. The residue was purified by column chromatography (hexane/ethyl acetate) to obtain the title compound (610 mg, 32%) as a colorless oil.
1H NMR (400 MHz, CDCl3): δ (ppm)=8.03 (2H, d, J=7.1 Hz), 7.55 (1H, dd, J=7.4 and 7.4 Hz), 7.43 (2H, dd, J=7.7 and 7.7 Hz), 7.34 (2H, d, J=8.6 Hz), 6.90 (2H, d, J=9.0 Hz), 5.66 (2H, s), 4.96-4.89 (1H, m), 3.80 (3H, s), 2.80 (2H, d, J=6.6 Hz), 2.13-2.09 (2H, m), 1.86-1.83 (3H, m), 1.54-1.44 (2H, m), 1.28-1.18 (2H, m).

(44d) trans-4-[2-(4-methoxy-benzyl)-2H-tetrazol-5-ylmethyl]-cyclohexanol

To a methanol (10 mL) solution of trans-benzoic acid 4-[2-(4-methoxy-benzyl)-2H-tetrazol-5-ylmethyl]-cyclohexyl ester (610 mg) obtained in Example (44c), sodium methoxide (28% methanol solution, 0.29 mL) was added at room temperature. After 2 days, the reaction mixture was concentrated. The residue was purified by column chromatography (hexane/ethyl acetate=5:1→1:1 and then dichloromethane/methanol=50:1) to obtain the title compound (396 mg, 87%) as a colorless oil.
1H NMR (400 MHz, CDCl3): δ (ppm)=7.33 (2H, d, J=8.2 Hz), 6.90 (2H, d, J=8.6 Hz), 5.65 (2H, s), 3.80 (3H, s), 3.59-3.53 (1H, m), 3.50 (1H, d, J=5.0 Hz), 2.75 (2H, d, J=6.7 Hz), 1.98-1.94 (2H, m), 1.78-1.74 (3H, m), 1.30-1.20 (2H, m), 1.14-1.03 (2H, m).

(44e) trans-6-[3-(2-fluoro-phenyl)-ureido]-3,4-dihydro-1H-isoquinoline-2-carboxylic acid 4-[2-(4-methoxy-benzyl)-2H-tetrazol-5-ylmethyl]-cyclohexyl ester The title compound (613 mg, quantitative yield) was obtained as a white solid in the same way as in Example (1e) from trans-4-[2-(4-methoxy-benzyl)-2H-tetrazol-5-ylmethyl]-cyclohexanol (396 mg) obtained in Example (44d) and 1-(2-fluoro-phenyl)-3-(1,2,3,4-tetrahydro-isoquinolin-6-yl)-urea hydrochloride (WO2006004200 A1) (321 mg).
1H NMR (400 MHz, DMSO-d6): δ (ppm)=9.01 (1H, s), 8.53 (1H, d, J=2.4 Hz), 8.16 (1H, dd, J=8.2 and 8.2 Hz), 7.34-7.30 (1H, m), 7.32 (2H, d, J=8.6 Hz), 7.27-7.21 (2H, m), 7.16-7.09 (1H, m), 7.03-6.98 (1H, m), 6.97-6.93 (1H, m), 6.95 (2H, d, J=9.0 Hz), 5.79 (2H, s), 4.49-4.46 (3H, m), 3.74 (3H, s), 3.56 (2H, t. J 5.9 Hz), 2.75 (2H, t, J=6.5 Hz), 2.73 (2H, d, J=6.7 Hz), 1.94-1.90 (2H, m), 1.72-1.68 (3H, m), 1.37-1.27 (2H, m), 1.18-1.10 (2H, m).

(44f) trans-6-[3-(2-fluoro-phenyl)-ureido]-3,4-dihydro-1H-isoquinoline-2-carboxylic acid 4-(2H-tetrazol-5-ylmethyl)-cyclohexyl ester An ethanol (6 mL) suspension of trans-6-[3-(2-fluoro-phenyl)-ureido]-3,4-dihydro-1H-isoquinoline-2-carboxylic acid 4-[2-(4-methoxy-benzyl)-2H-tetrazol-5-ylmethyl]-cyclohexyl ester (333 mg) obtained in Example (44e) and palladium carbon (55 mg) was stirred at room temperature for 3 days in a hydrogen atmosphere. The reaction mixture was filtered through Celite and concentrated. The residue was purified by column chromatography (dichloromethane/ethyl acetate=5:1→1:1 and then dichloromethane/methanol=25:1→5:1) to obtain the title compound (22 mg, 8%) as an off-white solid.
1H NMR (400 MHz, DMSO-d6): δ (ppm)=9.01 (1H, s), 8.53 (1H, d, J=2.7 Hz), 8.16 (1H, dd, J=8.2 and 8.2 Hz), 7.32 (1H, s), 7.26-7.21 (2H, m), 7.15-7.09 (2H, m), 7.03-6.98 (1H, m), 4.53-4.46 (3H, m), 3.56 (2H, t, J=6.0 Hz), 3.17 (1H, s), 2.77 (2H, t, J: 5.9 Hz), 2.77-2.73 (m, 2H), 1.96-1.91 (2H, m), 1.70-1.66 (3H, m), 1.37-1.28 (2H, m), 1.18-1.07 (2H, m);
MS (ESI) m/z: 494 (M+H)+.

Example 45 trans-6-[3-(2-fluoro-phenyl)-ureido]-3,4-dihydro-1H-isoquinoline-2-carboxylic acid 4-((S)-2,3-dihydroxy-propoxycarbonylmethyl)-cyclohexyl ester

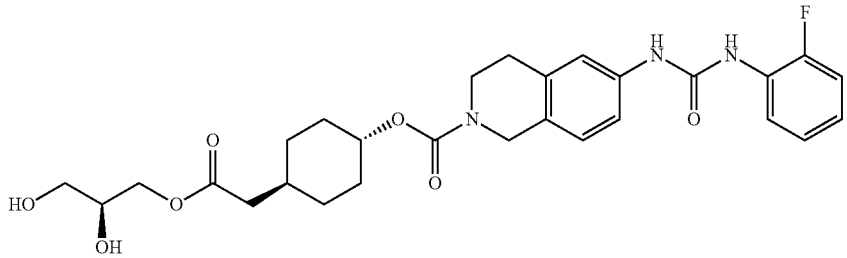 [SMILES: O=C(Nc1ccc2c(c1)CCN(C(=O)O[C@H]1CC[C@H](CC(=O)OC[C@@H](O)CO)CC1)C2)Nc1ccccc1F]

To a mixture of trans-6-[3-(2-fluoro-phenyl)-ureido]-3,4-dihydro-1H-isoquinoline-2-carboxylic acid 4-carboxymethyl-cyclohexyl ester (378 mg) obtained in Example 2 and acetonitrile (10 mL), p-toluenesulfonyl chloride (184 mg) and N-methylimidazole (0.19 mL) were added at 0° C. After 30 minutes, (R)-(2,2-dimethyl-[1,3]dioxolan-4-yl)-methanol (0.099 mL) and acetonitrile (2 mL) were added thereto. The reaction mixture was stirred for 30 minutes and then concentrated. The residue was diluted with ethyl acetate, washed with water and saturated brine, then dried over sodium sulfate, and then concentrated. The residue was purified by column chromatography (dichloromethane/methanol) to obtain ester (404 mg, 86%) as an orange oil. To a mixture of this ester (404 mg) and methanol (6 mL), 1 N hydrochloric acid (1.8 mL) was added. The reaction mixture was stirred overnight and concentrated. The residue was purified by column chromatography (dichloromethane/methanol) to obtain a yellow solid. This yellow solid was vigorously stirred in isopropyl ether, then collected by filtration, and then dried under reduced pressure to obtain the title compound (193 mg, 51%) as a yellow solid.

$^1$H NMR (400 MHz, DMSO-d6): δ (ppm)=9.03 (1H, s), 8.54 (1H, s), 8.15 (1H, dd, J=8.2 and 8.2 Hz), 7.32 (1H, s), 7.25 (1H, dd, J=8.2 and 1.2 Hz), 7.22 (1H, dd, J=8.2 and 1.6 Hz), 7.16-7.09 (2H, m), 7.03-6.98 (1H, m), 4.86 (1H, d, J=5.1 Hz), 4.62 (1H, t, J=5.9 Hz), 4.49-4.46 (3H, m), 4.05 (1H, dd, J=11.3 and 4.3 Hz), 3.91 (1H, dd, J=11.1 and 6.4 Hz), 3.65-3.62 (1H, m), 3.57 (2H, t, J=6.0 Hz), 3.38-3.31 (2H, m), 2.76 (2H, t, J=5.8 Hz), 2.22 (2H, d, J=7.0 Hz), 1.95-1.91 (2H, m), 1.77-1.73 (2H, m), 1.57-1.50 (1H, m), 1.39-1.30 (2H, m), 1.14-1.05 (2H, m);
MS (ESI) m/z: 544 (M+H)$^+$.

Example 46 trans-6-[3-(2-fluoro-phenyl)-ureido]-3,4-dihydro-1H-isoquinoline-2-carboxylic acid 4-((R)-2,3-dihydroxy-propoxycarbonylmethyl)-cyclohexyl ester

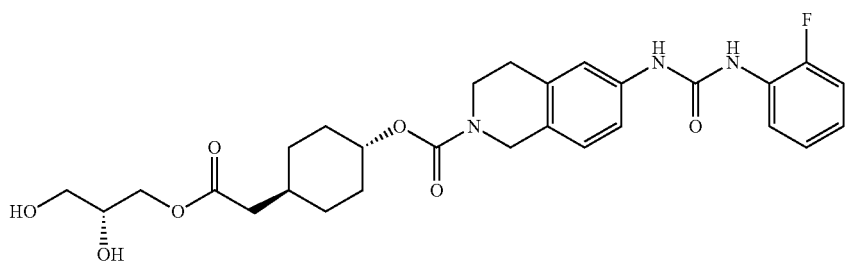 [SMILES: O=C(Nc1ccc2c(c1)CCN(C(=O)O[C@H]1CC[C@H](CC(=O)OC[C@H](O)CO)CC1)C2)Nc1ccccc1F]

Ester (427 mg, 92%) was obtained as an orange oil in the same way as in (Example 45) from trans-6-[3-(2-fluoro-phenyl)-ureido]-3,4-dihydro-1H-isoquinoline-2-carboxylic acid 4-carboxymethyl-cyclohexyl ester (378 mg) obtained in Example 2 and (S)-(2,2-dimethyl-[1,3]dioxolan-4-yl)-methanol (0.099 mL). From this ester (427 mg), the title compound (138 mg, 35%) was obtained as a white solid in the same way as in (Example 45).

$^1$H NMR (400 MHz, DMSO-d6): δ (ppm) 9.05 (1H, s), 8.56 (1H, s), 8.15 (1H, dd, J=8.4 and 8.4 Hz), 7.32 (1H, s), 7.26-7.21 (2H, m), 7.16-7.09 (2H, m), 7.03-6.98 (1H, m), 4.85 (1H, d, J=5.5 Hz), 4.61 (1H, t, J=5.6 Hz), 4.53-4.47 (3H, m), 4.07-4.04 (1H, m), 3.93-3.89 (1H, m), 3.66-3.62 (2H, m), 3.57 (2H, t, J=5.7 Hz), 3.37-3.32 (2H, m), 2.76 (2H, t, J=5.2 Hz), 2.23 (2H, d, J=6.7 Hz), 1.95-1.91 (2H, m), 1.77-1.67 (3H, m), 1.40-1.30 (2H, m), 1.15-1.03 (2H, m);
MS (ESI) m/z: 544 (M+H)$^+$.

Example 47 trans-6-(6-chloro-benzoxazol-2-ylamino)-3,4-dihydro-1H-isoquinoline-2-carboxylic acid 4-carboxymethyl-cyclohexyl ester

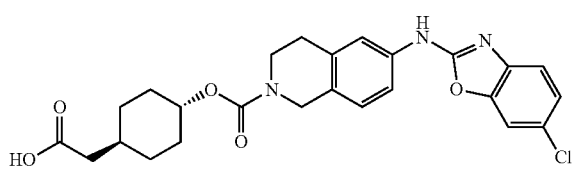 [SMILES: O=C(O)C[C@H]1CC[C@H](OC(=O)N2CCc3cc(Nc4nc5ccc(Cl)cc5o4)ccc3C2)CC1]

(47a) (6-chloro-benzoxazol-2-yl)-(1,2,3,4-tetrahydro-isoquinolin-6-yl)-amine hydrochloride The title compound (845 mg, 62%) was obtained as a light brown solid in the same way as in Example (25a) from 6-amino-2N-Boc-1,2,3,4-tetrahydroisoquinoline (1.00 g) and 2,6-dichlorobenzoxazole (761 mg).
MS (ESI) m/z: 300 (M+H)$^+$.

(47b) trans-6-(6-chloro-benzoxazol-2-ylamino)-3,4-dihydro-1H-isoquinoline-2-carboxylic acid 4-carboxymethyl-cyclohexyl ester Methyl ester (104 mg, 74%) was obtained in the same way as in Example (1e) from trans-(4-hydroxy-cyclohexyl)-acetic acid methyl/ester (74 mg) obtained in Example (1d) and (6-chloro-benzoxazol-2-yl)-(1,2,3,4-tetrahydro-isoquinolin-6-yl)-amine hydrochloride (103 mg) obtained in Example (47a). This methyl ester (79 mg) was hydrolyzed in the same way as in Example 2 to obtain the title compound (43 mg, 56%) as a white solid.
$^1$H NMR (400 MHz, DMSO-d6): δ (ppm)=12.1 (1H, brs), 10.7 (1H, s), 7.74-7.17 (7H, m), 4.50 (2H, s), 3.65-3.55 (2H, m), 2.87-2.77 (2H, m), 2.12 (2H, d, J=6.6 Hz), 1.99-1.90 (2H, m), 1.84-1.60 (3H, m), 1.45-1.27 (2H, m), 1.20-1.02 (2H, m).
MS (ESI) m/z: 484 (M+H)$^+$.

Example 48 trans-6-[3-(2-ethoxy-5-methyl-phenyl)-ureido]-3,4-dihydro-1H-isoquinoline-2-carboxylic acid 4-carboxymethyl-cyclohexyl ester

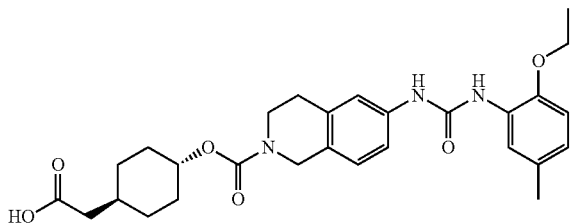 [SMILES: CCOc1ccc(C)cc1NC(=O)Nc1ccc2c(c1)CCN(C(=O)O[C@H]1CC[C@H](CC(=O)O)CC1)C2]

(48a) 6-[3-(2-ethoxy-5-methyl-phenyl)-ureido]-3,4-dihydro-1H-isoquinoline-2-carboxylic acid tert-butyl ester The title compound (1.70 g, quantitative yield) was obtained as a white solid in the same way as in Example (28a) from 6-amino-2N-Boc-1,2,3,4-tetrahydroisoquinoline (993 mg) and 2-ethoxy-5-methyl-aniline (605 mg).
$^1$H NMR (400 MHz, CDCl$_3$): δ (ppm)=7.97 (1H, d, J=1.6 Hz), 7.29-7.24 (3H, m), 7.06 (1H, d, J=7.1 Hz), 6.78 (1H, dd, J=8.6 and 2.0 Hz), 6.75 (1H, dd, J=9.3 and 9.3 Hz), 6.69 (1H, brs), 4.54 (2H, s), 4.01 (2H, q, J=6.8 Hz), 3.63 (2H, brs), 2.81 (2H, t, J=5.9 Hz), 2.29 (3H, s), 1.50 (9H, s), 1.34 (3H, t, J=7.1 Hz).

(48b) 1-(2-ethoxy-5-methyl-phenyl)-3-(1,2,3,4-tetrahydro-isoquinolin-6-yl)-urea hydrochloride The title compound (1.45 g, quantitative yield) was obtained as a white solid in the same way as in Example (22b) from 6-[3-(2-ethoxy-5-methyl-phenyl)-ureido]-3,4-dihydro-1H-isoquinoline-2-carboxylic acid tert-butyl ester (1.70 g) obtained in Example (48a).
$^1$H NMR (400 MHz, DMSO-d6): δ (ppm)=9.64 (1H, s), 9.27 (1H, brs), 8.13 (1H, s), 7.97 (1H, d, J=2.0 Hz), 7.45 (1H, d, J=1.5 Hz), 7.28 (1H, dd, J=8.4 and 2.2 Hz), 7.13 (1H, d, J=8.6 Hz), 6.88 (1H, d, J=8.2 Hz), 6.73 (1H, dd, J=8.2 and 2.4 Hz), 4.19 (2H, brs), 4.08 (2H, q, J=7.0 Hz), 3.36-3.33 (2H, m), 2.98 (2H, t, J=6.1 Hz), 2.22 (3H, s), 1.39 (3H, t, J=7.0 Hz).

(48c) trans-6-[3-(2-ethoxy-5-methyl-phenyl)-ureido]-3,4-dihydro-1H-isoquinoline-2-carboxylic acid 4-carboxymethyl-cyclohexyl ester Methyl ester (731 mg, 94%) was obtained in the same way as in Example (1e) from trans-(4-hydroxy-cyclohexyl)-acetic acid methyl ester (361 mg) obtained in Example (1d) and 1-(2-ethoxy-5-methyl-phenyl)-3-(1,2,3,4-tetrahydro-isoquinolin-6-yl)-urea hydrochloride (542 mg) obtained in Example (48b). This methyl ester (731 mg) was hydrolyzed in the same way as in Example 2 to obtain the title compound (602 mg, 85%) as a white solid.
$^1$H NMR (400 MHz, DMSO-d6): δ (ppm)=12.1 (1H, s), 9.34 (1H, s), 8.00 (2H, d, J=9.4 Hz), 7.37 (1H, s), 7.21 (1H, d, 7.8 Hz), 7.09 (1H, d, J=8.6 Hz), 7.09 (1H, d, J=8.6 Hz), 6.72 (1H, dd, J=8.2 and 2.0 Hz), 4.51-4.46 (3H, m), 4.09 (2H, q, J=7.1 Hz), 3.57 (2H, t, J=6.1 Hz), 2.76 (2H, t, J=5.7 Hz), 2.22 (3H, s), 2.11 (2H, d, J=7.1 Hz), 1.95-1.90 (2H, m), 1.77-1.73 (2H, m), 1.67-1.63 (1H, m), 1.39 (3H, t, J=6.8 Hz), 1.37-1.29 (2H, m), 1.12-1.01 (2H, m);
MS (ESI) m/z: 510 (M+H)$^+$.

Example 49 trans-6-[3-(3-methoxy-phenyl)-ureido]-3,4-dihydro-1H-isoquinoline-2-carboxylic acid 4-carboxymethyl-cyclohexyl ester

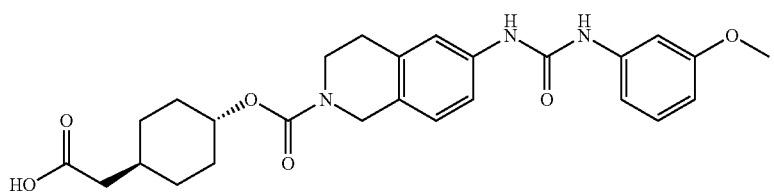 [SMILES: COc1cccc(NC(=O)Nc2ccc3c(c2)CCN(C(=O)O[C@H]2CC[C@H](CC(=O)O)CC2)C3)c1]

(49a) 6-[3-(3-methoxy-phenyl)-ureido]-3,4-dihydro-1H-isoquinoline-2-carboxylic acid tert-butyl ester The title compound (1.59 g, quantitative yield) was obtained as a white solid in the same way as in Example (26a) from 6-amino-2N-Boc-1,2,3,4-tetrahydroisoquinoline (993 mg) and 3-methoxy-phenyl isocyanate (0.63 mL).

$^1$H NMR (400 MHz, CDCl$_3$): δ (ppm)=7.29-7.20 (2H, m), 7.24 (1H, dd, J=6.8 and 6.8 Hz), 7.10-6.94 (2H, m), 7.07 (1H, s), 6.85 (1H, d, J=9.0 Hz), 6.77 (1H, brs), 6.66 (1H, dd, J=8.2 and 2.7 Hz), 4.52 (2H, s), 3.80 (3H, s), 3.61 (2H, t, J=5.2 Hz), 2.78 (2H, t, J=5.9 Hz), 1.50 (9H, s).

(49b) 1-(3-methoxy-phenyl)-3-(1,2,3,4-tetrahydro-isoquinolin-6-yl)-urea hydrochloride The title compound (1.34 g, quantitative yield) was obtained as a white solid in the same way as in Example (22b) from 6-[3-(3-methoxy-phenyl)-ureido]-3,4-dihydro-1H-isoquinoline-2-carboxylic acid tert-butyl ester (1.59 g) obtained in Example (49a).

$^1$H NMR (400 MHz, DMSO-d6): δ (ppm)=9.10 (1H, brs), 9.05 (2H, s), 7.40 (1H, d, J=1.9 Hz), 7.28 (1H, dd, J=8.4 and 2.1 Hz), 7.20 (1H, dd, J=2.2 and 2.2 Hz), 7.18 (1H, dd, J=8.2 and 8.2 Hz), 7.13 (1H, d, J=8.2 Hz), 6.92 (1H, dd, J=8.2 and 2.0 Hz), 6.55 (1H, dd, J=8.2 and 2.3 Hz), 4.19 (2H, s), 3.73 (3H, s), 3.36 (2H, t, J=6.2 Hz), 2.98 (2H, t, J=6.2 Hz).

(49c) trans-6-[3-(3-methoxy-phenyl)-ureido]-3,4-dihydro-1H-isoquinoline-2-carboxylic acid 4-carboxymethyl-cyclohexyl ester Methyl ester (743 mg, quantitative yield) was obtained in the same way as in Example (1e) from trans-(4-hydroxy-cyclohexyl)-acetic acid methyl ester (361 mg) obtained in Example (1d) and 1-(3-methoxy-phenyl)-3-(1,2,3,4-tetrahydro-isoquinolin-6-yl)-urea hydrochloride (500 mg) obtained in Example (49b). This methyl ester (743 mg) was hydrolyzed in the same way as in Example 2 to obtain the title compound (603 mg, 85%) as a white solid.

$^1$H NMR (400 MHz, DMSO-d6): δ (ppm)=12.1 (1H, s), 8.73 (1H, s), 8.66 (1H, s), 7.32 (1H, s), 7.23-7.19 (2H, m), 7.17 (1H, t, J=8.4 Hz), 7.08 (1H, d, J=8.3 Hz), 6.92 (1H, dd, J=7.7 and 1.3 Hz), 6.55 (1H, dd, J=7.8 and 2.4 Hz), 4.51-4.46 (3H, m), 3.73 (3H, s), 3.57 (2H, t, J=5.9 Hz), 2.75 (2H, t, J=5.7 Hz), 2.12 (2H, d, J=7.0 Hz), 1.95-1.91 (2H, m), 1.77-1.74 (2H, m), 1.68-1.62 (1H, m), 1.39-1.29 (2H, m), 1.11-1.02 (2H, m);

MS (ESI) m/z: 482 (M+H)$^+$.

Example 50 trans-6-(3-phenyl-ureido)-3,4-dihydro-1H-isoquinoline-2-carboxylic acid 4-carboxymethyl-cyclohexyl ester

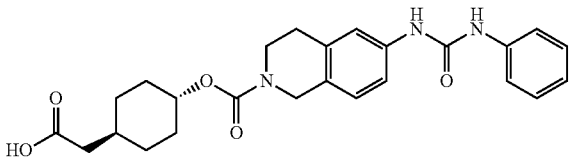 [SMILES: O=C(O)C[C@H]1CC[C@H](OC(=O)N2CCc3cc(NC(=O)Nc4ccccc4)ccc3C2)CC1]

(50a) 6-(3-phenyl-ureido)-3,4-dihydro-1H-isoquinoline-2-carboxylic acid tert-butyl ester The title compound (261 mg, quantitative yield) was obtained as a white solid in the same way as in Example (26a) from 6-amino-2N-Boc-1,2,3,4-tetrahydroisoquinoline (220 mg) and phenyl isocyanate (0.12 mL).

$^1$H NMR (400 MHz, CDCl$_3$): δ (ppm)=7.37-7.32 (3H, m), 7.31-7.01 (5H, m), 6.78-6.67 (2H, m), 4.52 (2H, s), 3.62 (2H, t, J=5.2 Hz), 2.79 (2H, t, J=5.9 Hz), 1.50 (9H, s).

(50b) 1-phenyl-3-(1,2,3,4-tetrahydro-isoquinolin-6-yl)-urea hydrochloride

The title compound (215 mg, quantitative yield) was obtained as a white solid in the same way as in Example (22b) from 6-(3-phenyl-ureido)-3,4-dihydro-1H-isoquinoline-2-carboxylic acid tert-butyl ester (261 mg) obtained in Example (50a).

$^1$H NMR (400 MHz, DMSO-d6): δ (ppm)=8.98 (2H, brs), 8.96 (1H, s), 7.45 (2H, d, J r 7.9 Hz), 7.40 (1H, d, J=2.0 Hz), 7.30-7.26 (3H, m), 7.13 (1H, d, J=8.6 Hz), 6.97 (1H, dd, J=7.4 and 7.4 Hz), 4.19 (2H, s), 3.37-3.31 (2H, m), 2.97 (2H, t, J=6.5 Hz).

(50c) trans-6-(3-phenyl-ureido)-3,4-dihydro-1H-isoquinoline-2-carboxylic acid 4-carboxymethyl-cyclohexyl ester Methyl ester (329 mg, quantitative yield) was obtained in the same way as in Example (1e) from trans-(4-hydroxy-cyclohexyl)-acetic acid methyl ester (171 mg) obtained in Example (1d) and 1-phenyl-3-(1,2,3,4-tetrahydro-isoquinolin-6-yl)-urea hydrochloride (215 mg) obtained in Example (50b). This methyl ester (329 mg) was hydrolyzed in the same way as in Example 2 to obtain the title compound (281 mg, 88%) as a white solid.

$^1$H NMR (400 MHz, DMSO-d6): δ (ppm)=12.1 (1H, s), 8.75 (1H, s), 8.71 (1H, s), 7.45 (2H, d, J=7.4 Hz), 7.32-7.22 (4H, m), 7.09 (1H, d, J=8.2 Hz), 6.96 (1H, dd, J=7.2 and 7.2 Hz), 4.51-4.46 (3H, m), 3.57 (2H, t, J=5.6 Hz), 2.75 (2H, t, J=5.9 Hz), 2.11 (2H, J=7.0 Hz), 1.95-1.91 (2H, m), 1.77-1.74 (2H, m), 1.68-1.62 (1H, m), 1.39-1.29 (2H, m), 1.12-1.02 (2H, m);

MS (ESI) m/z: 452 (M+H)$^+$.

Example 51 trans-6-[3-(3-difluoromethoxy-phenyl)-ureido]-3,4-dihydro-1H-isoquinoline-2-carboxylic acid 4-carboxymethyl-cyclohexyl ester

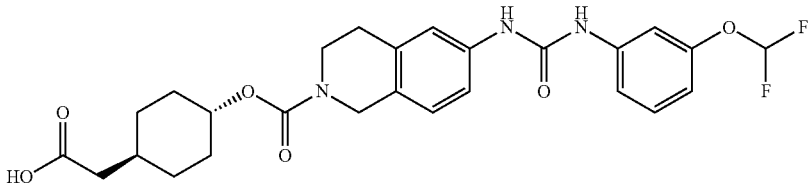 [SMILES: O=C(O)C[C@H]1CC[C@H](OC(=O)N2CCc3cc(NC(=O)Nc4cccc(OC(F)F)c4)ccc3C2)CC1]

(51a) 6-[3-(3-difluoromethoxy-phenyl)-ureido]-3,4-dihydro-1H-isoquinoline-2-carboxylic acid tert-butyl ester The title compound (1.63 g, 94%) was obtained as a white solid in the same way as in Example (28a) from 6-amino-2N-Boc-1,2,3,4-tetrahydroisoquinoline (992 mg) and 3-difluoromethoxy-aniline (0.49 mL).
$^1$H NMR (400 MHz, CDCl$_3$): δ (ppm)=7.41-6.59 (7H, m), 7.16 (1H, d, J=9.0 Hz), 6.81 (1H, dd, J=8.0 and 2.2 Hz), 6.49 (1H, dd, J=74.1 and 74.1 Hz), 4.50 (2H, s), 3.61 (2H, t, J=6.1 Hz), 2.76 (2H, s), 1.51 (9H, s).

(51b) 1-(3-difluoromethoxy-phenyl)-3-(1,2,3,4-tetrahydro-isoquinolin-6-yl)-urea hydrochloride The title compound (1.35 g, 98%) was obtained as a white solid in the same way as in Example (22b) from 6-[3-(3-difluoromethoxy-phenyl)-ureido]-3,4-dihydro-1H-isoquinoline-2-carboxylic acid tert-butyl ester (1.63 g) obtained in Example (51a).
$^1$H NMR (400 MHz, DMSO-d6): δ (ppm)=9.25 (1H, s), 9.08 (1H, s), 9.03 (1H, brs), 7.49 (1H, dd, J=2.1 and 2.1 Hz), 7.40 (1H, d, J=2.0 Hz), 7.21 (1H, dd, J=74.1 and 74.1 Hz), 7.32 (1H, dd, J=8.2 and 8.2 Hz), 7.29 (1H, dd, J=8.6 and 2.4 Hz), 7.19-7.16 (1H, m), 7.14 (1H, d, J=8.2 Hz), 6.78 (1H, dd, J=8.4 and 2.6 Hz), 4.20 (2H, s), 3.36 (2H, t, J=6.5 Hz), 2.98 (2H, t, J=6.1 Hz).

(51c) trans-6-[3-(3-difluoromethoxy-phenyl)-ureido]-3,4-dihydro-1H-isoquinoline-2-carboxylic acid 4-carboxymethyl-cyclohexyl ester Methyl ester (797 mg, quantitative yield) was obtained in the same way as in Example (1e) from trans-(4-hydroxy-cyclohexyl)-acetic acid methyl ester (361 mg) obtained in Example (1d) and 1-(3-difluoromethoxy-phenyl)-3-(1,2,3,4-tetrahydro-isoquinolin-6-yl)-urea hydrochloride (555 mg) obtained in Example (51b). This methyl ester (797 mg) was hydrolyzed in the same way as in Example 2 to obtain the title compound (619 mg, 80%) as a white solid.

$^1$H NMR (400 MHz, DMSO-d6): δ (ppm)=12.1 (1H, s), 9.08 (1H, brs), 8.88 (1H, brs), 7.49 (1H, d, J=2.3 Hz), 7.21 (1H, dd, J=74.1 and 74.1 Hz), 7.34-7.29 (2H, m), 7.25-7.18 (2H, m), 7.09 (1H, d, J=8.6 Hz), 6.76 (1H, d, J=10.2 Hz), 4.48-4.47 (3H, m), 3.57 (2H, t, J=5.8 Hz), 2.75 (2H, t, J=6.1 Hz), 2.11 (2H, d, J=7.5 Hz), 1.95-1.90 (2H, m), 1.78-1.74 (2H, m), 1.68-1.62 (1H, m), 1.39-1.29 (2H, m), 1.12-1.02 (2H, m);
MS (ESI) m/z: 518 (M+H)$^+$.

Example 52 trans-6-[3-(3-trifluoromethoxy-phenyl)-ureido]-3,4-dihydro-1H-isoquinoline-2-carboxylic acid 4-carboxymethyl-cyclohexyl ester

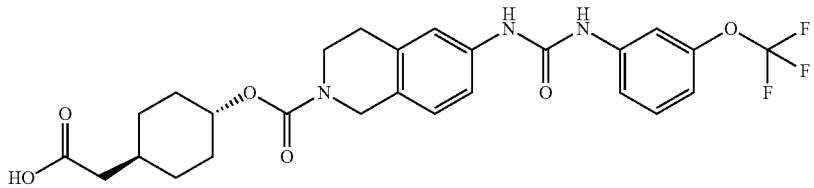 [SMILES: O=C(O)C[C@H]1CC[C@H](OC(=O)N2CCc3cc(NC(=O)Nc4cccc(OC(F)(F)F)c4)ccc3C2)CC1]

(52a) 6-[3-(3-trifluoromethoxy-phenyl)-ureido]-3,4-dihydro-1H-isoquinoline-2-carboxylic acid tert-butyl ester The title compound (1.72 g, 95%) was obtained as a white solid in the same way as in Example (28a) from 6-amino-2N-Boc-1,2,3,4-tetrahydroisoquinoline (992 mg) and 3-trifluoromethoxy-aniline (0.53 mL).
$^1$H NMR (400 MHz, CDCl$_3$): δ (ppm)=7.41 (1H, brs), 7.35-6.55 (7H, m), 6.91 (1H, d, J=7.8 Hz), 4.51 (2H, s), 3.62 (2H, t, J=6.0 Hz), 2.77 (2H, brs), 1.52 (9H, s).

(52b) 1-(3-trifluoromethoxy-phenyl)-3-(1,2,3,4-tetrahydro-isoquinolin-6-yl)-urea hydrochloride The title compound (1.47 g, quantitative yield) was obtained as a white solid in the same way as in Example (22b) from 6-[3-(3-trifluoromethoxy-phenyl)-ureido]-3,4-dihydro-1H-isoquinoline-2-carboxylic acid tert-butyl ester (1.72 g) obtained in Example (52a).
$^1$H NMR (400 MHz, DMSO-d6): δ (ppm)=9.36 (1H, s), 9.10 (1H, s), 8.99 (1H, brs), 7.72 (1H, s), 7.42-7.38 (2H, m), 7.30-7.26 (2H, m), 7.14 (1H, d, J=8.2 Hz), 6.96-6.93 (1H, m), 4.20 (2H, s), 3.36 (2H, t, J=6.4 Hz), 2.98 (2H, t, J=6.2 Hz).

(52c) trans-6-[3-(3-trifluoromethoxy-phenyl)-ureido]-3,4-dihydro-1H-isoquinoline-2-carboxylic acid 4-carboxymethyl-cyclohexyl ester Methyl ester (811 mg, 99%) was obtained in the same way as in Example (1e) from trans-(4-hydroxy-cyclohexyl)-acetic acid methyl ester (361 mg) obtained in Example (1d) and 1-(3-trifluoromethoxy-phenyl)-3-(1,2,3,4-tetrahydro-isoquinolin-6-yl)-urea hydrochloride (582 mg) obtained in Example (52b). This methyl ester (811 mg) was hydrolyzed in the same way as in Example 2 to obtain the title compound (625 mg, 79%) as a white solid.

$^1$H NMR (400 MHz, DMSO-d6): δ (ppm)=12.1 (1H, s), 9.05 (1H, s), 8.77 (1H, s), 7.71 (1H, s), 7.40 (1H, dd, J=8.2 and 8.2 Hz), 7.33 (1H, s), 7.28 (1H, dd, J=7.8 and 1.5 Hz), 7.22 (1H, dd, J=8.2 and 0.8 Hz), 7.10 (1H, d, J=8.6 Hz), 6.94 (1H, d, J=8.2 Hz), 4.51-4.47 (3H, m), 3.57 (2H, t, J=5.8 Hz), 2.76 (2H, t, J=5.7 Hz), 2.12 (2H, d, J=7.1 Hz), 1.95-1.91 (2H, m), 1.77-1.74 (2H, m), 1.67-1.62 (1H, m), 1.39-1.30 (2H, m), 1.11-1.03 (2H, m);

MS (ESI) m/z: 536 (M+H)$^+$.

Example 53 trans-6-[3-(3-ethoxy-2-methyl-phenyl)-ureido]-3,4-dihydro-1H-isoquinoline-2-carboxylic acid 4-carboxymethyl-cyclohexyl ester

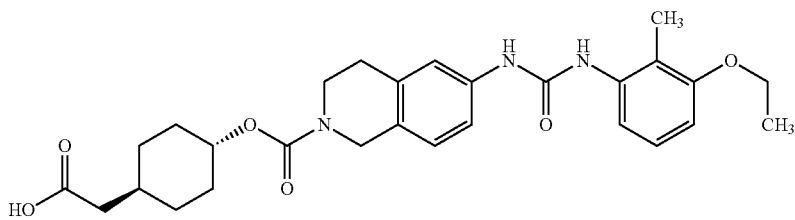 [SMILES: CCOc1cccc(NC(=O)Nc2ccc3c(c2)CCN(C(=O)O[C@H]2CC[C@H](CC(=O)O)CC2)C3)c1C]

(53a) 6-[3-(3-ethoxy-2-methyl-phenyl)-ureido]-3,4-dihydro-1H-isoquinoline-2-carboxylic acid tert-butyl ester The title compound (1.26 g, 78%) was obtained as a white solid in the same way as in Example (28a) from 6-amino-2N-Boc-1,2,3,4-tetrahydroisoquinoline (943 mg) and 3-ethoxy-2-methyl-aniline (EP1679308) (576 mg).

$^1$H NMR (400 MHz, CDCl$_3$): δ (ppm)=7.23-7.14 (2H, m), 7.19 (1H, dd, J=8.1 and 8.1 Hz), 7.06 (1H, d, J=8.3 Hz), 7.02 (1H, d, J=7.8 Hz), 6.78 (1H, d, J=8.3 Hz), 6.45 (1H, s), 6.18 (1H, s), 4.51 (2H, s), 4.06 (2H, q, J=7.0 Hz), 3.61 (2H, t, J=4.9 Hz), 2.79 (2H, t, J=5.7 Hz), 2.17 (3H, s), 1.44 (3H, t, J=7.1 Hz), 1.49 (9H, s).

(53b) 1-(3-ethoxy-2-methyl-phenyl)-3-(1,2,3,4-tetrahydro-isoquinolin-6-yl)-urea hydrochloride The title compound (1.08 g, quantitative yield) was obtained as an off-white solid in the same way as in Example (22b) from 6-[3-(3-ethoxy-2-methyl-phenyl)-ureido]-3,4-dihydro-1H-isoquinoline-2-carboxylic acid tert-butyl ester (1.26 g) obtained in Example (53a).

$^1$H NMR (400 MHz, DMSO-d6): δ (ppm)=9.28 (1H, s), 9.02 (1H, brs), 8.11 (1H, s), 7.42 (1H, d, J=4.3 Hz), 7.40 (1H, s), 7.28 (1H, dd, J=8.2 and 2.3 Hz), 7.12 (1H, d, J=8.6 Hz), 7.07 (1H, dd, J=8.1 and 8.0 Hz), 6.67 (1H, d, J==7.8 Hz), 4.19 (2H, s), 4.01 (2H, q, J=6.9 Hz), 3.37-3.34 (2H, m), 2.97 (2H, t, J=6.2 Hz), 2.09 (3H, s), 1.35 (3H, t, J=6.9 Hz).

(53c) trans-6-[3-(3-ethoxy-2-methyl-phenyl)-ureido]-3,4-dihydro-1H-isoquinoline-2-carboxylic acid 4-carboxymethyl-cyclohexyl ester Methyl ester (785 mg, quantitative yield) was obtained in the same way as in Example (1e) from trans-(4-hydroxy-cyclohexyl)-acetic acid methyl ester (361 mg) obtained in Example (1d) and 1-(3-ethoxy-2-methyl-phenyl)-3-(1,2,3,4-tetrahydro-isoquinolin-6-yl)-urea hydrochloride obtained in Example (53b). This methyl ester (785 mg) was hydrolyzed in the same way as in Example 2 to obtain the title compound (665 mg, 87%) as a white solid.

$^1$H NMR (400 MHz, DMSO-d6): δ (ppm)=12.1 (1H, s), 8.98 (1H, s), 7.96 (1H, s), 7.42 (1H, d, J=7.8 Hz), 7.33 (1H, s), 7.22 (1H, d, J=8.2 Hz), 7.08 (1H, d, J=8.2 Hz), 7.06 (1H, d, J=8.3 Hz), 6.67 (1H, d, J=8.2 Hz), 4.51-4.46 (3H, m), 4.01 (2H, q, J=7.0 Hz), 3.5.7 (2H, t, J=5.9 Hz), 2.75 (2H, t, J=5.7 Hz), 2.11 (2H, d, J=6.6 Hz), 2.08 (3H, s), 1.95-1.91 (2H, m), 1.77-1.74 (2H, m), 1.67-1.63 (1H, m), 1.39-1.29 (2H, m), 1.35 (3H, t, J=6.9 Hz), 1.11-1.01 (2H, m);

MS (ESI) m/z: 510 (M+H)+.

Example 54 trans-6-[3-(3-ethoxy-4-methyl-phenyl)-ureido]-3,4-dihydro-1H-isoquinoline-2-carboxylic acid 4-carboxymethyl-cyclohexyl ester

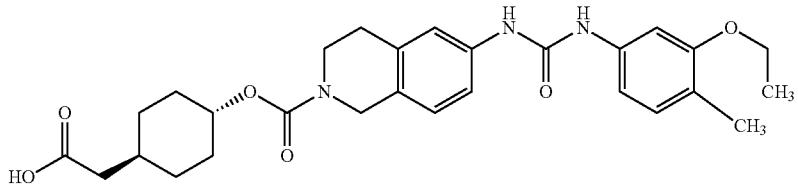 [SMILES: CCOc1cc(NC(=O)Nc2ccc3c(c2)CCN(C(=O)O[C@H]2CC[C@H](CC(=O)O)CC2)C3)ccc1C]

(54a) 6-[3-(3-ethoxy-4-methyl-phenyl)-ureido]-3,4-dihydro-1H-isoquinoline-2-carboxylic acid tert-butyl ester The title compound (1.55 g, 96%) was obtained as a pink solid in the same way as in Example (28a) from 6-amino-2N-Boc-1,2,3,4-tetrahydroisoquinoline (943 mg) and 3-ethoxy-4-methyl-aniline (Chemische Berichte 1906, 39, 3248.) (574 mg).

1H NMR (400 MHz, CDCl3): δ (ppm)=7.19-6.91 (3H, m), 7.07 (1H, d, J=7.8 Hz), 7.00 (1H, d, J=1.9 Hz), 6.69 (1H, brs), 6.67 (1H, d, J=2.0 Hz), 6.62 (1H, brs), 4.52 (2H, s), 4.01 (2H, q, J=6.9 Hz), 3.61 (2H, brs), 2.78 (2H, t, J=5.9 Hz), 2.19 (3H, s), 1.49 (9H, s), 1.41 (3H, t, J=6.9 Hz).

(54b) 1-(3-ethoxy-4-methyl-phenyl)-3-(1,2,3,4-tetrahydro-isoquinolin-6-yl)-urea hydrochloride The title compound (1.28 g, 98%) was obtained as an off-white solid in the same way as in Example (22b) from 6-[3-(3-ethoxy-4-methyl-phenyl)-ureido]-3,4-dihydro-1H-isoquinoline-2-carboxylic acid tert-butyl ester (1.55 g) obtained in Example (54a).

1H NMR (400 MHz, DMSO-d6): δ (ppm)=9.09 (1H, s), 8.98 (1H, s), 8.92 (1H, s), 7.41 (1H, d, J=1.6 Hz), 7.27 (1H, dd, J=8.4 and 2.1 Hz), 7.22 (1H, d, J=2.0 Hz), 7.12 (1H, d, J=8.6 Hz), 7.01 (1H, d, J=8.6 Hz), 6.79 (1H, dd, J=8.0 and 2.1 Hz), 4.19 (2H, brs), 3.99 (2H, q, J=6.9 Hz), 3.47 (2H, brs), 2.98 (2H, t, J=6.2 Hz), 2.08 (3H, s), 1.36 (3H, t, J=7.1 Hz).

(54c) trans-6-[3-(3-ethoxy-4-methyl-phenyl)-ureido]-3,4-dihydro-1H-isoquinoline-2-carboxylic acid 4-carboxymethyl-cyclohexyl ester Methyl ester (785 mg, quantitative yield) was obtained in the same way as in Example (1e) from trans-(4-hydroxy-cyclohexyl)-acetic acid methyl ester (361 mg) obtained in Example (1d) and 1-(3-ethoxy-4-methyl-phenyl)-3-(1,2,3,4-tetrahydro-isoquinolin-6-yl)-urea hydrochloride (543 mg) obtained in Example (54b). This methyl ester (785 mg) was hydrolyzed in the same way as in Example 2 to obtain the title compound (635 mg, 83%) as a white solid.

1H NMR (400 MHz, DMSO-d6): δ (ppm)=12.1 (1H, s), 8.65 (1H, s), 8.64 (1H, s), 7.33 (1H, s), 7.22 (1H, d, J=2.0 Hz), 7.20 (1H, d, J=9.0 Hz), 7.08 (1H, d, J=8.2 Hz), 7.00 (1H, d, J=8.2 Hz), 6.79 (1H, dd, J=8.0 and 2.1 Hz), 4.49-4.46 (3H, m), 3.99 (2H, q, J=6.9 Hz), 3.57 (2H, t, J=5.9 Hz), 2.75 (2H, t, J=6.0 Hz), 2.11 (2H, d, J=7.0 Hz), 2.07 (3H, s), 1.95-1.91 (2H, m), 1.77-1.74 (2H, m), 1.68-1.63 (1H, m), 1.39-1.29 (2H, m), 1.35 (3H, t, J=7.1 Hz), 1.11-1.02 (2H, m);

MS (ESI) m/z: 510 (M+H)+.

Example 55 trans-6-[3-(5-ethoxy-2-methyl-phenyl)-ureido]-3,4-dihydro-1H-isoquinoline-2-carboxylic acid 4-carboxymethyl-cyclohexyl ester

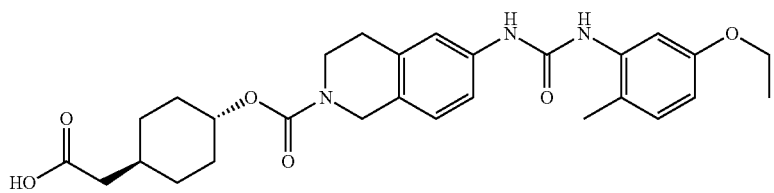 [SMILES: CCOc1ccc(C)c(NC(=O)Nc2ccc3c(c2)CCN(C(=O)O[C@H]2CC[C@H](CC(=O)O)CC2)C3)c1]

(55a) 6-[3-(5-ethoxy-2-methyl-phenyl)-ureido]-3,4-dihydro-1H-isoquinoline-2-carboxylic acid tert-butyl ester The title compound (1.60 g, 99%) was obtained as a white solid in the same way as in Example (28a) from 6-amino-2N-Boc-1,2,3,4-tetrahydroisoquinoline (943 mg) and 5-ethoxy-2-methyl-aniline (Chemische Berichte 1959, 92, 674.) (581 mg).

1H NMR (400 MHz, CDCl3): δ (ppm)=7.18-6.98 (2H, m), 7.16 (1H, brs), 7.13 (1H, d, J=8.6 Hz), 7.02 (1H, d, J=7.4 Hz), 6.71 (1H, dd, J=8.2 and 2.7 Hz), 6.54 (1H, brs), 6.26 (1H, brs), 4.52 (2H, s), 4.02 (2H, q, J=7.1 Hz), 3.62 (2H, brs), 2.79 (2H, t, J=5.9 Hz), 2.19 (3H, s), 1.49 (9H, s), 1.40 (3H, t, J=7.0 Hz).

(55b) 1-(5-ethoxy-2-methyl-phenyl)-3-(1,2,3,4-tetrahydro-isoquinolin-6-yl)-urea hydrochloride The title compound (1.36 g, quantitative yield) was obtained as a white solid in the same way as in Example (22b) from 6-[3-(5-ethoxy-2-methyl-phenyl)-ureido]-3,4-dihydro-1H-isoquinoline-2-carboxylic acid tert-butyl ester (1.60 g) obtained in Example (55a).

¹H NMR (400 MHz, DMSO-d6): δ (ppm)=9.52 (1H, s), 9.11 (1H, brs), 8.13 (1H, s), 7.59 (1H, d, J=2.8 Hz), 7.43 (1H, d, J=1.9 Hz), 7.29 (1H, dd. J=8.4 and 2.2 Hz), 7.13 (1H, d, J=8.2 Hz), 7.04 (1H, d, J=8.2 Hz), 6.50 (1H, dd, J=8.2 and 2.8 Hz), 4.20 (2H, s), 3.96 (2H, q, J=7.0 Hz), 3.38-3.34 (2H, m), 2.98 (2H, t, J=6.2 Hz), 2.18 (3H, s), 1.31 (3H, t, J=7.1 Hz).

(55c) trans-6-[3-(5-ethoxy-2-methyl-phenyl)-ureido]-3,4-dihydro-1H-isoquinoline-2-carboxylic acid 4-carboxymethyl-cyclohexyl ester Methyl ester (732 mg, 93%) was obtained in the same way as in Example (1e) from trans-(4-hydroxy-cyclohexyl)-acetic acid methyl ester (361 mg) obtained in Example (1d) and 1-(5-ethoxy-2-methyl-phenyl)-3-(1,2,3,4-tetrahydro-isoquinolin-6-yl)-urea hydrochloride (543 mg) obtained in Example (55b). This methyl ester (732 mg) was hydrolyzed in the same way as in Example 2 to obtain the title compound (579 mg, 81%) as a white solid.

¹H NMR (400 MHz, DMSO-d6): δ (ppm)=12.1 (1H, s), 9.07 (1H, s), 7.89 (1H, s), 7.59 (1H, d, J=2.3 Hz), 7.35 (1H, s), 7.21 (1H, d, J=7.8 Hz), 7.09 (1H, d, J=8.6 Hz), 7.04 (1H, d, J=9.0 Hz), 6.50 (1H, dd, J=8.2 and 2.7 Hz), 4.51-4.46 (3H, m), 3.96 (2H, q, J=6.8 Hz), 3.57 (2H, t, J=6.1 Hz), 2.76 (2H, t, J=5.6 Hz), 2.16 (3H, s), 2.11 (2H, d, J=7.0 Hz), 1.94-1.91 (2H, m), 1.77-1.74 (2H, m), 1.68-1.62 (1H, m), 1.39-1.29 (2H, m), 1.31 (3H, t, J=7.0 Hz), 1.12-1.03 (2H, m);

MS (ESI) m/z: 510 (M+H)⁺.

Example 56 trans-6-[3-(3-fluoro-5-methoxy-phenyl)-ureido]-3,4-dihydro-1H-isoquinoline-2-carboxylic acid 4-carboxymethyl-cyclohexyl ester

(56a) 6-[3-(3-fluoro-5-methoxy-phenyl)-ureido]-3,4-dihydro-1H-isoquinoline-2-carboxylic acid tert-butyl ester The title compound (938 mg, 57%) was obtained as a white solid in the same way as in Example (22a) from 6-amino-2N-Boc-1,2,3,4-tetrahydroisoquinoline (993 mg) and 3-fluoro-5-methoxy-benzoic acid (681 mg).

¹H NMR (400 MHz, CDCl₃): δ (ppm)=7.46-6.70 (4H, m), 7.21 (1H, hrs), 6.79 (1H, s), 6.57 (1H, brs), 6.34-6.30 (1H, m), 4.49 (2H, s), 3.75 (3H, s), 3.60 (2H, t, J=6.0 Hz), 2.75 (2H, hrs), 1.51 (9H, s).

(56b) 1-(3-fluoro-5-methoxy-phenyl)-3-(1,2,3,4-tetrahydro-isoquinolin-6-yl)-urea hydrochloride The title compound (742 mg, 94%) was obtained as an off-white solid in the same way as in Example (22b) from 6-[3-(3-fluoro-5-methoxy-phenyl)-ureido]-3,4-dihydro-1H-isoquinoline-2-carboxylic acid tert-butyl ester (938 mg) obtained in Example (56a).

¹H NMR (400 MHz, DMSO-d6): δ (ppm)=9.28 (1H, s), 9.10 (1H, s), 9.05 (1H, brs), 7.39 (1H, d, J=1.9 Hz), 7.28 (1H, dd, J=8.4 and 2.1 Hz), 7.13 (1H, d, J=8.2 Hz), 6.99-6.96 (1H, m), 6.83 (1H, s), 6.46-6.42 (1H, m), 4.19 (2H, s), 3.74 (3H, s), 3.38-3.34 (2H, m), 2.97 (2H, t, J=6.4 Hz).

(56c) trans-6-[3-(3-fluoro-5-methoxy-phenyl)-ureido]-3,4-dihydro-1H-isoquinoline-2-carboxylic acid 4-carboxymethyl-cyclohexyl ester Methyl ester (770 mg, quantitative yield) was obtained in the same way as in Example (1e) from trans-(4-hydroxy-cyclohexyl)-acetic acid methyl ester (361 mg) obtained in Example (1d) and 1-(3-fluoro-5-methoxy-phenyl)-3-(1,2,3,4-tetrahydro-isoquinolin-6-yl)-urea hydrochloride obtained in Example (56b). This methyl ester (770 mg) was hydrolyzed in the same way as in Example 2 to obtain the title compound (630 mg, 84%) as a white solid.

¹H NMR (400 MHz, DMSO-d6): δ (ppm)=12.1 (1H, s), 9.11 (1H, brs), 8.91 (1H, brs), 7.32 (1H, d, J=1.9 Hz), 7.23 (1H, dd, J=8.2 and 1.9 Hz), 7.09 (1H, d, J=8.6 Hz), 6.98 (1H, dt, J=11.6 and 2.0 Hz), 6.85 (1H, s), 6.42 (1H, dt, J=10.8 and 2.2 Hz), 4.48-4.46 (3H, m), 3.74 (3H, s), 3.57 (2H, t, J=5.9 Hz), 2.75 (2H, t, J=6.0 Hz), 2.11 (2H, d, J=6.7 Hz), 1.95-1.90 (2H, m), 1.77-1.74 (2H, m), 1.69-1.63 (1H, m), 1.39-1.29 (2H, m), 1.12-1.02 (2H, m);

MS (ESI) m/z: 500 (M+H)⁺.

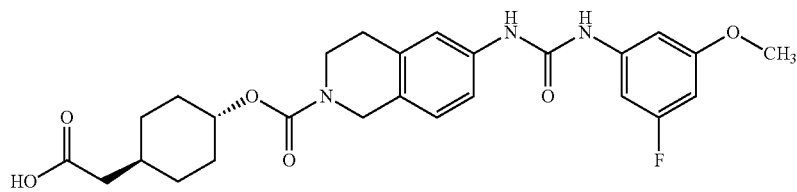 [SMILES: COc1cc(F)cc(NC(=O)Nc2ccc3c(c2)CCN(C(=O)O[C@H]2CC[C@H](CC(=O)O)CC2)C3)c1]

Example 57 trans-6-[3-(3,4-difluoro-phenyl)-ureido]-3,4-dihydro-1H-isoquinoline-2-carboxylic acid 4-carboxymethyl-cyclohexyl ester

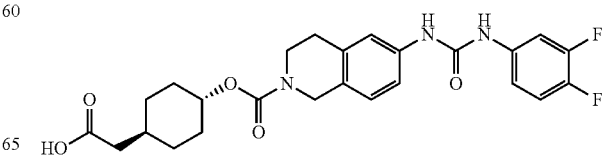

(57a) 6-[3-(3,4-difluoro-phenyl)-ureido]-3,4-dihydro-1H-isoquinoline-2-carboxylic acid tert-butyl ester The title compound (1.49 g, 92%) was obtained as a white solid in the same way as in Example (28a) from 6-amino-2N-Boc-1,2,3,4-tetrahydroisoquinoline (993 mg) and 3,4-difluoro-aniline (516 mg).

$^1$H NMR (400 MHz, CDCl$_3$): δ (ppm)=7.42 (1H, brs), 7.30-6.82 (6H, m), 6.56 (1H, brs), 4.51 (2H, s), 3.62 (2H, t, J=6.0 Hz), 2.78 (2H, brs), 1.51 (9H, s).

(57b) 1-(3,4-difluoro-phenyl)-3-(1,2,3,4-tetrahydro-isoquinolin-6-yl)-urea hydrochloride The title compound (1.25 g, quantitative yield) was obtained as an off-white solid in the same way as in Example (22b) from 6-[3-(3,4-difluoro-phenyl)-ureido]-3,4-dihydro-1H-isoquinoline-2-carboxylic acid tert-butyl ester (1.49 g) obtained in Example (57a).

$^1$H NMR (400 MHz, DMSO-d6): δ (ppm)=9.40 (1H, s), 9.18 (1H, s), 9.13 (1H, brs), 7.71-7.65 (1H, m), 7.39-7.32 (2H, m), 7.29 (1H, dd, J=8.6 and 1.9 Hz), 7.14 (1H, d, J=8.6 Hz), 7.12-7.08 (1H, m), 4.20 (2H, s), 3.38-3.34 (2H, m), 2.98 (2H, t, J=6.0 Hz).

(57c) trans-6-[3-(3,4-difluoro-phenyl)-ureido]-3,4-dihydro-1H-isoquinoline-2-carboxylic acid 4-carboxymethyl-cyclohexyl ester Methyl ester (752 mg, quantitative yield) was obtained in the same way as in Example (1e) from trans-(4-hydroxy-cyclohexyl)-acetic acid methyl ester (361 mg) obtained in Example (1d) and 1-(3,4-difluoro-phenyl)-3-(1,2,3,4-tetrahydro-isoquinolin-6-yl)-urea hydrochloride (510 mg) obtained in Example (57b). This methyl ester (752 mg) was hydrolyzed in the same way as in Example 2 to obtain the title compound (678 mg, 93%) as a white solid.

$^1$H NMR (400 MHz, DMSO-d6): δ (ppm)=12.1 (1H, s), 8.98 (1H, brs), 8.79 (1H, brs), 7.71-7.65 (1H, m), 7.38-7.31 (2H, m), 7.23 (1H, d, J=7.5 Hz), 7.14-7.08 (2H, m), 4.51-4.47 (3H, m), 3.57 (2H, t, J=5.8 Hz), 2.75 (2H, t, J=5.9 Hz), 2.12 (2H, d, J=7.1 Hz), 1.95-1.91 (2H, m), 1.77-1.74 (2H, m), 1.68-1.63 (1H, m), 1.39-1.29 (2H, m), 1.11-1.03 (2H, m); MS (ESI) m/z: 488 (M+H)$^+$.

Example 58 trans-6-[3-(4-fluoro-3-methoxy-phenyl)-ureido]-3,4-dihydro-1H-isoquinoline-2-carboxylic acid 4-carboxymethyl-cyclohexyl ester

(58a) 6-[3-(4-fluoro-3-methoxy-phenyl)-ureido]-3,4-dihydro-1H-isoquinoline-2-carboxylic acid tert-butyl ester The title compound (614 mg, 48%) was obtained as a white solid in the same way as in Example (22a) from 6-amino-2N-Boc-1,2,3,4-tetrahydroisoquinoline (760 mg) and 4-fluoro-3-methoxy-benzoic acid (521 mg).

$^1$H NMR (400 MHz, CDCl$_3$): δ (ppm)=7.31-6.82 (5H, m), 7.00 (1H, dd, J=9.8 and 9.8 Hz), 6.77 (1H, brs), 6.68 (1H, brs), 4.52 (2H, s), 3.88 (3H, s), 3.62 (2H, brs), 2.79 (2H, brs), 1.50 (9H, s).

(58b) 1-(4-fluoro-3-methoxy-phenyl)-3-(1,2,3,4-tetrahydro-isoquinolin-6-yl)-urea hydrochloride The title compound (507 mg, 98%) was obtained as a white solid in the same way as in Example (22b) from 6-[3-(4-fluoro-3-methoxy-phenyl)-ureido]-3,4-dihydro-1H-isoquinoline-2-carboxylic acid tert-butyl ester (614 mg) obtained in Example (58a).

$^1$H NMR (400 MHz, DMSO-d6): δ (ppm)=9.16 (1H, s), 9.13 (1H, brs), 9.11 (1H, s), 7.43 (1H, dd, J=8.0 and 2.6 Hz), 7.40 (1H, d, J=1.9 Hz), 7.28 (1H, dd, J=8.4 and 2.1 Hz), 7.12 (1H, d, J=8.6 Hz), 7.10 (1H, d, J=8.6 Hz), 6.88-6.84 (1H, m), 4.19 (2H, s), 3.81 (3H, s), 3.36 (2H, t, J=6.5 Hz), 2.98 (2H, t, J=6.0 Hz).

(58c) trans-6-[3-(4-fluoro-3-methoxy-phenyl)-ureido]-3,4-dihydro-1H-isoquinoline-2-carboxylic acid 4-carboxymethyl-cyclohexyl ester Methyl ester (616 mg, quantitative yield) was obtained in the same way as in Example (1e) from trans-(4-hydroxy-cyclohexyl)-acetic acid methyl ester (289 mg) obtained in Example (1d) and 1-(4-fluoro-3-methoxy-phenyl)-3-(1,2,3,4-tetrahydro-isoquinolin-6-yl)-urea hydrochloride (422 mg) obtained in Example (58b). This methyl ester (616 mg) was hydrolyzed in the same way as in Example 2 to obtain the title compound (536 mg, 89%) as a white solid.

$^1$H NMR (400 MHz, DMSO-d6): δ (ppm)=12.1 (1H, s), 8.81 (1H, s), 8.71 (1H, s), 7.43 (1H, dd, J=7.8 and 2.8 Hz), 7.34 (1H, s), 7.21 (1H, d, J=8.6 Hz), 7.13-7.08 (1H, m), 7.09 (1H, d, J=7.1 Hz), 6.88-6.84 (1H, m), 4.51-4.46 (3H, m), 3.81 (3H, s), 3.57 (2H, t, J=5.9 Hz), 2.75 (2H, t, J=5.6 Hz), 2.11 (2H, d, J=7.0 Hz), 1.95-1.91 (2H, m), 1.77-1.74 (2H, m), 1.68-1.62 (1H, m), 1.38-1.30 (2H, m), 1.11-1.02 (2H, m); MS (ESI) m/z: 500 (M+H)$^+$.

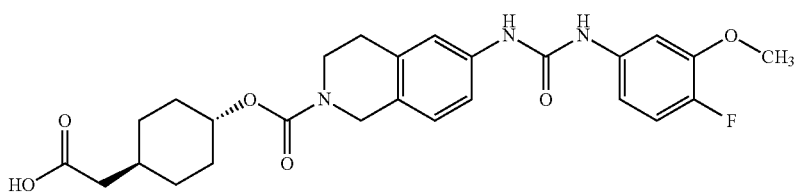 [SMILES: COc1cc(NC(=O)Nc2ccc3c(c2)CCN(C(=O)O[C@H]2CC[C@H](CC(=O)O)CC2)C3)ccc1F]

Example 59 trans-6-[3-(3-ethoxy-4-fluoro-phenyl)-ureido]-3,4-dihydro-1H-isoquinoline-2-carboxylic acid 4-carboxymethyl-cyclohexyl ester

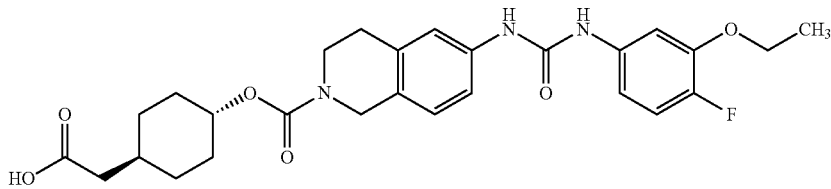 [SMILES: CCOc1cc(NC(=O)Nc2ccc3c(c2)CCN(C(=O)O[C@H]2CC[C@H](CC(=O)O)CC2)C3)ccc1F]

(59a) 6-[3-(3-ethoxy-4-fluoro-phenyl)-ureido]-3,4-dihydro-1H-isoquinoline-2-carboxylic acid tert-butyl ester The title compound (655 mg, 57%) was obtained as a pale yellow solid in the same way as in Example (22a) from 6-amino-2N-Boc-1,2,3,4-tetrahydroisoquinoline (672 mg) and 3-ethoxy-4-fluoro-benzoic acid (J. Med. Chem. 2002, 45, 3112.) (499 mg).

$^1$H NMR (400 MHz, CDCl$_3$): δ (ppm)=7.32-6.56 (5H, m), 7.01 (1H, d, J=9.0 Hz), 6.99 (1H, d, J=8.6 Hz), 6.82 (1H, brs), 4.53 (2H, s), 4.09 (2H, q, J=7.0 Hz), 3.62 (2H, t, J=6.1 Hz), 2.79 (2H, t, J=5.7 Hz), 1.50 (9H, s), 1.44 (3H, t, J=7.1 Hz).

(59b) 1-(3-ethoxy-4-fluoro-phenyl)-3-(1,2,3,4-tetrahydro-isoquinolin-6-yl)-urea hydrochloride The title compound (538 mg, 97%) was obtained as a white solid in the same way as in Example (22b) from 6-[3-(3-ethoxy-4-fluoro-phenyl)-ureido]-3,4-dihydro-1H-isoquinoline-2-carboxylic acid tert-butyl ester (654 mg) obtained in Example (59a).

$^1$H NMR (400 MHz, DMSO-d6): δ (ppm)=9.06-9.02 (3H, m), 7.42 (1H, d, J=2.3 Hz), 7.40 (1H, dd, J=2.6 and 2.6 Hz), 7.27 (1H, dd, J=8.3 and 2.4 Hz), 7.12 (1H, d, J=8.6 Hz), 7.09 (1H, d, J=8.6 Hz), 6.87-6.83 (1H, m), 4.19 (2H, s), 4.06 (2H, q, J=7.0 Hz), 3.37-3.34 (2H, m), 2.98-2.97 (2H, m), 1.36 (3H, t, J=7.1 Hz).

(59c) trans-6-[3-(3-ethoxy-4-fluoro-phenyl)-ureido]-3,4-dihydro-1H-isoquinoline-2-carboxylic acid 4-carboxymethyl-cyclohexyl ester Methyl ester (633 mg, quantitative yield) was obtained in the same way as in Example (1e) from trans-(4-hydroxy-cyclohexyl)-acetic acid methyl ester (289 mg) obtained in Example (1d) and 1-(3-ethoxy-4-fluoro-phenyl)-3-(1,2,3,4-tetrahydro-isoquinolin-6-yl)-urea hydrochloride obtained in Example (59b). This methyl ester (633 mg) was hydrolyzed in the same way as in Example 2 to obtain the title compound (523 mg, 85%) as a white solid.

$^1$H NMR (400 MHz, DMSO-d6): δ (ppm)=12.1 (1H, s), 8.82 (1H, s), 8.73 (1H, s), 7.42 (1H, dd, J=8.0 and 2.5 Hz), 7.33 (1H, d, J=1.2 Hz), 7.21 (1H, dd, J=8.2 and 2.0 Hz), 7.11 (1H, d, J=9.0 Hz), 7.08 (1H, d, J=9.0 Hz), 6.87-6.83 (1H, m), 4.48-4.46 (3H, m), 4.06 (2H, q, J=6.9 Hz), 3.57 (2H, J=5.9 Hz), 2.75 (2H, t, J=5.9 Hz), 2.11 (2H, d, J=6.6 Hz), 1.95-1.91 (2H, m), 1.77-1.74 (2H, m), 1.67-1.63 (1H, m), 1.36 (3H, J=6.9 Hz), 1.37-1.29 (2H, m), 1.12-1.02 (2H, m);

MS (ESI) m/z: 514 (M+H)$^+$.

Example 60 trans-6-[3-(2-fluoro-5-methoxy-phenyl)-ureido]-3,4-dihydro-1H-isoquinoline-2-carboxylic acid 4-carboxymethyl-cyclohexyl ester

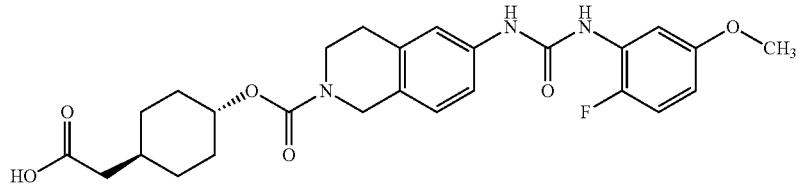 [SMILES: COc1ccc(F)c(NC(=O)Nc2ccc3c(c2)CCN(C(=O)O[C@H]2CC[C@H](CC(=O)O)CC2)C3)c1]

(60a) 6-[3-(2-fluoro-5-methoxy-phenyl)-ureido]-3,4-dihydro-1H-isoquinoline-2-carboxylic acid tert-butyl ester The title compound (1.27 g, 97%) was obtained as a white solid in the same way as in Example (28a) from 6-amino-2N-Boc-1,2,3,4-tetrahydroisoquinoline (782 mg) and 2-fluoro-5-methoxy-aniline (EP950657) (445 mg).

$^1$H NMR (400 MHz, CDCl$_3$): δ (ppm)=7.83 (1H, dd, J=6.7 and 3.2 Hz), 7.36-6.90 (3H, m), 6.98 (1H, d, J=9.0 Hz), 6.95 (1H, d, J=9.0 Hz), 6.86 (1H, brs), 6.53-6.49 (1H, m), 4.53 (2H, s), 3.79 (3H, s), 3.64 (2H; t, J=6.1 Hz), 2.81 (2H, t, J=5.1 Hz), 1.51 (9H, s).

(60b) 1-(2-fluoro-5-methoxy-phenyl)-3-(1,2,3,4-tetrahydro-isoquinolin-6-yl)-urea hydrochloride The title compound (1.08 g, quantitative yield) was obtained as a white solid in the same way as in Example (22b)

from 6-[3-(2-fluoro-5-methoxy-phenyl)-ureido]-3,4-dihydro-1H-isoquinoline-2-carboxylic acid tert-butyl ester (1.27 g) obtained in Example (60a).
¹H NMR (400 MHz, DMSO-d6): δ (ppm)=9.26 (1H, s), 8.94 (1H, brs), 8.64 (1H, d, J=2.4 Hz), 7.81 (1H, dd, J=7.0 and 3.1 Hz), 7.42 (1H, d, J=1.6 Hz), 7.27 (1H, dd, J=8.6 and 2.0 Hz), 7.19-7.13 (2H, m), 6.56-6.52 (1H, m), 4.20 (2H, s), 3.72 (3H, s), 3.37-3.34 (2H, m), 2.98 (2H, t, J=5.9 Hz).

(60c) trans-6-[3-(2-fluoro-5-methoxy-phenyl)-ureido]-3,4-dihydro-1H-isoquinoline-2-carboxylic acid 4-carboxymethyl-cyclohexyl ester Methyl ester (616 mg, quantitative yield) was obtained in the same way as in Example (1e) from trans-(4-hydroxy-cyclohexyl)-acetic acid methyl ester (289 mg) obtained in Example (1d) and 1-(2-fluoro-5-methoxy-phenyl)-3-(1,2,3,4-tetrahydro-isoquinolin-6-yl)-urea hydrochloride (422 mg) obtained in Example (60b). This methyl ester (616 mg) was hydrolyzed in the same way as in Example 2 to obtain the title compound (507 mg, 85%) as a white solid.
¹H NMR (400 MHz, DMSO-d6): δ (ppm)=12.1 (1H, brs), 9.09 (1H, s), 8.59 (1H, s), 7.83 (1H, dd, J=7.0 and 3.1 Hz), 7.34 (1H, s), 7.21 (1H, d, J=9.0 Hz), 7.18-7.09 (2H, m), 6.53 (1H, dt, J=9.0 and 3.3 Hz), 4.49-4.47 (3H, m), 3.72 (3H, s), 3.57 (2H, t, J=5.8 Hz), 2.76 (2H, t, J=5.9 Hz), 2.11 (2H, d, J=7.0 Hz), 1.95-1.90 (2H, m), 1.77-1.73 (2H, m), 1.68-1.62 (1H, m), 1.39-1.29 (2H, m), 1.12-1.01 (2H, m);
MS (ESI) m/z: 500 (M+H)⁺.

Example 61 trans-6-[3-(5-ethoxy-2-fluoro-phenyl)-ureido]-3,4-dihydro-1H-isoquinoline-2-carboxylic acid 4-carboxymethyl-cyclohexyl ester ¹H NMR (400 MHz, CDCl₃): δ (ppm)=6.87 (1H, dd, J=10.8 and 8.8 Hz), 6.33 (1H, dd, J=7.7 and 3.0 Hz), 6.20 (1H, dt, J=8.7 and 3.3 Hz), 3.95 (2H, q, J=7.0 Hz), 3.70 (2H, brs), 1.38 (3H, t, J=7.1 Hz).

(61c) 6-[3-(5-ethoxy-2-fluoro-phenyl)-ureido]-3,4-dihydro-1H-isoquinoline-2-carboxylic acid tert-butyl ester The title compound (1.37 g, quantitative yield) was obtained as a slightly purple solid in the same way as in Example (28a) from 6-amino-2N-Boc-1,2,3,4-tetrahydroisoquinoline (795 mg) and 5-ethoxy-2-fluoro-aniline (497 mg) obtained in Example (61b).
¹H NMR (400 MHz, CDCl₃): δ (ppm)=7.83-7.81 (1H, m), 7.37-6.81 (4H, m), 6.96 (1H, d, J=9.0 Hz), 6.93 (1H, d, J=9.0 Hz), 6.52-6.48 (1H, m), 4.52 (2H, s), 4.00 (2H, q, J=7.0 Hz), 3.63 (2H, t, J=5.9 Hz), 2.79 (2H, brs), 1.51 (9H, s), 1.37 (3H, t, J=7.0 Hz).

(61d) 1-(5-ethoxy-2-fluoro-phenyl)-3-(1,2,3,4-tetrahydro-isoquinolin-6-yl)-urea hydrochloride The title compound (1.17 g, quantitative yield) was obtained as a white solid in the same way as in Example (22b) from 6-[3-(5-ethoxy-2-fluoro-phenyl)-ureido]-3,4-dihydro-1H-isoquinoline-2-carboxylic acid tert-butyl ester (1.37 g) obtained in Example (61c).
¹H NMR (400 MHz, DMSO-d6): δ (ppm)-9.33 (1H, s), 9.04 (1H, brs), 8.65 (1H, d, J=2.7 Hz), 7.80 (1H, dd, J=6.8 and 2.9 Hz), 7.41 (1H, d, J=1.9 Hz), 7.27 (1H, dd, J=8.4 and 2.1 Hz), 7.15-7.10 (1H, m), 7.14 (1H, d, J=7.8 Hz), 6.54-6.50 (1H, m), 4.19 (2H, s), 3.97 (2H, q, J=6.8 Hz), 3.36 (2H, t, J=6.5 Hz), 2.98 (2H, t, J=6.1 Hz), 1.32 (3H, t, J=7.1 Hz).

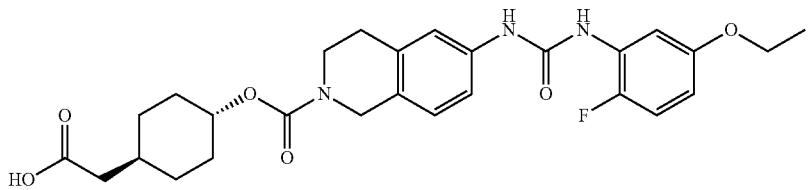 [SMILES: CCOc1ccc(F)c(NC(=O)Nc2ccc3c(c2)CCN(C(=O)O[C@H]2CC[C@H](CC(=O)O)CC2)C3)c1]

(61a) 4-ethoxy-1-fluoro-2-nitro-benzene

To a DMF (10 mL) solution of 4-fluoro-3-nitro-phenol (628 mg), sodium hydride (purity: 55% or higher, 209 mg) was added in small portions at room temperature. After 30 minutes, ethyl iodide (0.38 mL) was added thereto at room temperature. After 2 hours, the reaction mixture was diluted with ethyl acetate, washed with saturated sodium bicarbonate and saturated brine, then dried over sodium sulfate, and then concentrated. The residue was purified by column chromatography (hexane/ethyl acetate) to obtain the title compound (685 mg, 93%) as a yellow solid.
¹H NMR (400 MHz, CDCl₃): δ (ppm)=7.52 (1H, dd, J=5.9 and 3.1 Hz), 7.23-7.13 (2H, m), 4.07 (2H, q, J=7.0 Hz), 1.45 (3H, t, J=7.0 Hz).

(61b) 5-ethoxy-2-fluoro-phenylamine

4-Ethoxy-1-fluoro-2-nitro-benzene (685 mg) obtained in Example (61a) was reduced in the same way as in Example (1b) to obtain the title compound (498 mg, 87%) as a brown oil.

(61e) trans-6-[3-(5-ethoxy-2-fluoro-phenyl)-ureido]-3,4-dihydro-1H-isoquinoline-2-carboxylic acid 4-carboxymethyl-cyclohexyl ester Methyl ester (633 mg, quantitative yield) was obtained in the same way as in Example (1e) from trans-(4-hydroxy-cyclohexyl)-acetic acid methyl ester (289 mg) obtained in Example (1d) and 1-(5-ethoxy-2-fluoro-phenyl)-3-(1,2,3,4-tetrahydro-isoquinolin-6-yl)-urea hydrochloride (438 mg) obtained in Example (61d). This methyl ester (633 mg) was hydrolyzed in the same way as in Example 2 to obtain the title compound (507 mg, 82%) as a white solid.
¹H NMR (400 MHz, DMSO-d6): δ (ppm)=12.1 (1H, s), 9.09 (1H, s), 8.57 (1H, s), 7.82 (1H, dd, J=6.8 and 2.9 Hz), 7.33 (1H, s), 7.21 (1H, d, J=7.4 Hz), 7.15-7.09 (2H, m), 6.51 (1H, dt, J=9.0 and 3.5 Hz), 4.49-4.47 (3H, m), 3.97 (2H, q, J=7.0 Hz), 3.57 (2H, t, J=5.9 Hz), 2.76 (2H, t, J=5.9 Hz), 2.11 (2H, d, J=6.6 Hz), 2.12-2.10 (2H, m), 1.77-1.73 (2H, m), 1.68-1.62 (1H, m), 1.29-1.39 (2H, m), 1.32 (3H, t, J=6.9 Hz), 1.12-1.02 (2H, m);
MS (ESI) m/z: 514 (M+H)⁺.

Example 62 trans-6-[3-(4-methylsulfanyl-phenyl)-ureido]-3,4-dihydro-1H-isoquinoline-2-carboxylic acid 4-carboxymethyl-cyclohexyl ester

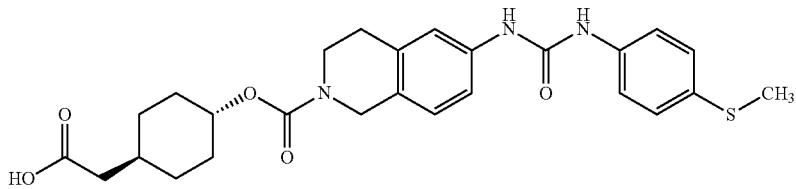

(62a) 6-[3-(4-methylsulfanyl-phenyl)-ureido]-3,4-dihydro-1H-isoquinoline-2-carboxylic acid tert-butyl ester The title compound (1.63 g, 98%) was obtained as a white solid in the same way as in Example (26a) from 6-amino-2N-Boc-1,2,3,4-tetrahydroisoquinoline (993 mg) and 4-methylsulfanyl isocyanate (0.67 mL).

$^1$H NMR (400 MHz, CDCl$_3$): δ (ppm)=7.29-7.00 (7H, m), 7.00 (1H, brs), 6.71 (1H, brs), 4.50 (2H, s), 3.59 (2H, t, J=5.1 Hz), 2.74 (2H, t, J=5.7 Hz), 2.44 (3H, s), 1.50 (9H, s).

(62b) 1-(4-methylsulfanyl-phenyl)-3-(1,2,3,4-tetrahydro-isoquinolin-6-yl)-urea hydrochloride The title compound (1.38 g, quantitative yield) was obtained as a white solid in the same way as in Example (22b) from 6-[3-(4-methylsulfanyl-phenyl)-ureido]-3,4-dihydro-1H-isoquinoline-2-carboxylic acid tert-butyl ester (1.63 g) obtained in Example (62a).

$^1$H NMR (400 MHz, DMSO-d6): δ (ppm)=9.08 (1H, brs), 9.05 (1H, d, J=4.7 Hz), 7.44-7.40 (1H, m), 7.43 (2H, d, J=8.6 Hz), 7.29 (1H, dd, J=8.4 and 2.2 Hz), 7.24-7.21 (1H, m), 7.22 (2H, d, J=8.6 Hz), 7.13 (1H, d, J=8.2 Hz), 4.20 (2H, s), 3.39-3.35 (2H, m), 2.98 (2H, t, J=6.0 Hz), 2.44 (3H, s).

(62c) trans-6-[3-(4-methylsulfanyl-phenyl)-ureido]-3,4-dihydro-1H-isoquinoline-2-carboxylic acid 4-carboxymethyl-cyclohexyl ester Methyl ester (2.01 g, quantitative yield) was obtained in the same way as in Example (1e) from trans-(4-hydroxy-cyclohexyl)-acetic acid methyl ester (947 mg) obtained in Example (1d) and 1-(4-methylsulfanyl-phenyl)-3-(1,2,3,4-tetrahydro-isoquinolin-6-yl)-urea hydrochloride obtained in Example (62b). This methyl ester (789 mg) was hydrolyzed in the same way as in Example 2 to obtain the title compound (456 mg, 60%) as a white solid.

$^1$H NMR (400 MHz, DMSO-d6): δ (ppm)=12.1 (1H, s), 8.75 (1H, s), 8.68 (1H, s), 7.42 (2H, d, J=8.6 Hz), 7.31 (1H, s), 7.22 (2H, d, J=8.6 Hz), 7.23-7.21 (1H, m), 7.08 (1H, d, J=8.6 Hz), 4.49-4.46 (3H, m), 3.57 (2H, t, J=5.9 Hz), 2.75 (2H, t, J=5.9 Hz), 2.44 (3H, s), 2.12 (2H, d, J=7.0 Hz), 1.95-1.91 (2H, m), 1.77-1.73 (2H, m), 1.68-1.62 (1H, m), 1.39-1.29 (2H, m), 1.12-1.03 (2H, m);

MS (ESI) m/z: 498 (M+H)$^+$.

Example 63 trans-6-[3-(4-methanesulfinyl-phenyl)-ureido]-3,4-dihydro-1H-isoquinoline-2-carboxylic acid 4-carboxymethyl-cyclohexyl ester

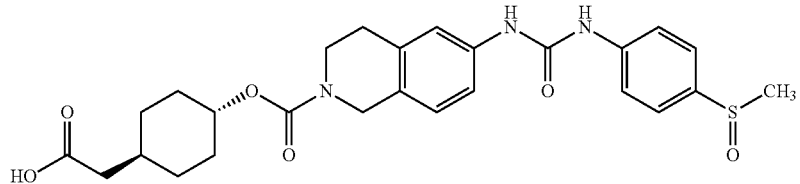 [SMILES: CS(=O)c1ccc(NC(=O)Nc2ccc3c(c2)CCN(C(=O)O[C@H]2CC[C@H](CC(=O)O)CC2)C3)cc1]

(63a) trans-6-[3-(4-methanesulfinyl-phenyl)-ureido]-3,4-dihydro-1H-isoquinoline-2-carboxylic acid 4-methoxycarbonylmethylcyclohexyl ester To a mixture of trans-6-[3-(4-methylsulfanyl-phenyl)-ureido]-3,4-dihydro-1H-isoquinoline-2-carboxylic acid 4-methoxycarbonylmethylcyclohexyl ester (1.85 g) obtained as an intermediate in Example (62c) and dichloromethane (20 mL), mCPBA (623 mg) was added at 0° C. The reaction mixture was warmed to room temperature, diluted with dichloromethane, washed with a saturated aqueous solution of sodium bicarbonate and saturated brine, then dried over sodium sulfate, and then concentrated. The residue was purified by column chromatography (dichloromethane/methanol=3:1 and then dichloromethane/methanol=4:1) to obtain the title compound (1.37 g, 72%) as a white solid.

$^1$H NMR (400 MHz, DMSO-d6): δ (ppm)=9.14 (1H, brs), 8.87 (1H, brs), 7.66 (2H, d, J=9.0 Hz), 7.60 (2H, d, J=8.7 Hz), 7.34 (1H, brs), 7.25 (1H, d, J=8.2 Hz), 7.10 (1H, d, J=8.2 Hz), 4.49-4.47 (3H, m), 3.58 (3H, s), 3.57 (2H, t, J=6.0 Hz), 2.76

(2H, t, J=5.9 Hz), 2.71 (3H, s), 2.22 (2H, d, J=6.6 Hz), 1.95-1.91 (2H, m), 1.75-1.65 (3H, m), 1.40-1.30 (2H, m), 1.14-1.04 (2H, m).

(63b) trans-6-[3-(4-methanesulfinyl-phenyl)-ureido]-3,4-dihydro-1H-isoquinoline-2-carboxylic acid 4-carboxymethyl-cyclohexyl ester trans-6-[3-(4-Methanesulfinyl-phenyl)-ureido]-3,4-dihydro-1H-isoquinoline-2-carboxylic acid 4-methoxycarbonyl-methylcyclohexyl ester (1.37 g) obtained in Example (63a) was hydrolyzed in the same way as in Example 2 to obtain the title compound (1.22 g, 92%) as a white solid.

$^1$H NMR (400 MHz, DMSO-d6): δ (ppm)=12.1 (1H, s), 9.09 (1H, s), 8.82 (1H, s), 7.65 (2H, d, J=8.6 Hz), 7.60 (2H, d, J=8.6 Hz), 7.34 (1H, brs), 7.24 (1H, d, J=8.6 Hz), 7.10 (1H, d, J=8.2 Hz), 4.51-4.47 (3H, m), 3.57 (2H, t, J=6.1 Hz), 2.76 (2H, t, J=6.2 Hz), 2.71 (3H, s), 2.12 (2H, d, J=6.6 Hz), 1.95-1.91 (2H, m), 1.77-1.74 (2H, m), 1.68-1.63 (1H, m), 1.39-1.30 (2H, m), 1.12-1.02 (2H, m);
MS (ESI) m/z: 514 (M+H)$^+$.

Example 64 trans-6-[3-(3-methylsulfanyl-phenyl)-ureido]-3,4-dihydro-1H-isoquinoline-2-carboxylic acid 4-carboxymethyl-cyclohexyl ester

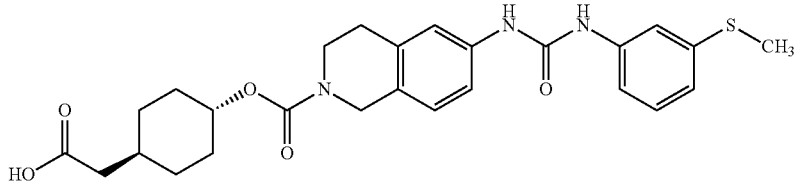 [SMILES: CSc1cccc(NC(=O)Nc2ccc3c(c2)CCN(C(=O)O[C@H]2CC[C@H](CC(=O)O)CC2)C3)c1]

(64a) 6-[3-(3-methylsulfanyl-phenyl)-ureido]-3,4-dihydro-1H-isoquinoline-2-carboxylic acid tert-butyl ester The title compound (1.43 g, 87%) was obtained as a pink solid in the same way as in Example (26a) from 6-amino-2N-Boc-1,2,3,4-tetrahydroisoquinoline (983 mg) and 3-methylsulfanyl-phenyl isocyanate (0.66 mL).

$^1$H NMR (400 MHz, CDCl$_3$): δ (ppm)=7.33-6.70 (5H, m), 7.31 (1H, brs), 7.20 (1H, dd, J=7.8 and 7.9 Hz), 7.11 (1H, d, J=8.3 Hz), 6.96 (1H, d, J=7.8 Hz), 4.50 (2H, s), 3.59 (2H, t, J=5.3 Hz), 2.75 (2H, t, J=5.1 Hz), 2.45 (3H, s), 1.51 (9H, s).

(64b) 1-(3-methylsulfanyl-phenyl)-3-(1,2,3,4-tetrahydro-isoquinolin-6-yl)-urea hydrochloride The title compound (566 mg, quantitative yield) was obtained as a gray solid in the same way as in Example (22b) from 6-[3-(3-methylsulfanyl-phenyl)-ureido]-3,4-dihydro-1H-isoquinoline-2-carboxylic acid tert-butyl ester (670 mg) obtained in Example (64a).

$^1$H NMR (400 MHz, DMSO-d6): δ (ppm)=9.32 (1H, s), 9.29 (1H, s), 9.23 (1H, brs), 7.49 (1H, dd, J=2.0 and 2.0 Hz), 7.39 (1H, d, J=2.0 Hz), 7.29 (1H, dd, J=8.6 and 2.3 Hz), 7.22 (1H, dd, J=7.8 and 7.8 Hz), 7.15-7.12 (2H, m), 6.87-6.84 (1H, m), 4.19 (2H, t, J=4.3 Hz), 3.38-3.34 (2H, m), 2.98 (2H, t, J=6.2 Hz), 2.46 (3H, s).

(64c) trans-6-[3-(3-methylsulfanyl-phenyl)-ureido]-3,4-dihydro-1H-isoquinoline-2-carboxylic acid 4-carboxymethyl-cyclohexyl ester Methyl ester (818 mg, quantitative yield) was obtained in the same way as in Example (1c) from trans-(4-hydroxy-cyclohexyl)-acetic acid methyl ester (390 mg) obtained in Example (1d) and 1-(3-methylsulfanyl-phenyl)-3-(1,2,3,4-tetrahydro-isoquinolin-6-yl)-urea hydrochloride (566 mg) obtained in Example (64b). This methyl ester (251 mg) was hydrolyzed in the same way as in Example 2 to obtain the title compound (135 mg, 56%) as a cream-colored solid.

$^1$H NMR (400 MHz, DMSO-d6): δ (ppm)=12.1 (1H, s), 8.81 (1H, s), 8.73 (1H, s), 7.48 (1H, dd, J=1.9 and 1.9 Hz), 7.33 (1H, s), 7.23-7.19 (2H, m), 7.14 (1H, d, J=9.0 Hz), 7.09 (1H, d, J=8.2 Hz), 6.85 (1H, d, J=7.8 Hz), 4.51-4.46 (3H, m), 3.57 (2H, t, J=6.1 Hz), 2.75 (2H, t, J=5.9 Hz), 2.46 (3H, s), 2.11 (2H, d, J=7.0 Hz), 1.95-1.91 (2H, m), 1.77-1.73 (2H, m), 1.68-1.62 (1H, m), 1.39-1.29 (2H, m), 1.12-1.02 (2H, m);
MS (ESI) m/z: 498 (M+H)$^+$.

Example 65 trans-6-[3-(3-methanesulfinyl-phenyl)-ureido]-3,4-dihydro-1H-isoquinoline-2-carboxylic acid 4-carboxymethyl-cyclohexyl ester

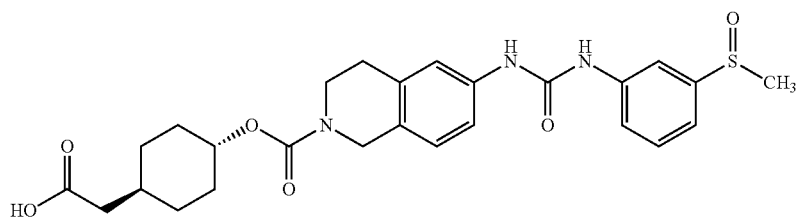 [SMILES: CS(=O)c1cccc(NC(=O)Nc2ccc3c(c2)CCN(C(=O)O[C@H]2CC[C@H](CC(=O)O)CC2)C3)c1]

(65a) trans-6-[3-(3-methanesulfinyl-phenyl)-ureido]-3,4-dihydro-1H-isoquinoline-2-carboxylic acid 4-methoxycarbonylmethylcyclohexyl ester The title compound (559 mg, 77%) was obtained as a pale pink solid in the same way as in Example (63a) from trans-6-[3-(3-methylsulfanyl-phenyl)-ureido]-3,4-dihydro-1H-isoquinoline-2-carboxylic acid 4-methoxycarbonylmethyl-cyclohexyl ester (700 mg) obtained as an intermediate in Example (64c).

$^1$H NMR (400 MHz, DMSO-d6): δ (ppm)=9.13 (1H, brs), 8.82 (1H, brs), 7.90 (1H, dd, J=2.0 and 2.0 Hz), 7.52-7.45 (2H, m), 7.48 (1H, d, J=7.5 Hz), 7.36 (1H, s), 7.24 (1H, d, J=7.5 Hz), 7.10 (1H, d, J=8.6 Hz), 4.51-4.47 (3H, m), 3.59 (3H, s), 3.59-3.55 (2H, m), 2.76 (2H, t, J=5.7 Hz), 2.73 (3H, s), 2.23 (2H, d, J=6.7 Hz), 1.95-1.90 (2H, m), 1.75-1.65 (3H, m), 1.40-1.30 (2H, m), 1.14-1.03 (2H, m).

(65b) trans-6-[3-(3-methanesulfinyl-phenyl)-ureido]-3,4-dihydro-1H-isoquinoline-2-carboxylic acid 4-carboxymethyl-cyclohexyl ester trans-6-[3-(3-Methanesulfinyl-phenyl)-ureido]-3,4-dihydro-1H-isoquinoline-2-carboxylic acid 4-methoxycarbonyl-methylcyclohexyl ester (559 mg) obtained in Example (65a) was hydrolyzed in the same way as in Example 2 to obtain the title compound (516 mg, 95%) as a white solid.

$^1$H NMR (400 MHz, DMSO-d6): δ (ppm)=12.1 (1H, s), 9.19 (1H, brs), 8.89 (1H, brs), 7.90 (1H, s), 7.52-7.45 (2H, m), 7.36 (1H, s), 7.26-7.23 (2H, m), 7.10 (1H, d, J=8.6 Hz), 4.51-4.47 (3H, m), 3.57 (2H, t, J=5.9 Hz), 2.76 (2H, t, J=5.9 Hz), 2.73 (3H, s), 2.11 (2H, d, J=7.0 Hz), 1.94-1.91 (2H, m), 1.78-1.74 (2H, m), 1.69-1.53 (1H, m), 1.40-1.28 (2H, m), 1.12-1.02 (2H, m);

MS (ESI) m/z: 514 (M+H)$^+$.

Example 66 trans-6-[3-(3-trifluoromethyl-phenyl)-ureido]-3,4-dihydro-1H-isoquinoline-2-carboxylic acid 4-carboxymethyl-cyclohexyl ester

(66a) 6-[3-(3-trifluoromethyl-phenyl)-ureido]-3,4-dihydro-1H-isoquinoline-2-carboxylic acid tert-butyl ester The title compound (1.31 g, quantitative yield) was obtained as a white solid in the same way as in Example (26a) from 6-amino-2N-Boc-1,2,3,4-tetrahydroisoquinoline (745 mg) and 3-trifluoromethyl-phenyl isocyanate (0.50 mL).

$^1$H NMR (400 MHz, CDCl$_3$): δ (ppm)=7.68 (1H, brs), 7.62 (1H, d, J=8.6 Hz), 7.42 (1H, dd, J=7.8 and 7.8 Hz), 7.31 (1H, d, J=7.5 Hz), 7.33-6.63 (5H, m), 4.53 (2H, s), 3.64 (2H, t, J=6.1 Hz), 2.80 (2H, brs), 1.52 (9H, s).

(66b) 1-(3-trifluoromethyl-phenyl)-3-(1,2,3,4-tetrahydro-isoquinolin-6-yl)-urea hydrochloride The title compound (1.12 g, quantitative yield) was obtained as a pale yellow solid in the same way as in Example (22b) from 6-[3-(3-trifluoromethyl-phenyl)-ureido]-3,4-dihydro-1H-isoquinoline-2-carboxylic acid tert-butyl ester (1.31 g) obtained in Example (66a).

$^1$H NMR (400 MHz, DMSO-d6): δ (ppm)=9.51 (1H, s), 9.21 (1H, s), 9.03 (1H, brs), 8.04 (1H, s), 7.56 (1H, d, J=8.2 Hz), 7.52 (1H, J=7.8 and 7.8 Hz), 7.42 (1H, d, J=1.9 Hz), 7.32 (1H, d, J=7.1 Hz), 7.29 (1H, dd, J=8.4 and 2.1 Hz), 7.14 (1H, d, J=8.2 Hz), 4.20 (2H, s), 3.36 (2H, t, J=6.4 Hz), 2.98 (2H, t, J=6.2 Hz).

(66c) trans-6-[3-(3-trifluoromethyl-phenyl)-ureido]-3,4-dihydro-1H-isoquinoline-2-carboxylic acid 4-carboxymethyl-cyclohexyl ester Methyl ester (640 mg, quantitative yield) was obtained in the same way as in Example (1e) from trans-(4-hydroxy-cyclohexyl)-acetic acid methyl ester (289 mg) obtained in Example (1d) and 1-(3-trifluoromethyl-phenyl)-3-(1,2,3,4-tetrahydro-isoquinolin-6-yl)-urea hydrochloride (446 mg) obtained in Example (66b). This methyl ester (640 mg) was hydrolyzed in the same way as in Example 2 to obtain the title compound (530 mg, 85%) as a white solid.

$^1$H NMR (400 MHz, DMSO-d6): δ (ppm)=12.1 (1H, s), 9.15 (1H, s), 8.85 (1H, s), 8.04 (1H, s), 7.57-7.49 (2H, m),

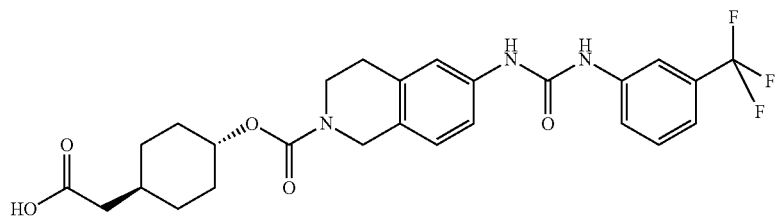 [SMILES: O=C(O)C[C@H]1CC[C@H](OC(=O)N2CCc3cc(NC(=O)Nc4cccc(C(F)(F)F)c4)ccc3C2)CC1]

7.35 (1H, s), 7.31 (1H, d, J=7.4 Hz), 7.23 (1H, dd, J=8.2 and 1.6 Hz), 7.10 (1H, d, J=8.2 Hz), 4.51-4.47 (3H, m), 3.57 (2H, t, J=5.9 Hz), 2.76 (2H, t, J=5.9 Hz), 2.12 (2H, d, J=7.4 Hz), 1.95-1.91 (2H, m), 1.77-1.74 (2H, m), 1.68-1.63 (1H, m), 1.40-1.29 (2H, m), 1.40-1.29 (2H, m);

MS (ESI) m/z: 520 (M+H)$^+$.

Example 67 trans-6-[3-(3-fluoro-phenyl)-ureido]-3,4-dihydro-1H-isoquinoline-2-carboxylic acid 4-carboxymethyl-cyclohexyl ester

Example 68 trans-6-(3-m-tolyl-ureido)-3,4-dihydro-1H-isoquinoline-2-carboxylic acid 4-carboxymethyl-cyclohexyl ester

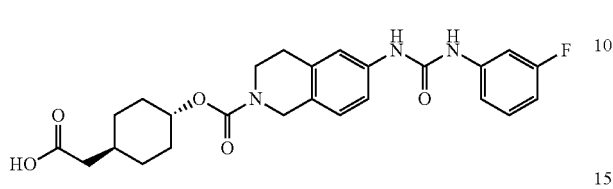

(67a) 6-[3-(3-fluoro-phenyl)-ureido]-3,4-dihydro-1H-isoquinoline-2-carboxylic acid tert-butyl ester The title compound (1.16 g, quantitative yield) was obtained as a white solid in the same way as in Example (26a) from 6-amino-2N-Boc-1,2,3,4-tetrahydroisoquinoline (745 mg) and 3-fluoro-phenyl isocyanate (0.41 mL).

$^1$H NMR (400 MHz, CDCl$_3$): δ (ppm)=7.39-6.59 (5H, m), 7.24-7.19 (2H, m), 7.04 (1H, d, J=7.8 Hz), 6.76 (1H, dd, J=8.5 and 8.5 Hz), 4.50 (2H, s), 3.61 (2H, t, J=5.9 Hz), 2.76 (2H, brs), 1.51 (9H, s)

(67b) 1-(3-fluoro-phenyl)-3-(1,2,3,4-tetrahydro-isoquinolin-6-yl)-urea hydrochloride The title compound (965 mg, quantitative yield) was obtained as a pale yellow solid in the same way as in Example (22b) from 6-[3-(3-fluoro-phenyl)-ureido]-3,4-dihydro-1H-isoquinoline-2-carboxylic acid tert-butyl ester (1.16 g) obtained in Example (67a).

$^1$H NMR (400 MHz, DMSO-d6): δ (ppm)=9.44 (1H, s), 9.24 (1H, s), 9.15 (1H, brs), 7.52-7.49 (1H, m), 7.39 (1H, d, J=1.9 Hz), 7.33-7.28 (2H, m), 7.14 (1H, d, J=8.6 Hz), 7.10 (1H, dd, J=7.4 and 1.9 Hz), 6.80-6.76 (1H, m), 4.20 (2H, s), 3.36 (2H, t, J=6.5 Hz), 2.98 (2H, t, J=6.2 Hz).

(67c) trans-6-[3-(3-fluoro-phenyl)-ureido]-3,4-dihydro-1H-isoquinoline-2-carboxylic acid 4-carboxymethyl-cyclohexyl ester Methyl ester (580 ring, quantitative yield) was obtained in the same way as in Example (1e) from trans-(4-hydroxy-cyclohexyl)-acetic acid methyl ester (289 mg) obtained in Example (1d) and 1-(3-fluoro-phenyl)-3-(1,2,3,4-tetrahydro-isoquinolin-6-yl)-urea hydrochloride (386 mg) obtained in Example (67b). This methyl ester (580 mg) was hydrolyzed in the same way as in Example 2 to obtain the title compound (500 mg, 89%) as a white solid.

$^1$H NMR (400 MHz, DMSO-d6): δ (ppm)=12.1 (1H, s), 8.97 (1H, s), 8.75 (1H, s), 7.50 (1H, dt, J=11.8 and 2.2 Hz), 7.33-7.27 (2H, m), 7.23 (1H, d, J=8.3 Hz), 7.11-7.08 (2H, m), 6.78 (1H, dt, J=12.0 and 4.3 Hz), 4.51-4.47 (3H, m), 3.57 (2H, t, J=6.0 Hz), 2.75 (2H, t, J=5.7 Hz), 2.12 (2H, d, J=7.0 Hz), 1.95-1.91 (2H, m), 1.77-1.73 (2H, m), 1.68-1.62 (1H, m), 1.39-1.30 (2H, m), 1.12-1.01 (2H, m);

MS (ESI) m/z: 470 (M+H)$^+$.

(68a) 6-(3-m-tolyl-ureido)-3,4-dihydro-1H-isoquinoline-2-carboxylic acid tert-butyl ester The title compound (1.13 g, 99%) was obtained as a white solid in the same way as in Example (26a) from 6-amino-2N-Boc-1,2,3,4-tetrahydroisoquinoline (745 mg) and m-tolyl isocyanate (0.45 mL).

$^1$H NMR (400 MHz, CDCl$_3$): δ (ppm)=7.36-6.74 (6H, m), 7.18 (1H, dd, J=7.7 and 7.6 Hz), 7.12 (1H, d, J=8.3 Hz), 6.90 (1H, d, J=7.4 Hz), 4.49 (2H, s), 3.58 (2H, brs), 2.73 (2H, t, J=5.7 Hz), 2.30 (3H, s), 1.50 (9H, s).

(68b) 1-(1,2,3,4-tetrahydro-isoquinolin-6-yl)-3-m-tolyl-urea hydrochloride

The title compound (918 mg, 97%) was obtained as a pale pink solid in the same way as in Example (22b) from 6-(3-m-tolyl-ureido)-3,4-dihydro-1H-isoquinoline-2-carboxylic acid tert-butyl ester (1.13 g) obtained in Example (68a).

$^1$H NMR (400 MHz, DMSO-d6): δ (ppm)=9.10 (1H, brs), 9.07 (1H, s), 8.97 (1H, s), 7.40 (1H, d, J=2.0 Hz), 7.30-7.27 (2H, m), 7.23 (1H, d, J=9.0 Hz), 7.15 dd, J=7.8 and 7.8 Hz), 7.12 (1H, d, J=8.2 Hz), 6.79 (1H, d, J=7.4 Hz), 4.19 (2H, s), 3.36 (2H, t, J=6.2 Hz), 2.97 (2H, t, J=6.1 Hz), 2.27 (3H, s).

(68c) trans-6-(3-m-tolyl-ureido)-3,4-dihydro-1H-isoquinoline-2-carboxylic acid 4-carboxymethyl-cyclohexyl ester Methyl ester (575 mg, quantitative yield) was obtained in the same way as in Example (1e) from trans-(4-hydroxy-cyclohexyl)-acetic acid methyl ester (289 mg) obtained in Example (1d) and 1-(1,2,3,4-tetrahydro-isoquinolin-6-yl)-3-m-tolyl-urea hydrochloride (381 mg) obtained in Example (68b). This methyl ester (575 mg) was hydrolyzed in the same way as in Example 2 to obtain the title compound (499 mg, 89%) as a yellow solid.

$^1$H NMR (400 MHz, DMSO-d6): δ (ppm)=12.1 (1H, s), 8.69 (1H, s), 8.67 (1H, s), 7.32 (2H, d, J=9.0 Hz), 7.22 (2H, d, J=8.6 Hz), 7.15 (1H, dd, J=7.6 and 7.7 Hz), 7.08 (1H, d, J=8.6 Hz), 6.78 (1H, d, J=7.4 Hz), 4.51-4.46 (3H, m), 3.57 (2H, t, J=5.9 Hz), 2.75 (2H, t, J=6.1 Hz), 2.27 (3H, s), 2.11 (2H, d, J=7.0 Hz), 1.95-1.91 (2H, m), 1.78-1.74 (2H, m), 1.68-1.62 (1H, m), 1.39-1.29 (2H, m), 1.11-1.02 (2H, m), MS (ESI) m/z: 466 (M+H)$^+$.

Example 69 trans-6-[3-(4-trifluoromethyl-phenyl)-ureido]-3,4-dihydro-1H-isoquinoline-2-carboxylic acid 4-carboxymethyl-cyclohexyl ester

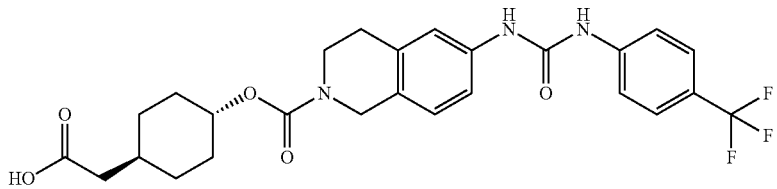 [SMILES: O=C(O)C[C@H]1CC[C@H](OC(=O)N2CCc3cc(NC(=O)Nc4ccc(C(F)(F)F)cc4)ccc3C2)CC1]

(69a) 6-[3-(4-trifluoromethyl-phenyl)-ureido]-3,4-dihydro-1H-isoquinoline-2-carboxylic acid tert-butyl ester The title compound (1.00 g, 77%) was obtained as a white solid in the same way as in Example (26a) from 6-amino-2N-Boc-1,2,3,4-tetrahydroisoquinoline (745 mg) and 4-trifluoromethyl-phenyl isocyanate (0.51 mL).

$^1$H NMR (400 MHz, CDCl$_3$): δ (ppm)=7.56-7.42 (5H, m), 7.33-6.55 (4H, m), 4.52 (2H, s), 3.63 (2H, 1, J=6.1 Hz), 2.78 (2H, brs), 1.52 (9H, s).

(69b) 1-(4-trifluoromethyl-phenyl)-3-(1,2,3,4-tetrahydro-isoquinolin-6-yl)-urea hydrochloride The title compound (851 mg, 99%) was obtained as a yellow solid in the same way as in Example (22b) from 6-[3-(4-trifluoromethyl-phenyl)-ureido]-3,4-dihydro-1H-isoquinoline-2-carboxylic acid tert-butyl ester (1.00 g) obtained in Example (69a).

$^1$H NMR (400 MHz, DMSO-d6): δ (ppm)=9.62 (1H, s), 9.30 (1H, s), 9.13 (1H, brs), 7.68-7.62 (4H, m), 7.40 (1H, d, J=1.9 Hz), 7.32 (1H, dd, J=8.4 and 2.1 Hz), 7.15 (1H, d, J=8.6 Hz), 4.20 (2H, s), 3.37-3.34 (2H, m), 3.00-2.99 (2H, m).

(69c) trans-6-[3-(4-trifluoromethyl-phenyl)-ureido]-3,4-dihydro-1H-isoquinoline-2-carboxylic acid 4-carboxymethyl-cyclohexyl ester Methyl ester (800 mg, quantitative yield) was obtained in the same way as in Example (1e) from trans-(4-hydroxy-cyclohexyl)-acetic acid methyl ester (362 mg) obtained in Example (1d) and 1-(4-trifluoromethyl-phenyl)-3-(1,2,3,4-tetrahydro-isoquinolin-6-yl)-urea hydrochloride (558 mg) obtained in Example (69b). This methyl ester (800 mg) was hydrolyzed in the same way as in Example 2 to obtain the title compound (651 mg, 84%) as a white solid.

$^1$H NMR (400 MHz, DMSO-d6): δ (ppm)=12.1 (1H, s), 9.28 (1H, s), 8.94 (1H, s), 7.68-7.62 (4H, m), 7.34 (1H, d, J=1.2 Hz), 7.25 (1H, dd, J=8.6 and 1.6 Hz), 7.11 (1H, d, J=8.6 Hz), 4.51-4.47 (3H, m), 3.57 (2H, t, J=6.1 Hz), 2.76 (2H, t, J=5.6 Hz), 2.11 (2H, d, J=6.6 Hz), 1.95-1.91 (2H, m), 1.78-1.74 (2H, m), 1.68-1.63 (1H, m), 1.39-1.29 (2H, m), 1.12-1.03 (2H, m);

MS (ESI) m/z: 520 (M+H)$^+$.

Example 70 trans-6-[3-(3-ethyl-phenyl)-ureido]-3,4-dihydro-1H-isoquinoline-2-carboxylic acid 4-carboxymethyl-cyclohexyl ester

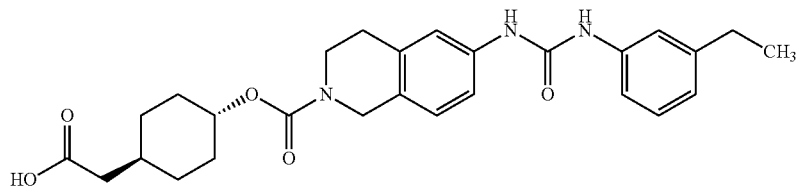 [SMILES: CCc1cccc(NC(=O)Nc2ccc3c(c2)CCN(C(=O)O[C@H]2CC[C@H](CC(=O)O)CC2)C3)c1]

(70a) 6-[3-(3-ethyl-phenyl)-ureido]-3,4-dihydro-1H-isoquinoline-2-carboxylic acid tort-butyl ester The title compound (1.19 g, quantitative yield) was obtained as a white solid in the same way as in Example (26a) from 6-amino-2N-Boc-1,2,3,4-tetrahydroisoquinoline (745 mg) and 3-ethyl-phenyl isocyanate (0.51 mL).

$^1$H NMR (400 MHz, CDCl$_3$): δ (ppm)=7.37 (1H, brs), 7.23 (1H, d, J=7.8 Hz), 7.21 (1H, d, J=7.5 Hz), 7.14 (1H, d, J=8.6 Hz), 7.10-6.89 (3H, m), 6.95 (1H, d, J=7.4 Hz), 6.75 (1H, brs), 4.50 (2H, s), 3.59 (2H, brs), 2.74 (2H, brs), 2.61 (2H, q, J=7.8 Hz), 1.50 (9H, s); 1.21 (3H, t, J=7.4 Hz).

(70b) 1-(3-ethyl-phenyl)-3-(1,2,3,4-tetrahydro-isoquinolin-6-yl)-urea hydrochloride The title compound (977 mg, 98%) was obtained as a white solid in the same way as in Example (22b) from 6-[3-(3-ethyl-phenyl)-ureido]-3,4-dihydro-1H-isoquinoline-2-carboxylic acid tert-butyl ester (1.19 g) obtained in Example (70a).

$^1$H NMR (400 MHz, DMSO-d6): δ (ppm)=9.06 (1H, brs), 8.99 (1H, s), 8.92 (1H, s), 7.41 (1H, d, J=1.6 Hz), 7.33 (1H, s), 7.29-7.23 (2H, m), 7.18 (1H, dd, J=7.8 and 7.8 Hz), 7.13 (1H, d, J=8.6 Hz), 6.83 (1H, d, J=7.0 Hz), 4.20 (2H, s), 3.39-3.35 (2H, m), 2.98 (2H, t, J=6.2 Hz), 2.57 (2H, q, J=7.5 Hz), 1.17 (3H, t, J=7.6 Hz).

(70c) trans-6-[3-(3-ethyl-phenyl)-ureido]-3,4-dihydro-1H-isoquinoline-2-carboxylic acid 4-carboxymethyl-cyclohexyl ester Methyl ester (740 mg, quantitative yield) was obtained in the same way as in Example (1e) from trans-(4-hydroxycyclohexyl)-acetic acid methyl ester (362 mg) obtained in Example (1d) and 1-(3-ethyl-phenyl)-3-(1,2,3,4-tetrahydro-isoquinolin-6-yl)-urea hydrochloride (498 mg) obtained in Example (70b). This methyl ester (740 mg) was hydrolyzed in the same way as in Example 2 to obtain the title compound (677 mg, 94%) as a white solid.

$^1$H NMR (400 MHz, DMSO-d6): δ (ppm)=12.1 (1H, s), 8.63 (2H, s), 7.33 (2H, s), 7.24-7.15 (3H, m), 7.08 (1H, d, J=8.6 Hz), 6.82 (1H, d, J=7.4 Hz), 4.52-4.46 (3H, m), 3.57 (2H, t, J=5.9 Hz), 2.75 (2H, t, J=5.8 Hz), 2.57 (2H, q, J=7.7 Hz), 2.12 (2H, d, J=7.1 Hz), 1.95-1.91 (2H, m), 1.77-1.73 (2H, m), 1.68-1.62 (1H, m), 1.39-1.29 (2H, m), 1.17 (3H, t, J=7.4 Hz), 1.12-1.02 (2H, m);

MS (ESI) m/z: 480 (M+H)$^+$.

Example 71 trans-6-(3-p-tolyl-ureido)-3,4-dihydro-1H-isoquinoline-2-carboxylic acid 4-carboxymethyl-cyclohexyl ester

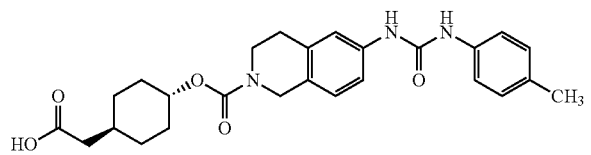 [SMILES: Cc1ccc(NC(=O)Nc2ccc3c(c2)CCN(C(=O)O[C@H]2CC[C@H](CC(=O)O)CC2)C3)cc1]

(71a) 6-(3-p-tolyl-ureido)-3,4-dihydro-1H-isoquinoline-2-carboxylic acid tert-butyl ester The title compound (1.14 g, quantitative yield) was obtained as a white solid in the same way as in Example (26a) from 6-amino-2N-Boc-1,2,3,4-tetrahydroisoquinoline (745 mg) and p-tolyl isocyanate (0.45 mL).

$^1$H NMR (400 MHz, CDCl$_3$): δ (ppm)=7.36-7.25 (1H, m), 7.23 (2H, d, J=8.2 Hz), 7.15 (2H, d, J=8.6 Hz), 7.06-6.85 (2H, m), 6.73-6.56 (2H, m), 4.51 s), 3.61 (2H, brs), 2.78 (2H, t, J=5.9 Hz), 2.33 (3H, s), 1.49 (9H, s).

(71b) 1-(1,2,3,4-tetrahydro-isoquinolin-6-yl)-3-p-tolyl-urea hydrochloride

The title compound (921 mg, 97%) was obtained as a white solid in the same way as in Example (22b) from 6-(3-p-tolyl-ureido)-3,4-dihydro-1H-isoquinoline-2-carboxylic acid tert-butyl ester (1.14 g) obtained in Example (71a).

$^1$H NMR (400 MHz, DMSO-d6): δ (ppm)=9.07 (1H, brs), 9.02 (1H, s), 8.92 (1H, s), 7.39 (1H, d, J=2.0 Hz), 7.34 (2H, d, J=8.6 Hz), 7.28 (1H, dd, J=8.5 and 2.2 Hz), 7.11 (1H, d, J=8.2 Hz), 7.08 (2H, d, J=8.6 Hz), 4.18 (2H, s), 3.37-3.31 (2H, m), 2.97 (2H, t, J=6.1 Hz), 2.24 (3H, s).

(71c) trans-6-(3-p-tolyl-ureido)-3,4-dihydro-1H-isoquinoline-2-carboxylic acid 4-carboxymethyl-cyclohexyl ester Methyl ester (719 mg, quantitative yield) was obtained in the same way as in Example (1e) from trans-(4-hydroxy-cyclohexyl)-acetic acid methyl ester (362 mg) obtained in Example (1d) and 1-(1,2,3,4-tetrahydro-isoquinolin-6-yl)-3-p-tolyl-urea hydrochloride (477 mg) obtained in Example (71b). This methyl ester (719 mg) was hydrolyzed in the same way as in Example 2 to obtain the title compound (635 mg, 91%) as a white solid.

$^1$H NMR (400 MHz, DMSO-d6): δ (ppm)=12.1 (1H, s), 8.61 (1H, s), 8.60 (1H, s), 7.34-7.31 (3H, m), 7.22-7.20 (1H, m), 7.09-7.07 (3H, m), 4.48-4.46 (3H, m), 3.56 (2H, t, J=4.3 Hz), 2.75 (2H, t, J=5.5 Hz), 2.24 (3H, s), 2.11 (2H, d, J=7.0 Hz), 1.95-1.91 (2H, m), 1.77-1.73 (2H, m), 1.68-1.62 (1H, m), 1.39-1.29 (2H, m), 1.12-1.02 (2H, m);

MS (ESI) m/z: 466 (M+H)$^+$.

Example 72 trans-6-[3-(4-isopropyl-phenyl)-ureido]-3,4-dihydro-1H-isoquinoline-2-carboxylic acid 4-carboxymethyl-cyclohexyl ester

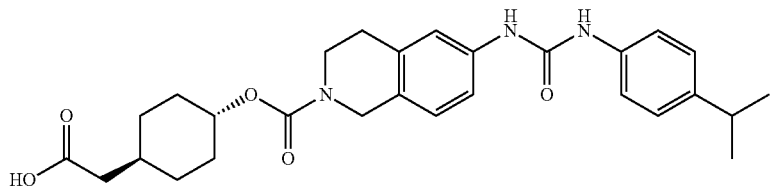 [SMILES: CC(C)c1ccc(NC(=O)Nc2ccc3c(c2)CCN(C(=O)O[C@H]2CC[C@H](CC(=O)O)CC2)C3)cc1]

(72a) 6-[3-(4-isopropyl-phenyl)-ureido]-1H-isoquinoline-2-carboxylic acid tert-butyl ester The title compound (1.23 g, quantitative yield) was obtained as a white solid in the same way as in Example (26a) from 6-amino-2N-Boc-1,2,3,4-tetrahydroisoquinoline (745 mg) and 4-isopropyl-phenyl isocyanate (0.58 mL).

$^1$H NMR (400 MHz, CDCl$_3$): δ (ppm)=7.37-6.75 (5H, m), 7.25 (2H, d, J=7.8 Hz), 7.16 (2H, d, J=8.6 Hz), 4.49 (2H, s), 3.57 (2H, brs), 2.90-2.83 (1H, m), 2.72 (2H, t, J=5.7 Hz), 1.50 (9H, s), 1.22 (6H, d, J=7.0 Hz).

(72b) 1-(4-isopropyl-phenyl)-3-(1,2,3,4-tetrahydro-isoquinolin-6-yl)-urea hydrochloride The title compound (1.04 g, quantitative yield) was obtained as a white solid in the same way as in Example (22b) from 6-[3-(3-isopropyl-phenyl)-ureido]-3,4-dihydro-1H-isoquinoline-2-carboxylic acid tert-butyl ester (1.23 g) obtained in Example (72a).

$^1$H NMR (400 MHz, DMSO-d6): δ (ppm)=9.11 (1H, brs), 9.00 (1H, s), 8.91 (1H, s), 7.39 (1H, d, J=2.0 Hz), 7.36 (2H, d, J=8.6 Hz), 7.28 (1H, dd, J=8.4 and 2.1 Hz), 7.15 (2H, d, J=8.6 Hz), 7.12 (1H, d, J=8.6 Hz), 4.19 (2H, s), 3.38-3.34 (2H, m), 2.97 (2H, t, J=6.2 Hz), 2.86-2.79 (1H, m), 1.18 (6H, d, J=7.0 Hz).

(72c) trans-6-[3-(4-isopropyl-phenyl)-ureido]-3,4-dihydro-1H-isoquinoline-2-carboxylic acid 4-carboxymethyl-cyclohexyl ester Methyl ester (761 mg, quantitative yield) was obtained in the same way as in Example (1e) from trans-(4-hydroxy-cyclohexyl)-acetic acid methyl ester (362 mg) obtained in Example (1d) and 1-(4-isopropyl-phenyl)-3-(1,2,3,4-tetrahydro-isoquinolin-6-yl)-urea hydrochloride (519 mg) obtained in Example (72b). This methyl ester (761 mg) was hydrolyzed in the same way as in Example 2 to obtain the title compound (640 mg, 87%) as a white solid.

$^1$H NMR (400 MHz, DMSO-d6): δ (ppm)=12.1 (1H, s), 8.63 (1H, s), 8.62 (1H, s), 7.36 (2H, d, J=8.6 Hz), 7.33 (1H, m), 7.21 (1H, d, J=8.3 Hz), 7.14 (2H, d, J=8.6 Hz), 7.08 (1H, d, J=8.2 Hz), 4.48-4.46 (3H, m), 3.56 (2H, t, J=5.9 Hz), 2.86-2.79 (1H, m), 2.75 (2H, t, J=5.9 Hz), 2.11 (2H, d, J=7.0 Hz), 1.95-1.91 (2H, m), 1.77-1.73 (2H, m), 1.68-1.62 (1H, m), 1.39-1.29 (2H, m), 1.18 (6H, d, J=6.6 Hz), 1.12-1.02 (2H, m);

MS (ESI) m/z: 494 (M+H)$^+$.

Example 73 trans-6-[3-(4-tert-butyl-phenyl)-ureido]-3,4-dihydro-1H-isoquinoline-2-carboxylic acid 4-carboxymethyl-cyclohexyl ester

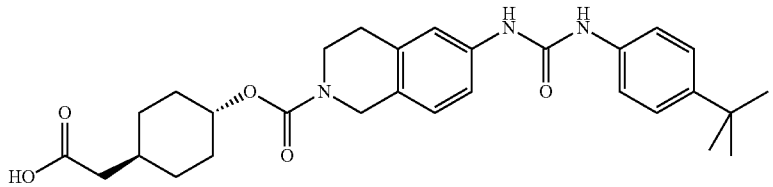 [SMILES: CC(C)(C)c1ccc(NC(=O)Nc2ccc3c(c2)CCN(C(=O)O[C@H]2CC[C@H](CC(=O)O)CC2)C3)cc1]

(73a) 6-[3-(4-tert-butyl-phenyl)-ureido]-3,4-dihydro-1H-isoquinoline-2-carboxylic acid tert-butyl ester The title compound (635 mg, quantitative yield) was obtained as a white solid in the same way as in Example (26a) from 6-amino-2N-Floc-1,2,3,4-tetrahydroisoquinoline (372 mg) and 4-tert-butyl-phenyl isocyanate (0.32 mL).

$^1$H NMR (400 MHz, CDCl$_3$): δ (ppm)=7.36 (2H, d, J=8.6 Hz), 7.27 (2H, d, J=8.2 Hz), 7.29-6.67 (5H, m), 4.51 (2H, s), 3.60 (2H, brs), 2.77 (2H, t, J=5.9 Hz), 1.5.0 (9H, s), 1.31 (9H, s).

(73b) 1-(4-tert-butyl-phenyl)-3-(1,2,3,4-tetrahydro-isoquinolin-6-yl)-urea hydrochloride The title compound (539 mg, quantitative yield) was obtained as a pale yellow solid in the same way as in Example (22b) from 6-[3-(4-tert-butyl-phenyl)-ureido]-3,4-dihydro-1H-isoquinoline-2-carboxylic acid tert-butyl ester (635 mg) obtained in Example (73a).

$^1$H NMR (400 MHz, DMSO-d6): δ (ppm)=9.13 (1H, brs), 9.02 (1H, s), 8.93 (1H, s), 7.40 (1H, d, J=1.6 Hz), 7.37 (2H, d, J=8.6 Hz), 7.29 (2H, d, J=8.7 Hz), 7.28 (1H, dd, J=8.6 and 2.7 Hz), 7.12 (1H, d, J=8.6 Hz), 4.19 (2H, brs), 3.39-3.36 (2H, m), 2.98 (2H, t, J=6.0 Hz), 1.26 (9H, s).

(73c) trans-6-[3-(4-tert-butyl-phenyl)-ureido]-3,4-dihydro-1H-isoquinoline-2-carboxylic acid 4-carboxymethyl-cyclohexyl ester Methyl ester (782 mg, quantitative yield) was obtained in the same way as in Example (1e) from trans-(4-hydroxy-cyclohexyl)-acetic acid methyl ester (361 mg) obtained in Example (1d) and 1-(4-tert-butyl-phenyl)-3-(1,2,3,4-tetrahydro-isoquinolin-6-yl)-urea hydrochloride (539 mg) obtained in Example (73b). This methyl ester (782 mg) was hydrolyzed in the same way as in Example 2 to obtain the title compound (653 mg, 86%) as a white solid.

$^1$H NMR (400 MHz, DMSO-d6): δ (ppm)=12.1 (1H, s), 8.74 (2H, brs), 7.37 (2H, d. J=9.0 Hz), 7.32 (1H, d, J=1.9 Hz), 7.29 (2H, d, J=9.0 Hz), 7.22 (1H, dd, J=8.2 and 2.0 Hz), 7.07 (1H, d, J=8.6 Hz), 4.51-4.46 (3H, m), 3.56 (2H, t, J=6.1 Hz), 2.75 (2H, t, J=6.0 Hz), 2.11 (2H, d, J=7.1 Hz), 1.95-1.90 (2H, m), 1.77-1.74 (2H, m), 1.68-1.63 (1H, m), 1.39-1.29 (2H, m), 1.26 (9H, s), 1.12-1.02 (2H, m);

MS (ESI) m/z: 508 (M+H)$^+$.

Example 74 trans-6-[3-(3-cyano-phenyl)-ureido]-3,4-dihydro-1H-isoquinoline-2-carboxylic acid 4-carboxymethyl-cyclohexyl ester

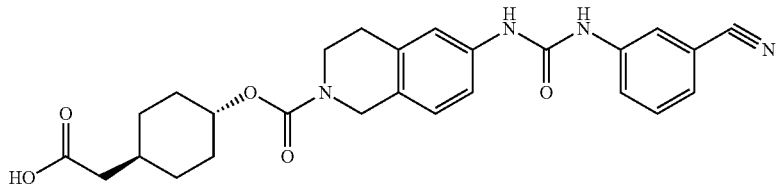 [SMILES: N#Cc1cccc(NC(=O)Nc2ccc3c(c2)CCN(C(=O)O[C@H]2CC[C@H](CC(=O)O)CC2)C3)c1]

(74a) 6-[3-(3-cyano-phenyl)-ureido]-3,4-dihydro-1H-isoquinoline-2-carboxylic acid tert-butyl ester The title compound (785 mg, quantitative yield) was obtained as a white solid in the same way as in Example (26a)

from 6-amino-2N-Roc-1,2,3,4-tetrahydroisoquinoline (497 mg) and 3-cyano-phenyl isocyanate (346 mg).

$^1$H NMR (400 MHz, CDCl$_3$): δ (ppm)=7.75-6.50 (6H, m), 7.65 (1H, d, J=8.6 Hz), 7.39 (1H, dd, J=7.8 and 7.8 Hz), 7.33 (1H, d, J=7.5 Hz), 4.51 (2H, s), 3.63 (2H, t, J=6.1 Hz), 2.79 (2H, brs), 1.53 (9H, s).

(74b) 1-(3-cyano-phenyl)-3-(1,2,3,4-tetrahydro-iso-quinolin-6-yl)-urea hydrochloride The title compound (657 mg, quantitative yield) was obtained as a pale yellow solid in the same way as in Example (22b) from 6-[3-(3-cyano-phenyl)-ureido]-3,4-dihydro-1H-isoquinoline-2-carboxylic acid tert-butyl ester (785 mg) obtained in Example (74a).

$^1$H NMR (400 MHz, DMSO-d6): δ (ppm)=H, s), 9.27 (1H, s), 9.12 (1H, brs), 8.00 (1H, dd, J=1.9 and 2.0 Hz), 7.66-7.63 (1H, m), 7.50 (1H, dd, J=8.0 and 8.0 Hz), 7.44-7.40 (2H, m), 7.30 (1H, dd, J=8.2 and 2.3 Hz), 7.15 (1H, d, J=8.2 Hz), 4.20 (2H, brs), 3.39-3.36 (2H, m), 2.98 (2H, t, J=6.3 Hz).

(74c) trans-6-[3-(3-cyano-phenyl)-ureido]-3,4-dihydro-1H-isoquinoline-2-carboxylic acid 4-carboxymethyl-cyclohexyl ester Methyl ester (498 mg, 81%) was obtained in the same way as in Example (1e) from trans-(4-hydroxy-cyclohexyl)-acetic acid methyl ester (301 mg) obtained in Example (1d) and 1-(3-cyano-phenyl)-3-(1,2,3,4-tetrahydro-isoquinolin-6-yl)-urea hydrochloride (411 mg) obtained in Example (74b). This methyl ester (498 mg) was hydrolyzed in the same way as in Example 2 to obtain the title compound (393 mg, 81%) as a pale yellow solid.

$^1$H NMR (400 MHz, DMSO-d6): δ (ppm)=12.1 (1H, s), 9.07 (1H, s), 8.85 (1H, s), 7.99 (1H, s), 7.67 (1H, d, J=8.6 Hz), 7.49 (1H, dd, J=8.0 and 8.0 Hz), 7.42 (1H, d, J=7.1 Hz), 7.33 (1H, s), 7.24 (1H, d, J=7.1 Hz), 7.11 (1H, d, J=8.6 Hz), 4.51-4.47 (3H, m), 3.57 (2H, t, J=5.7 Hz), 2.76 (2H, t, J=5.3 Hz), 2.12 (2H, d, J=7.1 Hz), 1.95-1.91 (2H, m), 1.77-1.74 (2H, m), 1.68-1.62 (1H, m), 1.39-1.29 (2H, m), 1.12-1.03 (2H, m);

MS (ESI) m/z: 477 (M+H)$^+$.

Example 75 trans-6-[3-(3-dimethylamino-phenyl)-ureido]-3,4-dihydro-1H-isoquinoline-2-carboxylic acid 4-carboxymethyl-cyclohexyl ester (75a) 6-[3-(3-dimethylamino-phenyl)-ureido]-3,4-dihydro-1H-isoquinoline-2-carboxylic acid tert-butyl ester The title compound (1.23 g, quantitative yield) was obtained as a white solid in the same way as in Example (28a) from 6-amino-2N-Boc-1,2,3,4-tetrahydroisoquinoline (745 mg) and 3-dimethylaminoaniline hydrochloride (627 mg).

$^1$H NMR (400 MHz, CDCl$_3$): δ (ppm)=7.33-7.15 (2H, m), 7.03-6.77 (4H, m), 6.61-6.50 (3H, m), 4.52 (2H, s), 3.62 (2H, brs), 2.96 (6H, s), 2.79 (2H, t, J=5.9 Hz), 1.49 (9H, s).

(75b) 1-(3-dimethylamino-phenyl)-3-(1,2,3,4-tetrahydro-isoquinolin-6-yl)-urea hydrochloride The title compound (1.15 g, quantitative yield) was obtained as a white solid in the same way as in Example (22b) from 6-[3-(3-dimethylamino-phenyl)-ureido]-3,4-dihydro-1H-isoquinoline-2-carboxylic acid tert-butyl ester (1.23 g) obtained in Example (75a).

$^1$H NMR (400 MHz, DMSO-d6): δ (ppm)=9.38 (1H, brs), 9.18 (2H, brs), 7.40 (1H, d, J=5.8 Hz), 7.29 (1H, d, J=8.2 Hz), 7.23-6.65 (4H, m), 7.13 (1H, d, J=8.3 Hz), 4.19 (2H, brs), 3.37 (2H, brs), 2.98 (8H, brs).

(75c) trans-6-[3-(3-dimethylamino-phenyl)-ureido]-3,4-dihydro-1H-isoquinoline-2-carboxylic acid 4-carboxymethyl-cyclohexyl ester Methyl ester (207 mg, 41%) was obtained in the same way as in Example (1e) from trans-(4-hydroxy-cyclohexyl)-acetic acid methyl ester (223 mg) obtained in Example (1d) and 1-(3-dimethylamino-phenyl)-3-(1,2,3,4-tetrahydro-isoquinolin-6-yl)-urea hydrochloride (383 mg) obtained in Example (75b). This methyl ester (207 mg) was hydrolyzed with an aqueous sodium hydroxide solution in the same way as in Example 2 to obtain the title compound (136 mg, 68%) as a gray solid.

$^1$H NMR (400 MHz, DMSO-d6): δ (ppm)=9.03 (1H, brs), 8.89 (1H, s), 7.38 (1H, brs), 7.32 (1H, s), 7.26 (1H, brs), 7.23 (1H, dd, J=8.5 and 1.8 Hz), 7.09 (1H, d, J=8.6 Hz), 7.04 (1H, brs), 6.82 (1H, brs), 4.52-4.45 (3H, m), 3.57 (2H, t, J=6.0 Hz), 3.01 (6H, s), 2.75 (2H, t, J=5.9 Hz), 2.12 (2H, d, J=7.1 Hz), 1.95-1.91 (2H, m), 1.77-1.74 (2H, m), 1.68-1.61 (1H, m), 1.39-1.30 (2H, m), 1.12-1.02 (2H, m);

MS (ESI) m/z: 495 (M+H)$^+$.

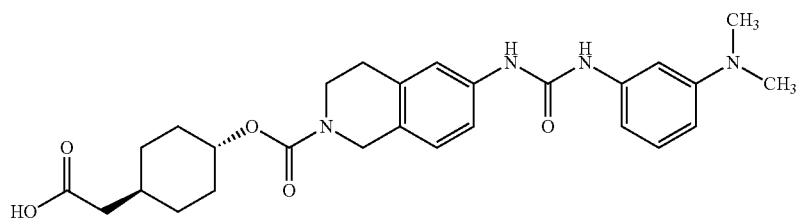

Example 76 trans-6-[3-(3-tert-butyl-phenyl)-ureido]-3,4-dihydro-1H-isoquinoline-2-carboxylic acid 4-carboxymethyl-cyclohexyl ester

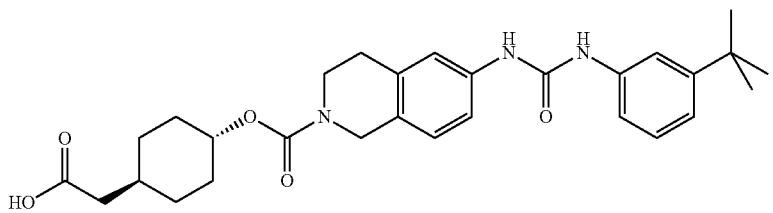 [SMILES: CC(C)(C)c1cccc(NC(=O)Nc2ccc3c(c2)CCN(C(=O)O[C@H]2CC[C@H](CC(=O)O)CC2)C3)c1]

(76a) 6-[3-(3-tert-butyl-phenyl)-ureido]-3,4-dihydro-1H-isoquinoline-2-carboxylic acid tert-butyl ester The title compound (1.24 g, 98%) was obtained as a white solid in the same way as in Example (28a) from 6-amino-2N-Boc-1,2,3,4-tetrahydroisoquinoline (745 mg) and 3-tert-butyl-aniline (448 mg).
$^1$H NMR (400 MHz, CDCl$_3$): δ (ppm)=7.36 (1H, dd, J=1.9 and 2.0 Hz), 7.30-6.88 (7H, m), 6.75 (1H, brs), 4.52 (2H, s), 3.62 (2H, brs), 2.79 (2H, t, J=5.9 Hz), 1.50 (9H, s), 1.31 (9H, s).

(76b) 1-(3-tert-butyl-phenyl)-3-(1,2,3,4-tetrahydro-isoquinolin-6-yl)-urea hydrochloride The title compound (1.06 g, quantitative yield) was obtained as an off-white solid in the same way as in Example (22b) from 6-[3-(3-tert-butyl-phenyl)-ureido]-3,4-dihydro-1H-isoquinoline-2-carboxylic acid tert-butyl ester (1.24 g) obtained in Example (76a).
$^1$H NMR (400 MHz, DMSO-d6): δ (ppm)=9.02 (1H, brs), 8.96 (1H, s), 8.93 (1H, s), 7.49 (1H, dd, J=2.0 and 2.0 Hz), 7.41 (1H, d, J=1.5 Hz), 7.29-7.25 (2H, m), 7.20 (1H, dd, J=7.8 and 7.8 Hz), 7.12 (1H, d, J=8.6 Hz), 7.01 (1H, d, J=7.8 Hz), 4.19 (2H, s), 3.38-3.32 (2H, m), 2.98 (2H, t, J=6.0 Hz), 1.27 (9H, s).

(76c) trans-6-[3-(3-tert-butyl-phenyl)-ureido]-3,4-dihydro-1H-isoquinoline-2-carboxylic acid 4-carboxymethyl-cyclohexyl ester Methyl ester (521 mg, quantitative yield) was obtained in the same way as in Example (1e) from trans-(4-hydroxy-cyclohexyl)-acetic acid methyl ester (223 mg) obtained in Example (1d) and 1-(3-tert-butyl-phenyl)-3-(1,2,3,4-tetrahydro-isoquinolin-6-yl)-urea hydrochloride (359 mg) obtained in Example (76b). This methyl ester (521 mg) was hydrolyzed with an aqueous sodium hydroxide solution in the same way as in Example 2 to obtain the title compound (395 mg, 78%) as a yellow solid.
$^1$H NMR (400 MHz, DMSO-d6): δ (ppm)=12.1 (1H, brs), 8.82 (1H, brs), 8.77 (1H, brs), 7.48 (1H, s), 7.34 (1H, s), 7.28 (1H, d, J=9.4 Hz), 7.24-7.17 (2H, m), 7.08 (1H, d, J=8.2 Hz), 7.00 (1H, d, J=7.8 Hz), 4.51-4.46 (3H, m), 3.57 (2H, t, J=5.9 Hz), 2.75 (2H, t, J=5.9 Hz), 2.11 (2H, d, J=7.1 Hz), 1.94-1.90 (2H, m), 1.78-1.74 (2H, m), 1.68-1.63 (1H, m), 1.40-1.29 (2H, m), 1.40 (9H, s), 1.12-1.01 (2H, m);
MS (ESI) m/z: 508 (M+H)$^+$.

Example 77 trans-6-(3-o-tolyl-ureido)-3,4-dihydro-1H-isoquinoline-2-carboxylic acid 4-carboxymethyl-cyclohexyl ester

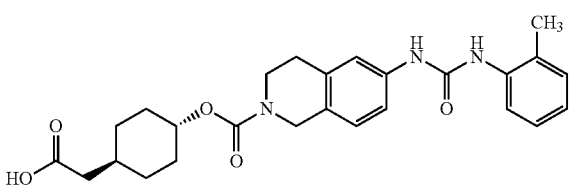 [SMILES: Cc1ccccc1NC(=O)Nc1ccc2c(c1)CCN(C(=O)O[C@H]1CC[C@H](CC(=O)O)CC1)C2]

(77a) 6-(3-o-tolyl-ureido)-3,4-dihydro-1H-isoquinoline-2-carboxylic acid tert-butyl ester The title compound (1.13 g, 99%) was obtained as a white solid in the same way as in Example (26a) from 6-amino-2N-Boc-1,2,3,4-tetrahydroisoquinoline (745 mg) and o-tolyl isocyanate (0.45 mL).
$^1$H NMR (400 MHz, CDCl$_3$): δ (ppm)=7.52 (1H, d, J=7.5 Hz), 7.30-7.15 (5H, m), 7.03 (1H, d, J=7.4 Hz), 6.47 (1H, brs), 6.25 (1H, brs), 4.52 (2H, s), 3.62 (2H, brs), 2.79 (2H, t, J=5.9 Hz), 2.29 (3H, s), 1.49 (9H, s).

(77b) 1-(1,2,3,4-tetrahydro-isoquinolin-6-yl)-3-o-tolyl-urea hydrochloride

The title compound (938 mg, quantitative yield) was obtained as a pale yellow solid in the same way as in Example (22b) from 6-(3-o-tolyl-ureido)-3,4-dihydro-1H-isoquinoline-2-carboxylic acid tert-butyl ester (1.13 g) obtained in Example (77a).
$^1$H NMR (400 MHz, DMSO-d6): δ (ppm)=9.50 (1H, s), 9.12 (1H, brs), 8.22 (1H, s), 7.84 (1H, d, J=7.8 Hz), 7.42 (1H, d, J=1.9 Hz), 7.30 (1H, dd, J=8.3 and 2.0 Hz), 7.18-7.12 (3H, m), 6.95 (1H, dd, J=7.2 and 7.2 Hz), 4.19 (2H, s), 3.38-3.31 (2H, m), 2.98 (2H, t, J=6.2 Hz), 2.26 (3H, s).

(77c) trans-6-(3-o-tolyl-ureido)-3,4-dihydro-1H-isoquinoline-2-carboxylic acid 4-carboxymethyl-cyclohexyl ester Methyl ester (719 mg, quantitative yield) was obtained in the same way as in Example (1e) from trans-(4-hydroxycyclohexyl)-acetic acid methyl ester (309 mg) obtained in Example (1d) and 1-(1,2,3,4-tetrahydro-isoquinolin-6-yl)-3-o-tolyl-urea hydrochloride (476 mg) obtained in Example (77b). This methyl ester (719 mg) was hydrolyzed with an aqueous sodium hydroxide solution in the same way as in Example 2 to obtain the title compound (638 mg, 91%) as a white solid.

$^1$H NMR (400 MHz, DMSO-d6): δ (ppm)=12.1 (1H, brs), 9.03 (1H, s), 7.97 (1H, s), 7.83 (1H, d, J=7.8 Hz), 7.34 (1H, s), 7.23 (1H, d, J=7.5 Hz), 7.17 (1H, d, J=8.2 Hz), 7.13 (1H, d, J=7.8 Hz), 7.09 (1H, d, J=8.6 Hz), 6.94 (1H, dd, J=7.5 and 7.5 Hz), 4.51-4.46 (3H, m), 3.57 (2H, t, J=5.8 Hz), 2.76 (2H, t, 7=5.7 Hz), 2.24 (3H, s), 2.11 (2H, d, J=6.6 Hz), 1.95-1.90 (2H, m), 1.77-1.73 (2H, m), 1.68-1.62 (1H, m), 1.39-1.30 (2H, m), 1.12-1.02 (2H, m);

MS (ESI) m/z: 466 (M+H)$^+$.

Example 78 trans-6-[3-(3,4-dimethyl-phenyl)-ureido]-3,4-dihydro-1H-isoquinoline-2-carboxylic acid 4-carboxymethyl-cyclohexyl ester

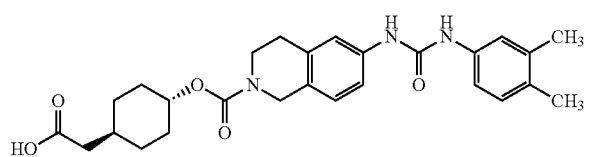 [SMILES: Cc1ccc(NC(=O)Nc2ccc3c(c2)CCN(C(=O)O[C@H]2CC[C@H](CC(=O)O)CC2)C3)cc1C]

(78a) 6-[3-(3,4-dimethyl-phenyl)-ureido]-3,4-dihydro-1H-isoquinoline-2-carboxylic acid tert-butyl ester The title compound (1.19 g, quantitative yield) was obtained as a white solid in the same way as in Example (26a) from 6-amino-2N-Boc-1,2,3,4-tetrahydroisoquinoline (745 mg) and 3,4-dimethyl-phenyl isocyanate (0.50 mL).

$^1$H NMR (400 MHz, CDCl$_3$): δ (ppm)=7.33-6.74 (5H, m), 7.12 (1H, brs), 7.08 (1H, dd, J=6.5 and 6.5 Hz), 6.84 (1H, brs), 4.50 (2H, s), 3.59 (2H, brs), 2.76 (2H, t, J=5.7 Hz), 2.22 (6H, s), 1.49 (9H, s).

(78b) 1-(3,4-dimethyl-phenyl)-3-(1,2,3,4-tetrahydro-isoquinolin-6-yl)-urea hydrochloride The title compound (993 mg, quantitative yield) was obtained as a pale yellow solid in the same way as in Example (22b) from 6-[3-(3,4-dimethyl-phenyl)-ureido]-3,4-dihydro-1H-isoquinoline-2-carboxylic acid tert-butyl ester (1.19 g) obtained in Example (78a).

$^1$H NMR (400 MHz, DMSO-d6): δ (ppm)=9.10 (1H, brs), 9.03 (1H, s), 8.86 (1H, s), 7.40 (1H, d, J=1.9 Hz), 7.27 (1H, dd, J=8.4 and 2.1 Hz), 7.24 (1H, d, J=1.9 Hz), 7.17 (1H, dd, J=8.2 and 2.4 Hz), 7.11 (1H, d, J=8.6 Hz), 7.02 (1H, d, J=8.2 Hz), 4.19 (2H, s), 3.37-3.31 (2H, m), 2.97 (2H, t, J=6.2 Hz), 2.18 (3H, s), 2.15 (3H, s).

(78c) trans-6-[3-(3,4-dimethyl-phenyl)-ureido]-3,4-dihydro-1H-isoquinoline-2-carboxylic acid 4-carboxymethyl-cyclohexyl ester Methyl ester (740 mg, quantitative yield) was obtained in the same way as in Example (1e) from trans-(4-hydroxy-cyclohexyl)-acetic acid methyl ester (309 mg) obtained in Example (1d) and 1-(3,4-dimethyl-phenyl)-3-(1,2,3,4-tetrahydro-isoquinolin-6-yl)-urea hydrochloride (498 mg) obtained in Example (78b). This methyl ester (740 mg) was hydrolyzed with an aqueous sodium hydroxide solution in the same way as in Example 2 to obtain the title compound (619 mg, 86%) as a white solid.

$^1$H NMR (400 MHz, DMSO-d6): δ (ppm)=12.1 (1H, brs), 8.64 (1H, s), 8.55 (1H, s), 7.33 (1H, s), 7.24 (1H, d, J=1.6 Hz), 7.21 (1H, d, J=8.6 Hz), 7.15 (1H, dd, J=8.4 and 2.2 Hz), 7.07 (1H, d, J=8.6 Hz), 7.02 (1H, d, 8.2 Hz), 4.52-4.46 (3H, m), 3.57 (2H, t, J=5.9 Hz), 2.75 (2H, t, J=5.5 Hz), 2.18 (3H, s), 2.15 (3H, s), 2.11 (2H, d, J=6.6 Hz), 1.95-1.91 (2H, m), 1.78-1.74 (2H, m), 1.68-1.62 (1H, m), 1.39-1.29 (2H, m), 1.12-1.02 (2H, m);

MS (ESI) m/z: 480 (M+H)$^+$.

Example 79 trans-6-[3-(4-methoxy-phenyl)-ureido]-3,4-dihydro-1H-isoquinoline-2-carboxylic acid 4-carboxymethyl-cyclohexyl ester

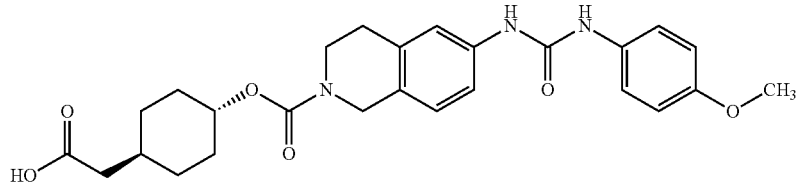 [SMILES: COc1ccc(NC(=O)Nc2ccc3c(c2)CCN(C(=O)O[C@H]2CC[C@H](CC(=O)O)CC2)C3)cc1]

(79a) 6-[3-(4-methoxy-phenyl)-ureido]-3,4-dihydro-1H-isoquinoline-2-carboxylic acid tert-butyl ester The title compound (747 mg, 94%) was obtained as a white solid in the same way as in Example (26a) from 6-amino-2N-Boc-1,2,3,4-tetrahydroisoquinoline (497 mg) and 4-methoxy-phenyl isocyanate (0.31 mL).

$^1$H NMR (400 MHz, CDCl$_3$): δ (ppm)=7.29-7.15 (2H, m), 7.25 (2H, d, J=8.6 Hz), 7.00 (1H, d, J=6.7 Hz), 6.89 (2H, d, J=8.6 Hz), 6.62 (1H, brs), 6.55 (1H, brs), 4.51 (2H, s), 3.81 (3H, s), 3.61 (2H, brs), 2.77 (2H, t, J=5.8 Hz), 1.49 (9H, s).

(79b) 1-(4-methoxy-phenyl)-3-(1,2,3,4-tetrahydro-isoquinolin-6-yl)-urea hydrochloride The title compound (621 mg, 99%) was obtained as a white solid in the same way as in Example (22b) from 6-[3-(4-methoxy-phenyl)-ureido]-3,4-dihydro-1H-isoquinoline-2-carboxylic acid tert-butyl ester (747 mg) obtained in Example (79a).

$^1$H NMR (400 MHz, DMSO-d6): δ (ppm)=9.15 (1H, brs), 9.02 (1H, s), 8.87 (1H, s), 7.36-7.31 (1H, m), 7.33 (2H, d, J=9.0 Hz), 7.26 (1H, dd, J=8.4 and 2.1 Hz), 7.09 (1H, d, J=8.6 Hz), 6.85 (2H, d, J=9.0 Hz), 4.16 (2H, s), 3.69 (3H, s), 3.35-3.31 (2H, m), 2.95 (2H, t, J=6.2 Hz).

(79c) trans-6-[3-(4-methoxy-phenyl)-ureido]-3,4-dihydro-1H-isoquinoline-2-carboxylic acid 4-carboxymethyl-cyclohexyl ester Methyl ester (407 mg, 82%) was obtained in the same way as in Example (1e) from trans-(4-hydroxy-cyclohexyl)-acetic acid methyl ester (206 mg) obtained in Example (1d) and 1-(4-methoxy-phenyl)-3-(1,2,3,4-tetrahydro-isoquinolin-6-yl)-urea hydrochloride (333 mg) obtained in Example (79b). This methyl ester (407 mg) was hydrolyzed with an aqueous sodium hydroxide solution in the same way as in Example 2 to obtain the title compound (378 mg, 96%) as a white solid.

$^1$H NMR (400 MHz, DMSO-d6): δ (ppm)=12.1 (1H, s), 8.57 (1H, s), 8.51 (1H, s), 7.35 (2H, d, J=9.0 Hz), 7.31 (1H, s), 7.21 (1H, d, J=8.6 Hz), 7.07 (1H, d, J=8.2 Hz), 6.87 (2H, d, J=9.0 Hz), 4.52-4.46 (3H, m), 3.72 (3H, s), 3.56 (2H, t, J=5.8 Hz), 2.74 (2H, t, J=5.9 Hz), 2.12 (2H, d, J=7.0 Hz), 1.95-1.91 (2H, m), 1.77-1.73 (2H, m), 1.69-1.62 (1H, m), 1.39-1.29 (2H, m), 1.12-1.02 (2H, m);

MS (ESI) m/z: 482 (M+H)$^+$.

Example 80 trans-6-[3-(4-ethoxy-phenyl)-ureido]-3,4-dihydro-1H-isoquinoline-2-carboxylic acid 4-carboxymethyl-cyclohexyl ester

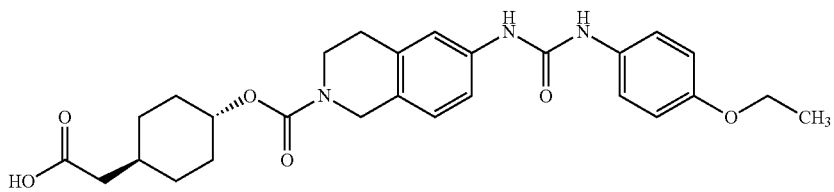 [SMILES: CCOc1ccc(NC(=O)Nc2ccc3c(c2)CCN(C(=O)O[C@H]2CC[C@H](CC(=O)O)CC2)C3)cc1]

(80a) 6-[3-(4-ethoxy-phenyl)-ureido]-3,4-dihydro-1H-isoquinoline-2-carboxylic acid tert-butyl ester The title compound (798 mg, 97%) was obtained as a white solid in the same way as in Example (26a) from 6-amino-2N-Boc-1,2,3,4-tetrahydroisoquinoline (497 mg) and 4-ethoxyphenyl isocyanate (0.35 mL).

$^1$H NMR (400 MHz, CDCl$_3$): δ (ppm)=7.28-7.15 (2H, m), 7.24 (2H, d, J=8.6 Hz), 7.02 (1H, d, J=7.8 Hz), 6.89 (2H, d, J=8.6 Hz), 6.47 (1H, brs), 6.37 (1H, brs), 4.52 (2H, s), 4.03 (2H, q, J=6.9 Hz), 3.61 (2H, t, J=5.5 Hz), 2.79 (2H, t, J=6.0 Hz), 1.49 (9H, s), 1.42 (3H, t, J=7.1 Hz).

(80b) 1-(4-ethoxy-phenyl)-3-(1,2,3,4-tetrahydro-isoquinolin-6-yl)-urea hydrochloride The title compound (674 mg, quantitative yield) was obtained as an off-white solid in the same way as in Example (22b) from 6-[3-(4-ethoxy-phenyl)-ureido]-3,4-dihydro-1H-isoquinoline-2-carboxylic acid tert-butyl ester (798 mg) obtained in Example (80a).

$^1$H NMR (400 MHz, DMSO-d6): δ (ppm)=9.17 (1H, brs), 9.04 (1H, s), 8.89 (1H, s), 7.35 (1H, d, J=1.9 Hz), 7.32 (2H, d, J=9.0 Hz), 7.26 (1H, dd, J=8.2 and 1.9 Hz), 7.09 (1H, d, J=8.2 Hz), 6.83 (2H, d, J=9.0 Hz), 4.16 (2H, t, J=4.1 Hz), 3.95 (2H, q, J=7.0 Hz), 3.41-3.31 (2H, m), 2.95 (2H, t, J=6.1 Hz), 1.28 (3H, t, J=6.8 Hz).

(80c) trans-6-[3-(4-ethoxy-phenyl)-ureido]-3,4-dihydro-1H-isoquinoline-2-carboxylic acid 4-carboxymethyl-cyclohexyl ester Methyl ester (488 mg, 96%) was obtained in the same way as in Example (1e) from trans-(4-hydroxy-cyclohexyl)-acetic acid methyl ester (206 mg) obtained in Example (1d) and 1-(4-ethoxy-phenyl)-3-(1,2,3,4-tetrahydro-isoquinolin-6-yl)-urea hydrochloride (347 mg) obtained in Example (80b). This methyl ester (488 mg) was hydrolyzed with an aqueous sodium hydroxide solution in the same way as in Example 2 to obtain the title compound (410 mg, 87%) as a white solid.

$^1$H NMR (400 MHz, DMSO-d6): δ (ppm)=12.1 (1H, brs), 8.59 (1H, s), 8.51 (1H, s), 7.36-7.30 (1H, m), 7.34 (2H, d, J=8.9 Hz), 7.21 (1H, dd, J=7.6 and 1.8 Hz), 7.07 (1H, d, J=8.6 Hz), 6.85 (2H, d, J=9.0 Hz), 4.51-4.45 (3H, m), 3.97 (2H, q, J=7.0 Hz), 3.56 (2H, t, J=5.9 Hz), 2.74 (2H, t, J=5.6 Hz), 2.11 (2H, d, J=6.6 Hz), 1.94-1.91 (2H, m), 1.77-1.73 (2H, m), 1.68-1.62 (1H, m), 1.39-1.31 (2H, m), 1.30 (3H, t, J=6.9 Hz), 1.12-1.01 (2H, m);

MS (ESI) m/z: 496 (M+H)$^+$.

Example 81 trans-6-(3-isopropyl-ureido)-3,4-dihydro-1H-isoquinoline-2-carboxylic acid 4-carboxymethyl-cyclohexyl ester

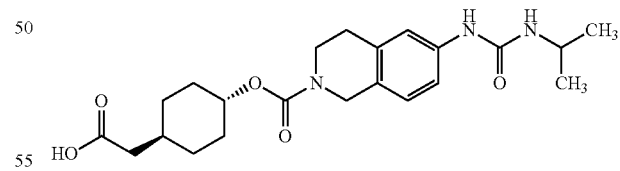

(81a) 6-(3-isopropyl-ureido)-3,4-dihydro-1H-isoquinoline-2-carboxylic acid tert-butyl ester The title compound (604 mg, 91%) was obtained as a white solid in the same way as in Example (28a) from 6-amino-2N-Boc-1,2,3,4-tetrahydroisoquinoline (496 mg) and isopropylamine (0.17 mL).

$^1$H NMR (400 MHz, CDCl$_3$): δ (ppm)=7.22-6.96 (4H, m), 6.08 (1H, s), 4.53 (2H, s), 4.04-3.95 (1H, m), 3.63 (2H, brs), 2.80 (2H, t, J'=6.1 Hz), 1.49 (9H, s), 1.18 (6H, d, J=6.6 Hz).

(81b) 1-isopropyl-3-(1,2,3,4-tetrahydro-isoquinolin-6-yl)-urea hydrochloride The title compound (488 mg, quantitative yield) was obtained as a white solid in the same way as in Example (22b) from 6-(3-isopropyl-ureido)-3,4-dihydro-1H-isoquinoline-2-carboxylic acid tert-butyl ester (604 mg) obtained in Example (81a).

$^1$H NMR (400 MHz, DMSO-d6): δ (ppm)=9.27 (1H, brs), 8.66 (1H, s), 7.32 (1H, d, J=2.0 Hz), 7.20 (1H, dd, J=8.4 and 2.1 Hz), 7.05 (1H, d, J=8.6 Hz), 4.77 (1H, brs), 4.15 (2H, t, J=4.3 Hz), 3.76-3.70 (1H, m), 3.35-3.30 (2H, m), 2.93 (2H, t, J=6.2 Hz), 1.08 (6H, d, J=6.7 Hz).

(81c) trans-6-(3-isopropyl-ureido)-3,4-dihydro-1H-isoquinoline-2-carboxylic acid 4-carboxymethyl-cyclohexyl ester Methyl ester (455 mg, 88%) was obtained in the same way as in Example (1e) from trans-(4-hydroxy-cyclohexyl)-acetic acid methyl ester (289 mg) obtained in Example (1d) and 1-isopropyl-3-(1,2,3,4-tetrahydro-isoquinolin-6-yl)-urea hydrochloride (324 mg) obtained in Example (81b). This methyl ester (455 mg) was hydrolyzed in the same way as in Example 2 to obtain the title compound (383 mg, 87%) as a white solid.

$^1$H NMR (400 MHz, DMSO-d6): δ (ppm)=12.1 (1H, s), 8.23 (1H, s), 7.24 (1H, s), 7.13 (1H, d, J=7.8 Hz), 7.01 (1H, d, J=8.6 Hz), 5.99 (1H, d, J=7.5 Hz), 4.50-4.43 (3H, m), 3.76-3.71 (1H, m), 3.55 (2H, t, J=6.0 Hz), 2.71 (2H, t, J=5.9 Hz), 2.11 (2H, d, J=6.6 Hz), 1.94-1.90 (2H, m), 1.77-1.73 (2H, m), 1.68-1.62 (1H, m), 1.38-1.29 (2H, m), 1.11-1.01 (2H, m), 1.08 (6H, d, J=6.7 Hz);
MS (ESI) m/z: 418 (M+H)$^+$.

Example 82 trans-6-(3-tert-butyl-ureido)-3,4-dihydro-1H-isoquinoline-2-carboxylic acid 4-carboxymethyl-cyclohexyl ester

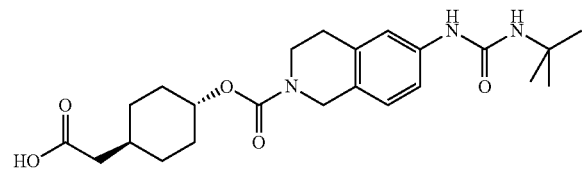 [SMILES: CC(C)(C)NC(=O)Nc1ccc2c(c1)CCN(C(=O)O[C@H]1CC[C@H](CC(=O)O)CC1)C2]

(82a) 6-(3-tert-butyl-ureido)-3,4-dihydro-1H-isoquinoline-2-carboxylic acid tert-butyl ester The title compound (434 mg, 63%) was obtained as a white solid in the same way as in Example (28a) from 6-amino-2N-Boc-1,2,3,4-tetrahydroisoquinoline (496 mg) and tert-butylamine (0.21

$^1$H NMR (400 MHz, CDCl$_3$): δ (ppm)=7.22-6.89 (4H, m), 6.03 (1H, s), 4.51 (2H, s), 3.62 (2H, brs), 2.80 (2H, t, J=5.8 Hz), 1.49 (9H, s), 1.37 (9H, s).

(82b) 1-tert-butyl-3-(1,2,3,4-tetrahydro-isoquinolin-6-yl)-urea hydrochloride The title compound (354 mg, quantitative yield) was obtained as a white solid in the same way as in Example (22b) from 6-(3-tert-butyl-ureido)-3,4-dihydro-1H-isoquinoline-2-carboxylic acid tert-butyl ester (434 mg) obtained in Example (82a).

$^1$H NMR (400 MHz, DMSO-d6): δ (ppm)=9.13 (1H, brs), 8.50 (1H, s), 7.34 (1H, d, J=1.9 Hz), 7.13 (1H, dd, J=8.4 and 2.1 Hz), 7.04 (1H, d, J=8.6 Hz), 6.17 (1H, brs), 4.15 (2H, brs), 3.36-3.31 (2H, m), 2.94 (2H, t, J=6.2 Hz), 1.28 (9H, s).

(82c) trans-6-(3-tert-butyl-ureido)-3,4-dihydro-1H-isoquinoline-2-carboxylic acid 4-carboxymethyl-cyclohexyl ester Methyl ester (557 mg, quantitative yield) was obtained in the same way as in Example (1e) from trans-(4-hydroxy-cyclohexyl)-acetic acid methyl ester (301 mg) obtained in Example (1d) and 1-tert-butyl-3-(1,2,3,4-tetrahydro-isoquinolin-6-yl)-urea hydrochloride (354 mg) obtained in Example (82b). This methyl ester (557 mg) was hydrolyzed in the same way as in Example 2 to obtain the title compound (451 mg, 84%) as a white solid.

$^1$H NMR (400 MHz, DMSO-d6): δ (ppm) 12.1 (1H, brs), 8.18 (1H, s), 7.26-7.07 (1H, m), 6.99 (2H, s), 5.97 (1H, s), 4.50-4.42 (3H, m), 3.54 (2H, t, J=5.9 Hz), 2.71 (2H, t, J=6.1 Hz), 2.11 (2H, d, J=6.6 Hz), 1.94-1.91 (2H, m), 1.77-1.73 (2H, m), 1.68-1.61 (1H, m), 1.38-1.24 (2H, m), 1.28 (9H, s), 1.11-1.01 (2H, m);
MS (ESI) m/z: 432 (M+H)$^+$.

Example 83 trans-6-(3-cyclopentyl-ureido)-3,4-dihydro-1H-isoquinoline-2-carboxylic acid 4-carboxymethyl-cyclohexyl ester

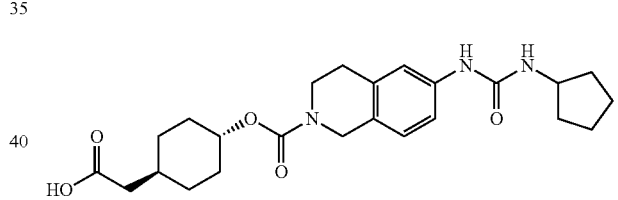

(83a) 6-(3-cyclopentyl-ureido)-3,4-dihydro-1H-isoquinoline-2-carboxylic acid tert-butyl ester The title compound (601 mg, 84%) was obtained as a white solid in the same way as in Example (28a) from 6-amino-2N-Boc-1,2,3,4-tetrahydroisoquinoline (496 mg) and aminocyclopentane (0.20 mL).

$^1$H NMR (400 MHz, CDCl$_3$): δ (ppm)=7.22-6.95 (4H, m), 6.17 (1H, s), 4.52 (2H, s), 4.14-4.08 (1H, m), 3.62 (2H, brs), 2.80 (2H, t, J=5.7 Hz), 2.02-1.97 (2H, m), 1.69-1.56 (4H, m), 1.49 (9H, s), 1.44-1.35 (2H, m).

(83b) 1-cyclopentyl-3-(1,2,3,4-tetrahydro-isoquinolin-6-yl)-urea hydrochloride The title compound (493 mg, quantitative yield) was obtained as a white solid in the same way as in Example (22b) from 6-(3-cyclopentyl-ureido)-3,4-dihydro-1H-isoquinoline-2-carboxylic acid tert-butyl ester (600 mg) obtained in Example (83a).

$^1$H NMR (400 MHz, DMSO-d6): δ (ppm)=9.14 (1H, brs), 8.53 (1H, s), 7.32 (1H, d, J=2.0 Hz), 7.19 (1H, dd, J=8.4 and 2.1 Hz), 7.05 (1H, d, J=8.6 Hz), 6.36 (1H, brs), 4.21-3.99 (1H, m), 3.91 (2H, t, J=7.2 Hz), 3.36-3.31 (2H, m), 2.93 (2H, t, J=6.2 Hz), 1.86-1.78 (2H, m), 1.66-1.61 (2H, m), 1.55-1.51 (2H, m), 1.39-1.31 (2H, m).

(83c) trans-6-(3-cyclopentyl-ureido)-3,4-dihydro-1H-isoquinoline-2-carboxylic acid 4-carboxymethyl-cyclohexyl ester Methyl ester (553 mg, 97%) was obtained in the same way as in Example (1e) from trans-(4-hydroxy-cyclohexyl)-acetic acid methyl ester (301 mg) obtained in Example (1d) and 1-cyclopentyl-3-(1,2,3,4-tetrahydro-isoquinolin-6-yl)-urea hydrochloride (369 mg) obtained in Example (83b). This methyl ester (553 mg) was hydrolyzed in the same way as in Example 2 to obtain the title compound (448 mg, 84%) as a pale yellow solid.

$^1$H NMR (400 MHz, DMSO-d6): δ (ppm)=12.1 (1H, brs), 8.20 (1H, s), 7.24 (1H, s), 7.13 (1H, d, J=8.6 Hz), 7.01 (1H, d, J=8.3 Hz), 6.14 (1H, d, J=7.4 Hz), 4.50-4.43 (3H, m), 3.94-3.89 (1H, m), 3.54 (2H, t, J=5.9 Hz), 2.71 (2H, t, J=5.8 Hz), 2.11 (2H, d, J=7.0 Hz), 1.93-1.90 (2H, m), 1.84-1.80 (2H, m), 1.76-1.73 (2H, m), 1.66-1.61 (3H, m), 1.56-1.51 (2H, m), 1.38-1.32 (4H, m), 1.11-1.01 (2H, m);

MS (ESI) m/z: 444 (M+H)$^+$.

Example 84 trans-6-(3-cyclohexyl-ureido)-3,4-dihydro-1H-isoquinoline-2-carboxylic acid 4-carboxymethyl-cyclohexyl ester

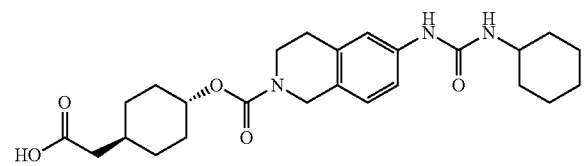 [SMILES: O=C(O)C[C@H]1CC[C@H](OC(=O)N2CCc3cc(NC(=O)NC4CCCCC4)ccc3C2)CC1]

(84a) 6-(3-cyclohexyl-ureido)-3,4-dihydro-1H-isoquinoline-2-carboxylic acid tert-butyl ester The title compound (1.14 g, quantitative yield) was obtained as a white solid in the same way as in Example (26a) from 6-amino-2N-Boc-1,2,3,4-tetrahydroisoquinoline (745 mg) and cyclohexyl isocyanate (0.46 mL).

$^1$H NMR (400 MHz, CDCl$_3$): δ (ppm)=7.33-6.96 (4H, m), 6.11 (1H, s), 4.53 (2H, s), 3.63 (2H, brs), 2.80 (2H, t, J=5.7 Hz), 1.99-1.95 (2H, m), 1.72-1.10 (9H, m), 1.49 (9H, s).

(84b) 1-cyclohexyl-3-(1,2,3,4-tetrahydro-isoquinolin-6-yl)-urea hydrochloride

The title compound (929 mg, quantitative yield) was obtained as a pale yellow solid in the same way as in Example (22b) from 6-(3-cyclohexyl-ureido)-3,4-dihydro-1H-isoquinoline-2-carboxylic acid tert-butyl ester (1.12 g) obtained in Example (84a).

$^1$H NMR (400 MHz, DMSO-d6): δ (ppm)=9.26 (1H, brs), 8.69 (1H, s), 7.30 (1H, d, J=1.9 Hz), 7.20 (1H, dd, J=8.4 and 2.1 Hz), 7.05 (1H, d, J=8.6 Hz), 5.12 (1H, brs), 4.14 (2H, s), 3.47-3.42 (2H, m), 3.35-3.30 (2H, m), 2.93 (2H, t, J=6.2 Hz), 1.79-1.76 (2H, m), 1.69-1.64 (2H, m), 1.54-1.51 (1H, m), 1.34-1.25 (2H, m), 1.22-1.11 (2H, m).

(84c) trans-6-(3-cyclohexyl-ureido)-3,4-dihydro-1H-isoquinoline-2-carboxylic acid 4-carboxymethyl-cyclohexyl ester Methyl ester (656 mg, 93%) was obtained in the same way as in Example (1e) from trans-(4-hydroxy-cyclohexyl)-acetic acid methyl ester (309 mg) obtained in Example (1d) and 1-cyclohexyl-3-(1,2,3,4-tetrahydro-isoquinolin-6-yl)-urea hydrochloride (464 mg) obtained in Example (84b). This methyl ester (656 mg) was hydrolyzed with an aqueous sodium hydroxide solution in the same way as in Example 2 to obtain the title compound (553 mg, 87%) as a white solid.

$^1$H NMR (400 MHz, DMSO-d6): δ (ppm)=12.1 (1H, s), 8.27 (1H, s), 7.23 (1H, s), 7.13 (1H, d, J=8.6 Hz), 7.01 (1H, d, J=8.6 Hz), 6.08 (1H, d, J=8.3 Hz), 4.50-4.43 (3H, m), 3.54 (2H, t, J=5.9 Hz), 3.45-3.40 (1H, m), 2.70 (2H, t, J=5.9 Hz), 2.10 (2H, d, J=7.0 Hz), 1.93-1.90 (2H, m), 1.80-1.73 (4H, m), 1.66-1.63 (3H, m), 1.56-1.51 (1H, m), 1.38-1.25 (4H, m), 1.21-1.01 (5H, m);

MS (ESI) m/z: 458 (M+H)$^+$.

Example 85 trans-6-(3-cyclohexylmethyl-ureido)-3,4-dihydro-1H-isoquinoline-2-carboxylic acid 4-carboxymethyl-cyclohexyl ester

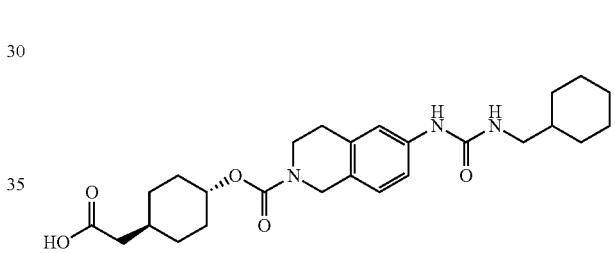

(85a) 6-(3-cyclohexylmethyl-ureido)-3,4-dihydro-1H-isoquinoline-2-carboxylic acid tert-butyl ester The title compound (774 mg, quantitative yield) was obtained as a white solid in the same way as in Example (28a) from 6-amino-2N-Boc-1,2,3,4-tetrahydroisoquinoline (496 mg) and cyclohexylmethylamine (0.26 mL).

$^1$H NMR (400 MHz, CDCl$_3$): δ (ppm)=7.22-6.97 (4H, m), 6.30 (1H, brs), 4.82 (1H, brs), 4.53 (2H, s), 3.63 (2H, brs), 3.09 (2H, d, J=6.7 Hz), 2.80 (2H, t, J=5.7 Hz), 1.74-1.47 (4H, m), 1.49 (9H, s), 1.28-1.16 (4H, m), 0.96-0.91 (2H, m).

(85b) 1-cyclohexylmethyl-3-(1,2,3,4-tetrahydro-isoquinolin-6-yl)-urea hydrochloride The title compound (540 mg, 83%) was obtained as a pink solid in the same way as in Example (22b) from 6-(3-cyclohexylmethyl-ureido)-3,4-dihydro-1H-isoquinoline-2-carboxylic acid tert-butyl ester (774 mg) obtained in Example (85a).

$^1$H NMR (400 MHz, DMSO-d6): δ (ppm)=9.15 (1H, brs), 8.68 (1H, s), 7.32 (1H, d, J=1.9 Hz), 7.20 (1H, dd, J=8.2 and 2.3 Hz), 7.05 (1H, d, J=8.6 Hz), 6.36 (1H, brs), 4.15-4.40 (1H, m), 4.12 (2H, s), 3.36-3.31 (2H, m), 2.92 (2H, d, J=6.7 Hz), 1.69-1.61 (5H, m), 1.39-1.33 (1H, m), 1.23-1.10 (4H, m), 0.93-0.84 (2H, m).

(85c) trans-6-(3-cyclohexylmethyl-ureido)-3,4-dihydro-1H-isoquinoline-2-carboxylic acid 4-carboxymethyl-cyclohexyl ester Methyl ester (679 mg, 84%) was obtained in the same way as in Example (1e) from trans-(4-hydroxy-cyclohexyl)-acetic acid methyl ester (344 mg) obtained in Example (1d) and 1-cyclohexylmethyl-3-(1,2,3,4-tetrahydro-isoquinolin-6-yl)-urea hydrochloride (539 mg) obtained in Example (85b). This methyl ester (679 mg) was hydrolyzed with an aqueous sodium hydroxide solution in the same way as in Example 2 to obtain the title compound (634 mg, 96%) as a white solid.

$^1$H NMR (400 MHz, DMSO-d6): δ (ppm)=12.1 (1H, s), 8.32 (1H, s), 7.24 (1H, s), 7.14 (1H, d, J=8.3 Hz), 7.01 (1H, d, J=8.2 Hz), 6.16 (1H, dd, J=5.6 and 5.6 Hz), 4.51-4.43 (3H, m), 3.54 (2H, t, J=5.9 Hz), 2.92 (2H, t, J=6.2 Hz), 2.71 (2H, t, J=6.0 Hz), 2.11 (2H, d, J=7.1 Hz), 1.94-1.90 (2H, m), 1.77-1.61 (9H, m), 1.39-1.29 (3H, m), 1.24-1.01 (4H, m), 0.93-0.84 (2H, m);

MS (ESI) m/z: 472 (M+H)$^+$.

Example 86 trans-6-(3-adamantan-1-yl-ureido)-3,4-dihydro-1H-isoquinoline-2-carboxylic acid 4-carboxymethyl-cyclohexyl ester

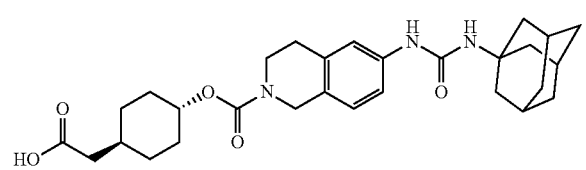 [SMILES: O=C(O)C[C@H]1CC[C@H](OC(=O)N2CCc3cc(NC(=O)NC45CC6CC(CC(C6)C4)C5)ccc3C2)CC1]

(86a) 6-(3-adamantan-1-yl-ureido)-3,4-dihydro-1H-isoquinoline-2-carboxylic acid tert-butyl ester The title compound (780 mg, 92%) was obtained as a white solid in the same way as in (Example 24b) from 6-(4-nitro-phenoxycarbonylamino)-3,4-dihydro-1H-isoquinoline-2-carboxylic acid tert-butyl ester (827 mg) obtained in Example (24a) and 1-aminoadamantane (303 mg).

$^1$H NMR (400 MHz, CDCl$_3$): δ (ppm)=7.25-6.90 (4H, m), 6.08 (1H, brs), 4.51 (2H, s), 3.61 (2H, brs), 2.79 (2H, t, J=5.6 Hz), 2.09 (2H, brs), 2.00 (4H, brs), 1.68 (5H, brs), 1.58 (2H, brs), 1.49 (2H, s).

(86b) 1-adamantan-1-yl-3-(1,2,3,4-tetrahydro-isoquinolin-6-yl)-urea hydrochloride The title compound (663 mg, quantitative yield) was obtained as a white solid in the same way as in Example (22b) from 6-(3-adamantan-1-yl-ureido)-3,4-dihydro-1H-isoquinoline-2-carboxylic acid tert-butyl ester (780 mg) obtained in Example (86a).

$^1$H NMR (400 MHz, DMSO-d6): δ (ppm)=9.14 (1H, brs), 8.52 (1H, s), 7.34 (1H, d, J=1.9 Hz), 7.11 (1H, dd, J=8.6 and 2.0 Hz), 7.04 (1H, d, J=8.6 Hz), 6.07 (1H, brs), 4.15 (2H, s), 4.07 (4H, brs), 3.35-3.31 (2H, m), 2.93 (2H, t, J=6.2 Hz), 2.02 (2H, brs), 1.92 (3H, brs), 1.92 (6H, brs).

(86c) trans-6-(3-adamantan-1-yl-ureido)-3,4-dihydro-1H-isoquinoline-2-carboxylic acid 4-carboxymethyl-cyclohexyl ester Methyl ester (895 mg, 93%) was obtained in the same way as in Example (1e) from trans-(4-hydroxy-cyclohexyl)-acetic acid methyl ester (378 mg) obtained in Example (1d) and 1-adamantan-1-yl-3-(1,2,3,4-tetrahydro-isoquinolin-6-yl)-urea hydrochloride (663 mg) obtained in Example (86b). This methyl ester (895 mg) was hydrolyzed with an aqueous sodium hydroxide solution in the same way as in Example 2 to obtain the title compound (841 mg, 97%) as a yellow solid.

$^1$H NMR (400 MHz, DMSO-d6): δ (ppm)=12.1 (1H, brs), 8.20 (1H, s), 7.26 (1H, s), 7.05 (1H, d, J=8.6 Hz), 7.00 (1H, d, J=8.6 Hz), 5.86 (1H, s), 4.50-4.42 (3H, m), 3.54 (2H, t, J=5.9 Hz), 2.70 (2H, t, J=5.9 Hz), 2.11 (2H, d, J=6.6 Hz), 2.02 (3H, brs), 1.92 (8H, brs), 1.77-1.73 (2H, m), 1.63 (7H, brs), 1.38-1.28 (2H, m), 1.11-1.01 (2H, m);

MS (ESI) m/z: 510 (M+H)$^+$.

Example 87 trans-6-(3-pyridin-3-yl-ureido)-3,4-dihydro-1H-isoquinoline-2-carboxylic acid 4-carboxymethyl-cyclohexyl ester

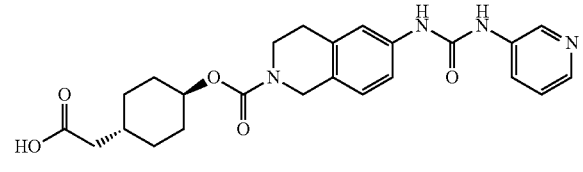 [SMILES: O=C(O)C[C@H]1CC[C@H](OC(=O)N2CCc3cc(NC(=O)Nc4cccnc4)ccc3C2)CC1]

(87a) 6-(3-pyridin-3-yl-ureido)-3,4-dihydro-1H-isoquinoline-2-carboxylic acid tert-butyl ester The title compound (448 mg, quantitative yield) was obtained as a pale yellow solid in the same way as in (Example 24b) from 6-(4-nitro-phenoxycarbonylamino)-3,4-dihydro-1H-isoquinoline-2-carboxylic acid tert-butyl ester (500 mg) obtained in Example (24a) and 3-aminopyridine (150 mg).

$^1$H NMR (400 MHz, DMSO-d6): δ (ppm)=1.43 (9H, s), 2.74 (2H, t, J=5.67 Hz), 3.53 (2H, t, J=5.87 Hz), 4.43 (2H, brs), 7.08 (1H, d, J=8.21 Hz), 7.22 (1H, d, J=7.43 Hz), 7.31 (2H, t, J=3.71 Hz), 7.93 (1H, ddd, J=8.41, 2.54, 1.56 Hz), 8.18 (1H, dd, J=4.69, 1.17 Hz), 8:59 (1H, d, J=1.95 Hz), 8.74 (1H, brs), 8.82 (1H, brs).

(87b) trans-6-(3-pyridin-3-yl-ureido)-3,4-dihydro-1H-isoquinoline-2-carboxylic acid 4-methoxycarbonylmethylcyclohexyl ester Amine was obtained in the same way as in Example (22b) from 6-(3-pyridin-3-yl-ureido)-3,4-dihydro-1H-isoquinoline-2-carboxylic acid tert-butyl ester (450 mg) obtained in Example (87a). From this amine (250 mg) and trans-(4-hydroxy-cyclohexyl)-acetic acid methyl ester (200 mg) obtained in Example (1d), the title compound (277 mg, 73%) was obtained as a white solid in the same way as in Example (1e).

$^1$H NMR (400 MHz, DMSO-d6): δ (ppm)=1.02-1.14 (1H, m), 1.27-1.41 (1H, m), 1.71 (3H, brs), 1.92 (2H, d, J=10.56 Hz), 2.22 (2H, d, J=6.65 Hz), 2.75 (2H, t, J=5.67 Hz), 3.50-3.60 (5H, m), 4.41-4.53 (3H, m), 7.09 (1H, d, J=8.21 Hz), 7.23 (1H, d, J=8.21 Hz), 7.32 (1H, d, J=4.30 Hz), 7.30 (1H, d, J=4.69 Hz), 7.89-7.99 (1H, m), 8.18 (1H, dd, J=4.69, 1.17 Hz), 8.59 (1H, d, J=2.35 Hz), 8.75 (1H, s), 8.82 (1H, s);

MS (FAB) m/z: 467 (M+H)$^+$.

(87c) trans-6-(3-pyridin-3-yl-ureido)-3,4-dihydro-1H-isoquinoline-2-carboxylic acid 4-carboxymethyl-cyclohexyl ester trans-6-(3-Pyridin-3-yl-ureido)-3,4-dihydro-1H-isoquinoline-2-carboxylic acid 4-methoxycarbonylmethylcyclohexyl ester (280 mg) obtained in Example (87b) was hydrolyzed in the same way as in Example 2 to obtain the title compound (186 mg, 67%) as a white solid.

$^1$H NMR (400 MHz, DMSO-d6): δ (ppm)=1.00-1.14 (2H, m), 1.28-1.41 (2H, m), 1.59-1.70 (1H, m), 1.75 (2H, d, J=11.73 Hz), 1.88-1.97 (2H, m), 2.12 (2H, d, J=7.04 Hz), 2.75 (2H, 1, J=5.47 Hz), 3.57 (2H, t, J=6.06 Hz), 4.42-4.53 (3H, m), 7.10 (1H, d, J=8.21 Hz), 7.23 (1H, d, J=7.82 Hz), 7.29-7.36 (2H, m), 7.91-7.98 (1H, m), 8.18 (1H, dd, J=4.69, 1.56 Hz), 8.60 (1H, d, J=2.74 Hz), 8.77 (1H, s), 8.85 (1H, s), 12.06 (1H, brs);

MS (FAB) m/z: 453 (M+H)$^+$.

Example 88 trans-6-(3-pyridin-2-yl-ureido)-3,4-dihydro-1H-isoquinoline-2-carboxylic acid 4-carboxymethyl-cyclohexyl ester

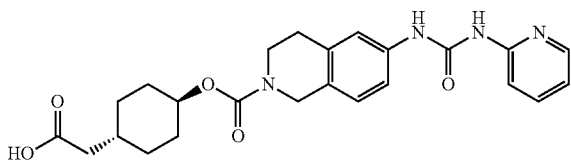 [SMILES: O=C(O)C[C@H]1CC[C@H](OC(=O)N2CCc3cc(NC(=O)Nc4ccccn4)ccc3C2)CC1]

(88a) 6-(3-pyridin-2-yl-ureido)-3,4-dihydro-1H-isoquinoline-2-carboxylic acid tert-butyl ester The title compound (395 mg, 89%) was obtained as a pale yellow solid in the same way as in (Example 24b) from 6-(4-nitro-phenoxycarbonylamino)-3,4-dihydro-1H-isoquinoline-2-carboxylic acid tert-butyl ester (500 mg) obtained in Example (24a) and 2-aminopyridine (150 mg).

$^1$H NMR (DMSO-d6, 400 MHz): δ ppm=10.55 (1H, brs), 9.46 (1H, s), 8.28 (1H, dd, J=5.08, 1.96 Hz), 7.72-7.77 (1H, m), 7.45 (1H, d, J=8.21 Hz), 7.37 (1H, s), 7.32 (1H, d, J=7.43 Hz), 7.10 (1H, d, J=8.21 Hz), 7.01 (1H, dd, J=6.84, 5.67 Hz), 4.44 (2H, brs), 3.54 (2H, t, J=5.87 Hz), 2.76 (2H, t, J=5.67 Hz), 1.43 (9H, s);

MS (FAB) m/z: 369 (M+H)$^+$.

(88b) trans-6-(3-pyridin-2-yl-ureido)-1H-isoquinoline-2-carboxylic acid 4-methoxycarbonylmethylcyclohexyl ester Amine (408 mg, quantitative yield) was obtained in the same way as in Example (22b) from 6-(3-pyridin-2-yl-ureido)-3,4-dihydro-1H-isoquinoline-2-carboxylic acid tert-butyl ester (400 mg) obtained in Example (88a). From this amine (280 mg) and trans-(4-hydroxy-cyclohexyl)-acetic acid methyl ester (200 mg) obtained in Example (1d), the title compound (168 mg, 39%) was obtained as a white solid in the same way as in Example (1e).

$^1$H NMR (DMSO-d6, 400 MHz): δ ppm=10.54 (1H, brs), 9.46 (1H, s), 8.24-8.32 (1H, m), 7.74 (1H, ddd, J=8.50, 7.14, 1.96 Hz), 7.45 (1H, d, J=8.21 Hz), 7.32 (1H, d, J=7.43 Hz), 7.38 (1H, d, J=1.17 Hz), 7.12 (1H, d, J=8.21 Hz), 7.01 (1H, ddd, J=7.23, 5.08, 0.98 Hz), 4.34-4.53 (3H, m), 3.40-3.60 (5H, m), 2.77 (2H, t, J=5.67 Hz), 2.22 (2H, d, J=7.04 Hz), 1.93 (2H, dd, J=11.93, 3.32 Hz), 1.62-1.81 (3H, m), 1.28-1.42 (2H, m), 1.01-1.15 (2H, m);

MS (FAB) m/z: 467 (M+H)$^+$.

(88c) trans-6-(3-pyridin-2-yl-ureido)-3,4-dihydro-1H-isoquinoline-2-carboxylic acid 4-carboxymethyl-cyclohexyl ester trans-6-(3-Pyridin-2-yl-ureido)-3,4-dihydro-1H-isoquinoline-2-carboxylic acid 4-methoxycarbonylmethylcyclohexyl ester (170 mg) obtained in Example (88b) was hydrolyzed in the same way as in Example 2 to obtain the title compound (121 mg, 74%) as a white solid.

$^1$H NMR (DMSO-d6, 500 MHz): δ ppm=10.47 (1H, brs), 9.67 (1H, brs), 8.29 (1H, dd, J=4.88, 1.46 Hz), 7.74-7.85 (1H, m), 7.47 (1H, d, J=8.30 Hz), 7.37 (1H, d, J=1.95 Hz), 7.32 (1H, d, J=8.30 Hz), 7.13 (1H, d, J=8.30 Hz), 7.03-7.08 (1H, m), 4.40-4.54 (3H, m), 3.57 (2H, t, J=5.86 Hz), 3.12-3.22 (1H, m), 2.77 (1H, t, J=5.86 Hz), 2.12 (2H, d, J=6.84 Hz), 1.93 (2H, dd, J=11.23, 2.93 Hz), 1.75 (1H, d, J=13.18 Hz), 1.26-1.40 (2H, m), 0.99-1.14 (2H, m);

MS (FAB) m/z: 453 (M+H)$^+$.

Example 89 trans-6-(3-pyridin-4-yl-ureido)-3,4-dihydro-1H-isoquinoline-2-carboxylic acid 4-carboxymethyl-cyclohexyl ester

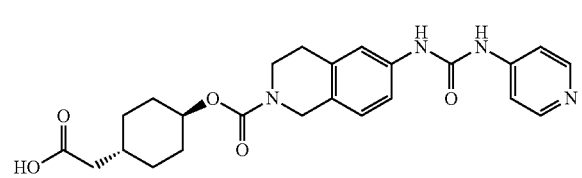 [SMILES: O=C(O)C[C@H]1CC[C@H](OC(=O)N2CCc3cc(NC(=O)Nc4ccncc4)ccc3C2)CC1]

(89a) 6-(3-pyridin-4-yl-ureido)-3,4-dihydro-1H-isoquinoline-2-carboxylic acid tert-butyl ester The title compound (380 mg, 85%) was obtained as a pale yellow solid in the same way as in (Example 24b) from 6-(4-nitro-phenoxycarbonylamino)-3,4-dihydro-1H-isoquinoline-2-carboxylic acid tert-butyl ester (500 mg) obtained in Example (24a) and 4-aminopyridine (150 mg).

$^1$H NMR (DMSO-d6, 500 MHz): δ ppm=9.07 (1H, s), 8.79 (1H, s), 8.35 (2H, dd, J=4.88, 1.47 Hz), 7.42 (2H, dd, J=4.64, 1.71 Hz), 7.31 (1H, brs), 7.23 (1H, d, J=7.32 Hz), 7.09 (1H, d, J=8.79 Hz), 4.43 (2H, brs), 3.53 (2H, t, J=5.86 Hz), 2.75 (2H, t, J=5.86 Hz), 1.43 (9H, s);

MS (FAB) m/z: 369 (M+H)$^+$.

(89b) trans-6-(3-pyridin-4-yl-ureido)-3,4-dihydro-1H-isoquinoline-2-carboxylic acid 4-methoxycarbonylmethylcyclohexyl ester Amine (324 mg) was obtained in the same way as in Example (22b) from 6-(3-pyridin-4-yl-ureido)-3,4-dihydro-1H-isoquinoline-2-carboxylic acid tert-butyl ester (380 mg) obtained in Example (89a). From this amine (324 mg) and trans-(4-hydroxy-cyclohexyl)-acetic acid methyl ester (180 mg) obtained in Example (1d), the title compound (346 mg, 72%, two steps) was obtained in the same way as in Example (1c).

¹H NMR (DMSO-d6, 400 MHz): δ ppm=9.08 (1H, s), 8.80 (1H, s), 8.35 (2H, dd, J=4.89, 1.37 Hz), 7.42 (2H, dd, J=4.69, 1.56 Hz), 7.31 (1H, s), 7.23 (1H, d, J=7.82 Hz), 7.10 (1H, d, J=8.21 Hz), 4.41-4.53 (3H, m), 3.34 (1H, s), 3.31 (4H, s), 2.76 (2H, J=5.87 Hz), 2.22 (2H, d, J=6.65 Hz), 1.92 (2H, d, J=11.73 Hz), 1.64-1.76 (3H, m), 1.28-1.42 (2H, m), 1.03-1.14 (2H, m);

MS (FAB) m/z: 467 (M+H)⁺.

(89c) trans-6-(3-pyridin-4-yl-ureido)-3,4-dihydro-1H-isoquinoline-2-carboxylic acid 4-carboxymethyl-cyclohexyl ester trans-6-(3-Pyridin-4-yl-ureido)-3,4-dihydro-1H-isoquinoline-2-carboxylic acid 4-methoxycarbonylmethylcyclohexyl ester (346 mg) obtained in Example (89b) was hydrolyzed in the same way as in Example 2 to obtain the title compound (323 mg, 96%) as a white solid.

¹H NMR (DMSO-d6, 500 MHz): δ ppm=9.83 (1H, brs), 9.14 (1H, brs), 8.47 (2H, d, J=6.35 Hz), 7.66 (2H, d, J=6.35 Hz), 7.32 (1H, s), 7.26 (1H, dd, J=8.30, 1.47 Hz), 7.13 (1H, d, J=8.30 Hz), 4.43-4.52 (3H, m), 3.57 (2H, t, J=5.86 Hz), 2.77 (2H, t, J=5.86 Hz), 2.12 (2H, d, J=6.84 Hz), 1.92 (2H, dd, J=11.96, 2.69 Hz), 1.75 (2H, d, J=12.70 Hz), 1.28-1.40 (2H, m), 1.01-1.12 (2H, m);

MS (FAB) m/z: 453 (M+H)⁺.

Example 90 trans-6-[3-(5-methyl-pyridin-3-yl)-ureido]-3,4-dihydro-1H-isoquinoline-2-carboxylic acid 4-carboxymethyl-cyclohexyl ester

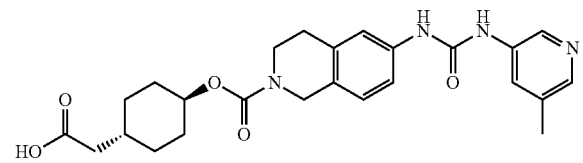 [SMILES: Cc1cncc(NC(=O)Nc2ccc3c(c2)CCN(C(=O)O[C@H]2CC[C@H](CC(=O)O)CC2)C3)c1]

(90a) 6-[3-(5-methyl-pyridin-3-yl)-ureido]-3,4-dihydro-1H-isoquinoline-2-carboxylic acid tert-butyl ester The title compound (446 mg, 96%) was obtained in the same way as in (Example 24b) from 6-(4-nitro-phenoxycarbonylamino)-3,4-dihydro-1H-isoquinoline-2-carboxylic acid tert-butyl ester (500 mg) obtained in Example (24a) and 5-methyl-pyridin-3-ylamine (130 mg).

¹H NMR (DMSO-d6, 400 MHz): δ ppm=8.75 (1H, s), 8.73 (1H, s), 8.38 (1H, d, J=2.35 Hz), 8.03 (1H, d, J=1.17 Hz), 7.79 (1H, s), 7.33 (1H, d, J=1.17 Hz), 7.21 (1H, d, J=7.04 Hz), 7.07 (1H, d, J=8.60 Hz), 4.43 (2H, brs), 3.53 (2H, t, J=5.87 Hz), 2.74 (2H, t, J=5.87 Hz), 2.27 (3H, s), 1.43 (9H, s).

MS (FAB) m/z: 383 (M+H)⁺.

(90b) trans-6-[3-(5-methyl-pyridin-3-yl)-ureido]-3,4-dihydro-1H-isoquinoline-2-carboxylic acid 4-methoxycarbonylmethylcyclohexyl ester Amine (386 mg, 93%) was obtained in the same way as in Example (22b) from 6-[3-(5-methyl-pyridin-3-yl)-ureido]-3,4-dihydro-1H-isoquinoline-2-carboxylic acid tert-butyl ester (450 mg) obtained in Example (90a). From this amine (420 mg) and trans-(4-hydroxy-cyclohexyl)-acetic acid methyl ester (200 mg) obtained in Example (1d), the title compound (406 mg, 72%) was obtained as a white solid in the same way as in Example (1e).

¹H NMR (DMSO-d6, 500 MHz): δ ppm=8.74 (1H, s), 8.72 (1H, s), 8.38 (1H, d, J=1.95 Hz), 8.03 (1H, s), 7.79 (1H, s), 7.33 (1H, brs), 7.21 (1H, d, J=7.32 Hz), 7.09 (1H, d, J=8.30 Hz), 4.43-4.51 (3H, m), 3.58 (3H, s), 3.56 (2H, t, J=5.86 Hz), 2.75 (2H, t, J=5.62 Hz), 2.27 (3H, s), 2.22 (2H, d, J=6.84 Hz), 1.92 (2H, d, J=11.23 Hz), 1.62-1.77 (3H, m), 1.30-1.39 (2H, m), 1.08 (2H, q, J=12.70 Hz);

MS (FAB) m/z: 481 (M+H)⁺.

(90c) trans-6-[3-(5-methyl-pyridin-3-yl)-ureido]-3,4-dihydro-1H-isoquinoline-2-carboxylic acid 4-carboxymethyl-cyclohexyl ester trans-6-[3-(5-Methyl-pyridin-3-yl)-ureido]-3,4-dihydro-1H-isoquinoline-2-carboxylic acid 4-methoxycarbonylmethylcyclohexyl ester (410 mg) obtained in Example (90b) was hydrolyzed in the same way as in Example 2 to obtain the title compound (342 mg, 87%) as a white solid.

¹H NMR (DMSO-d6, 400 MHz): δ ppm=9.04 (1H, s), 8.90 (1H, s), 8.55 (1H, s), 8.14 (1H, s), 7.90 (1H, s), 7.33 (1H, s), 7.23 (1H, d, J=8.21 Hz), 7.07-7.14 (1H, m), 4.42-4.54 (3H, m), 3.57 (2H, t, J=5.87 Hz), 2.75 (2H, t, J=5.87 Hz), 2.33 (3H, s), 2.12 (2H, d, J=6.65 Hz), 1.92 (2H, d, J=10.95 Hz), 1.75 (2H, d, J=12.90 Hz), 1.34 (2H, q, J=12.64 Hz), 1.00-1.13 (2H, m);

MS (FAB) m/z: 467 (M+H)⁺.

Example 91 trans-6-[3-(5-chloro-pyridin-2-yl)-ureido]-3,4-dihydro-1H-isoquinoline-2-carboxylic acid 4-carboxymethyl-cyclohexyl ester

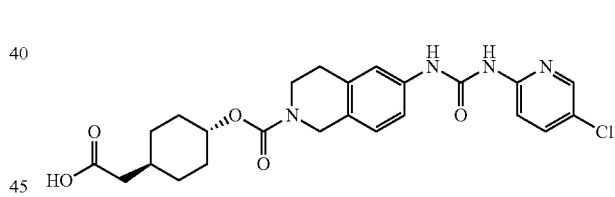

(91a) 6-[3-(5-chloro-pyridin-2-yl)-ureido]-3,4-dihydro-1H-isoquinoline-2-carboxylic acid tort-butyl ester The title compound (350 mg, 90%) was obtained in the same way as in (Example 24b) from 6-(4-nitro-phenoxycarbonylamino)-3,4-dihydro-1H-isoquinoline-2-carboxylic acid tert-butyl ester (400 mg) obtained in Example (24a) and 2-amino-5-chloropyridine (124 mg).

¹H NMR (400 MHz, CDCl₃): δ (ppm)=11.17 (1H, s), 8.22 (1H, d, J=2.7 Hz), 8.13 (1H, d, J=9.0 Hz), 7.59 (1H, dd, J=8.6, 2.7 Hz), 7.36 (1H, dd, J=8.8, 2.5 Hz), 7.04 (1H, d, J=8.6 Hz), 6.88 (1H, d, J=9.0 Hz), 6.74 (1H, d, J=9.0 Hz), 4.51 (2H, s), 3.65-3.56 (2H, m), 2.84-2.74 (2H, m), 1.46 (9H, s).

(91b) 1-(5-chloro-pyridin-2-yl)-3-(1,2,3,4-tetrahydro-isoquinolin-6-yl)-urea hydrochloride The title compound (325 mg, quantitative yield) was obtained in the same way as in Example (22b) from 6-[3-(5- chloro-pyridin-2-yl)-ureido]-3,4-dihydro-1H-isoquinoline-2-carboxylic acid tert-butyl ester (350 mg) obtained in Example (91a).

$^{1}$H NMR (400 MHz, DMSO-d6): δ (ppm)=9.20-9.08 (1H, m), 8.46 (1H, d, J=2.7 Hz), 7.95-7.92 (1H, m), 7.44-7.22 (3H, m), 7.13-6.99 (2H, m), 4.17 (1H, s), 3.37-3.29 (2H, m), 2.98-2.90 (2H, m).

(91c) trans-6-[3-(5-chloro-pyridin-2-yl)-ureido]-3,4-dihydro-1H-isoquinoline-2-carboxylic acid 4-methoxycarbonylmethylcyclohexyl ester The title compound (336 mg, 70%) was obtained as a white solid in the same way as in Example (1e) from 1-(5-chloro-pyridin-2-yl)-3-(1,2,3,4-tetrahydro-isoquinolin-6-yl)-urea hydrochloride (325 mg) obtained in Example (91b) and trans-(4-hydroxy-cyclohexyl)-acetic acid methyl ester (231 mg) obtained in Example (1d).

$^{1}$H NMR (400 MHz, DMSO-d6): δ (ppm)=8.59 (1H, s), 8.22 (1H, d, J=2.7 Hz), 7.99 (1H, d, J=2.3 Hz), 7.62-7.58 (1H, m), 7.41-7.27 (1H, m), 7.11-6.97 (1H, m), 6.90-6.84 (1H, m), 6.44 (1H, d, J=8.6 Hz), 4.64-4.45 (3H, m), 3.65 (3H, s), 3.60-3.46 (2H, m), 2.87-2.74 (2H, m), 2.20-2.16 (2H, m), 2.06-1.91 (2H, m), 1.82-1.67 (3H, m), 1.52-1.23 (2H, m), 1.15-0.98 (2H, m).

(91d) trans-6-[3-(5-chloro-pyridin-2-yl)-ureido]-3,4-dihydro-1H-isoquinoline-2-carboxylic acid 4-carboxymethyl-cyclohexyl ester trans-6-[3-(5-Chloro-pyridin-2-yl)-ureido]-3,4-dihydro-1H-isoquinoline-2-carboxylic acid 4-methoxycarbonylmethylcyclohexyl ester (371 mg) obtained in Example (91c) was hydrolyzed in the same way as in Example 2 to obtain the title compound (38 mg, 10%) as a white solid.

$^{1}$H NMR (400 MHz, DMSO-d6): δ (ppm)=12.08 (1H, s), 9.84 (1H, s), 9.52 (1H, s), 8.35 (1H, s), 7.92-7.87 (1H, m), 7.74-7.69 (1H, m), 7.37 (1H, s), 7.35-7.29 (1H, m), 7.18-7.13 (1H, m), 4.51 (3H, s), 3.63-3.58 (2H, m), 2.83-2.77 (2H, m), 2.15 (2H, d, J=6.8 Hz), 1.96 (2H, d, J=10.7 Hz), 1.78 (2H, d, J=12.2 Hz), 1.73-1.63 (1H, m), 1.37 (2H, q, J=12.2 Hz), 1.10 (2H, q, J=11.9 Hz).

MS (FAB) m/z: 509 (M+Na)$^{+}$.

Example 92 trans-6-[3-(6-chloro-pyridin-3-yl)-ureido]-3,4-dihydro-1H-isoquinoline-2-carboxylic acid 4-carboxymethyl-cyclohexyl ester

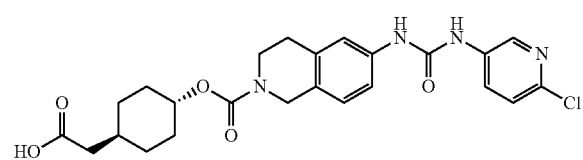 [SMILES: O=C(O)C[C@H]1CC[C@H](OC(=O)N2CCc3cc(NC(=O)Nc4ccc(Cl)nc4)ccc3C2)CC1]

(92a) 6-[3-(6-chloro-pyridin-3-yl)-ureido]-3,4-dihydro-1H-isoquinoline-2-carboxylic acid tert-butyl ester The title compound (430 mg, quantitative yield) was obtained in the same way as in (Example 24b) from 6-(4-nitro-phenoxycarbonylamino)-3,4-dihydro-1H-isoquinoline-2-carboxylic acid tert-butyl ester (400 mg) obtained in Example (24a) and 6-chloro-pyridin-3-ylamine (124 mg).

$^{1}$H NMR (400 MHz, CDCl$_{3}$): δ (ppm)=8.13 (1H, s), 8.03 (1H, dd, J=8.6, 2.7 Hz), 7.93 (1H, s), 7.83 (1H, d, J=3.1 Hz), 7.59 (1H, s), 7.21 (1H, d, J=8.6 Hz), 7.08 (1H, d, J=8.6 Hz), 6.98-6.93 (1H, m), 4.47 (2H, s), 3.59 (2H, t, J=6.1 Hz), 2.73 (2H, s), 1.49 (9H, s).

(92b) 1-(6-chloro-pyridin-3-yl)-3-(1,2,3,4-tetrahydro-isoquinolin-6-yl)-urea hydrochloride The title compound (287 mg, 87%) was obtained in the same way as in Example (22b) from 6-[3-(6-chloro-pyridin-3-yl)-ureido]-3,4-dihydro-1H-isoquinoline-2-carboxylic acid tert-butyl ester (400 mg) obtained in Example (92a).

$^{1}$H NMR (400 MHz, DMSO-d6): δ (ppm)=9.97 (1H, s), 9.64 (1H, s), 8.47 (1H, d, J=2.7 Hz), 7.93 (1H, dd, J=8.8, 2.9 Hz), 7.43-7.39 (2H, m), 7.35-7.33 (1H, m), 7.31-7.27 (1H, m), 7.12 (1H, d, J=8.6 Hz), 4.18-4.12 (2H, m), 3.36-3.28 (2H, m), 2.97 (2H, t, J=6.3 Hz).

(92c) trans-6-[3-(6-chloro-pyridin-3-yl)-ureido]-3,4-dihydro-1H-isoquinoline-2-carboxylic acid 4-methoxycarbonylmethylcyclohexyl ester The title compound (239 mg, 56%) was obtained as a colorless oil in the same way as in Example (1e) from 1-(6-chloro-pyridin-3-yl)-3-(1,2,3,4-tetrahydro-isoquinolin-6-yl)-urea hydrochloride (287 mg) obtained in Example (92b) and trans-(4-hydroxy-cyclohexyl)-acetic acid methyl ester (172 mg) obtained in Example (1d).

$^{1}$H NMR (400 MHz, CDCl$_{3}$): δ (ppm)=8.14-8.04 (1H, m), 8.03-7.98 (1H, m), 7.86 (1H, s), 7.58 (1H, s), 7.31 (1H, s), 7.20 (1H, d, J=9.0 Hz), 7.03-6.95 (1H, m), 6.89-6.69 (1H, m), 4.61-4.56 (1H, m), 4.50 (2H, s), 3.65 (3H, s), 3.61 (2H, t, J=5.5 Hz), 2.72 (2H, s), 2.18 (2H, d, J=6.6 Hz), 2.02 (2H, t, J=8.2 Hz), 1.84-1.71 (3H, m), 1.47-1.34 (2H, m), 1.12-0.99 (2H, m).

(92d) trans-6-[3-(6-chloro-pyridin-3-yl)-ureido]-3,4-dihydro-1H-isoquinoline-2-carboxylic acid 4-carboxymethyl-cyclohexyl ester trans-6-[3-(6-Chloro-pyridin-3-yl)-ureido]-3,4-dihydro-1H-isoquinoline-2-carboxylic acid 4-methoxycarbonylmethylcyclohexyl ester (371 mg) obtained in Example (92c) was hydrolyzed in the same way as in Example 2 to obtain the title compound (141 mg, 38%) as a white solid.

$^{1}$H NMR (400 MHz, DMSO-d6): δ (ppm)=12.04 (1H, s), 8.96 (1H, s), 8.79 (1H, s), 8.44 (1H, d, J=2.7 Hz), 7.95 (1H, dd, J=8.6, 2.7 Hz), 7.40 (1H, d, J=8.6 Hz), 7.29 (1H, s), 7.23-7.17 (1H, m), 7.10-7.06 (1H, m), 4.44 (3H, s), 3.54 (2H, t, J=5.9 Hz), 2.73 (2H, t, J=5.7 Hz), 2.10 (2H, d, J=6.6 Hz), 1.94-1.86 (2H, m), 1.77-1.68 (2H, m), 1.68-1.57 (1H, m), 1.38-1.26 (2H, m), 1.11-0.98 (2H, m).

MS (FAB) m/z: 509 (M+Na)$^{+}$.

Example 93 trans-6-[3-(5-chloro-pyridin-3-yl)-ureido]-3,4-dihydro-1H-isoquinoline-2-carboxylic acid 4-carboxymethyl-cyclohexyl ester

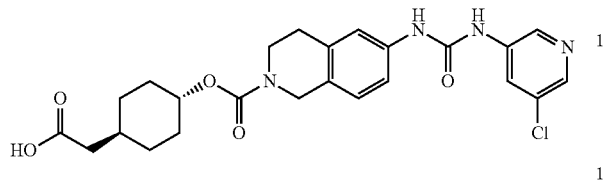

(93a) 6-[3-(5-chloro-pyridin-3-yl)-ureido]-3,4-dihydro-1H-isoquinoline-2-carboxylic acid tert-butyl ester The title compound (183 mg, 47%) was obtained in the same way as in (Example 24b) from 6-(4-nitro-phenoxycarbonylamino)-3,4-dihydro-1H-isoquinoline-2-carboxylic acid tert-butyl ester (400 mg) obtained in Example (24a) and 5-chloro-pyridin-3-ylamine (124 mg).
$^1$H NMR (400 MHz, CDCl$_3$): δ (ppm)=8.29-8.14 (3H, m), 8.10-7.81 (1H, m), 7.63-7.56 (1H, m), 7.42 (1H, brs), 7.10-6.58 (1H, m), 6.41 (1H, brs), 4.46 (2H, s), 3.59 (2H, t, J=5.9 Hz), 2.73 (2H, s), 1.50 (9H, s).

(93b) trans-6-[3-(5-chloro-pyridin-3-yl)-ureido]-3,4-dihydro-1H-isoquinoline-2-carboxylic acid 4-methoxycarbonylmethylcyclohexyl ester Amine (167 mg, quantitative yield) was obtained in the same way as in Example (22b) from 6-[3-(5-chloro-pyridin-3-yl)-ureido]-3,4-dihydro-1H-isoquinoline-2-carboxylic acid tert-butyl ester (183 mg) obtained in Example (93a). From this amine (167 mg) and trans-(4-hydroxy-cyclohexyl)-acetic acid methyl ester (121 mg) obtained in Example (1d), the title compound (220 mg, 88%) was obtained as a white solid in the same way as in Example (1c).
$^1$H NMR (400 MHz, CDCl$_3$): δ (ppm)=8.28-8.21 (3H, m), 7.84 (1H, brs), 7.56-7.35 (1H, m), 7.26-7.13 (1H, m), 7.11-7.04 (1H, m), 7.02-6.86 (1H, m), 4.64-4.45 (3H, m), 3.65 (3H, s), 3.60-3.46 (2H, m), 2.87-2.74 (2H, m), 2.20-2.16 (2H, m), 2.06-1.91 (2H, m), 1.82-1.67 (3H, m), 1.52-1.23 (2H, m), 1.15-0.98 (2H, m).

(93c) trans-6-[3-(5-chloro-pyridin-3-yl)-ureido]-3,4-dihydro-1H-isoquinoline-2-carboxylic acid 4-carboxymethyl-cyclohexyl ester trans-6-[3-(5-Chloro-pyridin-3-yl)-ureido]-3,4-dihydro-1H-isoquinoline-2-carboxylic acid 4-methoxycarbonylmethylcyclohexyl ester (121 mg) obtained in Example (93b) was hydrolyzed in the same way as in Example 2 to obtain the title compound (54 mg, 46%) as a white solid.
$^1$H NMR (400 MHz, DMSO-d6): δ (ppm)=9.07 (1H, s), 8.86 (1H, s), 8.47-8.44 (1H, m), 8.21-8.19 (1H, m), 8.16-8.13 (1H, m), 7.30 (1H, s), 7.24-7.18 (1H, m), 7.11-7.06 (1H, m), 4.51-4.40 (3H, m), 3.54 (2H, t, J=5.9 Hz), 2.76-2.71 (2H, m), 2.10 (2H, d, J=6.6 Hz), 1.95-1.87 (2H, m), 1.77-1.68 (2H, m), 1.68-1.58 (1H, m), 1.38-1.26 (2H, m), 1.11-0.99 (2H, m); MS (FAB) m/z: 525 (M+K)$^+$.

Example 94 trans-6-(3-pyrazin-2-yl-ureido)-3,4-dihydro-1H-isoquinoline-2-carboxylic acid 4-carboxymethyl-cyclohexyl ester

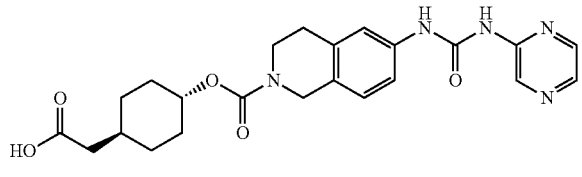 [SMILES: O=C(O)C[C@H]1CC[C@H](OC(=O)N2CCc3cc(NC(=O)Nc4cnccn4)ccc3C2)CC1]

(94a) 6-(3-pyrazin-2-yl-ureido)-3,4-dihydro-1H-isoquinoline-2-carboxylic acid tert-butyl ester The title compound (125 mg, 35%) was obtained as a white solid in the same way as in (Example 24b) from 6-(4-nitro-phenoxycarbonylamino)-3,4-dihydro-1H-isoquinoline-2-carboxylic acid tert-butyl ester (400 mg) obtained in Example (24a) and pyrazin-2-ylamine (92 mg).
$^1$H NMR (400 MHz, CDCl$_3$): δ (ppm)=10.95 (1H, s), 8.30 (1H, s), 8.23-8.21 (1H, m), 8.20-8.18 (1H, m), 7.92 (1H, s), 7.49-7.31 (2H, m), 7.08 (1H, d, J=8.2 Hz), 4.53 (2H, s), 3.67-3.59 (2H, m), 2.87-2.80 (2H, m), 1.48 (9H, s).

(94b) 1-pyrazin-2-yl-3-(1,2,3,4-tetrahydro-isoquinolin-6-yl)-urea hydrochloride The title compound (95 mg, 99%) was obtained in the same way as in Example (22b) from 6-[3-(5-chloro-pyridin-2-yl)-ureido]-3,4-dihydro-1H-isoquinoline-2-carboxylic acid tert-butyl ester (125 mg) obtained in Example (94a).
$^1$H NMR (400 MHz, DMSO-d6): δ (ppm)=9.98 (1H, s), 9.73 (1H, s), 9.21 (2H, s), 9.06 (1H, s), 8.30 (1H, t, J=2.0 Hz), 8.24 (1H, d, J=2.3 Hz), 7.42 (1H, s), 7.34 (1H, d, J=8.6 Hz), 7.15 (1H, d, J=8.6 Hz), 5.51 (1H, s), 4.19 (2H, s), 3.38-3.30 (2H, m), 2.98 (2H, t, J=5.9 Hz).

(94c) trans-6-(3-pyrazin-2-yl-ureido)-3,4-dihydro-1H-isoquinoline-2-carboxylic acid 4-methoxycarbonylmethylcyclohexyl ester The title compound (131 mg, 90%) was obtained as a white solid in the same way as in Example (1e) from 1-pyrazin-2-yl-3-(1,2,3,4-tetrahydro-isoquinolin-6-yl)-urea hydrochloride (95 mg) obtained in Example (94b) and trans-(4-hydroxy-cyclohexyl)-acetic acid methyl ester (75 mg) obtained in Example (1d).
$^1$H NMR (400 MHz, CDCl$_3$): δ (ppm)=10.99 (1H, s), 8.50 (1H, s), 8.35 (1H, s), 8.20 (2H, d, J=12.9 Hz), 7.28-7.47 (2H, m), 7.09 (1H, d, J=8.2 Hz), 4.64-4.50 (4H, m), 3.65 (3H, s), 3.58-3.45 (1H, m), 2.83 (1H, s), 2.25-2.15 (2H, m), 2.07-1.91 (2H, m), 1.83-1.70 (3H, m), 1.44-1.21 (2H, m), 1.16-0.97 (2H, m).

(94d) trans-6-(3-pyrazin-2-yl-ureido)-3,4-dihydro-1H-isoquinoline-2-carboxylic acid 4-carboxymethyl-cyclohexyl ester trans-6-(3-Pyrazin-2-yl-ureido)-3,4-dihydro-1H-isoquinoline-2-carboxylic acid 4-methoxycarbonylmethylcyclohexyl ester (131 mg) obtained in Example (94c) was hydrolyzed in the same way as in Example 2 to obtain the title compound (30 mg, 25%) as a white solid.

$^1$H NMR (400 MHz, DMSO-d6): δ (ppm)=2.03 (1H, s), 9.59 (1H, s), 9.54 (1H, s), 9.00 (1H, s), 8.30-8.28 (1H, m), 8.24-8.22 (1H, m), 7.34 (1H, s), 7.29-7.24 (1H, m), 7.13-7.08 (1H, m), 3.55 (2H, dd, J=6.3, 5.5 Hz), 3.33 (3H, s), 2.75 (2H, t, J=5.7 Hz), 2.10 (2H, d, J=7.0 Hz), 1.94-1.86 (2H, m), 1.77-1.69 (2H, m), 1.68-1.57 (1H, m), 1.38-1.26 (2H, m), 1.11-0.98 (2H, m).

MS (FAB) m/z: 454 (M+H)$^+$.

Example 95 trans-6-[3-(5-methyl-thiazol-2-yl)-ureido]-3,4-dihydro-1H-isoquinoline-2-carboxylic acid 4-carboxymethyl-cyclohexyl ester

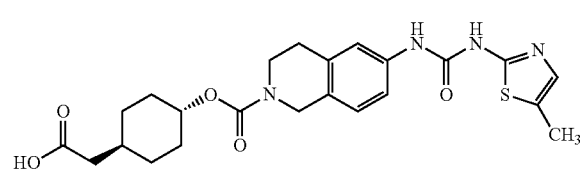 [SMILES: Cc1cnc(NC(=O)Nc2ccc3c(c2)CCN(C(=O)O[C@H]2CC[C@H](CC(=O)O)CC2)C3)s1]

(95a) 6-[3-(5-methyl-thiazol-2-yl)-ureido]-3,4-dihydro-1H-isoquinoline-2-carboxylic acid tert-butyl ester The title compound (561 mg, 96%) was obtained as an off-white solid in the same way as in (Example 24b) from 6-(4-nitro-phenoxycarbonylamino)-3,4-dihydro-1H-isoquinoline-2-carboxylic acid tert-butyl ester (620 mg) obtained in Example (24a) and 5-methyl-thiazol-2-ylamine (171 mg).

$^1$H NMR (400 MHz, CDCl$_3$): δ (ppm)=7.39 (1H, brs), 7.29-7.22 (2H, m), 7.08 (1H, d, J=8.6 Hz), 7.01 (1H, s), 5.30 (1H, s), 4.55 (2H, s), 3.65 (2H, brs), 2.84 (2H, t, J=5.4 Hz), 2.40 (3H, s), 1.50 (9H, s).

(95b) 1-(5-methyl-thiazol-2-yl)-3-(1,2,3,4-tetrahydro-isoquinolin-6-yl)-urea hydrochloride The title compound (468 mg, quantitative yield) was obtained as a white solid in the same way as in Example (22b) from 6-[3-(5-methyl-thiazol-2-yl)-ureido]-3,4-dihydro-1H-isoquinoline-2-carboxylic acid tert-butyl ester (561 mg) obtained in Example (95a).

$^1$H NMR (400 MHz, DMSO-d6): δ (ppm)=9.74 (1H, s), 9.30 (1H, brs), 7.41 (1H, d, J=2.0 Hz), 7.33 (1H, dd, J=8.5 and 2.1 Hz), 7.16 (1H, d, J=8.6 Hz), 7.08 (1H, d, J=1.1 Hz), 5.23 (1H, brs), 4.20 (2H, l, J=4.1 Hz), 3.38-3.33 (2H, m), 3.00 (2H, t, J=6.2 Hz), 2.32 (3H, s).

(95c) trans-6-[3-(5-methyl-thiazol-2-yl)-ureido]-3,4-dihydro-1H-isoquinoline-2-carboxylic acid 4-carboxymethyl-cyclohexyl ester Methyl ester (564 mg, 81%) was obtained in the same way as in Example (1e) from trans-(4-hydroxy-cyclohexyl)-acetic acid methyl ester (344 mg) obtained in Example (1d) and 1-(5-methyl-thiazol-2-yl)-3-(1,2,3,4-tetrahydro-isoquinolin-6-yl)-urea hydrochloride (468 mg) obtained in Example (95b). This methyl ester (564 mg) was hydrolyzed with an aqueous sodium hydroxide solution in the same way as in Example 2 to obtain the title compound (249 mg, 46%) as a white solid.

$^1$H NMR (400 MHz, DMSO-d6): δ (ppm)=11.9 (1H, s), 8.98 (2H, brs), 7.33 (1H, s), 7.25 (1H, d, J=9.0 Hz), 7.12 (1H, d, J=9.0 Hz), 7.03 (1H, s), 4.50-4.47 (3H, m), 3.57 (2H, t, J=5.8 Hz), 2.76 (2H, t, J=5.9 Hz), 2.31 (3H, s), 2.12 (2H, d, J=6.6 Hz), 1.94-1.91 (2H, m), 1.77-1.74 (2H, m), 1.67-1.62 (1H, m), 1.40-1.29 (2H, m), 1.11-1.03 (2H, m);

MS (ESI) m/z: 473 (M+H)$^+$.

Example 96 trans-6-[3-(2,5-dimethyl-2H-pyrazol-3-yl)-ureido]-3,4-dihydro-1H-isoquinoline-2-carboxylic acid 4-carboxymethyl-cyclohexyl ester

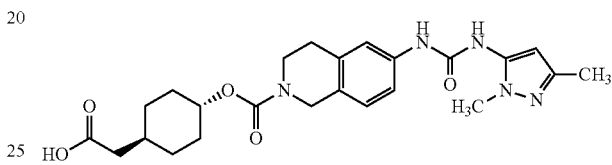

(96a) 6-[3-(2,5-dimethyl-2H-pyrazol-3-yl)-ureido]-3,4-dihydro-1H-isoquinoline-2-carboxylic acid tert-butyl ester The title compound (413 mg, 71%) was obtained as a white solid in the same way as in (Example 24b) from 6-(4-nitro-phenoxycarbonylamino)-3,4-dihydro-1H-isoquinoline-2-carboxylic acid tert-butyl ester (620 mg) obtained in Example (24a) and 2,5-dimethyl-2H-pyrazol-3-ylamine (166 mg).

$^1$H NMR (400 MHz, CDCl$_3$): δ (ppm)=7.17 (1H, brs), 7.04 (1H, d, J=7.5 Hz), 6.56 (1H, s), 6.12 (1H, brs), 6.03 (1H, s), 5.31 (1H, s), 4.52 (2H, s), 3.74 (3H, s), 3.62 (2H, t, J=5.6 Hz), 2.80 (2H, t, J=5.9 Hz), 2.27 (3H, s), 1.49 (9H, s).

(96b) 1-(2,5-dimethyl-2H-pyrazol-3-yl)-3-(1,2,3,4-tetrahydro-isoquinolin-6-yl)-urea hydrochloride The title compound (343 mg, quantitative yield) was obtained as a yellow solid in the same way as in Example (22b) from 6-[3-(2,5-dimethyl-2H-pyrazol-3-yl)-ureido]-3,4-dihydro-1H-isoquinoline-2-carboxylic acid tert-butyl ester (412 mg) obtained in Example (96a).

$^1$H NMR (400 MHz, DMSO-d6): δ (ppm)=9.54 (1H, s), 9.36 (1H, s), 9.13 (1H, brs), 7.38 (1H, d, J=1.9 Hz), 7.30 (1H, dd, J=8.3 and 2.0 Hz), 7.14 (1H, d, J=8.6 Hz), 6.08 (1H, s), 4.20 (2H, t, J=4.1 Hz), 3.66 (3H, s), 3.38-3.33 (2H, m), 2.98 (2H, t, J=6.0 Hz), 2.12 (3H, s).

(96c) trans-6-[3-(2,5-dimethyl-2H-pyrazol-3-yl)-ureido]-3,4-dihydro-1H-isoquinoline-2-carboxylic acid 4-carboxymethyl-cyclohexyl ester Methyl ester (514 mg, quantitative yield) was obtained in the same way as in Example (1e) from trans-(4-hydroxy-cyclohexyl)-acetic acid methyl ester (256 mg) obtained in Example (1d) and 1-(2,5-dimethyl-2H-pyrazol-3-yl)-3-(1,2,3,4-tetrahydro-isoquinolin-6-yl)-urea hydrochloride (342 mg) obtained in Example (96b). This methyl ester (514 mg) was hydrolyzed with an aqueous sodium hydroxide solution in the same way as in Example 2 to obtain the title compound (360 mg, 72%) as a pale pink solid.

¹H NMR (400 MHz, DMSO-d6): δ (ppm)=12.1 (1H, s), 8.86 (1H, s), 8.59 (1H, s), 7.32 (1H, s), 7.22 (1H, d, J=8.2 Hz), 7.09 (1H, d, J=8.6 Hz), 5.96 (1H, s), 4.51-4.46 (3H, m), 3.56 (2H, t, J=5.1 Hz), 3.57 (3H, s), 2.75 (2H, t, J=5.9 Hz), 2.11 (2H, d, J=7.0 Hz), 2.08 (3H, s), 1.95-1.90 (2H, m), 1.77-1.73 (2H, m), 1.68-1.62 (1H, m), 1.39-1.29 (2H, m), 1.12-1.02 (2H, m):

MS (ESI) m/z: 470 (M+H)⁺.

Example 97 trans-6-[3-(5-methyl-isoxazol-3-yl)-ureido]-3,4-dihydro-1H-isoquinoline-2-carboxylic acid 4-carboxymethyl-cyclohexyl ester

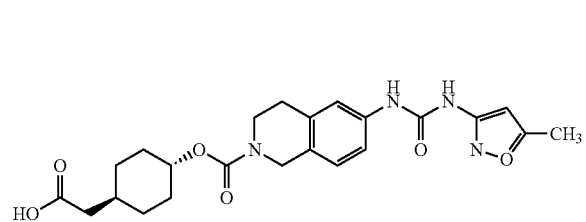

(97a) 6-[3-(5-methyl-isoxazol-3-yl)-ureido]-3,4-dihydro-1H-isoquinoline-2-carboxylic acid tert-butyl ester The title compound (143 mg, 26%) was obtained as a white solid in the same way as in (Example 24b) from 6-(4-nitrophenoxycarbonylamino)-3,4-dihydro-1H-isoquinoline-2-carboxylic acid tert-butyl ester (620 mg) obtained in Example (24a) and 5-methyl-isoxazol-3-ylamine (147 mg).

¹H NMR (400 MHz, CDCl₃): δ (ppm)=9.13 (1H, brs), 7.88 (1H, brs), 7.36 (1H, brs), 7.32-7.23 (1H, m), 7.07 (1H, d, J=8.3 Hz), 5.94 (1H, s), 4.54 (2H, s), 3.64 (2H, brs), 2.83 (2H, t, J=5.6 Hz), 2.41 (3H, s), 1.50 (9H, s)

(97b) 1-(5-methyl-isoxazol-3-yl)-3-(1,2,3,4-tetrahydro-isoquinolin-6-yl)-urea hydrochloride The title compound (110 mg, 93%) was obtained as a white solid in the same way as in Example (22b) from 6-[3-(5-methyl-isoxazol-3-yl)-ureido]-3,4-dihydro-1H-isoquinoline-2-carboxylic acid tert-butyl ester (143 mg) obtained in Example (97a):

¹H NMR (400 MHz, DMSO-d6): δ (ppm)=9.62 (1H, s), 9.14 (1H, s), 9.05 (1H, brs), 7.37 (1H, s), 7.30 (1H, d, J=8.6 Hz), 7.15 (1H, d, J=8.6 Hz), 6.53 (1H, s), 4.20 (2H, s), 3.37-3.31 (2H, m), 2.97 (2H, t, J=6.3 Hz), 2.36 (3H, s).

(97c) trans-6-[3-(5-methyl-isoxazol-3-yl)-ureido]-3,4-dihydro-1H-isoquinoline-2-carboxylic acid 4-carboxymethyl-cyclohexyl ester Methyl ester (167 mg, quantitative yield) was obtained in the same way as in Example (1e) from trans-(4-hydroxy-cyclohexyl)-acetic acid methyl ester (86 mg) obtained in Example (1d) and 1-(5-methyl-isoxazol-3-yl)-3-(1,2,3,4-tetrahydro-isoquinolin-6-yl)-urea hydrochloride (110 mg) obtained in Example (97b). This methyl ester (167 mg) was hydrolyzed with an aqueous sodium hydroxide solution in the same way as in Example 2 to obtain the title compound (143 mg, 88%) as an off-white solid.

¹H NMR (400 MHz, DMSO-d6): δ (ppm)=12.1 (1H, s), 9.54 (1H, s), 8.86 (1H, s), 7.30 (1H, s), 7.24 (1H, dd, J=8.4 and 1.7 Hz), 7.11 (1H, d, J=8.2 Hz), 6.53 (1H, s), 4.51-4.47 (3H, m), 3.57 (2H, t, J=5.9 Hz), 2.75 (2H, d, J=5.9 Hz), 2.36 (3H, s), 2.11 (2H, d, J=7.0 Hz), 1.94-1.91 (2H, m), 1.77-1.74 (2H, m), 1.68-1.62 (1H, m), 1.39-1.29 (2H, m), 1.12-1.01 (2H, m);

MS (ESI) m/z: 457 (M+H)⁺.

Example 98 trans-6-(benzothiazol-2-ylamino)-3,4-dihydro-1H-isoquinoline-2-carboxylic acid 4-carboxymethyl-cyclohexyl ester

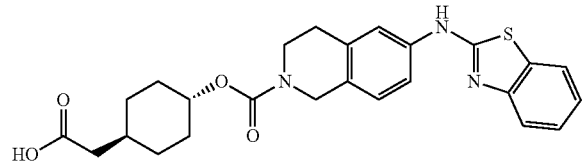 [SMILES: O=C(O)C[C@H]1CC[C@H](OC(=O)N2CCc3cc(Nc4nc5ccccc5s4)ccc3C2)CC1]

(98a) 6-(benzothiazol-2-ylamino)-3,4-dihydro-1H-isoquinoline-2-carboxylic acid tert-butyl ester A toluene solution of 6-amino-2N-Boc-1,2,3,4-tetrahydroisoquinoline (248 mg), 2-chlorobenzothiazole (186 mg), palladium acetate (22 mg), cesium carbonate (651 mg), and Xantphos (58 mg) was stirred at 120° C. for 1 hour under microwave irradiation. The reaction solution was purified by column chromatography to obtain the title compound (381 mg, quantitative yield).

¹H NMR (400 MHz, CDCl₃): δ (ppm)=7.77 (1H, d, J=8.2 Hz), 7.69 (1H, d, J=7.8 Hz), 7.40-7.29 (3H, m), 7.25-7.19 (2H, m), 4.69 (2H, s), 3.70 (2H, t, J=5.3 Hz), 2.90 (2H, t, J=5.7 Hz), 1.50 (9H, s).

(98b) benzothiazol-2-yl-(1,2,3,4-tetrahydro-isoquinolin-6-yl)-amine hydrochloride The title compound (124 mg, 66%) was obtained as a white solid in the same way as in Example (22b) from 6-(benzothiazol-2-ylamino)-3,4-dihydro-1H-isoquinoline-2-carboxylic acid tert-butyl ester (270 mg) obtained in Example (98a).

¹H NMR (400 MHz, DMSO-d6): δ (ppm)=9.25 (1H, s), 7.81-7.78 (1H, m), 7.67-7.56 (3H, m), 7.33-7.29 (1H, m), 7.20-7.13 (2H, m), 4.22-4.17 (2H, m), 3.39-3.32 (2H, m), 3.01 (2H, t, J=6.3 Hz).

(98c) trans-6-(benzothiazol-2-ylamino)-3,4-dihydro-1H-isoquinoline-2-carboxylic acid 4-methoxycarbonylmethyl-cyclohexyl ester The title compound (168 mg, 80%) was obtained in the same way as in Example (1e) from trans-(4-hydroxy-cyclohexyl)-acetic acid methyl ester (74 mg) obtained in Example (1d) and benzothiazol-2-yl-(1,2,3,4-tetrahydro-isoquinolin-6-yl)-amine hydrochloride (124 mg) obtained in Example (98b).

¹H NMR (400 MHz, CDCl₃): δ (ppm)=8.20-8.16 (1H, m), 7.50-7.44 (1H, m), 7.16-7.09 (2H, m), 7.09-7.02 (1H, m), 6.81 (1H, d, J=8.6 Hz), 6.74-6.69 (1H, m), 6.43 (1H, s), 4.66-4.52 (3H, m), 3.65 (3H, s), 3.57-3.50 (2H, m), 2.81 (2H, s), 2.23-2.16 (2H, m), 2.06-1.92 (2H, m), 1.82-1.69 (3H, m), 1.44-1.22 (2H, m), 1.16-0.99 (2H, m).

(98d) trans-6-(benzothiazol-2-ylamino)-3,4-dihydro-1H-isoquinoline-2-carboxylic acid 4-carboxymethyl-cyclohexyl ester trans-6-(Benzothiazol-2-ylamino)-3,4-dihydro-1H-isoquinoline-2-carboxylic acid 4-methoxycarbonylmethyl-cyclohexyl ester (168 mg) obtained in Example (98c) was hydrolyzed in the same way as in Example 2 to obtain the title compound (8 mg, 5%) as a white solid.

$^1$H NMR (400 MHz, DMSO-d6): δ (ppm)=7.80-7.76 (1H, m), 7.60-7.55 (3H, m), 7.33-7.28 (1H, m), 7.17-7.11 (2H, m), 4.53-4.44 (3H, m), 3.69-3.54 (2H, m), 2.83-2.73 (2H, m), 2.14-2.07 (2H, m), 1.98-1.87 (2H, m), 1.82-1.58 (2H, m), 1.42-1.28 (2H, m), 1.17-1.00 (2H, m).

Example 99

6-[3-(3-ethoxy-phenyl)-ureido]-3,4-dihydro-1H-isoquinoline-2-carboxylic acid t-4-carboxymethyl-t-2-methyl-r-1-cyclohexyl ester

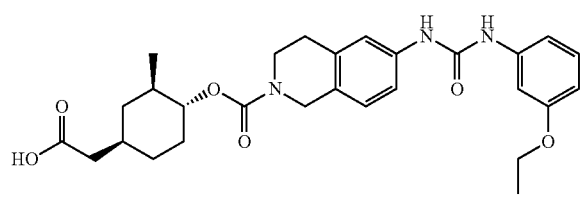 [SMILES: CCOc1cccc(NC(=O)Nc2ccc3c(c2)CCN(C(=O)O[C@@H]2CC[C@@H](CC(=O)O)C[C@H]2C)C3)c1]

Methyl ester (174 mg) was obtained in the same way as in Example (1e) from (t-4-hydroxy-c-3-methyl-cyclohexyl)-r-1-acetic acid methyl ester (94 mg) obtained in Example (16a) and 1-(3-ethoxy-phenyl)-3-(1,2,3,4-tetrahydro-isoquinolin-6-yl)-urea hydrochloride (WO2006004200 A1) (94 mg). This methyl ester was hydrolyzed in the same way as in Example 2 to obtain the title compound (117 mg, 85%, two steps) as a white solid.

$^1$H NMR (400 MHz, DMSO-d6): δ (ppm)=12.0 (1H, s), 8.65 (1H, s), 8.60 (1H, s), 7.32 (1H, s), 7.22-7.07 (4H, m), 6.89 (1H, d, J=9.4 Hz), 6.53 (1H, dd, J=8.4 and 2.1 Hz), 4.49 (2H, s), 4.22-4.15 (1H, m), 3.99 (2H, q, J=6.9 Hz), 3.62-3.55 (2H, m), 2.76 (2H, t, J=5.9 Hz), 2.11 (2H, d, J=6.3 Hz), 1.98-1.90 (1H, m), 1.79-1.70 (2H, m), 1.65-1.56 (1H, m), 1.32 (3H, t, J=7.1 Hz), 1.35-1.21 (2H, m), 1.11-1.01 (1H, m), 0.91-0.81 (4H, m).

MS (ESI) m/z: 510 (M+H)$^+$.

Example 100

6-[3-(3-ethoxy-phenyl)-ureido]-3,4-dihydro-1H-isoquinoline-2-carboxylic acid t-4-carboxymethyl-c-2-methyl-r-1-cyclohexyl ester

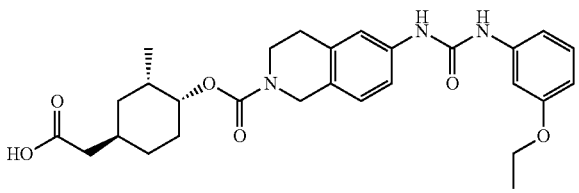 [SMILES: CCOc1cccc(NC(=O)Nc2ccc3c(c2)CCN(C(=O)O[C@@H]2CC[C@@H](CC(=O)O)C[C@@H]2C)C3)c1]

Methyl ester (155 mg, quantitative yield) was obtained in the same way as in Example (1e) from (t-4-hydroxy-t-3-methyl-cyclohexyl)-r-1-acetic acid methyl ester (83 mg) obtained in Example (14g) and 1-(3-ethoxy-phenyl)-3-(1,2,3,4-tetrahydro-isoquinolin-6-yl)-urea hydrochloride (WO2006004200 A1) (119 mg). This methyl ester was hydrolyzed in the same way as in Example 2.

MS (ESI) m/z: 510 (M+H)$^+$.

Example 101

6-[3-(3-methoxy-phenyl)-ureido]-3,4-dihydro-1H-isoquinoline-2-carboxylic acid t-4-carboxymethyl-t-2-methyl-r-1-cyclohexyl ester

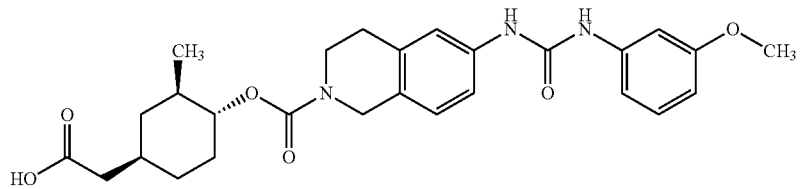 [SMILES: COc1cccc(NC(=O)Nc2ccc3c(c2)CCN(C(=O)O[C@@H]2CC[C@@H](CC(=O)O)C[C@H]2C)C3)c1]

Methyl ester (496 mg) was obtained in the same way as in Example (1e) from (t-4-hydroxy-c-3-methyl-cyclohexyl)-r-1-acetic acid methyl ester (261 mg) obtained in Example (16a) and 1-(3-methoxy-phenyl)-3-(1,2,3,4-tetrahydro-isoquinolin-6-yl)-urea hydrochloride (333 mg) obtained in Example (49b). This methyl ester was hydrolyzed with an aqueous sodium hydroxide solution in the same way as in Example 2 to obtain the title compound (438 mg, 91%, two steps) as a white solid.

$^1$H NMR (400 MHz, DMSO-d6): δ (ppm)=12.1 (1H, s), 8.74 (1H, s), 8.67 (1H, s), 7.33 (1H, s), 7.23-7.19 (2H, m), 7.16 (1H, d, J=8.3 Hz), 7.09 (1H, d, J=8.2 Hz), 6.92 (1H, d, J=7.9 Hz), 6.55 (1H, dd, J=8.2 and 2.4 Hz), 4.49 (2H, brs), 4.22-4.15 (1H, m), 3.73 (3H, s), 3.58 (2H, t, J=5.6 Hz), 2.76 (2H, t, J=6.0 Hz), 2.10 (2H, d, J=6.6 Hz), 1.96-1.91 (1H, m), 1.75-1.72 (3H, m), 1.64-1.57 (1H, m), 1.34-1.25 (1H, m), 1.10-1.04 (2H, m), 0.89-0.83 (3H, m);

MS (ESI) m/z: 496 (M+H)+.

Example 102

6-[3-(3-trifluoromethoxy-phenyl)-ureido]-3,4-dihydro-1H-isoquinoline-2-carboxylic acidt-4-carboxymethyl-t-2-methyl-r-1-cyclohexyl ester

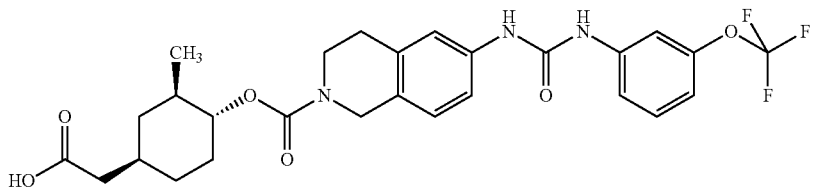 [SMILES: C[C@@H]1C[C@H](CC(=O)O)CC[C@H]1OC(=O)N1CCc2cc(NC(=O)Nc3cccc(OC(F)(F)F)c3)ccc2C1]

Methyl ester (553 mg) was obtained in the same way as in Example (1c) from (t-4-hydroxy-c-3-methyl-cyclohexyl)-r-1-acetic acid methyl ester (261 mg) obtained in Example (16a) and 1-(3-trifluoromethoxy-phenyl)-3-(1,2,3,4-tetrahydro-isoquinolin-6-yl)-urea hydrochloride (387 mg) obtained in Example (52b). This methyl ester was hydrolyzed with an aqueous sodium hydroxide solution in the same way as in Example 2 to obtain the title compound (477 mg, 88%, two steps) as a white solid.

1H NMR (400 MHz, DMSO-d6): δ (ppm)=12.1 (1H, s), 9.05 (1H, s), 8.76 (1H, s), 7.71 (1H, s), 7.40 (1H, dd, J=8.2 and 8.2 Hz), 7.33 (1H, s), 7.28 (1H, d, J=9.4 Hz), 7.23 (1H, d, J=7.9 Hz), 7.11 (1H, d, J=8.2 Hz), 6.94 (1H, d, J=8.2 Hz), 4.49 (2H, brs), 4.22-4.15 (1H, m), 3.61-3.57 (2H, m), 2.77 (2H, t, J=5.7 Hz), 2.10 (2H, d, J=6.6 Hz), 1.96-1.91 (1H, m), 1.74-1.72 (3H, m), 1.63-1.59 (1H, m), 1.34-1.24 (1H, m), 1.10-1.02 (2H, m), 0.89-0.80 (3H, m);

MS (ESI) m/z: 550 (M+H)+.

Example 103 trans-6-[3-(2-fluoro-phenyl)-ureido]-3,4-dihydro-1H-isoquinoline-2-carboxylic acid 4-(1-carboxy-ethyl)-cyclohexyl ester

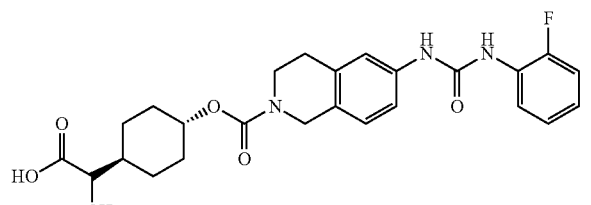

(103a)
2-(1,4-dioxa-spiro[4,5]dec-8-ylidene)-propionic acid ethyl ester

The title compound (7.01 g, 86%) was obtained as a colorless oil in the same way as in Example (1a) from 2-phosphonopropionate (8.0 mL) and 1,4-cyclohexanedione monoethylene ketal (5.28 g).

1H NMR (400 MHz, CDCl3): δ (ppm)=4.20 (2H, q, J=7.2 Hz), 3.94 (4H, s), 2.61 (2H, t, J=6.0 Hz), 2.39 (2H, t, J=6.4 Hz), 1.89 (3H, s), 1.76-1.71 (4H, m), 1.30 (3H, t, J=7.1 Hz);

MS (FAB) m/z: 241 (M+H)+.

(103b) 2-(1,4-dioxa-spiro[4,5]dec-8-yl)-propionic acid ethyl ester

The title compound (6.94 g, 98%) was obtained as a colorless oil in the same way as in Example (1b) from 2-(1,4-dioxa-spiro[4.5]dec-8-ylidene)-propionic acid ethyl ester (7.01 g) obtained in Example (103a).

1H NMR (400 MHz, CDCl3): δ (ppm)=4.18-4.10 (2H, m), 3.94 (4H, s), 2.26-2.20 (1H, m), 1.80-1.71 (3H, m), 1.64-1.49 (4H, m), 1.42-1.30 (2H, m), 1.26 (3H, t, J=7.0 Hz), 1.13 (3H, d, J=7.1 Hz);

MS (EI) m/z: 242 (M)+.

(103c) 2-(4-oxo-cyclohexyl)-propionic acid ethyl ester

The title compound (5.99 g, quantitative yield) was obtained as a colorless oil in the same way as in Example (1c) from 2-(1,4-dioxa-spiro[4.5]dec-8-yl)-propionic acid ethyl ester (6.94 g) obtained in Example (103b).

1H NMR (400 MHz, CDCl3): δ (ppm)=4.16 (2H, q, J=6.9 Hz), 2.47-2.30 (5H, m), 2.13-1.94 (3H, m), 1.59-1.43 (2H, m), 1.28 (3H, t, J=7.2 Hz), 1.19 (3H, d, J=7.0 Hz);

MS (EI) m/z: 198 (M)+.

(103d) trans-2-(4-hydroxy-cyclohexyl)-propionic acid ethyl ester

The title compound (762 mg, 44%) was obtained as a colorless oil in the same way as in Example (1d) from 2-(4-oxo-cyclohexyl)-propionic acid ethyl ester (1.70 g) obtained in Example (103c).

1H NMR (400 MHz, CDCl3): δ (ppm)=4.17-4.10 (2H, m), 3.62-3.50 (1H, m), 2.26-2.20 (1H, m), 2.06-1.95 (2H, m), 1.84-1.77 (1H, m), 1.71-1.65 (1H, m), 1.57-1.47 (1H, m), 1.40 (1H, s), 1.32-1.24 (2H, m), 1.27 (3H, d, J=7.1 Hz), 1.17-0.99 (2H, m), 1.12 (3H, d, J=7.1 Hz);

MS (FAB) m/z: 201 (M+H)+.

(103e) trans-6-[3-(2-fluoro-phenyl)-ureido]-3,4-dihydro-1H-isoquinoline-2-carboxylic acid 4-(1-carboxy-ethyl)-cyclohexyl ester Ethyl ester (88 mg, 55%) was obtained in the same way as in Example (1e) from trans-2-(4-hydroxy-cyclohexyl)-propionic acid ethyl ester (81 mg) obtained in Example (103d) and 1-(2-fluoro-phenyl)-3-(1,2,3,4-tetrahydro-isoquinolin-6-yl)-urea hydrochloride (WO2006004200 A1) (100 mg). This ethyl ester (88 mg) was hydrolyzed in the same way as in Example 2 to obtain the title compound (35 mg, 42%) as a white solid.

$^1$H NMR (400 MHz, DMSO-d6): δ (ppm)=12.1 (1H, s), 9.02 (1H, s), 8.54 (1H, s), 8.16 (1H, dd, J=8.2 and 8.2 Hz), 7.39-6.97 (6H, m), 4.55-4.40 (3H, m), 3.65-3.54 (2H, m), 2.85-2.73 (2H, m), 2.21-2.11 (1H, m), 2.04-1.91 (2H, m), 1.80-1.63 (1H, m), 1.57-1.41 (1H, m), 1.39-1.26 (2H, m), 1.19-0.99 (3H, m), 1.02 (3H, d, J=6.7 Hz);

MS (ESI) m/z: 484 (M+H)$^+$.

Example 104 trans-6-[3-(3-methoxy-phenyl)-ureido]-3,4-dihydro-1H-isoquinoline-2-carboxylic acid 4-(1-carboxy-ethyl)-cyclohexyl ester

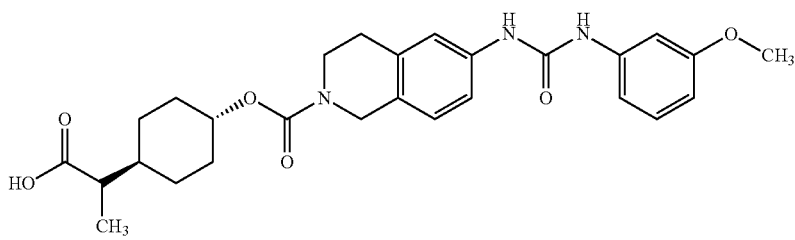 [SMILES: COc1cccc(NC(=O)Nc2ccc3c(c2)CCN(C(=O)O[C@H]2CC[C@H](C(C)C(=O)O)CC2)C3)c1]

Ethyl ester (331 mg, 79%) was obtained in the same way as in Example (1e) from trans-2-(4-hydroxy-cyclohexyl)-propionic acid ethyl ester (180 mg) obtained in Example (103d) and 1-(3-methoxy-phenyl)-3-(1,2,3,4-tetrahydro-isoquinolin-6-yl)-urea hydrochloride (267 mg) obtained in Example (49b). This ethyl ester (331 mg) was hydrolyzed with an aqueous sodium hydroxide solution in the same way as in Example 2 to obtain the title compound (249 mg, 79%) as an off-white solid.

$^1$H NMR (400 MHz, DMSO-d6): δ (ppm)=12.1 (1H, s), 8.67 (1H, s), 8.60 (1H, s), 7.32 (1H, brs), 7.22-7.15 (3H, m), 7.09 (1H, dd, J=8.3 and 4.3 Hz), 6.92 (1H, d, J=7.8 Hz), 6.55 (1H, dd, J=8.2 and 2.3 Hz), 4.51-4.43 (3H, m), 3.73 (3H, s), 3.56 (2H, t, J=5.5 Hz), 2.75 (2H, t, J=5.8 Hz), 2.15 (1H, t, J=7.1 Hz), 1.97-1.95 (1H, m), 1.83-1.64 (2H, m), 1.54-1.45 (2H, m), 1.37-1.27 (2H, m), 1.18-1.07 (2H, m), 1.04 (3H, d, J=5.9 Hz);

MS (ESI) m/z: 496 (M+H)$^+$.

Example 105 trans-6-(3-phenyl-ureido)-3,4-dihydro-1H-isoquinoline-2-carboxylic acid 4-(1-carboxy-ethyl)-cyclohexyl ester

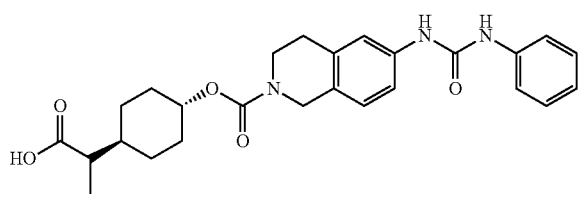 [SMILES: CC(C(=O)O)[C@H]1CC[C@H](OC(=O)N2CCc3cc(NC(=O)Nc4ccccc4)ccc3C2)CC1]

Ethyl ester (338 mg, 86%) was obtained in the same way as in Example (1e) from trans-2-(4-hydroxy-cyclohexyl)-propionic acid ethyl ester (180 mg) obtained in Example (103d) and 1-phenyl-3-(1,2,3,4-tetrahydro-isoquinolin-6-yl)-urea hydrochloride (243 mg) obtained in Example (50b). This ethyl ester (338 mg) was hydrolyzed with an aqueous sodium hydroxide solution in the same way as in Example 2 to obtain the title compound (204 mg, 64%) as an off-white solid.

$^1$H NMR (400 MHz, DMSO-d6): δ (ppm)=12.1 (1H, s), 8.64 (1H, s), 8.60 (1H, s), 7.45 (2H, d, J=8.6 Hz), 7.32 (1H, brs), 7.28 (2H, dd, J=8.0 and 8.0 Hz), 7.22 (1H, d, J=8.6 Hz), 7.09 (1H, dd, J=8.4 and 4.5 Hz), 6.97 (1H, dd, J=7.4 and 7.5 Hz), 4.49-4.44 (3H, m), 3.56 (2H, t, J=5.5 Hz), 2.75 (2H, t, J=6.0 Hz), 2.15 (1H, t, J=7.0 Hz), 1.99-1.93 (1H, m), 1.84-1.64 (2H, m), 1.48-1.37 (2H, m), 1.30-1.18 (2H, m), 1.06-1.05 (2H, m), 1.04 (3H, d, J=5.9 Hz);

MS (ESI) m/z: 466 (M+H)$^+$.

Example 106

[4-(2-{6-[3-(3-methoxy-phenyl)-ureido]-3,4-dihydro-1H-isoquinolin-2-yl}-1-methyl-2-oxy-ethyl)-cyclohexyl]-acetic acid

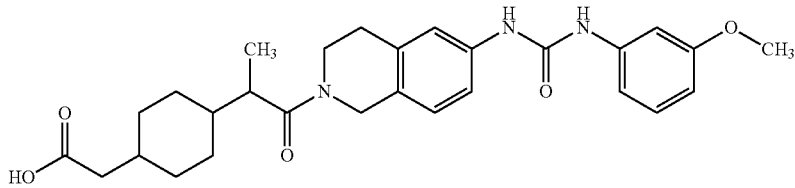 [SMILES: COc1cccc(NC(=O)Nc2ccc3c(c2)CCN(C(=O)C(C)C2CCC(CC(=O)O)CC2)C3)c1]

(106a) 2-(4-tert-butoxycarbonylmethyl-cyclohexyl)-propionic acid ethyl ester Olefin (6.16 g) was obtained in the same way as in Example (1a) from 2-(4-oxo-cyclohexyl)-propionic acid ethyl ester (4.13 g) obtained in Example (103c) and tert-butyl diethyl phosphonoacetate (4.99 g). This olefin (6.16 g) was reduced in the same way as in Example (1b) to obtain the title compound (4.17 g, 49%, two steps) as a colorless oil.

$^1$H NMR (400 MHz, CDCl$_3$): δ (ppm)=4.23-4.08 (2H, m), 2.51-2.37 (1H, m), 2.32-2.18 (2H, m), 2.14-2.04 (2H, m), 1.88-1.59 (4H, m), 1.45 (9H, s), 1.39-1.23 (5H, m), 1.19-0.86 (5H, m);

MS (FAB) m/z: 299 (M+H)$^+$.

(106b) 2-(4-tert-butoxycarbonylmethyl-cyclohexyl)-propionic acid 2-(4-Tert-butoxycarbonylmethyl-cyclohexyl)-propionic acid ethyl ester (2.46 g) obtained in Example (106a) was hydrolyzed with 1 N NaOH in the same way as in (Example 2) to obtain the title compound (1.72 g, 78%) as a colorless oil.

$^1$H NMR (400 MHz, CDCl$_3$): δ (ppm)=2.30-2.20 (1H, m), 2.12-2.05 (2H, m), 1.84-1.65 (3H, m), 1.57-1.49 (3H, m), 1.44 (9H, s), 1.30-1.22 (1H, m), 1.19-0.97 (4H, m), 1.14 (3H, d, J=6.6 Hz).

(106c) [4-(2-{6-[3-(3-methoxy-phenyl)-ureido]-3,4-dihydro-1H-isoquinolin-2-yl}-1-methyl-2-oxy-ethyl)-cyclohexyl]-acetic acid Tert-butyl ester (340 mg, 49%) was obtained in the same way as in Example 40 from 2-(4-tert-butoxycarbonylmethyl-cyclohexyl)-propionic acid (343 mg) obtained in Example (106b) and 1-(3-methoxy-phenyl)-3-(1,2,3,4-tetrahydro-isoquinolin-6-yl)-urea hydrochloride (425 mg) obtained in Example (49b). This tert-butyl ester (340 mg) was treated in the same way as in Example (22b) to obtain the title compound (148 mg, 48%) as a white solid. $^1$H NMR (400 MHz, DMSO-d6): δ (ppm)=12.0 (1H, s), 8.68 (1H, s), 8.60 (1H, s), 7.42-7.08 (5H, m), 6.92 (1H, d, J=7.4 Hz), 6.56 (1H, d, J=8.2 Hz), 4.71-4.53 (2H, m), 3.81 (3H, s), 3.73-3.65 (2H, m), 2.86-2.63 (3H, m), 2.13-2.04 (2H, m), 1.85-1.51 (4H, m), 1.46-1.31 (4H, m), 1.04-0.86 (5H, m);

MS (ESI) m/z: 494 (M+H)$^+$.

Example 107

2-[4-(2-{6-[3-(2-fluoro-phenyl)-ureido]-3,4-dihydro-1H-isoquinolin-2-yl}-2-oxo-ethyl)-cyclohexyl]-propionic acid

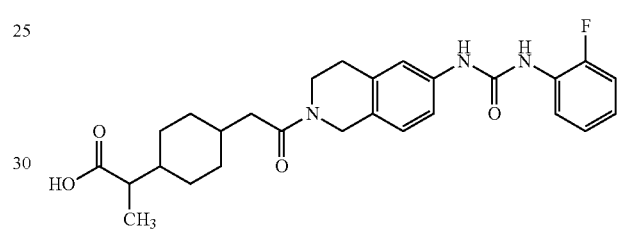

(107a) 2-(4-carbonylmethyl-cyclohexyl)-propionic acid ethyl ester

The title compound (1.53 g, quantitative yield) was obtained as a colorless oil in the same way as in Example (22b) from 2-(4-tert-butoxycarbonylmethyl-cyclohexyl)-propionic acid ethyl ester (1.68 g) obtained in Example (106a).

$^1$H NMR (400 MHz, CDCl$_3$): δ (ppm)=4.18-4.07 (2H, m), 2.44-2.32 (1H, m), 2.28-2.20 (2H, m), 2.14-2.06 (1H, m), 1.90-1.62 (3H, m), 1.90-1.62 (3H, m), 1.26 (3H, t, J=7.1 Hz), 1.15-1.10 (4H, m), 1.12-0.99 (3H, m);

MS (EI) m/z: 242 (M)$^+$.

(107b) [4-(2-{6-[3-(3-methoxy-phenyl)-ureido]-3,4-dihydro-1H-isoquinolin-2-yl}-1-methyl-2-oxy-ethyl)-cyclohexyl]-acetic acid Ethyl ester (304 mg, 82%) was obtained in the same way as in Example 40 from 2-(4-carbonylmethyl-cyclohexyl)-propionic acid ethyl ester (177 mg) obtained in Example (107a) and 1-(2-fluoro-phenyl)-3-(1,2,3,4-tetrahydro-isoquinolin-6-yl)-urea hydrochloride (WO2006004200 A1) (236 mg). This ethyl ester (304 mg) was hydrolyzed in the same way as in Example 2 to obtain the title compound (139 mg, 49%) as a white solid.

$^1$H NMR (400 MHz, DMSO-d6): δ (ppm)=12.0 (1H, s), 9.01 (1H, s), 8.53 (1H, s), 8.16 (1H, dd, J=8.2 and 8.2 Hz), 7.35-6.98 (6H, m), 4.61-4.50 (2H, m), 3.65 (2H, t, J=6.0 Hz), 2.85-2.70 (2H, m), 2.27 (2H, d, J=6.2 Hz), 2.15-2.06 (1H, m), 1.79-1.57 (4H, m), 1.79-1.57 (4H, m), 1.79-1.57 (5H, m);

MS (ESI) m/z: 482 (M+H)$^+$.

Example 108

[4-({6-[3-(2-fluoro-phenyl)-ureido]-3,4-dihydro-1H-isoquinoline-2-carbonyl}-methyl-amino)-cyclohexyl]-acetic acid

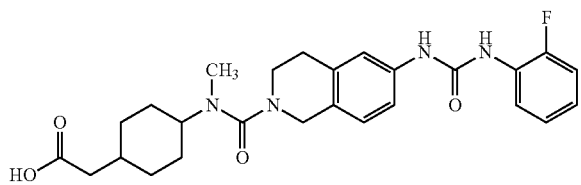 [SMILES: CN(C(=O)N1CCc2cc(NC(=O)Nc3ccccc3F)ccc2C1)C1CCC(CC(=O)O)CC1]

(108a) (4-methylamino-cyclohexyl)-acetic acid methyl ester

To a tetrahydrofuran (60 mL) solution of (4-oxo-cyclohexyl)-acetic acid methyl ester (2.14 g) obtained in Example (1c), methylamine (2.0 M tetrahydrofuran solution, 12.5 mL), acetic acid (0.72 mL), and sodium triacetoxyborohydride (2.67 g) were added at room temperature. After 4 hours, the reaction mixture was diluted with saturated sodium bicarbonate (100 mL). The organic solvent was removed under reduced pressure. The aqueous mixture was subjected to extraction with dichloromethane (×3). The dichloromethane layer was dried over sodium sulfate and then concentrated. The residue was purified by column chromatography (NH silica gel, dichloromethane/methanol) to obtain the title compound (822 mg, 35%) as a brown oil.

$^1$H NMR (400 MHz, CDCl$_3$): δ (ppm)=3.67 (3H, s), 2.62-2.57 (1H, m), 2.40 (3H, s), 2.28 (2H, d, J=7.4 Hz), 2.00-1.91 (1H, m), 1.83-1.75 (1H, m), 1.63-1.48 (4H, m), 1.45-1.35 (2H, m), 1.29-1.17 (1H, m), 1.15-1.01 (1H, m);

MS (EI) m/z: 185 (M)$^+$.

(108b) [4-({6-[3-(2-fluoro-phenyl)-ureido]-3,4-dihydro-1H-isoquinoline-2-carbonyl}-methyl-amino)-cyclohexyl]-acetic acid Methyl ester (322 mg, 88%) was obtained in the same way as in Example (1e) from (4-methylamino-cyclohexyl)-acetic acid methyl ester (190 mg) obtained in Example (108a) and 1-(2-fluoro-phenyl)-3-(1,2,3,4-tetrahydro-isoquinolin-6-yl)-urea hydrochloride (WO2006004200 A1) (238 mg). This methyl ester (322 mg) was hydrolyzed in the same way as in Example 2 to obtain the title compound (149 mg, 48%) as a pale yellow solid.

$^1$H NMR (400 MHz, DMSO-d6): δ (ppm)=12.0 (1H, s), 9.00 (1H, s), 8.53 (1H, s), 8.16 (1H, dd, J=8.8 and 8.8 Hz), 7.33-6.98 (6H, m), 4.22 (2H, s), 3.53-3.42 (1H, m), 2.82 (2H, t, J=5.2 Hz), 2.72 (3H, s), 2.33 (2H, d, J=7.9 Hz), 2.10 (2H, d, J=7.0 Hz), 1.82-1.37 (6H, m), 1.11-0.97 (1H, m), 1.04 (2H, d, J=6.3 Hz);

MS (ESI) m/z: 483 (M+H)$^+$.

Test Example 1

(1) Preparation of DGAT1 Enzyme

DGAT1 enzyme was prepared and stored according to the method described in US2007/0249620.

(2) DGAT1 Inhibitory Activity Test

A reaction solution having the following composition was incubated at room temperature (23° C.) for 30 minutes: 175 mM Tris-HCl (pH 8.0), 8 mM MgCl$_2$, 1 mg/ml BSA, 0.3 mM 1,2-dioleoyl-sn-glycerol (10-fold concentration of EtOH solution, 10% added), 10 μM [$^{14}$C]-oleoyl-CoA (approximately 50 mCi/mmol), 0.5% Triton X-100, the DGAT1 enzyme (10 μg) obtained in Test Example 1(1), and a test compound or vehicle (DMSO/MeOH, 7:3 solution, 5% added), 50 μA in total. A reaction stop solution (700 consisting of isopropanol/1-heptane/water (80:20:2, v/v/v) was added to the reaction solution and stirred. Subsequently, water (30 μl) and 1-heptane (100 μl) were added thereto and stirred. The 1-heptane layer (50 μl) was spotted onto a TLC plate and developed with a developing solvent consisting of 1-hexane/diethyl ether/acetic acid (85:15:1, v/v/v). The radioactivity of the triglyceride fraction was quantified using BAS2000 Bio Image Analyzer (FUJIFILM) and compared with the control. The inhibitory activity of the test compound was calculated according to the formula shown below. In this context, the radioactivity at no reaction (0 minute incubation) was used as background.

Inhibitory Rate=100−[(Radioactivity of sample supplemented with test compound)−(Background)]/[(Radioactivity of control)−(Background)]×100

The compounds of Examples 2-3, 5-45, 47-62, 64-80, 82-86, 90-95, 97-107, and 108 exhibited a 50% or higher inhibitory rate at the test compound concentration of 0.05 μg/ml.

In this context, the DGAT inhibitory activity test is not limited to the method described above. For example, microsomes prepared from the small intestine, fat tissue, or liver of animals (e.g., rats or mice) may be used as the DGAT enzyme. Moreover, microsomes prepared from cultured cells (3T3-L1 fat cells, primarily cultured fat cells, Caco2 cells, HepG2 cells, etc.) or cultured cells highly expressing DGAT can also be used as the DGAT enzyme. Furthermore, flush plates (PerkinElmer) that require no extraction procedure can be used for efficiently evaluating a large number of test compounds in a short time.

As is evident from these results, compounds of the present invention have excellent DGAT1 inhibitory bioactivity.

Test Example 2

The DGAT1 enzyme is important for the digestion and absorption of triglycerides, and the inhibition of DGAT1 in the small intestine suppresses the absorption of triglycerides. The in vivo activity of its DGAT1 inhibitory effect was evaluated with the suppressed absorption of triglycerides after fat loading as an index. Male C57BL/6N mice (7-12 weeks old, body weight: 17-25 g, Charles River Laboratories Japan Inc.) fasted overnight were assigned to Vehicle group 1, Vehicle group 2, and each test compound group, to which a vehicle (0.5% methylcellulose) or each test compound (1 to 10 mg/kg) suspended in vehicle was orally administered (5 mL/kg). After a given time, a lipoprotein lipase inhibitor (Pluronic-F127: Sigma-Aldrich Corp., 1 g/kg, 20% by weight dissolved in saline) was intraperitoneally administered (5 mL/kg) to each group. Immediately thereafter, distilled water for the Vehicle group 1 or a 20% fat-containing emulsion (Intralipid 20%: TERUMO CORP., Japan) for the Vehicle group 2 and the compound groups were orally administered thereto (0.2 mL/mouse). After a given time of 1 to 4 hours after administration, blood was collected from the tail vein or the right ventricle, and plasma was immediately separated and collected. Then, the triglyceride concentration in plasma was measured using a commercially available kit (Triglyceride E-Test Wako: Wako Pure Chemical Industries, Ltd.). In this method, the administration of the lipoprotein lipase inhibitor suppresses the hydrolysis of triglycerides in the blood such that the triglycerides are accumulated in the blood. These triglycerides are derived from two origins: exogenous triglycerides absorbed in the gastrointestinal tract and endogenous triglycerides released from the liver. The triglyceride absorption suppressive activity of each test compound was calculated based on the equation shown below by removing the influence of the endogenous triglycerides. In this context, each test compound was separately confirmed to have no influence on the concentration of the endogenous triglycerides.

Triglyceride absorption suppressive activity (%)=100–[(Triglyceride concentration of each test compound group)–(Triglyceride concentration of Vehicle group 1)]/[(Triglyceride concentration of Vehicle group 2)–(Triglyceride concentration of Vehicle group 1)]×100

The compounds of Examples 2, 5, 7, 8, 10, 11, 12, 13, 15, 16, 17, 20, 21, 22, 23, 24, 25, 26, 27, 28, 29, 30, 31, 32, 41, 43-62, 64, 66-78, 80-86, 90-92, 95, 97, 99-105, 107, and 108 exhibited 60% or higher triglyceride absorption suppressive activity at a dose of 10 mg/kg or lower.

As is evident from these results, compounds of the present invention have excellent triglyceride absorption suppressive activity.

Test Example 3

Male C57BL/6N mice (7-12 weeks old, body weight: 17-25 g, Charles River Laboratories Japan Inc.) were individually housed and fed on a high-fat diet (fat content: 45 kcal %: Research Diets, Inc. D12451) for 1 week or longer for acclimatization. Based on the food intake during the period, the animals were equally assigned to experimental groups and fasted overnight. Then, a vehicle (0.5% methylcellulose) or each test compound (1 to 10 mg/kg) suspended in vehicle was orally administered (10 mL/kg) to each group. 30 minutes after administration, the animals were fed on a high-fat diet, and the food intake was measured 6 hours after initiation of feeding. The feeding suppressant activity of each test compound was calculated based on the equation shown below.

Feeding suppressant activity (%)=[(Food intake of Vehicle group)–(Food intake of each test compound group)]/[(Food intake of Vehicle group)]×100

The compounds of Examples 2 and 20 exhibited 25% or higher feeding suppressant activity at a dose of 10 mg/kg or lower.

As is evident from these results, compounds of the present invention have an excellent feeding suppressant effect.

Formulation Example 1

Capsule

Compound of Example 2 or 3 50 mg
Lactose 128 mg
Corn starch 70 mg
Magnesium stearate 2 mg
- - -
a. 250 mg A powder of this formulation is mixed and passed through a 60-mesh sieve. Then, this powder is charged into 250 mg of gelatin capsule to prepare a capsule.

Formulation Example 2

Tablet

Compound of Example 2 or 3 50 mg
Lactose 126 mg
Corn starch 23 mg
Magnesium stearate 1 mg
- - -
a. 200 mg A powder of this formulation is mixed, granulated using a corn starch paste, then dried, and then compressed into a tablet (200 mg/tablet) using a tableting machine. This tablet can be sugar-coated according to need.

INDUSTRIAL APPLICABILITY

A compound of the present invention represented by the general formula (I) or a pharmacologically acceptable salt thereof has an excellent DGAT inhibitory effect and feeding suppressant effect and is thus useful as a pharmaceutical agent.

The invention claimed is:

1. A compound of formula (II), or a pharmacologically acceptable salt thereof:

(II)

wherein,
R represents a phenyl group optionally substituted with 1 to 5 groups each independently selected from Substituent Group A or a $C_3$-$C_6$ cycloalkyl group;
$R^3$ represents a carboxyl group;
X represents an oxygen atom; and
Substituent Group A is a group consisting of a halogen atom, a $C_1$-$C_6$ alkyl group, a $C_1$-$C_6$ halogenated alkyl group, a $C_1$-$C_6$ alkoxy group, a $C_1$-$C_6$ halogenated alkoxy group, a ($C_1$-$C_6$ alkoxy)-($C_1$-$C_6$ alkyl) group, a $C_1$-$C_6$ alkylthio group, a carboxyl group, a $C_2$-$C_7$ alkylcarbonyl group, a $C_2$-$C_7$ alkoxycarbonyl group, an amino group, a mono-$C_2$-$C_7$ alkylcarbonylamino group, a mono-$C_1$-$C_6$ alkylsulfonylamino group, a mono-$C_1$-$C_6$ alkylamino group, a di-($C_1$-$C_6$ alkyl)amino group, a cyano group, a nitro group, a hydroxy group, and a $C_1$-$C_6$ alkylsulfinyl group.

2. The compound or pharmacologically acceptable salt thereof according to claim 1, wherein R is a phenyl group optionally substituted with 1 to 3 groups each independently selected from a halogen atom, a $C_1$-$C_6$ alkyl group, a $C_1$-$C_6$ halogenated alkyl group, a $C_1$-$C_6$ alkoxy group, and a $C_1$-$C_6$ halogenated alkoxy group or a $C_3$-$C_6$ cycloalkyl group.

3. The compound or pharmacologically acceptable salt thereof according to claim 1, wherein R is a phenyl group, a 2-fluorophenyl group, a 3-fluorophenyl group, a 3-methylphenyl group, a 3-ethylphenyl group, a 3-methoxyphenyl group, a 3-ethoxyphenyl group, a 4-trifluoromethylphenyl group, a 3-trifluoromethoxyphenyl group, a 3,4-difluorophenyl group, a 2-fluoro-5-methoxyphenyl group, a 2,4,5-trifluorophenyl group, a 3,4,5-trifluorophenyl group or a cyclopentyl group.

4. The compound or pharmacologically acceptable salt thereof according to claim 1, wherein R is a phenyl group, a 2-fluorophenyl group, a 3-fluorophenyl group, a 3-methylphenyl group, a 3-ethylphenyl group, a 3-methoxyphenyl group, a 3-ethoxyphenyl group, a 3-trifluoromethoxyphenyl group, a 3,4-difluorophenyl group, a 2-fluoro-5-methoxyphenyl group or a 2,4,5-trifluorophenyl group.

5. The compound or pharmacologically acceptable salt thereof according to claim 1, wherein the compound of formula (II) is
trans-6-[3-(2-fluoro-phenyl)-ureido]-3,4-dihydro-1H-isoquinoline-2-carboxylic acid 4-carboxymethyl-cyclohexyl ester,
trans-6-[3-(3-ethoxy-phenyl)-ureido]-3,4-dihydro-1H-isoquinoline-2-carboxylic acid 4-carboxymethyl-cyclohexyl ester,
trans-6-[3-(2,4,5-trifluoro-phenyl)-ureido]-3,4-dihydro-1H-isoquinoline-2-carboxylic acid 4-carboxymethyl-cyclohexyl ester,
trans-6-[3-(3-methoxy-phenyl)-ureido]-3,4-dihydro-1H-isoquinoline-2-carboxylic acid 4-carboxymethyl-cyclohexyl ester,
trans-6-(3-phenyl-ureido)-3,4-dihydro-1H-isoquinoline-2-carboxylic acid 4-carboxymethyl-cyclohexyl ester,
trans-6-[3-(3-trifluoromethoxy-phenyl)-ureido]-3,4-dihydro-1H-isoquinoline-2-carboxylic acid 4-carboxymethyl-cyclohexyl ester,
trans-6-[3-(3,4-difluoro-phenyl)-ureido]-3,4-dihydro-1H-isoquinoline-2-carboxylic acid 4-carboxymethyl-cyclohexyl ester,
trans-6-[3-(2-fluoro-5-methoxy-phenyl)-ureido]-3,4-dihydro-1H-isoquinoline-2-carboxylic acid 4-carboxymethyl-cyclohexyl ester,
trans-6-[3-(3-fluoro-phenyl)-ureido]-3,4-dihydro-1H-isoquinoline-2-carboxylic acid 4-carboxymethyl-cyclohexyl ester,
trans-6-(3-m-tolyl-ureido)-3,4-dihydro-1H-isoquinoline-2-carboxylic acid 4-carboxymethyl-cyclohexyl ester or
trans-6-[3-(3-ethyl-phenyl)-ureido]-3,4-dihydro-1H-isoquinoline-2-carboxylic acid 4-carboxymethyl-cyclohexyl ester.

6. The compound according to claim 1, wherein the compound of formula (II) is
trans-6-[3-(2-fluoro-phenyl)-ureido]-3,4-dihydro-1H-isoquinoline-2-carboxylic acid 4-carboxymethyl-cyclohexyl ester,
trans-6-[3-(3-ethoxy-phenyl)-ureido]-3,4-dihydro-1H-isoquinoline-2-carboxylic acid 4-carboxymethyl-cyclohexyl ester,
trans-6-[3-(2,4,5-trifluoro-phenyl)-ureido]-3,4-dihydro-1H-isoquinoline-2-carboxylic acid 4-carboxymethyl-cyclohexyl ester,
trans-6-[3-(3-methoxy-phenyl)-ureido]-3,4-dihydro-1H-isoquinoline-2-carboxylic acid 4-carboxymethyl-cyclohexyl ester,
trans-6-(3-phenyl-ureido)-3,4-dihydro-1H-isoquinoline-2-carboxylic acid 4-carboxymethyl-cyclohexyl ester,
trans-6-[3-(3-trifluoromethoxy-phenyl)-ureido]-3,4-dihydro-1H-isoquinoline-2-carboxylic acid 4-carboxymethyl-cyclohexyl ester,
trans-6-[3-(3,4-difluoro-phenyl)-ureido]-3,4-dihydro-1H-isoquinoline-2-carboxylic acid 4-carboxymethyl-cyclohexyl ester,
trans-6-[3-(2-fluoro-5-methoxy-phenyl)-ureido]-3,4-dihydro-1H-isoquinoline-2-carboxylic acid 4-carboxymethyl-cyclohexyl ester,
trans-6-[3-(3-fluoro-phenyl)-ureido]-3,4-dihydro-1H-isoquinoline-2-carboxylic acid 4-carboxymethyl-cyclohexyl ester,
trans-6-(3-m-tolyl-ureido)-3,4-dihydro-1H-isoquinoline-2-carboxylic acid 4-carboxymethyl-cyclohexyl ester or
trans-6-[3-(3-ethyl-phenyl)-ureido]-3,4-dihydro-1H-isoquinoline-2-carboxylic acid 4-carboxymethyl-cyclohexyl ester.

7. The compound according to claim 6, wherein the compound is trans-6-[3-(2-fluoro-phenyl)-ureido]-3,4-dihydro-1H-isoquinoline-2-carboxylic acid 4-carboxymethyl-cyclohexyl ester.

8. The compound according to claim 6, wherein the compound is trans-6-[3-(3-ethoxy-phenyl)-ureido]-3,4-dihydro-1H-isoquinoline-2-carboxylic acid 4-carboxymethyl-cyclohexyl ester.

9. The compound according to claim 6, wherein the compound is trans-6-[3-(2,4,5-trifluoro-phenyl)-ureido]-3,4-dihydro-1H-isoquinoline-2-carboxylic acid 4-carboxymethyl-cyclohexyl ester.

10. The compound according to claim 6, wherein the compound is trans-6-[3-(3,4-difluoro-phenyl)-ureido]-3,4-dihydro-1H-isoquinoline-2-carboxylic acid 4-carboxymethyl-cyclohexyl ester.

11. The compound according to claim 6, wherein the compound is trans-6-[3-(2-fluoro-5-methoxy-phenyl)-ureido]-3,4-dihydro-1H-isoquinoline-2-carboxylic acid 4-carboxymethyl-cyclohexyl ester.

12. The compound according to claim 6, wherein the compound is trans-6-(3-m-tolyl-ureido)-3,4-dihydro-1H-isoquinoline-2-carboxylic acid 4-carboxymethyl-cyclohexyl ester.

13. The compound according to claim 6, wherein the compound is trans-6-[3-(3-ethyl-phenyl)-ureido]-3,4-dihydro-1H-isoquinoline-2-carboxylic acid 4-carboxymethyl-cyclohexyl ester.

14. The compound according to claim 1, wherein the compound is trans-6-[3-(2-methoxy-5-methyl-phenyl)-ureido]-3,4-dihydro-1H-isoquinoline-2-carboxylic acid 4-carboxymethyl-cyclohexyl ester.

15. The compound according to claim 1, wherein the compound is trans-6-[3-(5-ethoxy-2-fluoro-phenyl)-ureido]-3,4-dihydro-1H-isoquinoline-2-carboxylic acid 4-carboxymethyl-cyclohexyl ester.

16. The compound according to claim 1, wherein the compound is trans-6-(3-p-tolyl-ureido)-3,4-dihydro-1H-isoquinoline-2-carboxylic acid 4-carboxymethyl-cyclohexyl ester.

17. The compound according to claim 1, wherein the compound is trans-6-(3-o-tolyl-ureido)-3,4-dihydro-1H-isoquinoline-2-carboxylic acid 4-carboxymethyl-cyclohexyl ester.

18. The compound according to claim 1, wherein the compound is trans-6-[3-(3,4-dimethyl-phenyl)-ureido]-3,4-dihydro-1H-isoquinoline-2-carboxylic acid 4-carboxymethyl-cyclohexyl ester.

19. A pharmaceutical composition comprising a compound or pharmacologically acceptable salt thereof according to claim 1 and a pharmaceutically acceptable carrier.

20. The pharmaceutical composition according to claim 19, wherein the compound or pharmacologically acceptable salt is trans-6-[3-(2-fluoro-phenyl)-ureido]-3,4-dihydro-1H-isoquinoline-2-carboxylic acid 4-carboxymethyl-cyclohexyl ester.

21. The pharmaceutical composition according to claim 19, wherein the compound or pharmacologically acceptable salt is trans-6-[3-(2-methoxy-5-methyl-phenyl)-ureido]-3,4-dihydro-1H-isoquinoline-2-carboxylic acid 4-carboxymethyl-cyclohexyl ester.

22. The pharmaceutical composition according to claim 19, wherein the compound or pharmacologically acceptable salt is trans-6-[3-(2,4,5-trifluoro-phenyl)-ureido]-3,4-dihydro-1H-isoquinoline-2-carboxylic acid 4-carboxymethyl-cyclohexyl ester.

23. The pharmaceutical composition according to claim 19, wherein the compound or pharmacologically acceptable salt is trans-6-(3-p-tolyl-ureido)-3,4-dihydro-1H-isoquinoline-2-carboxylic acid 4-carboxymethyl-cyclohexyl ester.

24. A method for treating diabetes comprising administering a pharmacologically effective amount of a compound or pharmacologically acceptable salt thereof according to claim 1 to a warm-blooded animal.

25. A method for treating adiposity or obesity comprising administering a pharmacologically effective amount of a compound or pharmacologically acceptable salt thereof according to claim 1 to a warm-blooded animal.

26. The method according to claim 24, wherein the warm-blooded animal is a human.

27. The method according to claim 25, wherein the warm-blooded animal is a human.

28. A method for treating diabetes comprising administering a pharmacologically effective amount of a compound according to claim 7 or pharmacologically acceptable salt thereof to a human.

29. A method for treating diabetes comprising administering a pharmacologically effective amount of a compound according to claim 14 or pharmacologically acceptable salt thereof to a human.

30. A method for treating diabetes comprising administering a pharmacologically effective amount of a compound according to claim 9 or pharmacologically acceptable salt thereof to a human.

31. A method for treating diabetes comprising administering a pharmacologically effective amount of a compound according to claim 16 or pharmacologically acceptable salt thereof to a human.

32. A method for treating adiposity or obesity comprising administering a pharmacologically effective amount of a compound according to claim 7 or pharmacologically acceptable salt thereof to a human.

33. A method for treating adiposity or obesity comprising administering a pharmacologically effective amount of a compound according to claim 14 or pharmacologically acceptable salt thereof to a human.

34. A method for treating adiposity or obesity comprising administering a pharmacologically effective amount of a compound according to claim 9 or pharmacologically acceptable salt thereof to a human.

35. A method for treating adiposity or obesity comprising administering a pharmacologically effective amount of a compound according to claim 16 or pharmacologically acceptable salt thereof to a human.

36. A method for treating hypertriglyceridemia comprising administering a pharmacologically effective amount of a compound or pharmacologically acceptable salt thereof according to claim 1 to a warm-blooded animal.

37. The method according to claim 36, wherein the warm-blooded animal is a human.

38. A method for treating hypertriglyceridemia comprising administering a pharmacologically effective amount of a compound according to claim 7 or pharmacologically acceptable salt thereof to a human.

39. A method for treating hypertriglyceridemia comprising administering a pharmacologically effective amount of a compound according to claim 14 or pharmacologically acceptable salt thereof to a human.

40. A method for treating hypertriglyceridemia comprising administering a pharmacologically effective amount of a compound according to claim 9 or pharmacologically acceptable salt thereof to a human.

41. A method for treating hypertriglyceridemia comprising administering a pharmacologically effective amount of a compound according to claim 16 or pharmacologically acceptable salt thereof to a human.

* * * * *

UNITED STATES PATENT AND TRADEMARK OFFICE
CERTIFICATE OF CORRECTION

| | | |
|---|---|---|
| PATENT NO. | : 8,735,425 B2 | Page 1 of 1 |
| APPLICATION NO. | : 12/878170 | |
| DATED | : May 27, 2014 | |
| INVENTOR(S) | : Yoshikazu Uto, Hiroshi Karasawa and Kiyosumi Takaishi | |

It is certified that error appears in the above-identified patent and that said Letters Patent is hereby corrected as shown below:

On the title page of the patent at item (75), the city of residence for Inventor Yoshikazu Uto should be "Tokyo (JP)".

Signed and Sealed this
Fourth Day of November, 2014

Michelle K. Lee
*Deputy Director of the United States Patent and Trademark Office*